(12) United States Patent
Reddy et al.

(10) Patent No.: US 9,090,674 B2
(45) Date of Patent: Jul. 28, 2015

(54) RAPID ISOLATION OF MONOCLONAL ANTIBODIES FROM ANIMALS

(75) Inventors: Sai Reddy, Berkeley, IL (US); Xin Ge, Riverside, CA (US); Jason Lavinder, Round Rock, TX (US); Daniel Boutz, Austin, TX (US); Andrew D. Ellington, Austin, TX (US); Edward M. Marcotte, Austin, TX (US); George Georgiou, Austin, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 979 days.

(21) Appl. No.: 13/109,467

(22) Filed: May 17, 2011

(65) Prior Publication Data

US 2011/0312505 A1 Dec. 22, 2011

Related U.S. Application Data

(60) Provisional application No. 61/345,538, filed on May 17, 2010, provisional application No. 61/377,816, filed on Aug. 27, 2010.

(51) Int. Cl.
  C40B 30/04 (2006.01)
  C07K 16/06 (2006.01)
  G01N 33/68 (2006.01)
  C12Q 1/68 (2006.01)

(52) U.S. Cl.
  CPC ............ *C07K 16/065* (2013.01); *C12Q 1/6881* (2013.01); *G01N 33/6857* (2013.01); *C07K 2317/55* (2013.01); *C07K 2317/56* (2013.01); *C07K 2317/565* (2013.01); *C07K 2317/622* (2013.01); *C07K 2317/92* (2013.01); *C12Q 2600/16* (2013.01); *C40B 30/04* (2013.01)

(58) Field of Classification Search
  None
  See application file for complete search history.

(56) References Cited

U.S. PATENT DOCUMENTS

2006/0233812 A1 10/2006 Burnie et al.
2007/0172887 A1 7/2007 Takacs et al.

FOREIGN PATENT DOCUMENTS

| WO | WO 03-052416 | | 6/2003 |
|---|---|---|---|
| WO | WO03/052416 | † | 6/2003 |
| WO | WO 2005-084134 | | 9/2005 |
| WO | WO2008/079914 | † | 7/2008 |
| WO | WO 2008-079914 | | 7/2008 |

(Continued)

OTHER PUBLICATIONS

Meijer et. al. (2006) Journal of Molecular Biology vol. 358 pp. 764 to 772.*

(Continued)

*Primary Examiner* — Christian Boesen
(74) *Attorney, Agent, or Firm* — Parker Highlander PLLC

(57) ABSTRACT

Methods and compositions for identification of candidate antigen-specific variable regions as well as generation of antibodies or antigen-binding fragments that could have desired antigen specificity are provided. For example, in certain aspects methods for determining amino acid sequences of serum antibody CDR and abundancy level are described. In some aspects, methods for determining nucleic acid sequences of antibody variable region sequences and frequency are provided. Furthermore, the invention provides methods for identification and generation of antibody or antigen-binding fragments that comprise highly-represented CDR.

12 Claims, 11 Drawing Sheets

(56) References Cited

FOREIGN PATENT DOCUMENTS

| WO | WO2009/100896 | † | 8/2009 |
| WO | WO2010/083456 | † | 7/2010 |
| WO | WO 2010-083456 | | 7/2010 |
| WO | WO 2011-146514 | | 11/2011 |

OTHER PUBLICATIONS

Meijer et. al. (2006) Journal of Molecular Biology vol. 358 pp. 764 to 772 Supplementary Data.*
Arnaout, "Specificity and overlap in gene segment-defined antibody repertoires," *BMC Genomics*, 6:148, 2005.
Behrendt et al., "The role of somatic mutation in determining the affinity of anti-DNA antibodies," *Clin Exp Immunol*, 131:182-189, 2003.
Boudinot et al., "New perspectives for large-scale repertoire analysis of immune receptors," *Molecular Immunology*, 45:2437-2445, 2008.
Boyd et al., "Measurement and clinical monitoring of human lymphocyte clonality by massively parallel V-D-J pyrosequencing," *Science Translational Medicine*, 1(12):12ra23, 2009.
Burgoon et al., "Laser-capture microdissection of plasma cells from subacute sclerosing panencephalitis brain reveals intrathecal disease-relevant antibodies," *PNAS*, 102(20):7245-7250, 2005.
Campbell et al., "Subclonal phylogenetic structures in cancer revealed by ultra-deep sequencing," *PNAS*, 105(35):13081-13086, 2008.
Chapal et al., "Thyroid peroxidase autoantibodies obtained from random single chain Fv libraries contain the same heavy/light chain combinations as occur in vivo," *Endocrinology*, 142(11):4740-4750, 2001.
Clackson et al., "Making antibody fragments using phage display libraries," *Letters to Nature*, 352:624-628, 1991.
Correia-Neves et al., "The shaping of the T cell repertoire," *Immunity*, 14:21-32, 2001.
De Costa et al., "Sequencing and quantifying IgG fragments and antigen-binding regions by mass spectrometry," *Journal of Proteome Research*, 9:2937-2945, 2010.
Freeman et al., "Profiling the T-cell receptor beta-chain repertoire by massively parallel sequencing," *Genome Research*, 19:1817-1824, 2009.
Kurokawa et al., "Paired cloning of the T cell receptor α and β genes from a single T cell without the establishment of a T cell clone," *Clin Exp Immunol*, 123:340-345, 2001.
Matsutani et al., "Restricted usage of T-cell receptor α-chain variable region (TCRAV) and T-cell receptor β-chain variable region (TCRBV) repertoires after human allogeneic haematopoietic transplantation," *British Journal of Haematology*, 109:759-769, 2000.
McMahan et al., "Production, characterization, and immunogenicity of a soluble rat single chain T cell receptor specific for an encephalitogenic peptide," *The Journal of Biological Chemistry*, 278(33):30961-30970, 2003.
Obermeier et al., "Matching of oligoclonal immunoglobulin transcriptomes and proteomes of cerebrospinal fluid in multiple sclerosis," *Nature Medicine*, 14(6):688-693, 2008.
Packer and Muraro, "Optimized clonotypic analysis of T-cell receptor repertoire in immune reconstitution," *Experimental Hematology*, 35:516-521, 2007.
PCT International Search Report issued in International Application No. PCT/US2011/036852, mailed Sep. 26, 2012.
PCT Third Party Observation submitted in International Application No. PCT/US2011/036852 on Sep. 14, 2012.
Persson et al., "Generation of diverse high-affinity human monoclonal antibodies by repertoire cloning." *Proc. Natl. Acad. Sci. USA*, 88:2432-2436, 1991.
Schluter et al., "Sequence analysis of homogeneous peptides of shark immunoglobulin light chains by tandem mass spectrometry: correlation with gene sequence and homologies among variable and constant region peptides of sharks and mammals," *Molecular Immunology*, 27(1):17-23, 1990.
Weinstein et al., "High-throughput sequencing of the zebrafish antibody repertoire," *Science*, 324:807-810, 2009.
Cheung et al., "A proteomics approach for the identification and cloning of monoclonal antibodies from serum", *Nature Biotechnology*, 30(5):447-52, 2012.
DeKosky et al., "High-throughput sequencing of the paired human immunoglobulin heavy and light chain repertoire", *Nature Biotechnology*, 31(2):166-169, 2013.
Dornmair et al., "Novel approaches for identifying target antigens of autoreactive human B and T cells", *Seminars in Immunopathology*, 31(4):467-477, 2009.
Extended European Search Report issued in European Application No. 11784105.6, dated Sep. 11, 2013.
Fischer et al., "Sequencing antibody repertoires: the next generation", *MAbs*, 3(1):17-20, 2011.
Glanville et al., "Precise determination of the diversity of a combinatorial antibody library gives insight into the human immunoglobulin repertoire", *Proc Natl Acad Sci USA*, 106(48):20216-20221, 2009.
Ippolito et al., "Antibody repertoires in humanized NOD-scid-IL2Rγ(null) mice and human B cells reveals human-like diversification and tolerance checkpoints in the mouse", *PLoS One*, 7(4):e35497, 2012.
Maiolica et al., "Targeted proteome investigation via selected reaction monitoring mass spectrometry", *Journal of Proteomics*, 75(12):3495-3513, 2012.
Mouquet et al., "Complex-type N-glycan recognition by potent broadly neutralizing Hiv antibodies",*Proc Natl Acad Sci USA*, 109(47):E3268-E3277, 2012.
Nazabal et al., "Immunoassays with direct mass spectrometric detection", *Analytical Chemistry*, 78(11):3562-3570, 2006.
Office Communication issued in Australian Application No. 2011256290, dated Aug. 27, 2013.
Ravetch et al., "Structure of the human immunoglobulin mu locus: characterization of embryonic and rearranged J and D genes", *Cell*, 27:583-591, 1981.
Reddy et al., "Monoclonal antibodies isolated without screening by analyzing the variable-gene repertoire of plasma cells", *Nature Biotechnology*, 28(9):965-9, 2010.
Sato et al., "Proteomics-directed cloning of circulating antiviral human monoclonal antibodies", *Nature Biotechnology*, 30(11):1039-1043, 2012.
Willis et al., "Rapid molecular cloning of rearrangements of the IGHJ locus using long-distance inverse polymerase chain reaction", *Blood*, 90(6):2456-2464, 1997.
Wine et al., "Molecular deconvolution of the monoclonal antibodies that comprise the polyclonal serum response", *Proc Natl Acad Sci USA*, 110(8):2993-2998, 2013.
Schluter et al., Mol. Immunol. 27: 17-23 (1990).†
de Costa et al., J. Proteome Res. 9: 2937-2945 (2010; published on Web Apr. 14, 2010).†
Boyd et al., Science Translational Medicine 1(12): 12ra23; pp. 1-8 (Dec. 23, 2009).†
Weinstein et al., Science 324: 807-810 (May 8, 2009).†
Yates, TIG 16 (1): 5-8 (Jan. 2000) Elsevier Science.†
Peng J, "Protein Mixture Analysis by Tandem Mass Spectometry" In: The Bioinformatics of Brains: From Genes and Proteins to Behaviors (Williams RW, ed.) pp. 61-68 (2003); Washington, DC: Society for Neuroscience.†
Obermeier et al., Nature Medicine 14: 688-693 (May 1, 2008).†
Damoc et al., Proteomics 3: 1425-1433 (2003).†
Omenn et al., Proteomics 5: 3226-3245 (2005).†
List of 3020 proteins, http://www.ccmb.med.umich.edu/sites/default/files/ppp/Protein_list_3020.txt, retrieved Nov. 17, 2012 (HUPO Plasma Proteome Project (Omenn 2005) Dept. of Computational Medicine and Bioinformatics—U. Michigan Med. School.†
Huse et al., J. Biochem. Biophys. Methods 51: 217-231 (2002).†
Instructions for Product Nos. 21901 and 21902, Maleimide-PEG2-Biotin Sulfhydryl-reactive biotin labeling reagent with a polyethylene glycol (PEG) spacer arm, published by Thermo Fisher Scientific Inc. (2008).†

\* cited by examiner
† cited by third party

A. First Principle Component Vs. Second Principle Component

B. First Principle Component Vs. Third Principle Component

```
                        SEQUENCE LISTING

<160> NUMBER OF SEQ ID NOS: 806

<210> SEQ ID NO 1
<211> LENGTH: 22
<212> TYPE: DNA
<213> ORGANISM: Artificial Sequence
<220> FEATURE:
<223> OTHER INFORMATION: Synthetic primer

<400> SEQUENCE: 1
tgtgccttgg cagtctcagg gg                                              22

<210> SEQ ID NO 2
<211> LENGTH: 60
<212> TYPE: DNA
<213> ORGANISM: Artificial Sequence
<220> FEATURE:
<223> OTHER INFORMATION: Synthetic primer

<400> SEQUENCE: 2
ccatctcatc cctgcgtgtc tccgactcag acgagtgcgt acagttggtg cagcatcagc     60

<210> SEQ ID NO 3
<211> LENGTH: 60
<212> TYPE: DNA
<213> ORGANISM: Artificial Sequence
<220> FEATURE:
<223> OTHER INFORMATION: Synthetic primer

<400> SEQUENCE: 3
ccatctcatc cctgcgtgtc tccgactcag acgctcgaca acagttggtg cagcatcagc     60

<210> SEQ ID NO 4
<211> LENGTH: 60
<212> TYPE: DNA
<213> ORGANISM: Artificial Sequence
<220> FEATURE:
<223> OTHER INFORMATION: Synthetic primer

<400> SEQUENCE: 4
ccatctcatc cctgcgtgtc tccgactcag agacgcactc acagttggtg cagcatcagc     60

<210> SEQ ID NO 5
<211> LENGTH: 61
<212> TYPE: DNA
<213> ORGANISM: Artificial Sequence
<220> FEATURE:
<223> OTHER INFORMATION: Synthetic primer

<400> SEQUENCE: 5
ccatctcatc cctgcgtgtc tccgactcag acgagtgcgt gatagaccga tggggctgtt     60
g                                                                    61

<210> SEQ ID NO 6
<211> LENGTH: 61
<212> TYPE: DNA
<213> ORGANISM: Artificial Sequence
```

```
<220> FEATURE:
<223> OTHER INFORMATION: Synthetic primer

<400> SEQUENCE: 6
ccatctcatc cctgcgtgtc tccgactcag acgctcgaca gatagaccga tggggctgtt      60
g                                                                      61

<210> SEQ ID NO 7
<211> LENGTH: 61
<212> TYPE: DNA
<213> ORGANISM: Artificial Sequence
<220> FEATURE:
<223> OTHER INFORMATION: Synthetic primer

<400> SEQUENCE: 7
ccatctcatc cctgcgtgtc tccgactcag agacgcactc gatagaccga tggggctgtt      60
g                                                                      61

<210> SEQ ID NO 8
<211> LENGTH: 30
<212> TYPE: DNA
<213> ORGANISM: Artificial Sequence
<220> FEATURE:
<223> OTHER INFORMATION: Synthetic primer

<400> SEQUENCE: 8
cctatcccct gtgtgccttg gcagtctcag                                       30

<210> SEQ ID NO 9
<211> LENGTH: 22
<212> TYPE: DNA
<213> ORGANISM: Artificial Sequence
<220> FEATURE:
<223> OTHER INFORMATION: Synthetic primer

<400> SEQUENCE: 9
gagacacgca gggatgagat gg                                               22

<210> SEQ ID NO 10
<211> LENGTH: 9
<212> TYPE: PRT
<213> ORGANISM: Artificial Sequence
<220> FEATURE:
<223> OTHER INFORMATION: Synthetic peptide

<400> SEQUENCE: 10

His Asp Tyr Gly Asn Tyr Val Asp Tyr
1               5

<210> SEQ ID NO 11
<211> LENGTH: 11
<212> TYPE: PRT
<213> ORGANISM: Artificial Sequence
<220> FEATURE:
<223> OTHER INFORMATION: Synthetic peptide

<400> SEQUENCE: 11

Asp Gly Asn Tyr Gln Glu Asp Tyr Phe Asp Tyr
1               5                   10

<210> SEQ ID NO 12
<211> LENGTH: 9
<212> TYPE: PRT
<213> ORGANISM: Artificial Sequence
<220> FEATURE:
```

```
<223> OTHER INFORMATION: Synthetic peptide

<400> SEQUENCE: 12

Glu Gly Tyr Ala Tyr Asp Val Asp Tyr
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic peptide

<400> SEQUENCE: 13

Asp Asp Tyr Asp Trp Tyr Phe Asp Val
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic peptide

<400> SEQUENCE: 14

Asp Asn Trp Asp Trp Tyr Phe Asp Val
1               5

<210> SEQ ID NO 15
<211> LENGTH: 10
<212> TYPE: PRT
<213> ORGANISM: Artificial Sequence
<220> FEATURE:
<223> OTHER INFORMATION: Synthetic peptide

<400> SEQUENCE: 15

Asp Asp Gly Tyr Tyr Trp Tyr Phe Asp Val
1               5                   10

<210> SEQ ID NO 16
<211> LENGTH: 9
<212> TYPE: PRT
<213> ORGANISM: Artificial Sequence
<220> FEATURE:
<223> OTHER INFORMATION: Synthetic peptide

<400> SEQUENCE: 16

Tyr Asp Tyr Gly Lys Asp Phe Asp Tyr
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic peptide

<400> SEQUENCE: 17

Cys Ala Asp Gly Asn Tyr
1               5

<210> SEQ ID NO 18
<211> LENGTH: 12
<212> TYPE: PRT
<213> ORGANISM: Artificial Sequence
<220> FEATURE:
<223> OTHER INFORMATION: Synthetic peptide
```

```
<400> SEQUENCE: 18

Val Leu Gly Gln Gly Asp Tyr Tyr Ala Met Asp Tyr
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Synthetic peptide

<400> SEQUENCE: 19

Ser Asp Arg Tyr Asp Gly Tyr Phe Asp Tyr
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Synthetic peptide

<400> SEQUENCE: 20

Ser Asp Arg Phe Asp Gly Tyr Phe Asp Tyr
1               5                   10

<210> SEQ ID NO 21
<211> LENGTH: 6
<212> TYPE: PRT
<213> ORGANISM: Artificial Sequence
<220> FEATURE:
<223> OTHER INFORMATION: Synthetic peptide

<400> SEQUENCE: 21

Trp Leu Leu Leu Ala Tyr
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic peptide

<400> SEQUENCE: 22

Tyr Gly Asn Tyr Phe Asp Tyr
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic peptide

<400> SEQUENCE: 23

Ser Asp Gly Tyr Tyr Tyr Phe Asp Tyr
1               5

<210> SEQ ID NO 24
<211> LENGTH: 10
<212> TYPE: PRT
<213> ORGANISM: Artificial Sequence
<220> FEATURE:
<223> OTHER INFORMATION: Synthetic peptide
```

```
<400> SEQUENCE: 24

Ser Gly Gly Asn Tyr Asp Ala Met Asp Tyr
1               5                  10

<210> SEQ ID NO 25
<211> LENGTH: 12
<212> TYPE: PRT
<213> ORGANISM: Artificial Sequence
<220> FEATURE:
<223> OTHER INFORMATION: Synthetic peptide

<400> SEQUENCE: 25

Tyr Tyr Asp Tyr Asp Lys Ala Tyr Tyr Phe Asp Tyr
1               5                  10

<210> SEQ ID NO 26
<211> LENGTH: 112
<212> TYPE: PRT
<213> ORGANISM: Artificial Sequence
<220> FEATURE:
<223> OTHER INFORMATION: Synthetic peptide

<400> SEQUENCE: 26

Asp Val Leu Met Thr Gln Thr Pro Leu Ser Leu Pro Val Ser Leu Gly
1               5                  10                  15

Asp Gln Ala Ser Ile Ser Cys Arg Ser Ser Gln Ser Ile Val His Ser
            20                  25                  30

Asn Gly Asp Thr Tyr Leu Glu Trp Tyr Leu Gln Lys Pro Gly Gln Ser
        35                  40                  45

Pro Lys Leu Leu Val Tyr Lys Leu Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Ile Lys
            100                 105                 110

<210> SEQ ID NO 27
<211> LENGTH: 111
<212> TYPE: PRT
<213> ORGANISM: Artificial Sequence
<220> FEATURE:
<223> OTHER INFORMATION: Synthetic peptide

<400> SEQUENCE: 27

Asp Ile Val Met Thr Gln Ser Pro Ala Ser Leu Ala Val Ser Leu Gly
1               5                  10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Thr Thr Tyr Tyr Cys Gln Gln Ser Asn
                85                  90                  95

Glu Asp Pro Trp Thr Phe Gly Gly Gly Thr Lys Leu Glu Ile Lys
            100                 105                 110
```

<210> SEQ ID NO 28
<211> LENGTH: 111
<212> TYPE: PRT
<213> ORGANISM: Artificial Sequence
<220> FEATURE:
<223> OTHER INFORMATION: Synthetic peptide

<400> SEQUENCE: 28

```
Asp Ile Val Met Thr Gln Ser Pro Leu Thr Leu Thr Val Thr Ile Gly
1               5                   10                  15

Gln Pro Ala Ser Ile Ser Cys Lys Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Glu Phe Thr Leu Lys Thr
65                  70                  75                  80

Ser Arg Val Glu Ala Glu Asp Leu Gly Val Tyr Tyr Cys Trp Gln Gly
                85                  90                  95

Thr His Phe Pro His Phe Gly Gly Gly Thr Lys Leu Glu Ile Lys
            100                 105                 110
```

<210> SEQ ID NO 29
<211> LENGTH: 120
<212> TYPE: PRT
<213> ORGANISM: Artificial Sequence
<220> FEATURE:
<223> OTHER INFORMATION: Synthetic peptide

<400> SEQUENCE: 29

```
Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
        35                  40                  45

Gly Tyr Ile Asn Pro Ser Ser Gly Tyr Thr Asn Tyr Asn Gln Lys Phe
    50                  55                  60

Lys Asp Lys Ala Thr Leu Thr Ala Asp Lys Ser Ser Ser Thr Ala Asn
65                  70                  75                  80

Met Gln Leu Ser Ser Leu Thr Ser Glu Asp Ser Ala Val Tyr Tyr Cys
                85                  90                  95

Ala Arg Ser Asp Arg Tyr Asp Gly Tyr Phe Asp Tyr Trp Gly Gln Gly
            100                 105                 110

Thr Thr Leu Thr Val Ser Ser Ala
        115                 120
```

<210> SEQ ID NO 30
<211> LENGTH: 114
<212> TYPE: PRT
<213> ORGANISM: Artificial Sequence
<220> FEATURE:
<223> OTHER INFORMATION: Synthetic peptide

<400> SEQUENCE: 30

```
Glu Val Lys Leu Val Glu Ser Gly Gly Gly Phe Val Lys Pro Gly Gly
1               5                   10                  15
```

Ser Leu Lys Leu Ser Cys Ala Ala Ser Gly Phe Thr Phe Ser Thr Tyr
            20                  25                  30

Gly Met Ser Trp Val Arg Gln Thr Pro Glu Lys Arg Leu Glu Trp Val
            35                  40                  45

Ala Ser Ile Ser Ala Gly Gly Thr Thr Tyr Tyr Ser Asp Ser Val Lys
 50                      55                  60

Gly Arg Phe Thr Ile Ser Arg Asp Asn Ala Arg Asn Ile Leu Tyr Leu
 65                  70                  75                  80

Gln Met Ser Ser Leu Arg Ser Glu Asp Thr Ala Met Tyr Tyr Cys Ala
                85                  90                  95

Arg Trp Leu Leu Leu Ala Tyr Trp Gly Gln Gly Thr Leu Val Thr Ser
            100                 105                 110

Ser Ala

<210> SEQ ID NO 31
<211> LENGTH: 119
<212> TYPE: PRT
<213> ORGANISM: Artificial Sequence
<220> FEATURE:
<223> OTHER INFORMATION: Synthetic peptide

<400> SEQUENCE: 31

Gln Val Gln Leu Gln Gln Ser Gly Thr Val Leu Ala Arg Pro Gly Ala
 1               5                  10                  15

Ser Val Lys Met Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
            35                  40                  45

Gly Ala Ile Tyr Pro Gly Asn Ser Asp Thr Ser Tyr Asn Gln Lys Phe
 50                      55                  60

Lys Gly Lys Ala Lys Leu Thr Ala Val Thr Ser Thr Ser Thr Ala Tyr
 65                  70                  75                  80

Met Glu Leu Ser Ser Leu Thr Asn Glu Asp Ser Ala Val Tyr Tyr Cys
                85                  90                  95

Thr Arg Ser Asp Gly Tyr Tyr Tyr Phe Asp Tyr Trp Gly Gln Gly Thr
            100                 105                 110

Thr Leu Thr Val Ser Ser Ala
        115

<210> SEQ ID NO 32
<211> LENGTH: 107
<212> TYPE: PRT
<213> ORGANISM: Artificial Sequence
<220> FEATURE:
<223> OTHER INFORMATION: Synthetic peptide

<400> SEQUENCE: 32

Asp Ile Val Met Thr Gln Ser Pro Ser Ser Leu Ala Ser Leu Gly
 1               5                  10                  15

Glu Arg Val Ser Leu Thr Cys Arg Ala Ser Gln Asp Ile Gly Ser Ser
            20                  25                  30

Leu Asn Trp Leu Gln Gln Glu Pro Asp Gly Thr Ile Lys Arg Leu Ile
            35                  40                  45

Tyr Ala Thr Ser Ser Leu Asp Ser Gly Val Pro Lys Arg Phe Ser Gly
         50                  55                  60

Ser Arg Ser Gly Ser Asp Tyr Ser Leu Thr Ile Ser Ser Leu Glu Ser
 65                  70                  75                  80

Val Asp Phe Val Asp Tyr Tyr Cys Leu Gln Tyr Ala Ser Ser Pro Phe
                85                  90                  95

Thr Phe Gly Ser Gly Thr Lys Leu Glu Ile Lys
            100                 105

<210> SEQ ID NO 33
<211> LENGTH: 112
<212> TYPE: PRT
<213> ORGANISM: Artificial Sequence
<220> FEATURE:
<223> OTHER INFORMATION: Synthetic peptide

<400> SEQUENCE: 33

Asp Ile Val Met Thr Gln Ser Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Gly Asp Leu Gly Val Tyr Tyr Cys Trp Gln Gly
                85                  90                  95

Thr His Phe Pro Arg Thr Phe Gly Gly Gly Thr Lys Leu Glu Ile Lys
            100                 105                 110

<210> SEQ ID NO 34
<211> LENGTH: 111
<212> TYPE: PRT
<213> ORGANISM: Artificial Sequence
<220> FEATURE:
<223> OTHER INFORMATION: Synthetic peptide

<400> SEQUENCE: 34

Asp Ile Val Met Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Val Thr Tyr Tyr Cys Gln Gln Asn Asn
                85                  90                  95

Glu Asp Pro Arg Thr Phe Gly Gly Gly Thr Lys Leu Glu Ile Lys
            100                 105                 110

<210> SEQ ID NO 35
<211> LENGTH: 106
<212> TYPE: PRT
<213> ORGANISM: Artificial Sequence
<220> FEATURE:
<223> OTHER INFORMATION: Synthetic peptide

<400> SEQUENCE: 35

Asp Ile Val Met Thr Gln Ser Pro Ala Ile Met Ser Ala Ser Pro Gly

```
  1               5                   10                  15
Glu Lys Val Thr Ile Thr Cys Ser Ala Ser Ser Ser Val Ser Tyr Met
                20                  25                  30

His Trp Phe Gln Gln Lys Pro Gly Thr Ser Pro Lys Leu Trp Ile Tyr
            35                  40                  45

Ser Thr Ser Asn Leu Ala Ser Gly Val Pro Ala Arg Phe Ser Gly Ser
        50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Arg Ser Ser Tyr Pro Leu Thr
                85                  90                  95

Phe Gly Ala Gly Thr Lys Leu Glu Ile Lys
            100                 105

<210> SEQ ID NO 36
<211> LENGTH: 119
<212> TYPE: PRT
<213> ORGANISM: Artificial Sequence
<220> FEATURE:
<223> OTHER INFORMATION: Synthetic peptide

<400> SEQUENCE: 36

Glu Val Lys Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
                20                  25                  30

Gly Met Ser Trp Val Arg Gln Thr Pro Asp Lys Arg Leu Glu Trp Val
            35                  40                  45

Ala Thr Ile Ser Ser Gly Gly Ser Tyr Thr Tyr Tyr Pro Asp Ser Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Asp Tyr Gly Asn Tyr Val Asp Tyr Trp Gly Gln Gly Thr
            100                 105                 110

Thr Leu Thr Val Ser Ser Ala
        115

<210> SEQ ID NO 37
<211> LENGTH: 120
<212> TYPE: PRT
<213> ORGANISM: Artificial Sequence
<220> FEATURE:
<223> OTHER INFORMATION: Synthetic peptide

<400> SEQUENCE: 37

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
                20                  25                  30

Gly Met Ser Trp Val Arg Gln Thr Pro Asp Lys Arg Leu Glu Trp Val
            35                  40                  45

Ala Thr Ile Ser Ser Gly Gly Ser Tyr Thr Tyr Tyr Pro Asp Ser Val
        50                  55                  60

Lys Gly Arg Phe Thr Ile Ser Arg Asp Asn Ala Lys Asn Thr Leu Tyr
65                  70                  75                  80
```

-continued

Leu Gln Met Ser Ser Leu Lys Ser Glu Asp Thr Ala Met Tyr Tyr Cys
                85                  90                  95

Ala Arg Asp Gly Asn Tyr Gln Glu Asp Tyr Phe Asp Tyr Trp Gly Gln
            100                 105                 110

Gly Thr Thr Leu Thr Val Ser Ser
        115                 120

<210> SEQ ID NO 38
<211> LENGTH: 118
<212> TYPE: PRT
<213> ORGANISM: Artificial Sequence
<220> FEATURE:
<223> OTHER INFORMATION: Synthetic peptide

<400> SEQUENCE: 38

Glu Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Gly Ser Arg Thr Ile Tyr Ala Asp Ser Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Ile Tyr Tyr Cys
                85                  90                  95

Ala Arg Glu Gly Tyr Ala Tyr Asp Val Asp Tyr Trp Gly Gln Gly Thr
            100                 105                 110

Thr Leu Thr Val Ser Ser
        115

<210> SEQ ID NO 39
<211> LENGTH: 118
<212> TYPE: PRT
<213> ORGANISM: Artificial Sequence
<220> FEATURE:
<223> OTHER INFORMATION: Synthetic peptide

<400> SEQUENCE: 39

Glu Val Gln Gly Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Gly Ser Ser Asn Ile Phe Tyr Ser Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Tyr Asp Tyr Gly Lys Asp Phe Asp Tyr Trp Gly Gln Gly Thr
            100                 105                 110

Thr Leu Thr Val Ser Ser
        115

<210> SEQ ID NO 40

<211> LENGTH: 11
<212> TYPE: PRT
<213> ORGANISM: Artificial Sequence
<220> FEATURE:
<223> OTHER INFORMATION: Synthetic peptide

<400> SEQUENCE: 40

Cys Phe Gln Gly Ser His Val Pro Leu Thr Phe
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Synthetic peptide

<400> SEQUENCE: 41

Cys Trp Gln Gly Thr His Phe Pro His Phe
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Synthetic peptide

<400> SEQUENCE: 42

Cys Trp Gln Gly Thr His Phe Pro Thr Phe
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Synthetic peptide

<400> SEQUENCE: 43

Cys Trp Gln Gly Ile His Phe Pro Thr Phe
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Synthetic peptide

<400> SEQUENCE: 44

Cys Leu Gln Gly Ser His Val Pro Leu Thr Phe
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Synthetic peptide

<400> SEQUENCE: 45

Cys Trp Gln Gly Thr His Phe Pro Gln Thr Phe
1               5                   10

<210> SEQ ID NO 46
<211> LENGTH: 11

<212> TYPE: PRT
<213> ORGANISM: Artificial Sequence
<220> FEATURE:
<223> OTHER INFORMATION: Synthetic peptide

<400> SEQUENCE: 46

Cys Ser Gln Ser Thr His Val Pro Trp Thr Phe
1               5                   10

<210> SEQ ID NO 47
<211> LENGTH: 11
<212> TYPE: PRT
<213> ORGANISM: Artificial Sequence
<220> FEATURE:
<223> OTHER INFORMATION: Synthetic peptide

<400> SEQUENCE: 47

Cys Phe Gln Gly Ser His Val Pro Trp Thr Phe
1               5                   10

<210> SEQ ID NO 48
<211> LENGTH: 11
<212> TYPE: PRT
<213> ORGANISM: Artificial Sequence
<220> FEATURE:
<223> OTHER INFORMATION: Synthetic peptide

<400> SEQUENCE: 48

Cys Phe Gln Gly Ser His Val Pro Arg Thr Phe
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Synthetic peptide

<400> SEQUENCE: 49

Cys Trp Gln Gly Thr His Phe Pro Arg Thr Phe
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Synthetic peptide

<400> SEQUENCE: 50

Cys Phe Gln Gly Ser His Phe Pro Tyr Thr Phe
1               5                   10

<210> SEQ ID NO 51
<211> LENGTH: 11
<212> TYPE: PRT
<213> ORGANISM: Artificial Sequence
<220> FEATURE:
<223> OTHER INFORMATION: Synthetic peptide

<400> SEQUENCE: 51

Cys Phe Gln Gly Ser His Val Pro Tyr Thr Phe
1               5                   10

<210> SEQ ID NO 52
<211> LENGTH: 11
<212> TYPE: PRT

```
<213> ORGANISM: Artificial Sequence
<220> FEATURE:
<223> OTHER INFORMATION: Synthetic peptide

<400> SEQUENCE: 52

Cys Ser Gln Ser Thr His Val Pro Tyr Thr Phe
1               5                   10

<210> SEQ ID NO 53
<211> LENGTH: 11
<212> TYPE: PRT
<213> ORGANISM: Artificial Sequence
<220> FEATURE:
<223> OTHER INFORMATION: Synthetic peptide

<400> SEQUENCE: 53

Cys Gln Gln Ser Asn Glu Asp Pro Arg Thr Phe
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Synthetic peptide

<400> SEQUENCE: 54

Cys Gln Gln Ser Lys Glu Val Pro Trp Thr Phe
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Synthetic peptide

<400> SEQUENCE: 55

Cys Gln His His Tyr Gly Ile Pro Arg Thr Phe
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Synthetic peptide

<400> SEQUENCE: 56

Cys Ser Gln Ser Thr His Val Pro Phe Thr Phe
1               5                   10

<210> SEQ ID NO 57
<211> LENGTH: 11
<212> TYPE: PRT
<213> ORGANISM: Artificial Sequence
<220> FEATURE:
<223> OTHER INFORMATION: Synthetic peptide

<400> SEQUENCE: 57

Cys Gln His Ser Arg Glu Leu Pro Phe Thr Phe
1               5                   10

<210> SEQ ID NO 58
<211> LENGTH: 11
<212> TYPE: PRT
<213> ORGANISM: Artificial Sequence
```

```
<220> FEATURE:
<223> OTHER INFORMATION: Synthetic peptide

<400> SEQUENCE: 58

Cys Phe Gln Gly Ser His Val Pro Phe Thr Phe
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Synthetic peptide

<400> SEQUENCE: 59

Cys Gln Gln Ser Arg Lys Val Pro Trp Thr Phe
1               5                   10

<210> SEQ ID NO 60
<211> LENGTH: 9
<212> TYPE: PRT
<213> ORGANISM: Artificial Sequence
<220> FEATURE:
<223> OTHER INFORMATION: Synthetic peptide

<400> SEQUENCE: 60

Phe Gln Gly Ser His Val Pro Leu Thr
1               5

<210> SEQ ID NO 61
<211> LENGTH: 8
<212> TYPE: PRT
<213> ORGANISM: Artificial Sequence
<220> FEATURE:
<223> OTHER INFORMATION: Synthetic peptide

<400> SEQUENCE: 61

Trp Gln Gly Thr His Phe Pro His
1               5

<210> SEQ ID NO 62

<400> SEQUENCE: 62

000

<210> SEQ ID NO 63
<211> LENGTH: 9
<212> TYPE: PRT
<213> ORGANISM: Artificial Sequence
<220> FEATURE:
<223> OTHER INFORMATION: Synthetic peptide

<400> SEQUENCE: 63

Leu Gln Tyr Ala Ser Ser Pro Phe Thr
1               5

<210> SEQ ID NO 64
<211> LENGTH: 9
<212> TYPE: PRT
<213> ORGANISM: Artificial Sequence
<220> FEATURE:
<223> OTHER INFORMATION: Synthetic peptide

<400> SEQUENCE: 64

Trp Gln Gly Thr His Phe Pro Arg Thr
1               5
```

<210> SEQ ID NO 65
<211> LENGTH: 9
<212> TYPE: PRT
<213> ORGANISM: Artificial Sequence
<220> FEATURE:
<223> OTHER INFORMATION: Synthetic peptide

<400> SEQUENCE: 65

Gln Gln Arg Ser Ser Tyr Pro Leu Thr
1               5

<210> SEQ ID NO 66

<400> SEQUENCE: 66

000

<210> SEQ ID NO 67
<211> LENGTH: 34
<212> TYPE: DNA
<213> ORGANISM: Artificial Sequence
<220> FEATURE:
<223> OTHER INFORMATION: Synthetic primer

<400> SEQUENCE: 67
agccggccat ggcggayatc cagctgactc agcc                                 34

<210> SEQ ID NO 68
<211> LENGTH: 34
<212> TYPE: DNA
<213> ORGANISM: Artificial Sequence
<220> FEATURE:
<223> OTHER INFORMATION: Synthetic primer

<400> SEQUENCE: 68
agccggccat ggcggayatt gttctcwccc agtc                                 34

<210> SEQ ID NO 69
<211> LENGTH: 34
<212> TYPE: DNA
<213> ORGANISM: Artificial Sequence
<220> FEATURE:
<223> OTHER INFORMATION: Synthetic primer

<400> SEQUENCE: 69
agccggccat ggcggayatt gtgmtmactc agtc                                 34

<210> SEQ ID NO 70
<211> LENGTH: 34
<212> TYPE: DNA
<213> ORGANISM: Artificial Sequence
<220> FEATURE:
<223> OTHER INFORMATION: Synthetic primer

<400> SEQUENCE: 70
agccggccat ggcggayatt gtgytracac agtc                                 34

<210> SEQ ID NO 71
<211> LENGTH: 34
<212> TYPE: DNA
<213> ORGANISM: Artificial Sequence
<220> FEATURE:
<223> OTHER INFORMATION: Synthetic primer

<400> SEQUENCE: 71
agccggccat ggcggayatt gtratgacmc agtc                     34

<210> SEQ ID NO 72
<211> LENGTH: 34
<212> TYPE: DNA
<213> ORGANISM: Artificial Sequence
<220> FEATURE:
<223> OTHER INFORMATION: Synthetic primer

<400> SEQUENCE: 72
agccggccat ggcggayatt magatramcc agtc                     34

<210> SEQ ID NO 73
<211> LENGTH: 34
<212> TYPE: DNA
<213> ORGANISM: Artificial Sequence
<220> FEATURE:
<223> OTHER INFORMATION: Synthetic primer

<400> SEQUENCE: 73
agccggccat ggcggayatt cagatgaydc agtc                     34

<210> SEQ ID NO 74
<211> LENGTH: 34
<212> TYPE: DNA
<213> ORGANISM: Artificial Sequence
<220> FEATURE:
<223> OTHER INFORMATION: Synthetic primer

<400> SEQUENCE: 74
agccggccat ggcggayaty cagatgacac agac                     34

<210> SEQ ID NO 75
<211> LENGTH: 34
<212> TYPE: DNA
<213> ORGANISM: Artificial Sequence
<220> FEATURE:
<223> OTHER INFORMATION: Synthetic primer

<400> SEQUENCE: 75
agccggccat ggcggayatt gttctcawcc agtc                     34

<210> SEQ ID NO 76
<211> LENGTH: 34
<212> TYPE: DNA
<213> ORGANISM: Artificial Sequence
<220> FEATURE:
<223> OTHER INFORMATION: Synthetic primer

<400> SEQUENCE: 76
agccggccat ggcggayatt gwgctsaccc aatc                     34

<210> SEQ ID NO 77
<211> LENGTH: 34
<212> TYPE: DNA
<213> ORGANISM: Artificial Sequence
<220> FEATURE:
<223> OTHER INFORMATION: Synthetic primer

<400> SEQUENCE: 77
agccggccat ggcggayatt stratgaccc artc                     34

<210> SEQ ID NO 78
<211> LENGTH: 34
<212> TYPE: DNA
<213> ORGANISM: Artificial Sequence

```
<220> FEATURE:
<223> OTHER INFORMATION: Synthetic primer

<400> SEQUENCE: 78
agccggccat ggcggayrtt ktgatgaccc arac                        34

<210> SEQ ID NO 79
<211> LENGTH: 34
<212> TYPE: DNA
<213> ORGANISM: Artificial Sequence
<220> FEATURE:
<223> OTHER INFORMATION: Synthetic primer

<400> SEQUENCE: 79
agccggccat ggcggayatt gtgatgacbc agkc                        34

<210> SEQ ID NO 80
<211> LENGTH: 34
<212> TYPE: DNA
<213> ORGANISM: Artificial Sequence
<220> FEATURE:
<223> OTHER INFORMATION: Synthetic primer

<400> SEQUENCE: 80
agccggccat ggcggayatt gtgataacyc agga                        34

<210> SEQ ID NO 81
<211> LENGTH: 34
<212> TYPE: DNA
<213> ORGANISM: Artificial Sequence
<220> FEATURE:
<223> OTHER INFORMATION: Synthetic primer

<400> SEQUENCE: 81
agccggccat ggcggayatt gtgatgaccc agwt                        34

<210> SEQ ID NO 82
<211> LENGTH: 34
<212> TYPE: DNA
<213> ORGANISM: Artificial Sequence
<220> FEATURE:
<223> OTHER INFORMATION: Synthetic primer

<400> SEQUENCE: 82
agccggccat ggcggayatt gtgatgacac aacc                        34

<210> SEQ ID NO 83
<211> LENGTH: 34
<212> TYPE: DNA
<213> ORGANISM: Artificial Sequence
<220> FEATURE:
<223> OTHER INFORMATION: Synthetic primer

<400> SEQUENCE: 83
agccggccat ggcggayatt ttgctgactc agtc                        34

<210> SEQ ID NO 84
<211> LENGTH: 37
<212> TYPE: DNA
<213> ORGANISM: Artificial Sequence
<220> FEATURE:
<223> OTHER INFORMATION: Synthetic primer

<400> SEQUENCE: 84
agccggccat ggcggargct gttgtgactc aggaatc                     37
```

<210> SEQ ID NO 85
<211> LENGTH: 37
<212> TYPE: DNA
<213> ORGANISM: Artificial Sequence
<220> FEATURE:
<223> OTHER INFORMATION: Synthetic primer

<400> SEQUENCE: 85
gatggtgcgg ccgcagtacg tttgatttcc agcttgg					37

<210> SEQ ID NO 86
<211> LENGTH: 37
<212> TYPE: DNA
<213> ORGANISM: Artificial Sequence
<220> FEATURE:
<223> OTHER INFORMATION: Synthetic primer

<400> SEQUENCE: 86
gatggtgcgg ccgcagtacg ttttatttcc agcttgg					37

<210> SEQ ID NO 87
<211> LENGTH: 37
<212> TYPE: DNA
<213> ORGANISM: Artificial Sequence
<220> FEATURE:
<223> OTHER INFORMATION: Synthetic primer

<400> SEQUENCE: 87
gatggtgcgg ccgcagtacg ttttatttcc aactttg					37

<210> SEQ ID NO 88
<211> LENGTH: 37
<212> TYPE: DNA
<213> ORGANISM: Artificial Sequence
<220> FEATURE:
<223> OTHER INFORMATION: Synthetic primer

<400> SEQUENCE: 88
gatggtgcgg ccgcagtacg tttcagctcc agcttgg					37

<210> SEQ ID NO 89
<211> LENGTH: 37
<212> TYPE: DNA
<213> ORGANISM: Artificial Sequence
<220> FEATURE:
<223> OTHER INFORMATION: Synthetic primer

<400> SEQUENCE: 89
gatggtgcgg ccgcagtacc taggacagtc agtttgg					37

<210> SEQ ID NO 90
<211> LENGTH: 37
<212> TYPE: DNA
<213> ORGANISM: Artificial Sequence
<220> FEATURE:
<223> OTHER INFORMATION: Synthetic primer

<400> SEQUENCE: 90
gatggtgcgg ccgcagtacc taggacagtg accttgg					37

<210> SEQ ID NO 91
<211> LENGTH: 51
<212> TYPE: DNA
<213> ORGANISM: Artificial Sequence
<220> FEATURE:
<223> OTHER INFORMATION: Synthetic primer

```
<400> SEQUENCE: 91
gttattgcta gcggctcagc cggcaatggc ggakgtrmag cttcaggagt c        51

<210> SEQ ID NO 92
<211> LENGTH: 51
<212> TYPE: DNA
<213> ORGANISM: Artificial Sequence
<220> FEATURE:
<223> OTHER INFORMATION: Synthetic primer

<400> SEQUENCE: 92
gttattgcta gcggctcagc cggcaatggc ggaggtbcag ctbcagcagt c        51

<210> SEQ ID NO 93
<211> LENGTH: 51
<212> TYPE: DNA
<213> ORGANISM: Artificial Sequence
<220> FEATURE:
<223> OTHER INFORMATION: Synthetic primer

<400> SEQUENCE: 93
gttattgcta gcggctcagc cggcaatggc gcaggtgcag ctgaagsast c        51

<210> SEQ ID NO 94
<211> LENGTH: 51
<212> TYPE: DNA
<213> ORGANISM: Artificial Sequence
<220> FEATURE:
<223> OTHER INFORMATION: Synthetic primer

<400> SEQUENCE: 94
gttattgcta gcggctcagc cggcaatggc ggaggtccar ctgcaacart c        51

<210> SEQ ID NO 95
<211> LENGTH: 51
<212> TYPE: DNA
<213> ORGANISM: Artificial Sequence
<220> FEATURE:
<223> OTHER INFORMATION: Synthetic primer

<400> SEQUENCE: 95
gttattgcta gcggctcagc cggcaatggc gcaggtycag ctbcagcart c        51

<210> SEQ ID NO 96
<211> LENGTH: 51
<212> TYPE: DNA
<213> ORGANISM: Artificial Sequence
<220> FEATURE:
<223> OTHER INFORMATION: Synthetic primer

<400> SEQUENCE: 96
gttattgcta gcggctcagc cggcaatggc gcaggtycar ctgcagcagt c        51

<210> SEQ ID NO 97
<211> LENGTH: 51
<212> TYPE: DNA
<213> ORGANISM: Artificial Sequence
<220> FEATURE:
<223> OTHER INFORMATION: Synthetic primer

<400> SEQUENCE: 97
gttattgcta gcggctcagc cggcaatggc gcaggtccac gtgaagcagt c        51

<210> SEQ ID NO 98
```

<210> SEQ ID NO 98
<211> LENGTH: 51
<212> TYPE: DNA
<213> ORGANISM: Artificial Sequence
<220> FEATURE:
<223> OTHER INFORMATION: Synthetic primer

<400> SEQUENCE: 98
gttattgcta gcggctcagc cggcaatggc ggaggtgaas stggtggaat c          51

<210> SEQ ID NO 99
<211> LENGTH: 51
<212> TYPE: DNA
<213> ORGANISM: Artificial Sequence
<220> FEATURE:
<223> OTHER INFORMATION: Synthetic primer

<400> SEQUENCE: 99
gttattgcta gcggctcagc cggcaatggc ggavgtgawg ytggtggagt c          51

<210> SEQ ID NO 100
<211> LENGTH: 51
<212> TYPE: DNA
<213> ORGANISM: Artificial Sequence
<220> FEATURE:
<223> OTHER INFORMATION: Synthetic primer

<400> SEQUENCE: 100
gttattgcta gcggctcagc cggcaatggc ggaggtgcag skggtggagt c          51

<210> SEQ ID NO 101
<211> LENGTH: 51
<212> TYPE: DNA
<213> ORGANISM: Artificial Sequence
<220> FEATURE:
<223> OTHER INFORMATION: Synthetic primer

<400> SEQUENCE: 101
gttattgcta gcggctcagc cggcaatggc ggakgtgcam ctggtggagt c          51

<210> SEQ ID NO 102
<211> LENGTH: 51
<212> TYPE: DNA
<213> ORGANISM: Artificial Sequence
<220> FEATURE:
<223> OTHER INFORMATION: Synthetic primer

<400> SEQUENCE: 102
gttattgcta gcggctcagc cggcaatggc ggaggtgaag ctgatggart c          51

<210> SEQ ID NO 103
<211> LENGTH: 51
<212> TYPE: DNA
<213> ORGANISM: Artificial Sequence
<220> FEATURE:
<223> OTHER INFORMATION: Synthetic primer

<400> SEQUENCE: 103
gttattgcta gcggctcagc cggcaatggc ggaggtgcar cttgttgagt c          51

<210> SEQ ID NO 104
<211> LENGTH: 51
<212> TYPE: DNA
<213> ORGANISM: Artificial Sequence
<220> FEATURE:
<223> OTHER INFORMATION: Synthetic primer

<400> SEQUENCE: 104
gttattgcta gcggctcagc cggcaatggc ggargtraag cttctcgagt c    51

<210> SEQ ID NO 105
<211> LENGTH: 51
<212> TYPE: DNA
<213> ORGANISM: Artificial Sequence
<220> FEATURE:
<223> OTHER INFORMATION: Synthetic primer

<400> SEQUENCE: 105
gttattgcta gcggctcagc cggcaatggc ggaagtgaar sttgaggagt c    51

<210> SEQ ID NO 106
<211> LENGTH: 53
<212> TYPE: DNA
<213> ORGANISM: Artificial Sequence
<220> FEATURE:
<223> OTHER INFORMATION: Synthetic primer

<400> SEQUENCE: 106
gttattgcta gcggctcagc cggcaatggc gcaggttact ctraaagwgt stg    53

<210> SEQ ID NO 107
<211> LENGTH: 51
<212> TYPE: DNA
<213> ORGANISM: Artificial Sequence
<220> FEATURE:
<223> OTHER INFORMATION: Synthetic primer

<400> SEQUENCE: 107
gttattgcta gcggctcagc cggcaatggc gcaggtccaa ctvcagcarc c    51

<210> SEQ ID NO 108
<211> LENGTH: 51
<212> TYPE: DNA
<213> ORGANISM: Artificial Sequence
<220> FEATURE:
<223> OTHER INFORMATION: Synthetic primer

<400> SEQUENCE: 108
gttattgcta gcggctcagc cggcaatggc ggatgtgaac ttggaagtgt c    51

<210> SEQ ID NO 109
<211> LENGTH: 51
<212> TYPE: DNA
<213> ORGANISM: Artificial Sequence
<220> FEATURE:
<223> OTHER INFORMATION: Synthetic primer

<400> SEQUENCE: 109
gttattgcta gcggctcagc cggcaatggc ggaggtgaag gtcatcgagt c    51

<210> SEQ ID NO 110
<211> LENGTH: 35
<212> TYPE: DNA
<213> ORGANISM: Artificial Sequence
<220> FEATURE:
<223> OTHER INFORMATION: Synthetic primer

<400> SEQUENCE: 110
cccttgaagc ttgctgagga aacggtgacc gtggt    35

<210> SEQ ID NO 111
<211> LENGTH: 35
<212> TYPE: DNA

<213> ORGANISM: Artificial Sequence
<220> FEATURE:
<223> OTHER INFORMATION: Synthetic primer

<400> SEQUENCE: 111
cccttgaagc ttgctgagga gactgtgaga gtggt                              35

<210> SEQ ID NO 112
<211> LENGTH: 35
<212> TYPE: DNA
<213> ORGANISM: Artificial Sequence
<220> FEATURE:
<223> OTHER INFORMATION: Synthetic primer

<400> SEQUENCE: 112
cccttgaagc ttgctgcaga gacagtgacc agagt                              35

<210> SEQ ID NO 113
<211> LENGTH: 35
<212> TYPE: DNA
<213> ORGANISM: Artificial Sequence
<220> FEATURE:
<223> OTHER INFORMATION: Synthetic primer

<400> SEQUENCE: 113
cccttgaagc ttgctgagga gacggtgact gaggt                              35

<210> SEQ ID NO 114
<211> LENGTH: 9
<212> TYPE: PRT
<213> ORGANISM: Artificial Sequence
<220> FEATURE:
<223> OTHER INFORMATION: Synthetic peptide

<400> SEQUENCE: 114

Trp Gln Gly Thr His Phe Pro Leu Thr
1               5

<210> SEQ ID NO 115
<211> LENGTH: 9
<212> TYPE: PRT
<213> ORGANISM: Artificial Sequence
<220> FEATURE:
<223> OTHER INFORMATION: Synthetic peptide

<400> SEQUENCE: 115

Gln Gln Tyr Asn Ser Tyr Pro Leu Thr
1               5

<210> SEQ ID NO 116
<211> LENGTH: 9
<212> TYPE: PRT
<213> ORGANISM: Artificial Sequence
<220> FEATURE:
<223> OTHER INFORMATION: Synthetic peptide

<400> SEQUENCE: 116

Gln Gln Tyr Ser Ser Tyr Pro Leu Thr
1               5

<210> SEQ ID NO 117
<211> LENGTH: 8
<212> TYPE: PRT
<213> ORGANISM: Artificial Sequence
<220> FEATURE:
<223> OTHER INFORMATION: Synthetic peptide

```
<400> SEQUENCE: 117

Gln Gln Ser Asn Ser Trp Tyr Thr
1               5

<210> SEQ ID NO 118
<211> LENGTH: 9
<212> TYPE: PRT
<213> ORGANISM: Artificial Sequence
<220> FEATURE:
<223> OTHER INFORMATION: Synthetic peptide

<400> SEQUENCE: 118

Gln Asn Gly His Ser Phe Pro Leu Thr
1               5

<210> SEQ ID NO 119
<211> LENGTH: 10
<212> TYPE: PRT
<213> ORGANISM: Artificial Sequence
<220> FEATURE:
<223> OTHER INFORMATION: Synthetic peptide

<400> SEQUENCE: 119

Gln His His Tyr Gly Thr Pro Pro Trp Thr
1               5                   10

<210> SEQ ID NO 120
<211> LENGTH: 9
<212> TYPE: PRT
<213> ORGANISM: Artificial Sequence
<220> FEATURE:
<223> OTHER INFORMATION: Synthetic peptide

<400> SEQUENCE: 120

Gln Gln His Tyr Ser Thr Pro Trp Thr
1               5

<210> SEQ ID NO 121
<211> LENGTH: 8
<212> TYPE: PRT
<213> ORGANISM: Artificial Sequence
<220> FEATURE:
<223> OTHER INFORMATION: Synthetic peptide

<400> SEQUENCE: 121

His Gln Trp Ser Ser Tyr Pro Thr
1               5

<210> SEQ ID NO 122
<211> LENGTH: 9
<212> TYPE: PRT
<213> ORGANISM: Artificial Sequence
<220> FEATURE:
<223> OTHER INFORMATION: Synthetic peptide

<400> SEQUENCE: 122

Ser Gln Thr Thr His Val Pro Pro Thr
1               5

<210> SEQ ID NO 123
<211> LENGTH: 9
<212> TYPE: PRT
<213> ORGANISM: Artificial Sequence
<220> FEATURE:
<223> OTHER INFORMATION: Synthetic peptide

<400> SEQUENCE: 123
```

```
Trp Gln Gly Thr His Phe Pro Gln Thr
1               5
```

<210> SEQ ID NO 124
<211> LENGTH: 9
<212> TYPE: PRT
<213> ORGANISM: Artificial Sequence
<220> FEATURE:
<223> OTHER INFORMATION: Synthetic peptide

<400> SEQUENCE: 124

```
Ala Gln Phe Tyr Ser Tyr Pro Leu Thr
1               5
```

<210> SEQ ID NO 125
<211> LENGTH: 9
<212> TYPE: PRT
<213> ORGANISM: Artificial Sequence
<220> FEATURE:
<223> OTHER INFORMATION: Synthetic peptide

<400> SEQUENCE: 125

```
Met Gln His Leu Glu Tyr Pro Tyr Thr
1               5
```

<210> SEQ ID NO 126
<211> LENGTH: 9
<212> TYPE: PRT
<213> ORGANISM: Artificial Sequence
<220> FEATURE:
<223> OTHER INFORMATION: Synthetic peptide

<400> SEQUENCE: 126

```
Gln Gln Gly Gln Ser Tyr Pro Trp Thr
1               5
```

<210> SEQ ID NO 127
<211> LENGTH: 9
<212> TYPE: PRT
<213> ORGANISM: Artificial Sequence
<220> FEATURE:
<223> OTHER INFORMATION: Synthetic peptide

<400> SEQUENCE: 127

```
Gln Gln Trp Asn Tyr Pro Leu Ile Thr
1               5
```

<210> SEQ ID NO 128
<211> LENGTH: 9
<212> TYPE: PRT
<213> ORGANISM: Artificial Sequence
<220> FEATURE:
<223> OTHER INFORMATION: Synthetic peptide

<400> SEQUENCE: 128

```
Gln Gln Gly Asn Thr Leu Pro Trp Thr
1               5
```

<210> SEQ ID NO 129
<211> LENGTH: 10
<212> TYPE: PRT
<213> ORGANISM: Artificial Sequence
<220> FEATURE:
<223> OTHER INFORMATION: Synthetic peptide

<400> SEQUENCE: 129

```
Gln Gln Trp Ser Ser Tyr Pro Gln Leu Thr
1               5                   10

<210> SEQ ID NO 130
<211> LENGTH: 9
<212> TYPE: PRT
<213> ORGANISM: Artificial Sequence
<220> FEATURE:
<223> OTHER INFORMATION: Synthetic peptide

<400> SEQUENCE: 130

Gln Asn Asp His Ser Tyr Pro Leu Thr
1               5

<210> SEQ ID NO 131
<211> LENGTH: 9
<212> TYPE: PRT
<213> ORGANISM: Artificial Sequence
<220> FEATURE:
<223> OTHER INFORMATION: Synthetic peptide

<400> SEQUENCE: 131

Gln Gln Gly Gln Ser Tyr Pro Phe Thr
1               5

<210> SEQ ID NO 132
<211> LENGTH: 9
<212> TYPE: PRT
<213> ORGANISM: Artificial Sequence
<220> FEATURE:
<223> OTHER INFORMATION: Synthetic peptide

<400> SEQUENCE: 132

Gln Gln Ser Asn Glu Asp Pro Trp Thr
1               5

<210> SEQ ID NO 133
<211> LENGTH: 9
<212> TYPE: PRT
<213> ORGANISM: Artificial Sequence
<220> FEATURE:
<223> OTHER INFORMATION: Synthetic peptide

<400> SEQUENCE: 133

Gln Gln His Tyr Ser Thr Pro Phe Thr
1               5

<210> SEQ ID NO 134
<211> LENGTH: 9
<212> TYPE: PRT
<213> ORGANISM: Artificial Sequence
<220> FEATURE:
<223> OTHER INFORMATION: Synthetic peptide

<400> SEQUENCE: 134

Gln Gln Asn Asn Glu Asp Pro Arg Thr
1               5

<210> SEQ ID NO 135
<211> LENGTH: 9
<212> TYPE: PRT
<213> ORGANISM: Artificial Sequence
<220> FEATURE:
<223> OTHER INFORMATION: Synthetic peptide

<400> SEQUENCE: 135

Leu Gln Tyr Ala Ser Ser Pro Tyr Thr
```

```
1               5
```

<210> SEQ ID NO 136
<211> LENGTH: 9
<212> TYPE: PRT
<213> ORGANISM: Artificial Sequence
<220> FEATURE:
<223> OTHER INFORMATION: Synthetic peptide

<400> SEQUENCE: 136

```
Phe Gln Gly Ser His Val Pro Trp Thr
1               5
```

<210> SEQ ID NO 137
<211> LENGTH: 11
<212> TYPE: PRT
<213> ORGANISM: Artificial Sequence
<220> FEATURE:
<223> OTHER INFORMATION: Synthetic peptide

<400> SEQUENCE: 137

```
Thr Tyr Gly Ser Ser Tyr Tyr Ala Met Asp Tyr
1               5                   10
```

<210> SEQ ID NO 138
<211> LENGTH: 11
<212> TYPE: PRT
<213> ORGANISM: Artificial Sequence
<220> FEATURE:
<223> OTHER INFORMATION: Synthetic peptide

<400> SEQUENCE: 138

```
Thr Arg Leu Leu Trp Leu Tyr Ala Met Asp Tyr
1               5                   10
```

<210> SEQ ID NO 139
<211> LENGTH: 10
<212> TYPE: PRT
<213> ORGANISM: Artificial Sequence
<220> FEATURE:
<223> OTHER INFORMATION: Synthetic peptide

<400> SEQUENCE: 139

```
Asp Val Tyr Asp Gly Tyr Ala Met Asp Tyr
1               5                   10
```

<210> SEQ ID NO 140
<211> LENGTH: 7
<212> TYPE: PRT
<213> ORGANISM: Artificial Sequence
<220> FEATURE:
<223> OTHER INFORMATION: Synthetic peptide

<400> SEQUENCE: 140

```
Asn Pro Tyr Ala Met Asp Tyr
1               5
```

<210> SEQ ID NO 141
<211> LENGTH: 12
<212> TYPE: PRT
<213> ORGANISM: Artificial Sequence
<220> FEATURE:
<223> OTHER INFORMATION: Synthetic peptide

<400> SEQUENCE: 141

```
Arg Thr Thr Val Ser Arg Asp Trp Tyr Phe Asp Val
1               5                   10
```

<210> SEQ ID NO 142
<211> LENGTH: 10
<212> TYPE: PRT
<213> ORGANISM: Artificial Sequence
<220> FEATURE:
<223> OTHER INFORMATION: Synthetic peptide

<400> SEQUENCE: 142

Tyr Tyr Tyr Gly Ser Ser Ala Met Asp Tyr
1               5                   10

<210> SEQ ID NO 143
<211> LENGTH: 8
<212> TYPE: PRT
<213> ORGANISM: Artificial Sequence
<220> FEATURE:
<223> OTHER INFORMATION: Synthetic peptide

<400> SEQUENCE: 143

Asp Gly Trp Tyr Tyr Phe Asp Tyr
1               5

<210> SEQ ID NO 144
<211> LENGTH: 9
<212> TYPE: PRT
<213> ORGANISM: Artificial Sequence
<220> FEATURE:
<223> OTHER INFORMATION: Synthetic peptide

<400> SEQUENCE: 144

Glu Asp Asp Tyr Asp Leu Phe Ala Tyr
1               5

<210> SEQ ID NO 145
<211> LENGTH: 9
<212> TYPE: PRT
<213> ORGANISM: Artificial Sequence
<220> FEATURE:
<223> OTHER INFORMATION: Synthetic peptide

<400> SEQUENCE: 145

Gly Asn Tyr Tyr Tyr Ala Met Asp Tyr
1               5

<210> SEQ ID NO 146
<211> LENGTH: 10
<212> TYPE: PRT
<213> ORGANISM: Artificial Sequence
<220> FEATURE:
<223> OTHER INFORMATION: Synthetic peptide

<400> SEQUENCE: 146

Asp Met Ile Ser Tyr Trp Tyr Phe Asp Val
1               5                   10

<210> SEQ ID NO 147
<211> LENGTH: 11
<212> TYPE: PRT
<213> ORGANISM: Artificial Sequence
<220> FEATURE:
<223> OTHER INFORMATION: Synthetic peptide

<400> SEQUENCE: 147

Glu Asp Tyr Gly Asn Tyr Trp Tyr Phe Asp Val
1               5                   10

<210> SEQ ID NO 148
<211> LENGTH: 12
<212> TYPE: PRT
<213> ORGANISM: Artificial Sequence
<220> FEATURE:
<223> OTHER INFORMATION: Synthetic peptide

<400> SEQUENCE: 148

Glu Gly Tyr Tyr Tyr Gly Ser Ser Tyr Phe Asp Tyr
1               5                   10

<210> SEQ ID NO 149
<211> LENGTH: 10
<212> TYPE: PRT
<213> ORGANISM: Artificial Sequence
<220> FEATURE:
<223> OTHER INFORMATION: Synthetic peptide

<400> SEQUENCE: 149

Arg Gly Asp Gly Asn Tyr Phe Phe Asp Tyr
1               5                   10

<210> SEQ ID NO 150
<211> LENGTH: 8
<212> TYPE: PRT
<213> ORGANISM: Artificial Sequence
<220> FEATURE:
<223> OTHER INFORMATION: Synthetic peptide

<400> SEQUENCE: 150

Gly Asp Glu Ala Trp Phe Ala Tyr
1               5

<210> SEQ ID NO 151
<211> LENGTH: 6
<212> TYPE: PRT
<213> ORGANISM: Artificial Sequence
<220> FEATURE:
<223> OTHER INFORMATION: Synthetic peptide

<400> SEQUENCE: 151

Glu Gly Asp Phe Asp Tyr
1               5

<210> SEQ ID NO 152
<211> LENGTH: 10
<212> TYPE: PRT
<213> ORGANISM: Artificial Sequence
<220> FEATURE:
<223> OTHER INFORMATION: Synthetic peptide

<400> SEQUENCE: 152

Gly Gly Asn Tyr Asp Tyr Ala Met Asp Tyr
1               5                   10

<210> SEQ ID NO 153
<211> LENGTH: 9
<212> TYPE: PRT
<213> ORGANISM: Artificial Sequence
<220> FEATURE:
<223> OTHER INFORMATION: Synthetic peptide

<400> SEQUENCE: 153

Gly Ser Ser Tyr Tyr Ala Met Asp Tyr
1               5

```
<210> SEQ ID NO 154
<211> LENGTH: 12
<212> TYPE: PRT
<213> ORGANISM: Artificial Sequence
<220> FEATURE:
<223> OTHER INFORMATION: Synthetic peptide

<400> SEQUENCE: 154

Asp Tyr Tyr Gly Ser Ser Tyr Trp Tyr Phe Asp Val
1               5                   10

<210> SEQ ID NO 155
<211> LENGTH: 9
<212> TYPE: PRT
<213> ORGANISM: Artificial Sequence
<220> FEATURE:
<223> OTHER INFORMATION: Synthetic peptide

<400> SEQUENCE: 155

Leu Leu Trp Leu Tyr Ala Met Asp Tyr
1               5

<210> SEQ ID NO 156
<211> LENGTH: 9
<212> TYPE: PRT
<213> ORGANISM: Artificial Sequence
<220> FEATURE:
<223> OTHER INFORMATION: Synthetic peptide

<400> SEQUENCE: 156

Asp Asp Gly Tyr Trp Tyr Phe Asp Val
1               5

<210> SEQ ID NO 157
<211> LENGTH: 10
<212> TYPE: PRT
<213> ORGANISM: Artificial Sequence
<220> FEATURE:
<223> OTHER INFORMATION: Synthetic peptide

<400> SEQUENCE: 157

Tyr Tyr Tyr Gly Ser Ser Tyr Phe Asp Val
1               5                   10

<210> SEQ ID NO 158
<211> LENGTH: 8
<212> TYPE: PRT
<213> ORGANISM: Artificial Sequence
<220> FEATURE:
<223> OTHER INFORMATION: Synthetic peptide

<400> SEQUENCE: 158

Trp Gln Gly Thr His Phe Pro Thr
1               5

<210> SEQ ID NO 159
<211> LENGTH: 9
<212> TYPE: PRT
<213> ORGANISM: Artificial Sequence
<220> FEATURE:
<223> OTHER INFORMATION: Synthetic peptide

<400> SEQUENCE: 159

Asp Gly Tyr Asp Trp Tyr Phe Asp Val
1               5

<210> SEQ ID NO 160
```

```
<211> LENGTH: 12
<212> TYPE: PRT
<213> ORGANISM: Artificial Sequence
<220> FEATURE:
<223> OTHER INFORMATION: Synthetic peptide

<400> SEQUENCE: 160

Gln Gly Tyr Asp Tyr Asp Pro Tyr Ala Met Asp Tyr
1               5                   10

<210> SEQ ID NO 161
<211> LENGTH: 5
<212> TYPE: PRT
<213> ORGANISM: Artificial Sequence
<220> FEATURE:
<223> OTHER INFORMATION: Synthetic peptide

<400> SEQUENCE: 161

Thr Gly Phe Asp Tyr
1               5

<210> SEQ ID NO 162
<211> LENGTH: 11
<212> TYPE: PRT
<213> ORGANISM: Artificial Sequence
<220> FEATURE:
<223> OTHER INFORMATION: Synthetic peptide

<400> SEQUENCE: 162

Lys Gly Ser Thr Thr Ala Thr Tyr Phe Asp Tyr
1               5                   10

<210> SEQ ID NO 163
<211> LENGTH: 9
<212> TYPE: PRT
<213> ORGANISM: Artificial Sequence
<220> FEATURE:
<223> OTHER INFORMATION: Synthetic peptide

<400> SEQUENCE: 163

Leu Gln His Gly Glu Ser Pro Phe Thr
1               5

<210> SEQ ID NO 164
<211> LENGTH: 9
<212> TYPE: PRT
<213> ORGANISM: Artificial Sequence
<220> FEATURE:
<223> OTHER INFORMATION: Synthetic peptide

<400> SEQUENCE: 164

Gln Gln Gly Gln Ser Tyr Pro Leu Thr
1               5

<210> SEQ ID NO 165
<211> LENGTH: 9
<212> TYPE: PRT
<213> ORGANISM: Artificial Sequence
<220> FEATURE:
<223> OTHER INFORMATION: Synthetic peptide

<400> SEQUENCE: 165

Gln Gln Ser Lys Glu Val Pro Pro Thr
1               5

<210> SEQ ID NO 166
<211> LENGTH: 7
```

<212> TYPE: PRT
<213> ORGANISM: Artificial Sequence
<220> FEATURE:
<223> OTHER INFORMATION: Synthetic peptide

<400> SEQUENCE: 166

Gln Asn Asp Tyr Ser Phe Thr
1               5

<210> SEQ ID NO 167
<211> LENGTH: 9
<212> TYPE: PRT
<213> ORGANISM: Artificial Sequence
<220> FEATURE:
<223> OTHER INFORMATION: Synthetic peptide

<400> SEQUENCE: 167

Trp Gln Gly Thr His Phe Pro Trp Thr
1               5

<210> SEQ ID NO 168
<211> LENGTH: 9
<212> TYPE: PRT
<213> ORGANISM: Artificial Sequence
<220> FEATURE:
<223> OTHER INFORMATION: Synthetic peptide

<400> SEQUENCE: 168

Phe Gln Gly Ser His Val Pro Phe Thr
1               5

<210> SEQ ID NO 169
<211> LENGTH: 9
<212> TYPE: PRT
<213> ORGANISM: Artificial Sequence
<220> FEATURE:
<223> OTHER INFORMATION: Synthetic peptide

<400> SEQUENCE: 169

Leu Gln Gly Ser His Val Pro Leu Thr
1               5

<210> SEQ ID NO 170
<211> LENGTH: 9
<212> TYPE: PRT
<213> ORGANISM: Artificial Sequence
<220> FEATURE:
<223> OTHER INFORMATION: Synthetic peptide

<400> SEQUENCE: 170

Leu Gln His Gly Glu Ser Pro Tyr Thr
1               5

<210> SEQ ID NO 171
<211> LENGTH: 9
<212> TYPE: PRT
<213> ORGANISM: Artificial Sequence
<220> FEATURE:
<223> OTHER INFORMATION: Synthetic peptide

<400> SEQUENCE: 171

Ser Gln Ser Thr His Val Pro Trp Thr
1               5

<210> SEQ ID NO 172
<211> LENGTH: 28
<212> TYPE: DNA

<210> SEQ ID NO 172
<211> LENGTH: 28
<212> TYPE: DNA
<213> ORGANISM: Artificial Sequence
<220> FEATURE:
<223> OTHER INFORMATION: Synthetic primer

<400> SEQUENCE: 172
gggaagactg acggagcctt aggttgcc                                28

<210> SEQ ID NO 173
<211> LENGTH: 28
<212> TYPE: DNA
<213> ORGANISM: Artificial Sequence
<220> FEATURE:
<223> OTHER INFORMATION: Synthetic primer

<400> SEQUENCE: 173
ggaagactga tggagcctta ggttgccc                                28

<210> SEQ ID NO 174
<211> LENGTH: 28
<212> TYPE: DNA
<213> ORGANISM: Artificial Sequence
<220> FEATURE:
<223> OTHER INFORMATION: Synthetic primer

<400> SEQUENCE: 174
gggtacagag ttggagatga caggctca                                28

<210> SEQ ID NO 175
<211> LENGTH: 29
<212> TYPE: DNA
<213> ORGANISM: Artificial Sequence
<220> FEATURE:
<223> OTHER INFORMATION: Synthetic primer

<400> SEQUENCE: 175
gggtacagag ttggagatga caggctcac                               29

<210> SEQ ID NO 176
<211> LENGTH: 28
<212> TYPE: DNA
<213> ORGANISM: Artificial Sequence
<220> FEATURE:
<223> OTHER INFORMATION: Synthetic primer

<400> SEQUENCE: 176
ggtagacttt cggggtgtt gttgaggc                                 28

<210> SEQ ID NO 177
<211> LENGTH: 22
<212> TYPE: DNA
<213> ORGANISM: Artificial Sequence
<220> FEATURE:
<223> OTHER INFORMATION: Synthetic primer

<400> SEQUENCE: 177
ctttcggggc tgtggtggag gc                                      22

<210> SEQ ID NO 178
<211> LENGTH: 28
<212> TYPE: DNA
<213> ORGANISM: Artificial Sequence
<220> FEATURE:
<223> OTHER INFORMATION: Synthetic primer

<400> SEQUENCE: 178
ggaagacttt cgggtgagat tcactttc                                28

<210> SEQ ID NO 179
<211> LENGTH: 20
<212> TYPE: DNA
<213> ORGANISM: Artificial Sequence
<220> FEATURE:
<223> OTHER INFORMATION: Synthetic primer

<400> SEQUENCE: 179
gatggggccg tcttgggggc                                              20

<210> SEQ ID NO 180
<211> LENGTH: 20
<212> TYPE: DNA
<213> ORGANISM: Artificial Sequence
<220> FEATURE:
<223> OTHER INFORMATION: Synthetic primer

<400> SEQUENCE: 180
aatggggccg tcttgggggc                                              20

<210> SEQ ID NO 181
<211> LENGTH: 26
<212> TYPE: DNA
<213> ORGANISM: Artificial Sequence
<220> FEATURE:
<223> OTHER INFORMATION: Synthetic primer

<400> SEQUENCE: 181
gtagagattc ggggcagact ggctct                                       26

<210> SEQ ID NO 182
<211> LENGTH: 26
<212> TYPE: DNA
<213> ORGANISM: Artificial Sequence
<220> FEATURE:
<223> OTHER INFORMATION: Synthetic primer

<400> SEQUENCE: 182
ggacgggaag tcctggatgt tctggc                                       26

<210> SEQ ID NO 183
<211> LENGTH: 12
<212> TYPE: PRT
<213> ORGANISM: Artificial Sequence
<220> FEATURE:
<223> OTHER INFORMATION: Synthetic peptide

<400> SEQUENCE: 183

Asp Thr Thr Val Val Glu Gly Asp Tyr Phe Asp Tyr
1               5                   10

<210> SEQ ID NO 184
<211> LENGTH: 26
<212> TYPE: DNA
<213> ORGANISM: Artificial Sequence
<220> FEATURE:
<223> OTHER INFORMATION: Synthetic primer

<400> SEQUENCE: 184
cagtgggaag actgacggag ccttag                                       26

<210> SEQ ID NO 185
<211> LENGTH: 26
<212> TYPE: DNA
<213> ORGANISM: Artificial Sequence

```
<220> FEATURE:
<223> OTHER INFORMATION: Synthetic primer

<400> SEQUENCE: 185
cagtgggaag actgatggag ccttag                                          26

<210> SEQ ID NO 186
<211> LENGTH: 26
<212> TYPE: DNA
<213> ORGANISM: Artificial Sequence
<220> FEATURE:
<223> OTHER INFORMATION: Synthetic primer

<400> SEQUENCE: 186
ggagacgagc gggtacagag ttggag                                          26

<210> SEQ ID NO 187
<211> LENGTH: 24
<212> TYPE: DNA
<213> ORGANISM: Artificial Sequence
<220> FEATURE:
<223> OTHER INFORMATION: Synthetic primer

<400> SEQUENCE: 187
tggtgggaag akgaggacag tagg                                            24

<210> SEQ ID NO 188
<211> LENGTH: 23
<212> TYPE: DNA
<213> ORGANISM: Artificial Sequence
<220> FEATURE:
<223> OTHER INFORMATION: Synthetic primer

<400> SEQUENCE: 188 caaggggcg accacaggct gac                                              23

<210> SEQ ID NO 189
<211> LENGTH: 25
<212> TYPE: DNA
<213> ORGANISM: Artificial Sequence
<220> FEATURE:
<223> OTHER INFORMATION: Synthetic primer

<400> SEQUENCE: 189
gtgaaggagt gactacgggt tgacc                                           25

<210> SEQ ID NO 190
<211> LENGTH: 22
<212> TYPE: DNA
<213> ORGANISM: Artificial Sequence
<220> FEATURE:
<223> OTHER INFORMATION: Synthetic primer

<400> SEQUENCE: 190 gaggggtca ccgcgggctg ac                                               22

<210> SEQ ID NO 191
<211> LENGTH: 23
<212> TYPE: DNA
<213> ORGANISM: Artificial Sequence
<220> FEATURE:
<223> OTHER INFORMATION: Synthetic primer

<400> SEQUENCE: 191
gactttcggg ggtgttgttg agg                                             23
```

```
<210> SEQ ID NO 192
<211> LENGTH: 23
<212> TYPE: DNA
<213> ORGANISM: Artificial Sequence
<220> FEATURE:
<223> OTHER INFORMATION: Synthetic primer

<400> SEQUENCE: 192
gactttcggg gctgtggtgg agg                                              23

<210> SEQ ID NO 193
<211> LENGTH: 28
<212> TYPE: DNA
<213> ORGANISM: Artificial Sequence
<220> FEATURE:
<223> OTHER INFORMATION: Synthetic primer

<400> SEQUENCE: 193 ccaggggaa gactttcggg tgagattc                                          28

<210> SEQ ID NO 194
<211> LENGTH: 32
<212> TYPE: DNA
<213> ORGANISM: Artificial Sequence
<220> FEATURE:
<223> OTHER INFORMATION: Synthetic primer

<400> SEQUENCE: 194
gatggtttga agagggagac ggatggctga gc                                    32

<210> SEQ ID NO 195
<211> LENGTH: 27
<212> TYPE: DNA
<213> ORGANISM: Artificial Sequence
<220> FEATURE:
<223> OTHER INFORMATION: Synthetic primer

<400> SEQUENCE: 195
acagggtgac cgagggtgcg gacttgg                                          27

<210> SEQ ID NO 196
<211> LENGTH: 23
<212> TYPE: DNA
<213> ORGANISM: Artificial Sequence
<220> FEATURE:
<223> OTHER INFORMATION: Synthetic primer

<400> SEQUENCE: 196
gactttcggg ggtgtggtgg agg                                              23

<210> SEQ ID NO 197
<211> LENGTH: 28
<212> TYPE: DNA
<213> ORGANISM: Artificial Sequence
<220> FEATURE:
<223> OTHER INFORMATION: Synthetic primer

<400> SEQUENCE: 197 ccaggggaa gactttcggg tgagattc                                          28

<210> SEQ ID NO 198
<211> LENGTH: 32
<212> TYPE: DNA
<213> ORGANISM: Artificial Sequence
<220> FEATURE:
<223> OTHER INFORMATION: Synthetic primer
```

-continued

<400> SEQUENCE: 198
gatggtttga agagggagac ggatggctga gc        32

<210> SEQ ID NO 199
<211> LENGTH: 27
<212> TYPE: DNA
<213> ORGANISM: Artificial Sequence
<220> FEATURE:
<223> OTHER INFORMATION: Synthetic primer

<400> SEQUENCE: 199
acagggtgac tgagggtgcg gacttgg        27

<210> SEQ ID NO 200
<211> LENGTH: 21
<212> TYPE: PRT
<213> ORGANISM: Artificial Sequence
<220> FEATURE:
<223> OTHER INFORMATION: Synthetic peptide

<400> SEQUENCE: 200

Ala Arg Gly Leu Asn Ala Ala Gly Tyr Thr Thr Phe Ala Tyr Gly Thr
1               5                   10                  15

Thr Val Met Asp Leu
            20

<210> SEQ ID NO 201
<211> LENGTH: 13
<212> TYPE: PRT
<213> ORGANISM: Artificial Sequence
<220> FEATURE:
<223> OTHER INFORMATION: Syhthetic peptide

<400> SEQUENCE: 201

Ala Arg Asp Met Asp Gly Gly Asn Val Gly Tyr Gly Met
1               5                   10

<210> SEQ ID NO 202
<211> LENGTH: 15
<212> TYPE: PRT
<213> ORGANISM: Artificial Sequence
<220> FEATURE:
<223> OTHER INFORMATION: Synthetic peptide

<400> SEQUENCE: 202

Ala Arg Phe Asp Ala Ala Tyr Ala Asp Phe Gly Val Ala Asn Leu
1               5                   10                  15

<210> SEQ ID NO 203
<211> LENGTH: 19
<212> TYPE: PRT
<213> ORGANISM: Artificial Sequence
<220> FEATURE:
<223> OTHER INFORMATION: Synthetic peptide

<400> SEQUENCE: 203

Ala Arg Ala Asp Arg Gly Phe Tyr Ala Gly Thr Ser Asp Tyr Thr Gly
1               5                   10                  15

Tyr Asn Leu

<210> SEQ ID NO 204
<211> LENGTH: 19
<212> TYPE: PRT
<213> ORGANISM: Artificial Sequence

```
<220> FEATURE:
<223> OTHER INFORMATION: Synthetic peptide

<400> SEQUENCE: 204

Ala Arg Ala Asp Arg Gly Phe Tyr Ala Gly Thr Ser Asp Tyr Ser Gly
1               5                   10                  15

Tyr Asn Leu

<210> SEQ ID NO 205
<211> LENGTH: 14
<212> TYPE: PRT
<213> ORGANISM: Artificial Sequence
<220> FEATURE:
<223> OTHER INFORMATION: Synthetic peptide

<400> SEQUENCE: 205

Ala Arg Asp Ala Gly Gly Ser Tyr Ser Tyr Tyr Phe Asp Leu
1               5                   10

<210> SEQ ID NO 206
<211> LENGTH: 16
<212> TYPE: PRT
<213> ORGANISM: Artificial Sequence
<220> FEATURE:
<223> OTHER INFORMATION: Synthetic peptide

<400> SEQUENCE: 206

Ala Arg Asp Ala Gly Gly Tyr Thr Gly Asp Gly Tyr Tyr Phe Lys Leu
1               5                   10                  15

<210> SEQ ID NO 207
<211> LENGTH: 11
<212> TYPE: PRT
<213> ORGANISM: Artificial Sequence
<220> FEATURE:
<223> OTHER INFORMATION: Synthetic peptide

<400> SEQUENCE: 207

Ala Arg Gly Gly Pro Ile His Tyr Ser Asn Leu
1               5                   10

<210> SEQ ID NO 208
<211> LENGTH: 12
<212> TYPE: PRT
<213> ORGANISM: Artificial Sequence
<220> FEATURE:
<223> OTHER INFORMATION: Synthetic peptide

<400> SEQUENCE: 208

Ala Arg Gly Ser Gly Trp Tyr Gly Gly Leu Asn Leu
1               5                   10

<210> SEQ ID NO 209
<211> LENGTH: 17
<212> TYPE: PRT
<213> ORGANISM: Artificial Sequence
<220> FEATURE:
<223> OTHER INFORMATION: Synthetic peptide

<400> SEQUENCE: 209

Ala Ser Asn Tyr Ala Asp Pro Pro Gly Tyr Asn Tyr Thr Pro Phe Asn
1               5                   10                  15

Leu

<210> SEQ ID NO 210
```

-continued

```
<211> LENGTH: 14
<212> TYPE: PRT
<213> ORGANISM: Artificial Sequence
<220> FEATURE:
<223> OTHER INFORMATION: Synthetic peptide

<400> SEQUENCE: 210

Ala Thr Asp Arg Gly Pro Ser Gly Ser Gly Pro Leu Asp Leu
1               5                   10

<210> SEQ ID NO 211
<211> LENGTH: 19
<212> TYPE: PRT
<213> ORGANISM: Artificial Sequence
<220> FEATURE:
<223> OTHER INFORMATION: Synthetic peptide

<400> SEQUENCE: 211

Ser Arg Asp Gly Lys Tyr Ala Gly Ile Ala Gly Tyr Gly Ser Thr Tyr
1               5                   10                  15

Phe Asp Leu

<210> SEQ ID NO 212
<211> LENGTH: 16
<212> TYPE: PRT
<213> ORGANISM: Artificial Sequence
<220> FEATURE:
<223> OTHER INFORMATION: Synthetic peptide

<400> SEQUENCE: 212

Ala Gly Asp Gly Arg Ser Tyr Tyr Ala Asp Tyr Ala Phe Val Asp Leu
1               5                   10                  15

<210> SEQ ID NO 213
<211> LENGTH: 17
<212> TYPE: PRT
<213> ORGANISM: Artificial Sequence
<220> FEATURE:
<223> OTHER INFORMATION: Synthetic peptide

<400> SEQUENCE: 213

Ala Arg Asp Pro Val Thr Arg Leu Val Ala Gly Ala Asp Tyr Phe Asp
1               5                   10                  15

Leu

<210> SEQ ID NO 214
<211> LENGTH: 18
<212> TYPE: PRT
<213> ORGANISM: Artificial Sequence
<220> FEATURE:
<223> OTHER INFORMATION: Synthetic peptide

<400> SEQUENCE: 214

Ala Arg Asp Val Tyr Thr Tyr Asp Ala Asp Gly Asp Tyr Arg His Phe
1               5                   10                  15

Asn Leu

<210> SEQ ID NO 215
<211> LENGTH: 19
<212> TYPE: PRT
<213> ORGANISM: Artificial Sequence
<220> FEATURE:
<223> OTHER INFORMATION: Synthetic peptide

<400> SEQUENCE: 215
```

```
Ala Arg Ala Pro Val Tyr Tyr Asn Gly Gly Tyr Ala Gly Phe Arg Glu
1               5                   10                  15

Phe Asn Leu

<210> SEQ ID NO 216
<211> LENGTH: 10
<212> TYPE: PRT
<213> ORGANISM: Artificial Sequence
<220> FEATURE:
<223> OTHER INFORMATION: Synthetic peptide

<400> SEQUENCE: 216

Ala Arg Asp Gly Gly Trp Gly Tyr Asn Leu
1               5                   10

<210> SEQ ID NO 217
<211> LENGTH: 13
<212> TYPE: PRT
<213> ORGANISM: Artificial Sequence
<220> FEATURE:
<223> OTHER INFORMATION: Synthetic peptide

<400> SEQUENCE: 217

Ala Arg Asp Ser Phe Asp Gly Tyr Gly Asp Phe Asn Leu
1               5                   10

<210> SEQ ID NO 218
<211> LENGTH: 11
<212> TYPE: PRT
<213> ORGANISM: Artificial Sequence
<220> FEATURE:
<223> OTHER INFORMATION: Synthetic peptide

<400> SEQUENCE: 218

Ala Arg Val Gly Asn His Tyr Gly Met Asp Leu
1               5                   10

<210> SEQ ID NO 219
<211> LENGTH: 19
<212> TYPE: PRT
<213> ORGANISM: Artificial Sequence
<220> FEATURE:
<223> OTHER INFORMATION: Synthetic peptide

<400> SEQUENCE: 219

Ala Arg Gly Ala Ala Gly Tyr Ala Gly Tyr Ala Tyr Ala Tyr Tyr Tyr
1               5                   10                  15

Phe Asp Phe

<210> SEQ ID NO 220
<211> LENGTH: 10
<212> TYPE: PRT
<213> ORGANISM: Artificial Sequence
<220> FEATURE:
<223> OTHER INFORMATION: Synthetic peptide

<400> SEQUENCE: 220

Ala Arg Asp Trp Asn Tyr Gly Met Asp Leu
1               5                   10

<210> SEQ ID NO 221
<211> LENGTH: 6
<212> TYPE: PRT
<213> ORGANISM: Artificial Sequence
<220> FEATURE:
<223> OTHER INFORMATION: Synthetic peptide
```

<400> SEQUENCE: 221

Ala Arg Asn Phe Ala Leu
1               5

<210> SEQ ID NO 222
<211> LENGTH: 15
<212> TYPE: PRT
<213> ORGANISM: Artificial Sequence
<220> FEATURE:
<223> OTHER INFORMATION: Synthetic peptide

<400> SEQUENCE: 222

Ala Arg Asp Leu Asn Ala Ala His Arg Thr Asn Ser Pro Lys Leu
1               5                   10                  15

<210> SEQ ID NO 223
<211> LENGTH: 5
<212> TYPE: PRT
<213> ORGANISM: Artificial Sequence
<220> FEATURE:
<223> OTHER INFORMATION: Synthetic peptide

<400> SEQUENCE: 223

Trp Ile Thr Asn Leu
1               5

<210> SEQ ID NO 224
<211> LENGTH: 12
<212> TYPE: PRT
<213> ORGANISM: Artificial Sequence
<220> FEATURE:
<223> OTHER INFORMATION: Synthetic peptide

<400> SEQUENCE: 224

Ala Arg Gly Phe Ser Leu Leu Gly Tyr Leu Thr Leu
1               5                   10

<210> SEQ ID NO 225
<211> LENGTH: 14
<212> TYPE: PRT
<213> ORGANISM: Artificial Sequence
<220> FEATURE:
<223> OTHER INFORMATION: Synthetic peptide

<400> SEQUENCE: 225

Ala Arg Asp Pro Tyr Gly Arg Ser Gly Asp Asp Phe Val Leu
1               5                   10

<210> SEQ ID NO 226
<211> LENGTH: 13
<212> TYPE: PRT
<213> ORGANISM: Artificial Sequence
<220> FEATURE:
<223> OTHER INFORMATION: Synthetic peptide

<400> SEQUENCE: 226

Ala Arg Gly Tyr Asp Asp Tyr Gly Asp Tyr Leu Asp Leu
1               5                   10

<210> SEQ ID NO 227
<211> LENGTH: 17
<212> TYPE: PRT
<213> ORGANISM: Artificial Sequence
<220> FEATURE:
<223> OTHER INFORMATION: Synthetic peptide

```
<400> SEQUENCE: 227

Ala Arg Ser Ala Tyr Asn Asp Phe Gly Asp Tyr Val Ser Pro Leu Thr
1               5                   10                  15

Leu

<210> SEQ ID NO 228
<211> LENGTH: 6
<212> TYPE: PRT
<213> ORGANISM: Artificial Sequence
<220> FEATURE:
<223> OTHER INFORMATION: Synthetic peptide

<400> SEQUENCE: 228

Ala Arg Gln Tyr Leu Leu
1               5

<210> SEQ ID NO 229
<211> LENGTH: 11
<212> TYPE: PRT
<213> ORGANISM: Artificial Sequence
<220> FEATURE:
<223> OTHER INFORMATION: Synthetic peptide

<400> SEQUENCE: 229

Ala Arg Gly Ser Val Ile Tyr Val Gly Glu Leu
1               5                   10

<210> SEQ ID NO 230
<211> LENGTH: 13
<212> TYPE: PRT
<213> ORGANISM: Artificial Sequence
<220> FEATURE:
<223> OTHER INFORMATION: Synthetic peptide

<400> SEQUENCE: 230

Ala Arg Gly Arg Ser Asp Thr Asn Tyr Arg Leu Asn Leu
1               5                   10

<210> SEQ ID NO 231
<211> LENGTH: 17
<212> TYPE: PRT
<213> ORGANISM: Artificial Sequence
<220> FEATURE:
<223> OTHER INFORMATION: Synthetic peptide

<400> SEQUENCE: 231

Gly Arg Ser Val Glu Ala Val Gln Gly Ala Ser Asn Trp Tyr Phe Asp
1               5                   10                  15

Ile

<210> SEQ ID NO 232
<211> LENGTH: 13
<212> TYPE: PRT
<213> ORGANISM: Artificial Sequence
<220> FEATURE:
<223> OTHER INFORMATION: Synthetic peptide

<400> SEQUENCE: 232

Gly Lys Thr Ser Thr Ile Asp Ser Asp Tyr Tyr Asn Leu
1               5                   10

<210> SEQ ID NO 233
<211> LENGTH: 13
<212> TYPE: PRT
<213> ORGANISM: Artificial Sequence
```

```
<220> FEATURE:
<223> OTHER INFORMATION: Synthetic peptide

<400> SEQUENCE: 233

Ala Arg Gly Gly Phe Thr Asp Arg Thr Tyr Ala Asn Ile
1               5                   10

<210> SEQ ID NO 234
<211> LENGTH: 12
<212> TYPE: PRT
<213> ORGANISM: Artificial Sequence
<220> FEATURE:
<223> OTHER INFORMATION: Synthetic peptide

<400> SEQUENCE: 234

Ala Arg Asn Ala Gly Gly Asn Asp Tyr Phe Arg Leu
1               5                   10

<210> SEQ ID NO 235
<211> LENGTH: 12
<212> TYPE: PRT
<213> ORGANISM: Artificial Sequence
<220> FEATURE:
<223> OTHER INFORMATION: Synthetic peptide

<400> SEQUENCE: 235

Gly Arg Tyr Gly Gly Asn Val Gly Ala Phe Asp Met
1               5                   10

<210> SEQ ID NO 236
<211> LENGTH: 18
<212> TYPE: PRT
<213> ORGANISM: Artificial Sequence
<220> FEATURE:
<223> OTHER INFORMATION: Synthetic peptide

<400> SEQUENCE: 236

Ala Arg Gly Asn Ser Val Thr Asp Thr Tyr Leu Ile Asp Ser Gly Met
1               5                   10                  15

Asp Leu

<210> SEQ ID NO 237
<211> LENGTH: 13
<212> TYPE: PRT
<213> ORGANISM: Artificial Sequence
<220> FEATURE:
<223> OTHER INFORMATION: Synthetic peptide

<400> SEQUENCE: 237

Ala Lys Ser Ala Tyr Asn Thr Ala Gly Tyr Ser Pro Leu
1               5                   10

<210> SEQ ID NO 238
<211> LENGTH: 18
<212> TYPE: PRT
<213> ORGANISM: Artificial Sequence
<220> FEATURE:
<223> OTHER INFORMATION: Synthetic peptide

<400> SEQUENCE: 238

Ala Arg Asp Leu Ser Tyr Asp Pro Tyr Gly Asp Leu Gly Thr Arg Leu
1               5                   10                  15

Asp Leu

<210> SEQ ID NO 239
```

```
<211> LENGTH: 14
<212> TYPE: PRT
<213> ORGANISM: Artificial Sequence
<220> FEATURE:
<223> OTHER INFORMATION: Synthetic peptide

<400> SEQUENCE: 239

Ala Arg Arg Asn Pro Asn Tyr Asp Thr Gly His Phe Asn Ile
1               5                   10

<210> SEQ ID NO 240
<211> LENGTH: 20
<212> TYPE: PRT
<213> ORGANISM: Artificial Sequence
<220> FEATURE:
<223> OTHER INFORMATION: Synthetic peptide

<400> SEQUENCE: 240

Gly Arg Gly Arg Tyr Gly Gly Gly Tyr Asp Tyr Asp Phe Phe Gln Tyr
1               5                   10                  15

Gly Val Asp Val
            20

<210> SEQ ID NO 241
<211> LENGTH: 19
<212> TYPE: PRT
<213> ORGANISM: Artificial Sequence
<220> FEATURE:
<223> OTHER INFORMATION: Synthetic peptide

<400> SEQUENCE: 241

Ala Arg Arg Cys Gly Glu Gly Asp Gly Tyr Gly Tyr Asn Pro Asp Cys
1               5                   10                  15

Tyr Asp Tyr

<210> SEQ ID NO 242
<211> LENGTH: 19
<212> TYPE: PRT
<213> ORGANISM: Artificial Sequence
<220> FEATURE:
<223> OTHER INFORMATION: Synthetic peptide

<400> SEQUENCE: 242

Val Arg Cys Tyr Thr His Trp Ser Asp Asn Asn Gly Arg Cys Tyr Gly
1               5                   10                  15

Pro Met Tyr

<210> SEQ ID NO 243
<211> LENGTH: 16
<212> TYPE: PRT
<213> ORGANISM: Artificial Sequence
<220> FEATURE:
<223> OTHER INFORMATION: Synthetic peptide

<400> SEQUENCE: 243

Ala Arg Glu Arg Ser Gly Trp Tyr Ser Pro Tyr Gly Ala Val Asp Val
1               5                   10                  15

<210> SEQ ID NO 244
<211> LENGTH: 17
<212> TYPE: PRT
<213> ORGANISM: Artificial Sequence
<220> FEATURE:
<223> OTHER INFORMATION: Synthetic peptide

<400> SEQUENCE: 244
```

```
Ala Lys Tyr Phe Trp Thr Asn Asn Tyr Ala Asp Tyr Val Phe Phe Asp
1               5                   10                  15

Ile

<210> SEQ ID NO 245
<211> LENGTH: 17
<212> TYPE: PRT
<213> ORGANISM: Artificial Sequence
<220> FEATURE:
<223> OTHER INFORMATION: Synthetic peptide

<400> SEQUENCE: 245

Ala Arg Asp Gly Asp Gly Ala Gly Gly Ala Leu Ser Ser Gly Leu Asp
1               5                   10                  15

Val

<210> SEQ ID NO 246
<211> LENGTH: 14
<212> TYPE: PRT
<213> ORGANISM: Artificial Sequence
<220> FEATURE:
<223> OTHER INFORMATION: Synthetic peptide

<400> SEQUENCE: 246

Gly Arg Asp Gly Tyr Tyr Ser Asp Tyr Tyr Ala Val Asp Val
1               5                   10

<210> SEQ ID NO 247
<211> LENGTH: 13
<212> TYPE: PRT
<213> ORGANISM: Artificial Sequence
<220> FEATURE:
<223> OTHER INFORMATION: Synthetic peptide

<400> SEQUENCE: 247

Ala Arg Ser Asn Gly Gly Gly Ile Gly Asp Val Asp Val
1               5                   10

<210> SEQ ID NO 248
<211> LENGTH: 9
<212> TYPE: PRT
<213> ORGANISM: Artificial Sequence
<220> FEATURE:
<223> OTHER INFORMATION: Synthetic peptide

<400> SEQUENCE: 248

Gly Arg Gly Tyr Asp Gln Val Val Ser
1               5

<210> SEQ ID NO 249
<211> LENGTH: 17
<212> TYPE: PRT
<213> ORGANISM: Artificial Sequence
<220> FEATURE:
<223> OTHER INFORMATION: Synthetic peptide

<400> SEQUENCE: 249

Val Arg Ser Asp Tyr Gly Tyr Gly Ala Gly Tyr Gly Trp Gly Phe His
1               5                   10                  15

His

<210> SEQ ID NO 250
<211> LENGTH: 10
<212> TYPE: PRT
```

```
<213> ORGANISM: Artificial Sequence
<220> FEATURE:
<223> OTHER INFORMATION: Synthetic peptide

<400> SEQUENCE: 250

Ala Asp Gly Tyr Ser Tyr Pro Asn Ala Tyr
1               5                   10

<210> SEQ ID NO 251

<400> SEQUENCE: 251

000

<210> SEQ ID NO 252
<211> LENGTH: 14
<212> TYPE: PRT
<213> ORGANISM: Artificial Sequence
<220> FEATURE:
<223> OTHER INFORMATION: Synthetic peptide

<400> SEQUENCE: 252

Thr Lys Ser Trp Asp Tyr Asp Tyr Ala Asn Gly Ala Glu Phe
1               5                   10

<210> SEQ ID NO 253
<211> LENGTH: 16
<212> TYPE: PRT
<213> ORGANISM: Artificial Sequence
<220> FEATURE:
<223> OTHER INFORMATION: Synthetic peptide

<400> SEQUENCE: 253

Val Arg Glu Ala Tyr Gly Ser Asp Gly Leu Tyr Tyr Gly Ile Asp Val
1               5                   10                  15

<210> SEQ ID NO 254
<211> LENGTH: 4
<212> TYPE: PRT
<213> ORGANISM: Artificial Sequence
<220> FEATURE:
<223> OTHER INFORMATION: Synthetic peptide

<400> SEQUENCE: 254

Gly Arg Asp Val
1

<210> SEQ ID NO 255
<211> LENGTH: 12
<212> TYPE: PRT
<213> ORGANISM: Artificial Sequence
<220> FEATURE:
<223> OTHER INFORMATION: Synthetic peptide

<400> SEQUENCE: 255

Val Thr Gly Gly Asn Gly Tyr Gly Tyr Asp Ala Pro
1               5                   10

<210> SEQ ID NO 256
<211> LENGTH: 17
<212> TYPE: PRT
<213> ORGANISM: Artificial Sequence
<220> FEATURE:
<223> OTHER INFORMATION: Synthetic peptide

<400> SEQUENCE: 256

Ala Arg Gly Tyr Ser Asp Tyr Ala Tyr Phe Tyr Gly Gly Ala Ile Glu
```

```
1               5                   10                  15
Val

<210> SEQ ID NO 257

<400> SEQUENCE: 257

000

<210> SEQ ID NO 258
<211> LENGTH: 14
<212> TYPE: PRT
<213> ORGANISM: Artificial Sequence
<220> FEATURE:
<223> OTHER INFORMATION: Synthetic peptide

<400> SEQUENCE: 258

Gly Lys Gly Val Tyr Tyr Asn Tyr Gly Ala Asp Val Glu Asp
1               5                   10

<210> SEQ ID NO 259
<211> LENGTH: 15
<212> TYPE: PRT
<213> ORGANISM: Artificial Sequence
<220> FEATURE:
<223> OTHER INFORMATION: Synthetic peptide

<400> SEQUENCE: 259

Ala Ser Ala Tyr Gly Tyr Ser Trp Asn Ser Tyr Gly Ile Asp Asp
1               5                   10                  15

<210> SEQ ID NO 260
<211> LENGTH: 19
<212> TYPE: PRT
<213> ORGANISM: Artificial Sequence
<220> FEATURE:
<223> OTHER INFORMATION: Synthetic peptide

<400> SEQUENCE: 260

Ala Arg Gly Pro Asp Tyr Ser Thr Tyr Gly Thr Ala Tyr Ile Tyr Tyr
1               5                   10                  15

Leu Asp Tyr

<210> SEQ ID NO 261
<211> LENGTH: 10
<212> TYPE: PRT
<213> ORGANISM: Artificial Sequence
<220> FEATURE:
<223> OTHER INFORMATION: Synthetic peptide

<400> SEQUENCE: 261

Ala Ser Ser Ile Leu Ala Ile Ser Asn Tyr
1               5                   10

<210> SEQ ID NO 262
<211> LENGTH: 19
<212> TYPE: PRT
<213> ORGANISM: Artificial Sequence
<220> FEATURE:
<223> OTHER INFORMATION: Synthetic peptide

<400> SEQUENCE: 262

Ala Arg Gly Pro Asp Tyr Ser Thr Tyr Gly Ser Tyr Tyr Leu Tyr Tyr
1               5                   10                  15

Leu Asp Tyr
```

<210> SEQ ID NO 263
<211> LENGTH: 13
<212> TYPE: PRT
<213> ORGANISM: Artificial Sequence
<220> FEATURE:
<223> OTHER INFORMATION: Synthetic peptide

<400> SEQUENCE: 263

Ala Thr Ser Ala Cys Gly Tyr Thr His Cys Ile Asp Tyr
1               5                   10

<210> SEQ ID NO 264
<211> LENGTH: 7
<212> TYPE: PRT
<213> ORGANISM: Artificial Sequence
<220> FEATURE:
<223> OTHER INFORMATION: Synthetic peptide

<400> SEQUENCE: 264

Ala Arg Gly Gly Gly Asp Tyr
1               5

<210> SEQ ID NO 265
<211> LENGTH: 13
<212> TYPE: PRT
<213> ORGANISM: Artificial Sequence
<220> FEATURE:
<223> OTHER INFORMATION: Synthetic peptide

<400> SEQUENCE: 265

Ala Arg Tyr Arg Tyr Phe Ala Glu Ser Leu Ile Asp Tyr
1               5                   10

<210> SEQ ID NO 266

<400> SEQUENCE: 266

000

<210> SEQ ID NO 267
<211> LENGTH: 12
<212> TYPE: PRT
<213> ORGANISM: Artificial Sequence
<220> FEATURE:
<223> OTHER INFORMATION: Synthetic peptide

<400> SEQUENCE: 267

Val Thr Gly Asn Met Tyr Ser Cys Asp Val Asp Phe
1               5                   10

<210> SEQ ID NO 268
<211> LENGTH: 18
<212> TYPE: PRT
<213> ORGANISM: Artificial Sequence
<220> FEATURE:
<223> OTHER INFORMATION: Synthetic peptide

<400> SEQUENCE: 268

Ala Arg Cys His Tyr Gly Gly His Cys Glu Thr Tyr Gly Leu Pro Met
1               5                   10                  15

Asp Tyr

<210> SEQ ID NO 269
<211> LENGTH: 10
<212> TYPE: PRT

<213> ORGANISM: Artificial Sequence
<220> FEATURE:
<223> OTHER INFORMATION: Synthetic peptide

<400> SEQUENCE: 269

Ala Arg Gly Leu Met Pro Ile Phe Asp Arg
1               5                   10

<210> SEQ ID NO 270
<211> LENGTH: 16
<212> TYPE: PRT
<213> ORGANISM: Artificial Sequence
<220> FEATURE:
<223> OTHER INFORMATION: Synthetic peptide

<400> SEQUENCE: 270

Val Arg Asp Tyr Glu Glu Tyr Asn His Ala Tyr Ala Tyr Gly Gly Tyr
1               5                   10                  15

<210> SEQ ID NO 271
<211> LENGTH: 14
<212> TYPE: PRT
<213> ORGANISM: Artificial Sequence
<220> FEATURE:
<223> OTHER INFORMATION: Synthetic peptide

<400> SEQUENCE: 271

Ile Arg Glu Gly Gly Gly Gly Tyr Gly Phe Asn Ile Asp Tyr
1               5                   10

<210> SEQ ID NO 272
<211> LENGTH: 16
<212> TYPE: PRT
<213> ORGANISM: Artificial Sequence
<220> FEATURE:
<223> OTHER INFORMATION: Synthetic peptide

<400> SEQUENCE: 272

Glu Cys Tyr Asn Gly Tyr Gly Tyr Ala Tyr Gly Tyr Asn Ile Asp Thr
1               5                   10                  15

<210> SEQ ID NO 273
<211> LENGTH: 16
<212> TYPE: PRT
<213> ORGANISM: Artificial Sequence
<220> FEATURE:
<223> OTHER INFORMATION: Synthetic peptide

<400> SEQUENCE: 273

Val Arg Val Arg Arg Gly Tyr Gly His Ala Tyr Gly Tyr Asn Asp Tyr
1               5                   10                  15

<210> SEQ ID NO 274
<211> LENGTH: 19
<212> TYPE: PRT
<213> ORGANISM: Artificial Sequence
<220> FEATURE:
<223> OTHER INFORMATION: Synthetic peptide

<400> SEQUENCE: 274

Gly Arg Glu Gly Asn Ile Ala Tyr Gly Tyr Asp Tyr Gly Pro His Asn
1               5                   10                  15

Ile Asp Tyr

<210> SEQ ID NO 275

```
<400> SEQUENCE: 275

000

<210> SEQ ID NO 276
<211> LENGTH: 15
<212> TYPE: PRT
<213> ORGANISM: Artificial Sequence
<220> FEATURE:
<223> OTHER INFORMATION: Synthetic peptide

<400> SEQUENCE: 276

Ala Arg Asn Thr Gly Arg Tyr Gly Ile Cys Ser Thr Ile Asp Ala
1               5                   10                  15

<210> SEQ ID NO 277
<211> LENGTH: 19
<212> TYPE: PRT
<213> ORGANISM: Artificial Sequence
<220> FEATURE:
<223> OTHER INFORMATION: Synthetic peptide

<400> SEQUENCE: 277

Gly Arg Glu Ser Arg Ser Val Ser Gly Tyr Gly His Gly Val Thr Asn
1               5                   10                  15

Phe Asp Phe

<210> SEQ ID NO 278
<211> LENGTH: 9
<212> TYPE: PRT
<213> ORGANISM: Artificial Sequence
<220> FEATURE:
<223> OTHER INFORMATION: Synthetic peptide

<400> SEQUENCE: 278

Ala Arg Gly Cys Leu Leu Ile Asp Tyr
1               5

<210> SEQ ID NO 279

<400> SEQUENCE: 279

000

<210> SEQ ID NO 280
<211> LENGTH: 21
<212> TYPE: PRT
<213> ORGANISM: Artificial Sequence
<220> FEATURE:
<223> OTHER INFORMATION: Synthetic peptide

<400> SEQUENCE: 280

Ala Arg Gly Leu Asn Ala Ala Gly Tyr Thr Thr Phe Ala Tyr Gly Thr
1               5                   10                  15

Thr Val Met Asp Leu
            20

<210> SEQ ID NO 281
<211> LENGTH: 12
<212> TYPE: PRT
<213> ORGANISM: Artificial Sequence
<220> FEATURE:
<223> OTHER INFORMATION: Synthetic peptide

<400> SEQUENCE: 281

Ala Thr Tyr Asp Gly Ser Ile Ala Tyr Leu Ala Leu
```

<210> SEQ ID NO 282
<211> LENGTH: 13
<212> TYPE: PRT
<213> ORGANISM: Artificial Sequence
<220> FEATURE:
<223> OTHER INFORMATION: Synthetic peptide

<400> SEQUENCE: 282

Ala Arg Asp Met Asp Gly Gly Asn Val Gly Tyr Gly Met
1               5                   10

<210> SEQ ID NO 283
<211> LENGTH: 18
<212> TYPE: PRT
<213> ORGANISM: Artificial Sequence
<220> FEATURE:
<223> OTHER INFORMATION: Synthetic peptide

<400> SEQUENCE: 283

Ala Lys Tyr Ser Ala Ser Ser Gly Ala Tyr Tyr Asp Gly Tyr Tyr Phe
1               5                   10                  15

Asn Leu

<210> SEQ ID NO 284
<211> LENGTH: 15
<212> TYPE: PRT
<213> ORGANISM: Artificial Sequence
<220> FEATURE:
<223> OTHER INFORMATION: Synthetic peptide

<400> SEQUENCE: 284

Ala Arg Phe Asp Ala Ala Tyr Ala Asp Phe Gly Val Ala Asn Leu
1               5                   10                  15

<210> SEQ ID NO 285
<211> LENGTH: 18
<212> TYPE: PRT
<213> ORGANISM: Artificial Sequence
<220> FEATURE:
<223> OTHER INFORMATION: Synthetic peptide

<400> SEQUENCE: 285

Ala Arg Ala Ser Ser Ser Ser Gly His Tyr Tyr Asp Gly Tyr Tyr Phe
1               5                   10                  15

Asn Leu

<210> SEQ ID NO 286
<211> LENGTH: 19
<212> TYPE: PRT
<213> ORGANISM: Artificial Sequence
<220> FEATURE:
<223> OTHER INFORMATION: Synthetic peptide

<400> SEQUENCE: 286

Ala Arg Ala Asp Arg Gly Phe Tyr Ala Gly Thr Ser Asp Tyr Thr Gly
1               5                   10                  15

Tyr Asn Leu

<210> SEQ ID NO 287
<211> LENGTH: 10
<212> TYPE: PRT
<213> ORGANISM: Artificial Sequence
<220> FEATURE:

<223> OTHER INFORMATION: Synthetic peptide

<400> SEQUENCE: 287

Ala Arg Gly Gly Tyr Ser Thr Phe Asp Leu
1               5                   10

<210> SEQ ID NO 288
<211> LENGTH: 19
<212> TYPE: PRT
<213> ORGANISM: Artificial Sequence
<220> FEATURE:
<223> OTHER INFORMATION: Synthetic peptide

<400> SEQUENCE: 288

Ala Arg Ala Asp Arg Gly Phe Tyr Ala Gly Thr Ser Asp Tyr Ser Gly
1               5                   10                  15

Tyr Asn Leu

<210> SEQ ID NO 289
<211> LENGTH: 10
<212> TYPE: PRT
<213> ORGANISM: Artificial Sequence
<220> FEATURE:
<223> OTHER INFORMATION: Synthetic peptide

<400> SEQUENCE: 289

Ala Arg Asp Leu Val Met Leu Ser Tyr Leu
1               5                   10

<210> SEQ ID NO 290
<211> LENGTH: 14
<212> TYPE: PRT
<213> ORGANISM: Artificial Sequence
<220> FEATURE:
<223> OTHER INFORMATION: Synthetic peptide

<400> SEQUENCE: 290

Ala Arg Asp Ala Gly Gly Ser Tyr Ser Tyr Tyr Phe Asp Leu
1               5                   10

<210> SEQ ID NO 291
<211> LENGTH: 17
<212> TYPE: PRT
<213> ORGANISM: Artificial Sequence
<220> FEATURE:
<223> OTHER INFORMATION: Synthetic peptide

<400> SEQUENCE: 291

Ala Ser Asn Tyr Ala Gly Asn Pro Gly Tyr Gly Tyr Ala Pro Phe Asn
1               5                   10                  15

Leu

<210> SEQ ID NO 292
<211> LENGTH: 16
<212> TYPE: PRT
<213> ORGANISM: Artificial Sequence
<220> FEATURE:
<223> OTHER INFORMATION: Synthetic peptide

<400> SEQUENCE: 292

Ala Arg Asp Ala Gly Gly Tyr Thr Gly Asp Gly Tyr Tyr Phe Lys Leu
1               5                   10                  15

<210> SEQ ID NO 293
<211> LENGTH: 19

```
<212> TYPE: PRT
<213> ORGANISM: Artificial Sequence
<220> FEATURE:
<223> OTHER INFORMATION: Synthetic peptide

<400> SEQUENCE: 293

Ala Arg Ala Asp Arg Gly Phe Tyr Ala Gly Thr Ser Asp Tyr Ser Gly
1               5                   10                  15

Tyr Asn Leu

<210> SEQ ID NO 294
<211> LENGTH: 11
<212> TYPE: PRT
<213> ORGANISM: Artificial Sequence
<220> FEATURE:
<223> OTHER INFORMATION: Synthetic peptide

<400> SEQUENCE: 294

Ala Arg Gly Gly Pro Ile His Tyr Ser Asn Leu
1               5                   10

<210> SEQ ID NO 295
<211> LENGTH: 6
<212> TYPE: PRT
<213> ORGANISM: Artificial Sequence
<220> FEATURE:
<223> OTHER INFORMATION: Synthetic peptide

<400> SEQUENCE: 295

Ala Arg Asn Phe Lys Leu
1               5

<210> SEQ ID NO 296
<211> LENGTH: 12
<212> TYPE: PRT
<213> ORGANISM: Artificial Sequence
<220> FEATURE:
<223> OTHER INFORMATION: Synthetic peptide

<400> SEQUENCE: 296

Ala Arg Gly Ser Gly Trp Tyr Gly Gly Leu Asn Leu
1               5                   10

<210> SEQ ID NO 297
<211> LENGTH: 13
<212> TYPE: PRT
<213> ORGANISM: Artificial Sequence
<220> FEATURE:
<223> OTHER INFORMATION: Synthetic peptide

<400> SEQUENCE: 297

Ala Arg Gly Asp Asp Asp Tyr Trp Tyr Tyr Leu Asn Leu
1               5                   10

<210> SEQ ID NO 298
<211> LENGTH: 17
<212> TYPE: PRT
<213> ORGANISM: Artificial Sequence
<220> FEATURE:
<223> OTHER INFORMATION: Synthetic peptide

<400> SEQUENCE: 298

Ala Ser Asn Tyr Ala Asp Pro Pro Gly Tyr Asn Tyr Thr Pro Phe Asn
1               5                   10                  15

Leu
```

<210> SEQ ID NO 299
<211> LENGTH: 12
<212> TYPE: PRT
<213> ORGANISM: Artificial Sequence
<220> FEATURE:
<223> OTHER INFORMATION: Synthetic peptide

<400> SEQUENCE: 299

Glu Arg His Arg His Gly Asp Ala Tyr Pro Asn Leu
1               5                   10

<210> SEQ ID NO 300
<211> LENGTH: 14
<212> TYPE: PRT
<213> ORGANISM: Artificial Sequence
<220> FEATURE:
<223> OTHER INFORMATION: Synthetic peptide

<400> SEQUENCE: 300

Ala Thr Asp Arg Gly Pro Ser Gly Ser Gly Pro Leu Asp Leu
1               5                   10

<210> SEQ ID NO 301
<211> LENGTH: 13
<212> TYPE: PRT
<213> ORGANISM: Artificial Sequence
<220> FEATURE:
<223> OTHER INFORMATION: Synthetic peptide

<400> SEQUENCE: 301

Ala Arg Glu Gly Gly Asn Ser Asp Trp Ser Phe Thr Leu
1               5                   10

<210> SEQ ID NO 302
<211> LENGTH: 19
<212> TYPE: PRT
<213> ORGANISM: Artificial Sequence
<220> FEATURE:
<223> OTHER INFORMATION: Synthetic peptide

<400> SEQUENCE: 302

Ser Arg Asp Gly Lys Tyr Ala Gly Ile Ala Gly Tyr Gly Ser Thr Tyr
1               5                   10                  15

Phe Asp Leu

<210> SEQ ID NO 303
<211> LENGTH: 16
<212> TYPE: PRT
<213> ORGANISM: Artificial Sequence
<220> FEATURE:
<223> OTHER INFORMATION: Synthetic peptide

<400> SEQUENCE: 303

Ala Arg Asp Ser Ser Tyr Asn Tyr Trp Val Pro Asp Tyr Phe Asp Leu
1               5                   10                  15

<210> SEQ ID NO 304
<211> LENGTH: 16
<212> TYPE: PRT
<213> ORGANISM: Artificial Sequence
<220> FEATURE:
<223> OTHER INFORMATION: Synthetic peptide

<400> SEQUENCE: 304

Ala Gly Asp Gly Arg Ser Tyr Tyr Ala Asp Tyr Ala Phe Val Asp Leu
1               5                   10                  15

<210> SEQ ID NO 305
<211> LENGTH: 13
<212> TYPE: PRT
<213> ORGANISM: Artificial Sequence
<220> FEATURE:
<223> OTHER INFORMATION: Synthetic peptide

<400> SEQUENCE: 305

Ala Arg Glu His Asp Asp Asp Asn Gly Ala Leu Thr Leu
1               5                   10

<210> SEQ ID NO 306
<211> LENGTH: 17
<212> TYPE: PRT
<213> ORGANISM: Artificial Sequence
<220> FEATURE:
<223> OTHER INFORMATION: Synthetic peptide

<400> SEQUENCE: 306

Ala Arg Asp Pro Val Thr Arg Leu Val Ala Gly Ala Asp Tyr Phe Asp
1               5                   10                  15

Leu

<210> SEQ ID NO 307
<211> LENGTH: 14
<212> TYPE: PRT
<213> ORGANISM: Artificial Sequence
<220> FEATURE:
<223> OTHER INFORMATION: Synthetic peptide

<400> SEQUENCE: 307

Ala Arg Tyr Tyr Ile Tyr Arg Gly Asp Trp Ser Gly Asn Leu
1               5                   10

<210> SEQ ID NO 308
<211> LENGTH: 18
<212> TYPE: PRT
<213> ORGANISM: Artificial Sequence
<220> FEATURE:
<223> OTHER INFORMATION: Synthetic peptide

<400> SEQUENCE: 308

Ala Arg Asp Val Tyr Thr Tyr Asp Ala Asp Gly Asp Tyr Arg His Phe
1               5                   10                  15

Asn Leu

<210> SEQ ID NO 309
<211> LENGTH: 12
<212> TYPE: PRT
<213> ORGANISM: Artificial Sequence
<220> FEATURE:
<223> OTHER INFORMATION: Synthetic peptide

<400> SEQUENCE: 309

Ala Arg Met Gly Gly Ser Asp Glu Asp Tyr His Leu
1               5                   10

<210> SEQ ID NO 310
<211> LENGTH: 19
<212> TYPE: PRT
<213> ORGANISM: Artificial Sequence
<220> FEATURE:
<223> OTHER INFORMATION: Synthetic peptide

<400> SEQUENCE: 310

Ala Arg Ala Pro Val Tyr Tyr Asn Gly Gly Tyr Ala Gly Phe Arg Glu
1               5                   10                  15

Phe Asn Leu

<210> SEQ ID NO 311
<211> LENGTH: 18
<212> TYPE: PRT
<213> ORGANISM: Artificial Sequence
<220> FEATURE:
<223> OTHER INFORMATION: Synthetic peptide

<400> SEQUENCE: 311

Ala Arg Asp Pro Phe Ala Ser Ser Ser Gly Tyr Tyr Trp Trp Gly Met
1               5                   10                  15

Asp Leu

<210> SEQ ID NO 312
<211> LENGTH: 10
<212> TYPE: PRT
<213> ORGANISM: Artificial Sequence
<220> FEATURE:
<223> OTHER INFORMATION: Synthetic peptide

<400> SEQUENCE: 312

Ala Arg Asp Gly Gly Trp Gly Tyr Asn Leu
1               5                   10

<210> SEQ ID NO 313
<211> LENGTH: 14
<212> TYPE: PRT
<213> ORGANISM: Artificial Sequence
<220> FEATURE:
<223> OTHER INFORMATION: Synthetic peptide

<400> SEQUENCE: 313

Ala Arg Asp Ser Ser Ser Gly Gly Asn Arg Gly Phe Asp Leu
1               5                   10

<210> SEQ ID NO 314
<211> LENGTH: 13
<212> TYPE: PRT
<213> ORGANISM: Artificial Sequence
<220> FEATURE:
<223> OTHER INFORMATION: Synthetic peptide

<400> SEQUENCE: 314

Ala Arg Asp Ser Phe Asp Gly Tyr Gly Asp Phe Asn Leu
1               5                   10

<210> SEQ ID NO 315
<211> LENGTH: 14
<212> TYPE: PRT
<213> ORGANISM: Artificial Sequence
<220> FEATURE:
<223> OTHER INFORMATION: Synthetic peptide

<400> SEQUENCE: 315

Ala Arg Leu Arg Ser Ser Ser Gly Tyr Phe Ile Tyr Asp Leu
1               5                   10

<210> SEQ ID NO 316
<211> LENGTH: 11
<212> TYPE: PRT
<213> ORGANISM: Artificial Sequence
<220> FEATURE:

<223> OTHER INFORMATION: Synthetic peptide

<400> SEQUENCE: 316

Ala Arg Val Gly Asn His Tyr Gly Met Asp Leu
1               5                   10

<210> SEQ ID NO 317
<211> LENGTH: 11
<212> TYPE: PRT
<213> ORGANISM: Artificial Sequence
<220> FEATURE:
<223> OTHER INFORMATION: Synthetic peptide

<400> SEQUENCE: 317

Ala Arg Gly Glu Tyr Gly Thr Lys Leu Asp Val
1               5                   10

<210> SEQ ID NO 318
<211> LENGTH: 19
<212> TYPE: PRT
<213> ORGANISM: Artificial Sequence
<220> FEATURE:
<223> OTHER INFORMATION: Synthetic peptide

<400> SEQUENCE: 318

Ala Arg Gly Ala Ala Gly Tyr Ala Gly Tyr Ala Tyr Ala Tyr Tyr
1               5                   10                  15

Phe Asp Phe

<210> SEQ ID NO 319
<211> LENGTH: 13
<212> TYPE: PRT
<213> ORGANISM: Artificial Sequence
<220> FEATURE:
<223> OTHER INFORMATION: Synthetic peptide

<400> SEQUENCE: 319

Ala Arg Cys Gly Gly Phe Gly Ile Glu Tyr Phe Asn Leu
1               5                   10

<210> SEQ ID NO 320
<211> LENGTH: 19
<212> TYPE: PRT
<213> ORGANISM: Artificial Sequence
<220> FEATURE:
<223> OTHER INFORMATION: Synthetic peptide

<400> SEQUENCE: 320

Val Arg Cys Tyr Thr His Trp Ser Asp Asn Asn Gly Arg Cys Tyr Gly
1               5                   10                  15

Pro Met Tyr

<210> SEQ ID NO 321
<211> LENGTH: 14
<212> TYPE: PRT
<213> ORGANISM: Artificial Sequence
<220> FEATURE:
<223> OTHER INFORMATION: Synthetic peptide

<400> SEQUENCE: 321

Gly Arg Asp Gly Tyr Tyr Ser Asp Tyr Tyr Ala Val Asp Val
1               5                   10

<210> SEQ ID NO 322
<211> LENGTH: 10

```
<212> TYPE: PRT
<213> ORGANISM: Artificial Sequence
<220> FEATURE:
<223> OTHER INFORMATION: Synthetic peptide

<400> SEQUENCE: 322

Ala Asp Gly Tyr Ser Tyr Pro Asn Ala Tyr
1               5                   10

<210> SEQ ID NO 323
<211> LENGTH: 4
<212> TYPE: PRT
<213> ORGANISM: Artificial Sequence
<220> FEATURE:
<223> OTHER INFORMATION: Synthetic peptide

<400> SEQUENCE: 323

Gly Arg Asp Val
1

<210> SEQ ID NO 324
<211> LENGTH: 17
<212> TYPE: PRT
<213> ORGANISM: Artificial Sequence
<220> FEATURE:
<223> OTHER INFORMATION: Synthetic peptide

<400> SEQUENCE: 324

Ala Arg Gly Tyr Ser Asp Tyr Ala Tyr Phe Tyr Gly Gly Ala Ile Glu
1               5                   10                  15

Val

<210> SEQ ID NO 325
<211> LENGTH: 14
<212> TYPE: PRT
<213> ORGANISM: Artificial Sequence
<220> FEATURE:
<223> OTHER INFORMATION: Synthetic peptide

<400> SEQUENCE: 325

Gly Lys Gly Val Tyr Tyr Asn Tyr Gly Ala Asp Val Glu Asp
1               5                   10

<210> SEQ ID NO 326
<211> LENGTH: 18
<212> TYPE: PRT
<213> ORGANISM: Artificial Sequence
<220> FEATURE:
<223> OTHER INFORMATION: Synthetic peptide

<400> SEQUENCE: 326

Ala Arg Asp Thr Ser Ile Asp Tyr Ala Tyr Arg Tyr Asn Tyr Glu Ile
1               5                   10                  15

Asp Tyr

<210> SEQ ID NO 327
<211> LENGTH: 16
<212> TYPE: PRT
<213> ORGANISM: Artificial Sequence
<220> FEATURE:
<223> OTHER INFORMATION: Synthetic peptide

<400> SEQUENCE: 327

Ala Arg Gly Ile Ser Asp Trp Asp Tyr Gly Leu Val Gly Leu Asn Val
1               5                   10                  15
```

<210> SEQ ID NO 328
<211> LENGTH: 13
<212> TYPE: PRT
<213> ORGANISM: Artificial Sequence
<220> FEATURE:
<223> OTHER INFORMATION: Synthetic peptide

<400> SEQUENCE: 328

Ala Arg Ser Asn Gly Gly Gly Ile Gly Asp Val Asp Ile
1               5                   10

<210> SEQ ID NO 329
<211> LENGTH: 13
<212> TYPE: PRT
<213> ORGANISM: Artificial Sequence
<220> FEATURE:
<223> OTHER INFORMATION: Synthetic peptide

<400> SEQUENCE: 329

Val Thr Gly Gly Asn Gly Tyr Gly Tyr Asp Ala Pro Phe
1               5                   10

<210> SEQ ID NO 330
<211> LENGTH: 14
<212> TYPE: PRT
<213> ORGANISM: Artificial Sequence
<220> FEATURE:
<223> OTHER INFORMATION: Synthetic peptide

<400> SEQUENCE: 330

Ala Arg Asp Lys Glu Trp Pro Gly Ala Ser Ser Ile Asp Tyr
1               5                   10

<210> SEQ ID NO 331
<211> LENGTH: 15
<212> TYPE: PRT
<213> ORGANISM: Artificial Sequence
<220> FEATURE:
<223> OTHER INFORMATION: Synthetic peptide

<400> SEQUENCE: 331

Ile Ser Gly Arg Ser Gly Val Gly Asp Asp Trp Ala Ala His Tyr
1               5                   10                  15

<210> SEQ ID NO 332
<211> LENGTH: 17
<212> TYPE: PRT
<213> ORGANISM: Artificial Sequence
<220> FEATURE:
<223> OTHER INFORMATION: Synthetic peptide

<400> SEQUENCE: 332

Val Gly Gly Ser Gly Tyr Asn Tyr Arg Tyr Val Tyr Asp Gly Val Asp
1               5                   10                  15

Ile

<210> SEQ ID NO 333
<211> LENGTH: 19
<212> TYPE: PRT
<213> ORGANISM: Artificial Sequence
<220> FEATURE:
<223> OTHER INFORMATION: Synthetic peptide

<400> SEQUENCE: 333

Ala Arg Asp Arg Thr Cys Cys Gly Ala Gly Tyr Gly Ser Arg Pro Asp
1               5                   10                  15

Ile Glu Val

<210> SEQ ID NO 334
<211> LENGTH: 17
<212> TYPE: PRT
<213> ORGANISM: Artificial Sequence
<220> FEATURE:
<223> OTHER INFORMATION: Synthetic peptide

<400> SEQUENCE: 334

Ala Arg Val Tyr Ala Asp Asp Thr Tyr Asp Tyr Glu Asp Ala Phe Asp
1               5                   10                  15

Tyr

<210> SEQ ID NO 335
<211> LENGTH: 21
<212> TYPE: PRT
<213> ORGANISM: Artificial Sequence
<220> FEATURE:
<223> OTHER INFORMATION: Synthetic peptide

<400> SEQUENCE: 335

Ala Arg Gly Arg Tyr Ser Gly Tyr Gly Tyr Gly Tyr Gly Tyr Asp Gln
1               5                   10                  15

Tyr Tyr Ile Asp Tyr
            20

<210> SEQ ID NO 336
<211> LENGTH: 13
<212> TYPE: PRT
<213> ORGANISM: Artificial Sequence
<220> FEATURE:
<223> OTHER INFORMATION: Synthetic peptide

<400> SEQUENCE: 336

Ala Arg Ser Asn Gly Gly Gly Ile Gly Asp Val Asp Val
1               5                   10

<210> SEQ ID NO 337
<211> LENGTH: 20
<212> TYPE: PRT
<213> ORGANISM: Artificial Sequence
<220> FEATURE:
<223> OTHER INFORMATION: Synthetic peptide

<400> SEQUENCE: 337

Thr Ser Cys Tyr Ser Val Tyr Gly Tyr Asn Cys Ala Asp Arg Asp Tyr
1               5                   10                  15

Gly Ala Asn Phe
            20

<210> SEQ ID NO 338
<211> LENGTH: 19
<212> TYPE: PRT
<213> ORGANISM: Artificial Sequence
<220> FEATURE:
<223> OTHER INFORMATION: Synthetic peptide

<400> SEQUENCE: 338

Ala Arg Gly Pro Asp Tyr Ser Thr Tyr Gly Thr Ala Tyr Ile Tyr Tyr
1               5                   10                  15

Leu Asp Tyr

```
<210> SEQ ID NO 339
<211> LENGTH: 19
<212> TYPE: PRT
<213> ORGANISM: Artificial Sequence
<220> FEATURE:
<223> OTHER INFORMATION: Synthetic peptide

<400> SEQUENCE: 339

Ala Arg Gly Pro Asp Tyr Ser Thr Tyr Gly Ser Tyr Tyr Leu Tyr Tyr
1               5                   10                  15

Leu Asp Tyr

<210> SEQ ID NO 340
<211> LENGTH: 7
<212> TYPE: PRT
<213> ORGANISM: Artificial Sequence
<220> FEATURE:
<223> OTHER INFORMATION: Synthetic peptide

<400> SEQUENCE: 340

Ala Arg Gly Gly Gly Asp Tyr
1               5

<210> SEQ ID NO 341
<211> LENGTH: 10
<212> TYPE: PRT
<213> ORGANISM: Artificial Sequence
<220> FEATURE:
<223> OTHER INFORMATION: Synthetic peptide

<400> SEQUENCE: 341

Ala Ser Ser Ile Leu Ala Ile Ser Asn Tyr
1               5                   10

<210> SEQ ID NO 342
<211> LENGTH: 18
<212> TYPE: PRT
<213> ORGANISM: Artificial Sequence
<220> FEATURE:
<223> OTHER INFORMATION: Synthetic peptide

<400> SEQUENCE: 342

Ala Arg Cys His Tyr Gly Gly His Cys Glu Thr Tyr Gly Leu Pro Met
1               5                   10                  15

Asp Tyr

<210> SEQ ID NO 343
<211> LENGTH: 16
<212> TYPE: PRT
<213> ORGANISM: Artificial Sequence
<220> FEATURE:
<223> OTHER INFORMATION: Synthetic peptide

<400> SEQUENCE: 343

Val Arg Asp Tyr Glu Glu Tyr Asn His Ala Tyr Ala Tyr Gly Gly Tyr
1               5                   10                  15

<210> SEQ ID NO 344
<211> LENGTH: 16
<212> TYPE: PRT
<213> ORGANISM: Artificial Sequence
<220> FEATURE:
<223> OTHER INFORMATION: Synthetic peptide

<400> SEQUENCE: 344

Glu Cys Tyr Asn Gly Tyr Gly Tyr Ala Tyr Gly Tyr Asn Ile Asp Thr
```

<210> SEQ ID NO 345
<211> LENGTH: 19
<212> TYPE: PRT
<213> ORGANISM: Artificial Sequence
<220> FEATURE:
<223> OTHER INFORMATION: Synthetic peptide

<400> SEQUENCE: 345

Gly Arg Glu Gly Asn Ile Ala Tyr Gly Tyr Asp Tyr Gly Pro His Asn
1               5                   10                  15

Ile Asp Tyr

<210> SEQ ID NO 346
<211> LENGTH: 12
<212> TYPE: PRT
<213> ORGANISM: Artificial Sequence
<220> FEATURE:
<223> OTHER INFORMATION: Synthetic peptide

<400> SEQUENCE: 346

Val Thr Gly Asn Met Tyr Ser Cys Asp Val Asp Phe
1               5                   10

<210> SEQ ID NO 347
<211> LENGTH: 13
<212> TYPE: PRT
<213> ORGANISM: Artificial Sequence
<220> FEATURE:
<223> OTHER INFORMATION: Synthetic peptide

<400> SEQUENCE: 347

Ala Thr Ser Ala Cys Gly Tyr Thr His Cys Ile Asp Tyr
1               5                   10

<210> SEQ ID NO 348
<211> LENGTH: 14
<212> TYPE: PRT
<213> ORGANISM: Artificial Sequence
<220> FEATURE:
<223> OTHER INFORMATION: Synthetic peptide

<400> SEQUENCE: 348

Ala Gly Ser Ile Arg Trp Phe Asp Arg Pro Thr Ser Gly Val
1               5                   10

<210> SEQ ID NO 349
<211> LENGTH: 16
<212> TYPE: PRT
<213> ORGANISM: Artificial Sequence
<220> FEATURE:
<223> OTHER INFORMATION: Synthetic peptide

<400> SEQUENCE: 349

Val Arg Val Arg Arg Gly Tyr Gly His Ala Tyr Gly Tyr Asn Asp Tyr
1               5                   10                  15

<210> SEQ ID NO 350
<211> LENGTH: 16
<212> TYPE: PRT
<213> ORGANISM: Artificial Sequence
<220> FEATURE:
<223> OTHER INFORMATION: Synthetic peptide

<400> SEQUENCE: 350

Val Arg Gly Tyr Tyr Ser Pro Pro Gly Tyr Asp Ile Cys Phe Asp Asp
1               5                   10                  15

<210> SEQ ID NO 351
<211> LENGTH: 10
<212> TYPE: PRT
<213> ORGANISM: Artificial Sequence
<220> FEATURE:
<223> OTHER INFORMATION: Synthetic peptide

<400> SEQUENCE: 351

Ala Arg Gly Leu Met Pro Ile Phe Asp Arg
1               5                   10

<210> SEQ ID NO 352
<211> LENGTH: 11
<212> TYPE: PRT
<213> ORGANISM: Artificial Sequence
<220> FEATURE:
<223> OTHER INFORMATION: Synthetic peptide

<400> SEQUENCE: 352

Ala Arg Gly Ile Gly Ile Pro Arg Leu Asp Tyr
1               5                   10

<210> SEQ ID NO 353
<211> LENGTH: 13
<212> TYPE: PRT
<213> ORGANISM: Artificial Sequence
<220> FEATURE:
<223> OTHER INFORMATION: Synthetic peptide

<400> SEQUENCE: 353

Thr Arg Asn Asp Ile Gly Tyr Ser Tyr Leu Pro Asp Tyr
1               5                   10

<210> SEQ ID NO 354
<211> LENGTH: 16
<212> TYPE: PRT
<213> ORGANISM: Artificial Sequence
<220> FEATURE:
<223> OTHER INFORMATION: Synthetic peptide

<400> SEQUENCE: 354

Val Arg Asp Tyr Tyr Gly Gly Val Gly Val Ala Val Ser Gly Asp Tyr
1               5                   10                  15

<210> SEQ ID NO 355
<211> LENGTH: 9
<212> TYPE: PRT
<213> ORGANISM: Artificial Sequence
<220> FEATURE:
<223> OTHER INFORMATION: Synthetic peptide

<400> SEQUENCE: 355

Ala Arg Gly Leu Tyr Asp Val Ser Ile
1               5

<210> SEQ ID NO 356
<211> LENGTH: 15
<212> TYPE: PRT
<213> ORGANISM: Artificial Sequence
<220> FEATURE:
<223> OTHER INFORMATION: Synthetic peptide

<400> SEQUENCE: 356

Ala Arg Ala Ala Gly Phe Thr Arg Ala Ala Ala Asp Val Asp Tyr

<210> SEQ ID NO 357
<211> LENGTH: 17
<212> TYPE: PRT
<213> ORGANISM: Artificial Sequence
<220> FEATURE:
<223> OTHER INFORMATION: Synthetic peptide

<400> SEQUENCE: 357

Ala Arg Gly Phe Tyr Ser Thr Asn Ser Val Ala Arg Tyr Tyr Ala Asp
1               5                   10                  15

Tyr

<210> SEQ ID NO 358
<211> LENGTH: 15
<212> TYPE: PRT
<213> ORGANISM: Artificial Sequence
<220> FEATURE:
<223> OTHER INFORMATION: Synthetic peptide

<400> SEQUENCE: 358

Val Arg Asp Asp Gly Thr Ile Gly Tyr Ala Gly Ser Ile Asp Tyr
1               5                   10                  15

<210> SEQ ID NO 359
<211> LENGTH: 19
<212> TYPE: PRT
<213> ORGANISM: Artificial Sequence
<220> FEATURE:
<223> OTHER INFORMATION: Synthetic peptide

<400> SEQUENCE: 359

Gly Arg Glu Ser Arg Ser Val Ser Gly Tyr Gly His Gly Val Thr Asn
1               5                   10                  15

Phe Asp Phe

<210> SEQ ID NO 360
<211> LENGTH: 17
<212> TYPE: PRT
<213> ORGANISM: Artificial Sequence
<220> FEATURE:
<223> OTHER INFORMATION: Synthetic peptide

<400> SEQUENCE: 360

Val Ser Leu Ser Thr Leu Cys Asp Ala Ala Gly Ala Phe Tyr Gly Glu
1               5                   10                  15

Tyr

<210> SEQ ID NO 361
<211> LENGTH: 15
<212> TYPE: PRT
<213> ORGANISM: Artificial Sequence
<220> FEATURE:
<223> OTHER INFORMATION: Synthetic peptide

<400> SEQUENCE: 361

Ala Arg Tyr Ser Asp Phe Gly Ser Ala Gly Asn Tyr Leu Asp Tyr
1               5                   10                  15

<210> SEQ ID NO 362
<211> LENGTH: 13
<212> TYPE: PRT
<213> ORGANISM: Artificial Sequence
<220> FEATURE:

<223> OTHER INFORMATION: Synthetic peptide

<400> SEQUENCE: 362

Ala Arg Asp Met Asp Gly Gly Asn Val Gly Tyr Gly Met
1               5                   10

<210> SEQ ID NO 363
<211> LENGTH: 19
<212> TYPE: PRT
<213> ORGANISM: Artificial Sequence
<220> FEATURE:
<223> OTHER INFORMATION: Synthetic peptide

<400> SEQUENCE: 363

Ala Arg Ala Asp Arg Gly Phe Tyr Ala Gly Thr Ser Asp Tyr Thr Gly
1               5                   10                  15

Tyr Asn Leu

<210> SEQ ID NO 364
<211> LENGTH: 19
<212> TYPE: PRT
<213> ORGANISM: Artificial Sequence
<220> FEATURE:
<223> OTHER INFORMATION: Synthetic peptide

<400> SEQUENCE: 364

Ala Arg Ala Asp Arg Gly Phe Tyr Ala Gly Thr Ser Asp Tyr Ser Gly
1               5                   10                  15

Tyr Asn Leu

<210> SEQ ID NO 365
<211> LENGTH: 12
<212> TYPE: PRT
<213> ORGANISM: Artificial Sequence
<220> FEATURE:
<223> OTHER INFORMATION: Synthetic peptide

<400> SEQUENCE: 365

Ala Arg Gly Ser Gly Trp Tyr Gly Gly Leu Asn Leu
1               5                   10

<210> SEQ ID NO 366
<211> LENGTH: 17
<212> TYPE: PRT
<213> ORGANISM: Artificial Sequence
<220> FEATURE:
<223> OTHER INFORMATION: Synthetic peptide

<400> SEQUENCE: 366

Ala Ser Asn Tyr Ala Asp Pro Pro Gly Tyr Asn Tyr Thr Pro Phe Asn
1               5                   10                  15

Leu

<210> SEQ ID NO 367
<211> LENGTH: 19
<212> TYPE: PRT
<213> ORGANISM: Artificial Sequence
<220> FEATURE:
<223> OTHER INFORMATION: Synthetic peptide

<400> SEQUENCE: 367

Ala Arg Leu Tyr Ala Gly Ser Ser Tyr Ser Ile Ser Pro Asp Tyr Gly
1               5                   10                  15

Met Asp Leu

<210> SEQ ID NO 368
<211> LENGTH: 18
<212> TYPE: PRT
<213> ORGANISM: Artificial Sequence
<220> FEATURE:
<223> OTHER INFORMATION: Synthetic peptide

<400> SEQUENCE: 368

Ala Arg Asp Ser Tyr Val Gly Asp Glu Ile Thr Thr Gly Tyr Ser Phe
1               5                   10                  15

Asn Leu

<210> SEQ ID NO 369
<211> LENGTH: 20
<212> TYPE: PRT
<213> ORGANISM: Artificial Sequence
<220> FEATURE:
<223> OTHER INFORMATION: Synthetic peptide

<400> SEQUENCE: 369

Ala Arg Asn Tyr Ala Gly Tyr Gly Gly Tyr Val Tyr Leu Ser Glu Tyr
1               5                   10                  15

His Phe Asn Leu
            20

<210> SEQ ID NO 370
<211> LENGTH: 17
<212> TYPE: PRT
<213> ORGANISM: Artificial Sequence
<220> FEATURE:
<223> OTHER INFORMATION: Synthetic peptide

<400> SEQUENCE: 370

Ala Ser Asn Tyr Ala Asp Gly Pro Gly Tyr Gly Phe Ala Pro Phe Asn
1               5                   10                  15

Leu

<210> SEQ ID NO 371
<211> LENGTH: 14
<212> TYPE: PRT
<213> ORGANISM: Artificial Sequence
<220> FEATURE:
<223> OTHER INFORMATION: Synthetic peptide

<400> SEQUENCE: 371

Ala Arg Asp Tyr Tyr Ser Ser Gly Trp Gly Gly Phe Asn Leu
1               5                   10

<210> SEQ ID NO 372
<211> LENGTH: 11
<212> TYPE: PRT
<213> ORGANISM: Artificial Sequence
<220> FEATURE:
<223> OTHER INFORMATION: Synthetic peptide

<400> SEQUENCE: 372

Ala Arg Leu Asn Ile Gly Gly Ala Asp Gly Leu
1               5                   10

<210> SEQ ID NO 373
<211> LENGTH: 14
<212> TYPE: PRT
<213> ORGANISM: Artificial Sequence
<220> FEATURE:

```
<223> OTHER INFORMATION: Synthetic peptide

<400> SEQUENCE: 373

Ala Arg Asp Tyr Gly Ser Ser Gly Trp Gly Gly Phe Asn Leu
1               5                   10

<210> SEQ ID NO 374
<211> LENGTH: 17
<212> TYPE: PRT
<213> ORGANISM: Artificial Sequence
<220> FEATURE:
<223> OTHER INFORMATION: Synthetic peptide

<400> SEQUENCE: 374

Ala Ser Asn Tyr Ala Gly Asp Ala Gly Tyr Gly Tyr Ala Pro Phe Asn
1               5                   10                  15
Leu

<210> SEQ ID NO 375
<211> LENGTH: 17
<212> TYPE: PRT
<213> ORGANISM: Artificial Sequence
<220> FEATURE:
<223> OTHER INFORMATION: Synthetic peptide

<400> SEQUENCE: 375

Ala Arg Asp Leu Gly Ala Ala Glu Tyr Gly Tyr Gly Ser Pro Phe Asn
1               5                   10                  15
Leu

<210> SEQ ID NO 376
<211> LENGTH: 13
<212> TYPE: PRT
<213> ORGANISM: Artificial Sequence
<220> FEATURE:
<223> OTHER INFORMATION: Synthetic peptide

<400> SEQUENCE: 376

Ala Ser Ser His Leu Ser Asp Asp Tyr Tyr Phe Asn Leu
1               5                   10

<210> SEQ ID NO 377
<211> LENGTH: 15
<212> TYPE: PRT
<213> ORGANISM: Artificial Sequence
<220> FEATURE:
<223> OTHER INFORMATION: Synthetic peptide

<400> SEQUENCE: 377

Ala Arg Gly Leu Val Met Leu Val Met Ser Ile Leu Pro Asp Leu
1               5                   10                  15

<210> SEQ ID NO 378
<211> LENGTH: 17
<212> TYPE: PRT
<213> ORGANISM: Artificial Sequence
<220> FEATURE:
<223> OTHER INFORMATION: Synthetic peptide

<400> SEQUENCE: 378

Ala Thr Tyr Thr Tyr Asp Tyr Ala Gly Tyr Ser His Ala Gly Phe Asn
1               5                   10                  15
Leu
```

```
<210> SEQ ID NO 379
<211> LENGTH: 16
<212> TYPE: PRT
<213> ORGANISM: Artificial Sequence
<220> FEATURE:
<223> OTHER INFORMATION: Synthetic peptide

<400> SEQUENCE: 379

Ala Arg Asp Pro Pro Gly Tyr Gly Ile Asn Phe Val Ala Met Asp Leu
1               5                   10                  15

<210> SEQ ID NO 380
<211> LENGTH: 11
<212> TYPE: PRT
<213> ORGANISM: Artificial Sequence
<220> FEATURE:
<223> OTHER INFORMATION: Synthetic peptide

<400> SEQUENCE: 380

Ala Arg Glu Phe Ala Ala Gly Ser Phe Asn Phe
1               5                   10

<210> SEQ ID NO 381
<211> LENGTH: 14
<212> TYPE: PRT
<213> ORGANISM: Artificial Sequence
<220> FEATURE:
<223> OTHER INFORMATION: Synthetic peptide

<400> SEQUENCE: 381

Ala Thr Asp Arg Gly Pro Ser Gly Ser Gly Pro Leu Asp Leu
1               5                   10

<210> SEQ ID NO 382
<211> LENGTH: 19
<212> TYPE: PRT
<213> ORGANISM: Artificial Sequence
<220> FEATURE:
<223> OTHER INFORMATION: Synthetic peptide

<400> SEQUENCE: 382

Ser Arg Asp Gly Lys Tyr Ala Gly Ile Ala Gly Tyr Gly Ser Thr Tyr
1               5                   10                  15

Phe Asp Leu

<210> SEQ ID NO 383
<211> LENGTH: 16
<212> TYPE: PRT
<213> ORGANISM: Artificial Sequence
<220> FEATURE:
<223> OTHER INFORMATION: Synthetic peptide

<400> SEQUENCE: 383

Ala Gly Asp Gly Arg Ser Tyr Tyr Ala Asp Tyr Ala Phe Val Asp Leu
1               5                   10                  15

<210> SEQ ID NO 384
<211> LENGTH: 17
<212> TYPE: PRT
<213> ORGANISM: Artificial Sequence
<220> FEATURE:
<223> OTHER INFORMATION: Synthetic peptide

<400> SEQUENCE: 384

Ala Arg Asp Pro Val Thr Arg Leu Val Ala Gly Ala Asp Tyr Phe Asp
1               5                   10                  15
```

Leu

<210> SEQ ID NO 385
<211> LENGTH: 18
<212> TYPE: PRT
<213> ORGANISM: Artificial Sequence
<220> FEATURE:
<223> OTHER INFORMATION: Synthetic peptide

<400> SEQUENCE: 385

Ala Arg Asp Val Tyr Thr Tyr Asp Ala Asp Gly Asp Tyr Arg His Phe
1               5                   10                  15

Asn Leu

<210> SEQ ID NO 386
<211> LENGTH: 19
<212> TYPE: PRT
<213> ORGANISM: Artificial Sequence
<220> FEATURE:
<223> OTHER INFORMATION: Synthetic peptide

<400> SEQUENCE: 386

Ala Arg Ala Pro Val Tyr Tyr Asn Gly Gly Tyr Ala Gly Phe Arg Glu
1               5                   10                  15

Phe Asn Leu

<210> SEQ ID NO 387
<211> LENGTH: 11
<212> TYPE: PRT
<213> ORGANISM: Artificial Sequence
<220> FEATURE:
<223> OTHER INFORMATION: Synthetic peptide

<400> SEQUENCE: 387

Ala Arg Val Gly Asn His Tyr Gly Met Asp Leu
1               5                   10

<210> SEQ ID NO 388
<211> LENGTH: 19
<212> TYPE: PRT
<213> ORGANISM: Artificial Sequence
<220> FEATURE:
<223> OTHER INFORMATION: Synthetic peptide

<400> SEQUENCE: 388

Ala Arg Gly Ala Ala Gly Tyr Ala Gly Tyr Ala Tyr Ala Tyr Tyr Tyr
1               5                   10                  15

Phe Asp Phe

<210> SEQ ID NO 389
<211> LENGTH: 17
<212> TYPE: PRT
<213> ORGANISM: Artificial Sequence
<220> FEATURE:
<223> OTHER INFORMATION: Synthetic peptide

<400> SEQUENCE: 389

Ala Arg Asp Pro Val Asn Arg Leu Gln Ala Gly Ala Asp Tyr Phe Asn
1               5                   10                  15

Leu

<210> SEQ ID NO 390
<211> LENGTH: 19
<212> TYPE: PRT

```
<213> ORGANISM: Artificial Sequence
<220> FEATURE:
<223> OTHER INFORMATION: Synthetic peptide

<400> SEQUENCE: 390

Ala Arg Asp Phe Ser Tyr Gly Tyr Ala Gly Gln Ala Tyr Val Thr Pro
1               5                   10                  15
Phe Ile Leu

<210> SEQ ID NO 391
<211> LENGTH: 10
<212> TYPE: PRT
<213> ORGANISM: Artificial Sequence
<220> FEATURE:
<223> OTHER INFORMATION: Synthetic peptide

<400> SEQUENCE: 391

Ala Arg Gln Pro Tyr Thr Gly Thr Thr Leu
1               5                   10

<210> SEQ ID NO 392
<211> LENGTH: 13
<212> TYPE: PRT
<213> ORGANISM: Artificial Sequence
<220> FEATURE:
<223> OTHER INFORMATION: Synthetic peptide

<400> SEQUENCE: 392

Val Arg Asp Ser Phe Leu Asp Tyr Gly Asp Phe Gly Leu
1               5                   10

<210> SEQ ID NO 393
<211> LENGTH: 11
<212> TYPE: PRT
<213> ORGANISM: Artificial Sequence
<220> FEATURE:
<223> OTHER INFORMATION: Synthetic peptide

<400> SEQUENCE: 393

Ala Arg Gly Gly Gly Arg Gly Glu Leu Asn Leu
1               5                   10

<210> SEQ ID NO 394
<211> LENGTH: 14
<212> TYPE: PRT
<213> ORGANISM: Artificial Sequence
<220> FEATURE:
<223> OTHER INFORMATION: Synthetic peptide

<400> SEQUENCE: 394

Ala Arg Asp Phe Gly Ala Ser Ser Tyr Tyr Leu Phe Asp Leu
1               5                   10

<210> SEQ ID NO 395
<211> LENGTH: 18
<212> TYPE: PRT
<213> ORGANISM: Artificial Sequence
<220> FEATURE:
<223> OTHER INFORMATION: Synthetic peptide

<400> SEQUENCE: 395

Ala Arg Gly Val Ile Tyr Asp Asp Phe Gly Asp Tyr Pro Tyr Tyr Leu
1               5                   10                  15
Asp Leu
```

```
<210> SEQ ID NO 396
<211> LENGTH: 15
<212> TYPE: PRT
<213> ORGANISM: Artificial Sequence
<220> FEATURE:
<223> OTHER INFORMATION: Synthetic peptide

<400> SEQUENCE: 396

Ala Arg Asp Leu Asp Gly Tyr Gly Asp Phe Ile Tyr Phe Gly Leu
1               5                   10                  15

<210> SEQ ID NO 397
<211> LENGTH: 12
<212> TYPE: PRT
<213> ORGANISM: Artificial Sequence
<220> FEATURE:
<223> OTHER INFORMATION: Synthetic peptide

<400> SEQUENCE: 397

Ala Lys Tyr Asp Asp Tyr Ala His Tyr Phe His Leu
1               5                   10

<210> SEQ ID NO 398
<211> LENGTH: 18
<212> TYPE: PRT
<213> ORGANISM: Artificial Sequence
<220> FEATURE:
<223> OTHER INFORMATION: Synthetic peptide

<400> SEQUENCE: 398

Ala Arg Asp Gly Phe Pro Cys Ala Ser Asp Tyr Tyr Arg Ala Cys Leu
1               5                   10                  15

Asp Leu

<210> SEQ ID NO 399
<211> LENGTH: 15
<212> TYPE: PRT
<213> ORGANISM: Artificial Sequence
<220> FEATURE:
<223> OTHER INFORMATION: Synthetic peptide

<400> SEQUENCE: 399

Ala Arg Thr Leu Ile Tyr Ala Ser Arg Pro Asn Tyr Phe Asp Leu
1               5                   10                  15

<210> SEQ ID NO 400
<211> LENGTH: 13
<212> TYPE: PRT
<213> ORGANISM: Artificial Sequence
<220> FEATURE:
<223> OTHER INFORMATION: Synthetic peptide

<400> SEQUENCE: 400

Ala Arg Asp Gly Asp Gly Gly Ser Phe Gly Tyr Thr Leu
1               5                   10

<210> SEQ ID NO 401
<211> LENGTH: 6
<212> TYPE: PRT
<213> ORGANISM: Artificial Sequence
<220> FEATURE:
<223> OTHER INFORMATION: Synthetic peptide

<400> SEQUENCE: 401

Ala Arg Asp Phe Asn Leu
1               5
```

<210> SEQ ID NO 402
<211> LENGTH: 14
<212> TYPE: PRT
<213> ORGANISM: Artificial Sequence
<220> FEATURE:
<223> OTHER INFORMATION: Synthetic peptide

<400> SEQUENCE: 402

Ala Thr Asn Val Gly Gly Gly Tyr Val Ala Arg Leu Asp Leu
1               5                   10

<210> SEQ ID NO 403
<211> LENGTH: 12
<212> TYPE: PRT
<213> ORGANISM: Artificial Sequence
<220> FEATURE:
<223> OTHER INFORMATION: Synthetic peptide

<400> SEQUENCE: 403

Ala Arg Asp Met Leu Val Val Val Gly Leu Asn Leu
1               5                   10

<210> SEQ ID NO 404
<211> LENGTH: 16
<212> TYPE: PRT
<213> ORGANISM: Artificial Sequence
<220> FEATURE:
<223> OTHER INFORMATION: Synthetic peptide

<400> SEQUENCE: 404

Ala Lys Tyr Asn Tyr Asp Asp Tyr Gly Asp Gln Tyr Tyr Phe Asn Leu
1               5                   10                  15

<210> SEQ ID NO 405
<211> LENGTH: 6
<212> TYPE: PRT
<213> ORGANISM: Artificial Sequence
<220> FEATURE:
<223> OTHER INFORMATION: Synthetic peptide

<400> SEQUENCE: 405

Ala Arg Asp Tyr Asn Leu
1               5

<210> SEQ ID NO 406
<211> LENGTH: 11
<212> TYPE: PRT
<213> ORGANISM: Artificial Sequence
<220> FEATURE:
<223> OTHER INFORMATION: Synthetic peptide

<400> SEQUENCE: 406

Ala Gly Arg Ser Gly Trp Asp Gly Phe Asn Leu
1               5                   10

<210> SEQ ID NO 407
<211> LENGTH: 17
<212> TYPE: PRT
<213> ORGANISM: Artificial Sequence
<220> FEATURE:
<223> OTHER INFORMATION: Synthetic peptide

<400> SEQUENCE: 407

Thr Arg Glu Phe Ala Tyr Ala Tyr Ser Ser Gly Tyr Tyr Gly Phe Asn
1               5                   10                  15

Leu

<210> SEQ ID NO 408
<211> LENGTH: 16
<212> TYPE: PRT
<213> ORGANISM: Artificial Sequence
<220> FEATURE:
<223> OTHER INFORMATION: Synthetic peptide

<400> SEQUENCE: 408

Ala Arg Tyr Asn Tyr Asp Asp Tyr Gly Asp Gln Tyr Tyr Phe Asn Leu
1               5                   10                  15

<210> SEQ ID NO 409
<211> LENGTH: 16
<212> TYPE: PRT
<213> ORGANISM: Artificial Sequence
<220> FEATURE:
<223> OTHER INFORMATION: Synthetic peptide

<400> SEQUENCE: 409

Ala Ser Tyr Gly Gly Gly Ser Phe Ile Ser Pro Asp Tyr Leu Asn Leu
1               5                   10                  15

<210> SEQ ID NO 410
<211> LENGTH: 15
<212> TYPE: PRT
<213> ORGANISM: Artificial Sequence
<220> FEATURE:
<223> OTHER INFORMATION: Synthetic peptide

<400> SEQUENCE: 410

Ala Arg Gly Asn Tyr Asp Asp Tyr Gly Ala Glu Tyr Phe Gly Leu
1               5                   10                  15

<210> SEQ ID NO 411
<211> LENGTH: 21
<212> TYPE: PRT
<213> ORGANISM: Artificial Sequence
<220> FEATURE:
<223> OTHER INFORMATION: Synthetic peptide

<400> SEQUENCE: 411

Thr Arg Gly Gly Ser Tyr Thr Asp Gly Asp Val Gly Ala Val Tyr Ala
1               5                   10                  15

Thr Asp Phe Asn Leu
            20

<210> SEQ ID NO 412
<211> LENGTH: 18
<212> TYPE: PRT
<213> ORGANISM: Artificial Sequence
<220> FEATURE:
<223> OTHER INFORMATION: Synthetic peptide

<400> SEQUENCE: 412

Ala Arg Asp Leu Gly Asp Thr Tyr Tyr Ser Gly Ala Leu Trp Tyr Trp
1               5                   10                  15

Asn Leu

<210> SEQ ID NO 413
<211> LENGTH: 20
<212> TYPE: PRT
<213> ORGANISM: Artificial Sequence
<220> FEATURE:
<223> OTHER INFORMATION: Synthetic peptide

```
<400> SEQUENCE: 413

Ala Arg Phe Ala Tyr Ser Tyr Gly Tyr Ala Gly Asn Ile Asp Tyr Tyr
1               5                   10                  15

Gly Met Asp Leu
            20

<210> SEQ ID NO 414
<211> LENGTH: 23
<212> TYPE: PRT
<213> ORGANISM: Artificial Sequence
<220> FEATURE:
<223> OTHER INFORMATION: Synthetic peptide

<400> SEQUENCE: 414

Ala Arg Val Asp Leu Ala Tyr Tyr Asn Gly Gly Asp Thr Thr Thr Pro
1               5                   10                  15

Tyr Ala Thr Glu Phe Thr Leu
            20

<210> SEQ ID NO 415
<211> LENGTH: 18
<212> TYPE: PRT
<213> ORGANISM: Artificial Sequence
<220> FEATURE:
<223> OTHER INFORMATION: Synthetic peptide

<400> SEQUENCE: 415

Ala Arg Gly Thr Tyr Thr Tyr Asp Asp Tyr Gly Asp Tyr Arg Ala Phe
1               5                   10                  15

Asp Pro

<210> SEQ ID NO 416
<211> LENGTH: 9
<212> TYPE: PRT
<213> ORGANISM: Artificial Sequence
<220> FEATURE:
<223> OTHER INFORMATION: Synthetic peptide

<400> SEQUENCE: 416

Gln Gly Tyr Ser Ser Tyr Pro Leu Thr
1               5

<210> SEQ ID NO 417
<211> LENGTH: 12
<212> TYPE: PRT
<213> ORGANISM: Artificial Sequence
<220> FEATURE:
<223> OTHER INFORMATION: Synthetic peptide

<400> SEQUENCE: 417

Gln Cys Thr Arg Tyr Asp Arg Ser Asp Gly Gly Ala
1               5                   10

<210> SEQ ID NO 418
<211> LENGTH: 13
<212> TYPE: PRT
<213> ORGANISM: Artificial Sequence
<220> FEATURE:
<223> OTHER INFORMATION: Synthetic peptide

<400> SEQUENCE: 418

Gln Ser Ala Tyr Phe Ser Val Thr Gly Asp Ser Tyr Ala
1               5                   10
```

```
<210> SEQ ID NO 419
<211> LENGTH: 13
<212> TYPE: PRT
<213> ORGANISM: Artificial Sequence
<220> FEATURE:
<223> OTHER INFORMATION: Synthetic peptide

<400> SEQUENCE: 419

Gln Ser Ala Tyr Asp Ala Ser Thr Tyr Val Pro Ser Ala
1               5                   10

<210> SEQ ID NO 420
<211> LENGTH: 12
<212> TYPE: PRT
<213> ORGANISM: Artificial Sequence
<220> FEATURE:
<223> OTHER INFORMATION: Synthetic peptide

<400> SEQUENCE: 420

Gln Thr Ala Tyr Gly Ser Ser Ser Ser Asp Asn Val
1               5                   10

<210> SEQ ID NO 421
<211> LENGTH: 11
<212> TYPE: PRT
<213> ORGANISM: Artificial Sequence
<220> FEATURE:
<223> OTHER INFORMATION: Synthetic peptide

<400> SEQUENCE: 421

Leu Gly Gly Tyr Ser Gly Ser Ala Asp Leu Thr
1               5                   10

<210> SEQ ID NO 422
<211> LENGTH: 11
<212> TYPE: PRT
<213> ORGANISM: Artificial Sequence
<220> FEATURE:
<223> OTHER INFORMATION: Synthetic peptide

<400> SEQUENCE: 422

Ala Gly Gly Tyr Ser Ser Ser Ser Asp Asn Ala
1               5                   10

<210> SEQ ID NO 423
<211> LENGTH: 10
<212> TYPE: PRT
<213> ORGANISM: Artificial Sequence
<220> FEATURE:
<223> OTHER INFORMATION: Synthetic peptide

<400> SEQUENCE: 423

Gly Gly Asp Leu Gly Gly Gly Met Asp Ala
1               5                   10

<210> SEQ ID NO 424
<211> LENGTH: 11
<212> TYPE: PRT
<213> ORGANISM: Artificial Sequence
<220> FEATURE:
<223> OTHER INFORMATION: Synthetic peptide

<400> SEQUENCE: 424

Leu Gly Gly Tyr Ser Ser Ser Thr Gly Thr Thr
1               5                   10

<210> SEQ ID NO 425
```

```
<211> LENGTH: 10
<212> TYPE: PRT
<213> ORGANISM: Artificial Sequence
<220> FEATURE:
<223> OTHER INFORMATION: Synthetic peptide

<400> SEQUENCE: 425

Leu Gly Gly Tyr Ser Tyr Gly Ser Asn Thr
1               5                   10

<210> SEQ ID NO 426
<211> LENGTH: 9
<212> TYPE: PRT
<213> ORGANISM: Artificial Sequence
<220> FEATURE:
<223> OTHER INFORMATION: Synthetic peptide

<400> SEQUENCE: 426

Gln Gln Gly Tyr Ser Thr Pro Leu Thr
1               5

<210> SEQ ID NO 427
<211> LENGTH: 9
<212> TYPE: PRT
<213> ORGANISM: Artificial Sequence
<220> FEATURE:
<223> OTHER INFORMATION: Synthetic peptide

<400> SEQUENCE: 427

Gln Gly Tyr Arg Arg Tyr Pro His Thr
1               5

<210> SEQ ID NO 428
<211> LENGTH: 11
<212> TYPE: PRT
<213> ORGANISM: Artificial Sequence
<220> FEATURE:
<223> OTHER INFORMATION: Synthetic peptide

<400> SEQUENCE: 428

Leu Gly Gly Asp Thr Ser Arg Thr Gly Leu Thr
1               5                   10

<210> SEQ ID NO 429
<211> LENGTH: 12
<212> TYPE: PRT
<213> ORGANISM: Artificial Sequence
<220> FEATURE:
<223> OTHER INFORMATION: Synthetic peptide

<400> SEQUENCE: 429

Leu Gly Gly Val Ser Gly Ser Ala Asp Phe Val Ser
1               5                   10

<210> SEQ ID NO 430
<211> LENGTH: 12
<212> TYPE: PRT
<213> ORGANISM: Artificial Sequence
<220> FEATURE:
<223> OTHER INFORMATION: Synthetic peptide

<400> SEQUENCE: 430

Gln Ser Ala Tyr Tyr Ser Ser Asn Pro Asp Ile Thr
1               5                   10

<210> SEQ ID NO 431
<211> LENGTH: 12
```

```
<212> TYPE: PRT
<213> ORGANISM: Artificial Sequence
<220> FEATURE:
<223> OTHER INFORMATION: Synthetic peptide

<400> SEQUENCE: 431

Leu Gly Gly Val Ser Gly Ser Ala Asp Phe Leu Ser
1               5                   10

<210> SEQ ID NO 432
<211> LENGTH: 13
<212> TYPE: PRT
<213> ORGANISM: Artificial Sequence
<220> FEATURE:
<223> OTHER INFORMATION: Synthetic peptide

<400> SEQUENCE: 432

Gln Ser Ala Asp Tyr Thr Thr Phe Thr Asp Ser His Ala
1               5                   10

<210> SEQ ID NO 433
<211> LENGTH: 12
<212> TYPE: PRT
<213> ORGANISM: Artificial Sequence
<220> FEATURE:
<223> OTHER INFORMATION: Synthetic peptide

<400> SEQUENCE: 433

Gln Ser Ala Tyr Tyr Gly Ser Ser Gly Lys Ile Thr
1               5                   10

<210> SEQ ID NO 434
<211> LENGTH: 12
<212> TYPE: PRT
<213> ORGANISM: Artificial Sequence
<220> FEATURE:
<223> OTHER INFORMATION: Synthetic peptide

<400> SEQUENCE: 434

Gln Ser Ala Tyr Tyr Ser Ser Ala Asp Asn Ala
1               5                   10

<210> SEQ ID NO 435
<211> LENGTH: 12
<212> TYPE: PRT
<213> ORGANISM: Artificial Sequence
<220> FEATURE:
<223> OTHER INFORMATION: Synthetic peptide

<400> SEQUENCE: 435

Gln Ser Ala Tyr Tyr Ser Ser Ala Asp Asn Ala
1               5                   10

<210> SEQ ID NO 436
<211> LENGTH: 11
<212> TYPE: PRT
<213> ORGANISM: Artificial Sequence
<220> FEATURE:
<223> OTHER INFORMATION: Synthetic peptide

<400> SEQUENCE: 436

Leu Gly Gly Tyr Ile Ser Ala Ser Asp Asn Gly
1               5                   10

<210> SEQ ID NO 437
<211> LENGTH: 14
<212> TYPE: PRT
```

```
<213> ORGANISM: Artificial Sequence
<220> FEATURE:
<223> OTHER INFORMATION: Synthetic peptide

<400> SEQUENCE: 437

Ala Gly Ala Tyr Thr Thr Ser Val Ser Asp Ala Val Arg Ala
1               5                   10

<210> SEQ ID NO 438
<211> LENGTH: 13
<212> TYPE: PRT
<213> ORGANISM: Artificial Sequence
<220> FEATURE:
<223> OTHER INFORMATION: Synthetic peptide

<400> SEQUENCE: 438

Gln Gly Gly Tyr Asp Cys Ser Ser Ala Asp Cys His Val
1               5                   10

<210> SEQ ID NO 439
<211> LENGTH: 12
<212> TYPE: PRT
<213> ORGANISM: Artificial Sequence
<220> FEATURE:
<223> OTHER INFORMATION: Synthetic peptide

<400> SEQUENCE: 439

Leu Gly Gly Tyr Asn Tyr Asp Gly Thr Gly Arg Thr
1               5                   10

<210> SEQ ID NO 440
<211> LENGTH: 9
<212> TYPE: PRT
<213> ORGANISM: Artificial Sequence
<220> FEATURE:
<223> OTHER INFORMATION: Synthetic peptide

<400> SEQUENCE: 440

Gln Gly Tyr Ser Asn Tyr His Leu Thr
1               5

<210> SEQ ID NO 441
<211> LENGTH: 10
<212> TYPE: PRT
<213> ORGANISM: Artificial Sequence
<220> FEATURE:
<223> OTHER INFORMATION: Synthetic peptide

<400> SEQUENCE: 441

Gln Gly Gly Tyr Ser Gly Asn Ile Tyr Asp
1               5                   10

<210> SEQ ID NO 442
<211> LENGTH: 10
<212> TYPE: PRT
<213> ORGANISM: Artificial Sequence
<220> FEATURE:
<223> OTHER INFORMATION: Synthetic peptide

<400> SEQUENCE: 442

Gln Gly Tyr Trp His Asp Gly Ile Trp Ala
1               5                   10

<210> SEQ ID NO 443
<211> LENGTH: 14
<212> TYPE: PRT
<213> ORGANISM: Artificial Sequence
```

```
<220> FEATURE:
<223> OTHER INFORMATION: Synthetic peptide

<400> SEQUENCE: 443

Leu Gly Val Gly Thr Tyr Ile Asn Gly Asp Gly Arg Gly Val
1               5                   10

<210> SEQ ID NO 444
<211> LENGTH: 13
<212> TYPE: PRT
<213> ORGANISM: Artificial Sequence
<220> FEATURE:
<223> OTHER INFORMATION: Synthetic peptide

<400> SEQUENCE: 444

Leu Gly Ser Tyr Asp Cys Asp Arg Ala Asp Cys Thr Ala
1               5                   10

<210> SEQ ID NO 445
<211> LENGTH: 13
<212> TYPE: PRT
<213> ORGANISM: Artificial Sequence
<220> FEATURE:
<223> OTHER INFORMATION: Synthetic peptide

<400> SEQUENCE: 445

Gln Phe Thr His Ser Ser Ser Asn Ser Asp Gly Asn Pro
1               5                   10

<210> SEQ ID NO 446
<211> LENGTH: 11
<212> TYPE: PRT
<213> ORGANISM: Artificial Sequence
<220> FEATURE:
<223> OTHER INFORMATION: Synthetic peptide

<400> SEQUENCE: 446

Gln Ser Tyr Val Tyr Gly Ala Asp Thr Pro Ala
1               5                   10

<210> SEQ ID NO 447
<211> LENGTH: 14
<212> TYPE: PRT
<213> ORGANISM: Artificial Sequence
<220> FEATURE:
<223> OTHER INFORMATION: Synthetic peptide

<400> SEQUENCE: 447

Gln Cys Ser Phe Val Thr Asn Gly Asp Asn Ser His Asn Thr
1               5                   10

<210> SEQ ID NO 448
<211> LENGTH: 11
<212> TYPE: PRT
<213> ORGANISM: Artificial Sequence
<220> FEATURE:
<223> OTHER INFORMATION: Synthetic peptide

<400> SEQUENCE: 448

Gln Ser Tyr Tyr Gly Val Ala Ser Lys His Ala
1               5                   10

<210> SEQ ID NO 449
<211> LENGTH: 12
<212> TYPE: PRT
<213> ORGANISM: Artificial Sequence
<220> FEATURE:
```

```
<223> OTHER INFORMATION: Synthetic peptide

<400> SEQUENCE: 449

Gln Gln Glu Tyr Glu Ser Arg Asp Val Pro Asn Pro
1               5                   10

<210> SEQ ID NO 450
<211> LENGTH: 12
<212> TYPE: PRT
<213> ORGANISM: Artificial Sequence
<220> FEATURE:
<223> OTHER INFORMATION: Synthetic peptide

<400> SEQUENCE: 450

Gln Gln Ser Tyr Thr Arg His Asn Ala Glu Asn Ile
1               5                   10

<210> SEQ ID NO 451
<211> LENGTH: 12
<212> TYPE: PRT
<213> ORGANISM: Artificial Sequence
<220> FEATURE:
<223> OTHER INFORMATION: Synthetic peptide

<400> SEQUENCE: 451

Gln Thr Ser Asn Ala Ile Thr Thr Tyr Gly Ala Ala
1               5                   10

<210> SEQ ID NO 452
<211> LENGTH: 14
<212> TYPE: PRT
<213> ORGANISM: Artificial Sequence
<220> FEATURE:
<223> OTHER INFORMATION: Synthetic peptide

<400> SEQUENCE: 452

Leu Gly Val Asp Thr Asp Ile Asn Gly Asp Thr Thr Trp Ala
1               5                   10

<210> SEQ ID NO 453
<211> LENGTH: 12
<212> TYPE: PRT
<213> ORGANISM: Artificial Sequence
<220> FEATURE:
<223> OTHER INFORMATION: Synthetic peptide

<400> SEQUENCE: 453

Gln Cys Thr Ser Tyr Gly Ser Thr Tyr Val Gly Pro
1               5                   10

<210> SEQ ID NO 454
<211> LENGTH: 10
<212> TYPE: PRT
<213> ORGANISM: Artificial Sequence
<220> FEATURE:
<223> OTHER INFORMATION: Synthetic peptide

<400> SEQUENCE: 454

Ala Gly Asp Phe Gly Ala Ser Ile Val Ala
1               5                   10

<210> SEQ ID NO 455
<211> LENGTH: 14
<212> TYPE: PRT
<213> ORGANISM: Artificial Sequence
<220> FEATURE:
<223> OTHER INFORMATION: Synthetic peptide
```

<400> SEQUENCE: 455

Gln Ser Tyr Asp Tyr Ser Ser Ser Ser Thr Tyr Val Asn Ile
1               5                   10

<210> SEQ ID NO 456
<211> LENGTH: 8
<212> TYPE: PRT
<213> ORGANISM: Artificial Sequence
<220> FEATURE:
<223> OTHER INFORMATION: Synthetic peptide

<400> SEQUENCE: 456

Tyr Asp Ser Ser Ser Ser Gly Val
1               5

<210> SEQ ID NO 457
<211> LENGTH: 8
<212> TYPE: PRT
<213> ORGANISM: Artificial Sequence
<220> FEATURE:
<223> OTHER INFORMATION: Synthetic peptide

<400> SEQUENCE: 457

Phe Asp Ser Ser Ser Asn Tyr Ile
1               5

<210> SEQ ID NO 458
<211> LENGTH: 9
<212> TYPE: PRT
<213> ORGANISM: Artificial Sequence
<220> FEATURE:
<223> OTHER INFORMATION: Synthetic peptide

<400> SEQUENCE: 458

Tyr Asp Ser Thr Tyr Gly Gly Ser Ile
1               5

<210> SEQ ID NO 459
<211> LENGTH: 8
<212> TYPE: PRT
<213> ORGANISM: Artificial Sequence
<220> FEATURE:
<223> OTHER INFORMATION: Synthetic peptide

<400> SEQUENCE: 459

Phe Ser Thr Asp Tyr Ile Asp Val
1               5

<210> SEQ ID NO 460
<211> LENGTH: 8
<212> TYPE: PRT
<213> ORGANISM: Artificial Sequence
<220> FEATURE:
<223> OTHER INFORMATION: Synthetic peptide

<400> SEQUENCE: 460

Tyr Asp Ser Ser Ser Thr Gly Val
1               5

<210> SEQ ID NO 461
<211> LENGTH: 8
<212> TYPE: PRT
<213> ORGANISM: Artificial Sequence
<220> FEATURE:
<223> OTHER INFORMATION: Synthetic peptide

<400> SEQUENCE: 461

Thr Asp Ser Asn Asn Asn Ala Val
1               5

<210> SEQ ID NO 462
<211> LENGTH: 8
<212> TYPE: PRT
<213> ORGANISM: Artificial Sequence
<220> FEATURE:
<223> OTHER INFORMATION: Synthetic peptide

<400> SEQUENCE: 462

Tyr Ser Ser Ser Asn Tyr Gly Val
1               5

<210> SEQ ID NO 463
<211> LENGTH: 8
<212> TYPE: PRT
<213> ORGANISM: Artificial Sequence
<220> FEATURE:
<223> OTHER INFORMATION: Synthetic peptide

<400> SEQUENCE: 463

Tyr Asp Ser Asp Ser Ser Tyr Ile
1               5

<210> SEQ ID NO 464
<211> LENGTH: 8
<212> TYPE: PRT
<213> ORGANISM: Artificial Sequence
<220> FEATURE:
<223> OTHER INFORMATION: Synthetic peptide

<400> SEQUENCE: 464

Tyr Gln Ser Asp Trp Ser Leu Leu
1               5

<210> SEQ ID NO 465
<211> LENGTH: 8
<212> TYPE: PRT
<213> ORGANISM: Artificial Sequence
<220> FEATURE:
<223> OTHER INFORMATION: Synthetic peptide

<400> SEQUENCE: 465

Ile Gln Ser Asp Trp Thr Gly Val
1               5

<210> SEQ ID NO 466
<211> LENGTH: 8
<212> TYPE: PRT
<213> ORGANISM: Artificial Sequence
<220> FEATURE:
<223> OTHER INFORMATION: Synthetic peptide

<400> SEQUENCE: 466

Tyr Asp Ser Ser Ser Tyr Thr Val
1               5

<210> SEQ ID NO 467
<211> LENGTH: 8
<212> TYPE: PRT
<213> ORGANISM: Artificial Sequence
<220> FEATURE:
<223> OTHER INFORMATION: Synthetic peptide

<400> SEQUENCE: 467

Tyr Arg Ser Pro Tyr Thr Gly Val
1               5

<210> SEQ ID NO 468
<211> LENGTH: 7
<212> TYPE: PRT
<213> ORGANISM: Artificial Sequence
<220> FEATURE:
<223> OTHER INFORMATION: Synthetic peptide

<400> SEQUENCE: 468

Tyr Lys Ser Gly Gly Ile Val
1               5

<210> SEQ ID NO 469
<211> LENGTH: 8
<212> TYPE: PRT
<213> ORGANISM: Artificial Sequence
<220> FEATURE:
<223> OTHER INFORMATION: Synthetic peptide

<400> SEQUENCE: 469

Tyr Asp Asn Asn Asn Ser Asn Leu
1               5

<210> SEQ ID NO 470
<211> LENGTH: 7
<212> TYPE: PRT
<213> ORGANISM: Artificial Sequence
<220> FEATURE:
<223> OTHER INFORMATION: Synthetic peptide

<400> SEQUENCE: 470

Asp Asp Thr Ser Asp Ser Leu
1               5

<210> SEQ ID NO 471
<211> LENGTH: 8
<212> TYPE: PRT
<213> ORGANISM: Artificial Sequence
<220> FEATURE:
<223> OTHER INFORMATION: Synthetic peptide

<400> SEQUENCE: 471

Tyr Arg Ser Pro Gly Thr Val Val
1               5

<210> SEQ ID NO 472
<211> LENGTH: 8
<212> TYPE: PRT
<213> ORGANISM: Artificial Sequence
<220> FEATURE:
<223> OTHER INFORMATION: Synthetic peptide

<400> SEQUENCE: 472

Tyr Lys Thr Pro Tyr Thr Gly Val
1               5

<210> SEQ ID NO 473
<211> LENGTH: 8
<212> TYPE: PRT
<213> ORGANISM: Artificial Sequence
<220> FEATURE:
<223> OTHER INFORMATION: Synthetic peptide

<400> SEQUENCE: 473

Tyr Asp Ser Ser Ser Tyr Gly Val
1               5

<210> SEQ ID NO 474
<211> LENGTH: 8
<212> TYPE: PRT
<213> ORGANISM: Artificial Sequence
<220> FEATURE:
<223> OTHER INFORMATION: Synthetic peptide

<400> SEQUENCE: 474

Tyr Lys Ser Gly Gly Thr Gly Val
1               5

<210> SEQ ID NO 475
<211> LENGTH: 8
<212> TYPE: PRT
<213> ORGANISM: Artificial Sequence
<220> FEATURE:
<223> OTHER INFORMATION: Synthetic peptide

<400> SEQUENCE: 475

Tyr Asp Ser Gly Ser Tyr Gly Val
1               5

<210> SEQ ID NO 476
<211> LENGTH: 19
<212> TYPE: PRT
<213> ORGANISM: Artificial Sequence
<220> FEATURE:
<223> OTHER INFORMATION: Synthetic peptide

<400> SEQUENCE: 476

Ala Arg Gly Pro Asp Tyr Ser Thr Tyr Gly Thr Ala Tyr Ile Tyr Tyr
1               5                   10                  15

Leu Asp Tyr

<210> SEQ ID NO 477
<211> LENGTH: 19
<212> TYPE: PRT
<213> ORGANISM: Artificial Sequence
<220> FEATURE:
<223> OTHER INFORMATION: Synthetic peptide

<400> SEQUENCE: 477

Ala Arg Gly Pro Asp Tyr Ser Thr Tyr Gly Ser Tyr Tyr Leu Tyr Tyr
1               5                   10                  15

Leu Asp Tyr

<210> SEQ ID NO 478
<211> LENGTH: 7
<212> TYPE: PRT
<213> ORGANISM: Artificial Sequence
<220> FEATURE:
<223> OTHER INFORMATION: Synthetic peptide

<400> SEQUENCE: 478

Ala Arg Gly Gly Gly Asp Tyr
1               5

<210> SEQ ID NO 479
<211> LENGTH: 10
<212> TYPE: PRT
<213> ORGANISM: Artificial Sequence
<220> FEATURE:
<223> OTHER INFORMATION: Synthetic peptide

```
<400> SEQUENCE: 479

Ala Ser Ser Ile Leu Ala Ile Ser Asn Tyr
1               5                   10

<210> SEQ ID NO 480
<211> LENGTH: 18
<212> TYPE: PRT
<213> ORGANISM: Artificial Sequence
<220> FEATURE:
<223> OTHER INFORMATION: Synthetic peptide

<400> SEQUENCE: 480

Ala Arg Cys His Tyr Gly Gly His Cys Glu Thr Tyr Gly Leu Pro Met
1               5                   10                  15

Asp Tyr

<210> SEQ ID NO 481
<211> LENGTH: 16
<212> TYPE: PRT
<213> ORGANISM: Artificial Sequence
<220> FEATURE:
<223> OTHER INFORMATION: Synthetic peptide

<400> SEQUENCE: 481

Val Arg Asp Tyr Glu Glu Tyr Asn His Ala Tyr Ala Tyr Gly Gly Tyr
1               5                   10                  15

<210> SEQ ID NO 482
<211> LENGTH: 16
<212> TYPE: PRT
<213> ORGANISM: Artificial Sequence
<220> FEATURE:
<223> OTHER INFORMATION: Synthetic peptide

<400> SEQUENCE: 482

Glu Cys Tyr Asn Gly Tyr Gly Tyr Ala Tyr Gly Tyr Asn Ile Asp Thr
1               5                   10                  15

<210> SEQ ID NO 483
<211> LENGTH: 8
<212> TYPE: PRT
<213> ORGANISM: Artificial Sequence
<220> FEATURE:
<223> OTHER INFORMATION: Synthetic peptide

<400> SEQUENCE: 483

Tyr Asp Ser Ser Ser Tyr Thr Val
1               5

<210> SEQ ID NO 484
<211> LENGTH: 8
<212> TYPE: PRT
<213> ORGANISM: Artificial Sequence
<220> FEATURE:
<223> OTHER INFORMATION: Synthetic peptide

<400> SEQUENCE: 484

Tyr Arg Ser Pro Tyr Thr Gly Val
1               5

<210> SEQ ID NO 485
<211> LENGTH: 7
<212> TYPE: PRT
<213> ORGANISM: Artificial Sequence
<220> FEATURE:
```

```
<223> OTHER INFORMATION: Synthetic peptide

<400> SEQUENCE: 485

Tyr Lys Ser Gly Gly Ile Val
1               5

<210> SEQ ID NO 486
<211> LENGTH: 8
<212> TYPE: PRT
<213> ORGANISM: Artificial Sequence
<220> FEATURE:
<223> OTHER INFORMATION: Synthetic peptide

<400> SEQUENCE: 486

Tyr Asp Asn Asn Ser Asn Leu
1               5

<210> SEQ ID NO 487
<211> LENGTH: 8
<212> TYPE: PRT
<213> ORGANISM: Artificial Sequence
<220> FEATURE:
<223> OTHER INFORMATION: Synthetic peptide

<400> SEQUENCE: 487

Asp Asp Thr Ser Asp Ser Val Leu
1               5

<210> SEQ ID NO 488
<211> LENGTH: 10
<212> TYPE: PRT
<213> ORGANISM: Artificial Sequence
<220> FEATURE:
<223> OTHER INFORMATION: Synthetic peptide

<400> SEQUENCE: 488

Ala Ser Ser Ile Leu Ala Ile Ser Asn Tyr
1               5                   10

<210> SEQ ID NO 489
<211> LENGTH: 116
<212> TYPE: PRT
<213> ORGANISM: Artificial Sequence
<220> FEATURE:
<223> OTHER INFORMATION: Synthetic peptide

<400> SEQUENCE: 489

Gln Val Arg Leu Gln Glu Ser Gly Pro Ser Leu Val Lys Pro Ser Gln
1               5                   10                  15

Thr Leu Ser Leu Thr Cys Thr Val Ser Arg Phe Ser Leu Thr Asn Tyr
            20                  25                  30

Gly Val Gly Trp Val Arg Gln Ala Pro Gly Lys Ala Leu Glu Trp Leu
        35                  40                  45

Gly Gly Ile Asp Lys Asp Gly Asp Thr Gly Tyr Asn Pro Ala Leu Lys
    50                  55                  60

Ser Arg Leu Ser Ile Thr Arg Asp Thr Ser Lys Ser Gln Val Ser Leu
65                  70                  75                  80

Ser Leu Ser Ser Thr Thr Thr Glu Asp Thr Ala Val Tyr Tyr Cys Ala
                85                  90                  95

Ser Ser Ile Leu Ala Ile Ser Asn Tyr Trp Gly Pro Gly Val Leu Val
            100                 105                 110

Thr Val Ser Ser
        115
```

<210> SEQ ID NO 490
<211> LENGTH: 16
<212> TYPE: PRT
<213> ORGANISM: Artificial Sequence
<220> FEATURE:
<223> OTHER INFORMATION: Synthetic peptide

<400> SEQUENCE: 490

```
Val Arg Asp Tyr Glu Glu Tyr Asn His Ala Tyr Ala Tyr Gly Gly Tyr
 1               5                  10                  15
```

<210> SEQ ID NO 491
<211> LENGTH: 122
<212> TYPE: PRT
<213> ORGANISM: Artificial Sequence
<220> FEATURE:
<223> OTHER INFORMATION: Synthetic peptide

<400> SEQUENCE: 491

```
Gln Val Gln Leu Gln Glu Ser Gly Pro Ser Leu Val Lys Pro Ser Gln
 1               5                  10                  15

Thr Leu Ser Leu Thr Cys Thr Val Ser Gly Phe Ser Leu Lys Thr His
            20                  25                  30

Gly Val Gly Trp Val Arg Gln Ala Pro Gly Lys Ala Leu Glu Ser Val
        35                  40                  45

Gly Ile Ile Phe Thr Gly Gly Thr Gly Tyr Asn Pro Ala Leu Lys
    50                  55                  60

Ser Arg Leu Ser Ile Thr Arg Asp Thr Ser Lys Ser Gln Val Ser Leu
65                  70                  75                  80

Ser Leu Ser Ser Val Thr Thr Glu Asp Thr Ala Val Tyr Tyr Cys Val
                85                  90                  95

Arg Asp Tyr Glu Glu Tyr Asn His Ala Tyr Ala Tyr Gly Gly Tyr Trp
            100                 105                 110

Gly Pro Gly Leu Leu Val Thr Val Ser Ser
        115                 120
```

<210> SEQ ID NO 492
<211> LENGTH: 19
<212> TYPE: PRT
<213> ORGANISM: Artificial Sequence
<220> FEATURE:
<223> OTHER INFORMATION: Synthetic peptide

<400> SEQUENCE: 492

```
Ala Arg Gly Pro Asp Tyr Ser Thr Tyr Gly Ser Tyr Tyr Leu Tyr Tyr
 1               5                  10                  15

Leu Asp Tyr
```

<210> SEQ ID NO 493
<211> LENGTH: 125
<212> TYPE: PRT
<213> ORGANISM: Artificial Sequence
<220> FEATURE:
<223> OTHER INFORMATION: Synthetic peptide

<400> SEQUENCE: 493

```
Gln Val Gln Leu Gln Glu Ser Gly Pro Ser Leu Val Lys Pro Ser Gln
 1               5                  10                  15

Thr Leu Ser Leu Ala Cys Thr Val Ser Val Phe Ser Leu Thr Ser Tyr
            20                  25                  30
```

Thr Val Gly Trp Val Arg Gln Ala Pro Gly Lys Ala Pro Glu Trp Val
            35                  40                  45

Gly Ser Ile Gly Gly Ser Gly Arg Arg Val Tyr Asn Pro Ala Leu Lys
 50                  55                  60

Ser Arg Val Ser Ile Ala Arg Asp Thr Ser Lys Asn Gln Val Ser Leu
 65                  70                  75                  80

Ser Leu Ser Ser Val Thr Thr Glu Asp Thr Ala Val Tyr Tyr Cys Ala
                 85                  90                  95

Arg Gly Pro Asp Tyr Ser Thr Tyr Gly Ser Tyr Tyr Leu Tyr Tyr Leu
            100                 105                 110

Asp Tyr Trp Gly Pro Gly Leu Leu Val Thr Val Ser Ser
            115                 120                 125

<210> SEQ ID NO 494
<211> LENGTH: 19
<212> TYPE: PRT
<213> ORGANISM: Artificial Sequence
<220> FEATURE:
<223> OTHER INFORMATION: Synthetic peptide

<400> SEQUENCE: 494

Ala Arg Gly Pro Asp Tyr Ser Thr Tyr Gly Thr Ala Tyr Ile Tyr Tyr
 1               5                  10                  15

Leu Asp Tyr

<210> SEQ ID NO 495
<211> LENGTH: 125
<212> TYPE: PRT
<213> ORGANISM: Artificial Sequence
<220> FEATURE:
<223> OTHER INFORMATION: Synthetic peptide

<400> SEQUENCE: 495

Gln Val Gln Leu Gln Glu Ser Gly Pro Ser Leu Val Lys Pro Ser Gln
 1               5                  10                  15

Thr Leu Ser Leu Ala Cys Thr Val Ser Val Phe Ser Leu Asn Ser Tyr
             20                  25                  30

Thr Val Gly Trp Val Arg Gln Ala Pro Gly Lys Ala Leu Glu Trp Val
            35                  40                  45

Gly Ser Ile Gly Gly Ser Gly Arg Arg Val Tyr Asn Pro Ala Leu Lys
 50                  55                  60

Ser Arg Val Ser Ile Ala Arg Asp Thr Ser Lys Ser Gln Val Ser Leu
 65                  70                  75                  80

Ser Leu Ser Ser Val Thr Ala Glu Asp Thr Ala Val Tyr Tyr Cys Ala
                 85                  90                  95

Arg Gly Pro Asp Tyr Ser Thr Tyr Gly Thr Ala Tyr Ile Tyr Tyr Leu
            100                 105                 110

Asp Tyr Val Gly Pro Arg Thr Pro Gly His Arg Leu Leu
            115                 120                 125

<210> SEQ ID NO 496
<211> LENGTH: 18
<212> TYPE: PRT
<213> ORGANISM: Artificial Sequence
<220> FEATURE:
<223> OTHER INFORMATION: Synthetic peptide

<400> SEQUENCE: 496

Ala Arg Cys His Tyr Gly Gly His Cys Glu Thr Tyr Gly Leu Pro Met
 1               5                  10                  15

Asp Tyr

<210> SEQ ID NO 497
<211> LENGTH: 124
<212> TYPE: PRT
<213> ORGANISM: Artificial Sequence
<220> FEATURE:
<223> OTHER INFORMATION: Synthetic peptide

<400> SEQUENCE: 497

Gln Val Arg Leu Gln Glu Ser Gly Pro Ser Leu Val Lys Pro Ser Gln
1               5                   10                  15

Thr Leu Ser Leu Thr Cys Thr Val Ser Gly Phe Pro Leu Thr Ser Asn
            20                  25                  30

Ala Val Gly Trp Val Arg Gln Ala Pro Gly Lys Val Pro Glu Trp Leu
        35                  40                  45

Gly Gly Ile Ser Thr Arg Gly Ser Thr Tyr Tyr Asn Ser Ala Leu Lys
    50                  55                  60

Ser Arg Leu Ser Ile Thr Arg Asp Thr Ser Lys Ser Gln Val Ser Leu
65                  70                  75                  80

Phe Leu Ser Ser Val Thr Thr Glu Asp Thr Ala Leu Tyr Tyr Cys Ala
                85                  90                  95

Arg Cys His Tyr Gly Gly His Cys Glu Thr Tyr Gly Leu Pro Met Asp
            100                 105                 110

Tyr Trp Gly Pro Gly Leu Leu Val Thr Val Ser Ser
        115                 120

<210> SEQ ID NO 498
<211> LENGTH: 7
<212> TYPE: PRT
<213> ORGANISM: Artificial Sequence
<220> FEATURE:
<223> OTHER INFORMATION: Synthetic peptide

<400> SEQUENCE: 498

Ala Arg Gly Gly Gly Asp Tyr
1               5

<210> SEQ ID NO 499
<211> LENGTH: 113
<212> TYPE: PRT
<213> ORGANISM: Artificial Sequence
<220> FEATURE:
<223> OTHER INFORMATION: Synthetic peptide

<400> SEQUENCE: 499

Gln Val Gln Leu Gln Glu Ser Gly Pro Ser Leu Val Lys Pro Ser Gln
1               5                   10                  15

Thr Leu Ser Leu Thr Cys Thr Ile Ser Gly Phe Ser Leu Thr Asp His
            20                  25                  30

Asp Val Glu Trp Val Arg Gln Ala Pro Gly Lys Ala Leu Glu Trp Val
        35                  40                  45

Gly Ala Ile Tyr Asp Ser Gly Asn Ala Tyr Tyr Asn Pro Ala Leu Lys
    50                  55                  60

Ser Arg Leu Ser Ile Thr Arg Asp Thr Ser Arg Ser Arg Val Ser Leu
65                  70                  75                  80

Ser Leu Ser Asn Val Thr Thr Glu Asp Thr Ala Leu Tyr Tyr Cys Ala
                85                  90                  95

Arg Gly Gly Gly Asp Tyr Trp Gly Pro Gly Leu Leu Val Thr Val Ser 100                 105                 110
Ser

<210> SEQ ID NO 500
<211> LENGTH: 16
<212> TYPE: PRT
<213> ORGANISM: Artificial Sequence
<220> FEATURE:
<223> OTHER INFORMATION: Synthetic peptide

<400> SEQUENCE: 500

Glu Cys Tyr Asn Gly Tyr Gly Tyr Ala Tyr Gly Tyr Asn Ile Asp Thr
1               5                   10                  15

<210> SEQ ID NO 501
<211> LENGTH: 122
<212> TYPE: PRT
<213> ORGANISM: Artificial Sequence
<220> FEATURE:
<223> OTHER INFORMATION: Synthetic peptide

<400> SEQUENCE: 501

Gln Val Gln Leu Gln Glu Ser Gly Pro Ser Leu Val Lys Pro Ser Gln
1               5                   10                  15

Thr Leu Ser Leu Thr Cys Thr Val Ser Gly Phe Ser Leu Thr Arg Tyr
            20                  25                  30

Gly Val Gly Trp Val Arg Gln Ala Pro Gly Lys Ala Leu Glu Trp Val
        35                  40                  45

Gly Tyr Ile Tyr Ser Asp Gly Gly Ile Tyr Tyr Asn Pro Ala Leu Lys
    50                  55                  60

Ser Arg Leu Ser Ile Thr Arg Asp Thr Ser Lys Ser Gln Val Ser Leu
65                  70                  75                  80

Ser Leu Ser Ser Val Thr Thr Glu Asp Thr Ala Val Tyr Tyr Cys Glu
                85                  90                  95

Cys Tyr Asn Gly Tyr Gly Tyr Ala Tyr Gly Tyr Asn Ile Asp Thr Trp
            100                 105                 110

Gly Pro Gly Leu Leu Val Thr Val Ser Ser
        115                 120

<210> SEQ ID NO 502
<211> LENGTH: 8
<212> TYPE: PRT
<213> ORGANISM: Artificial Sequence
<220> FEATURE:
<223> OTHER INFORMATION: Synthetic peptide

<400> SEQUENCE: 502

Tyr Asp Ser Ser Ser Tyr Thr Val
1               5

<210> SEQ ID NO 503
<211> LENGTH: 110
<212> TYPE: PRT
<213> ORGANISM: Artificial Sequence
<220> FEATURE:
<223> OTHER INFORMATION: Synthetic peptide

<400> SEQUENCE: 503

Gln Ala Val Leu Thr Gln Pro Ser Ser Val Ser Arg Ser Leu Gly Gln
1               5                   10                  15

Ser Val Ser Ile Thr Cys Ser Gly Ser Ser Ser Asn Val Gly Tyr Gly
            20                  25                  30

Ser Tyr Val Gly Trp Phe Gln Gln Val Pro Gly Ser Ala Pro Lys Leu
            35                  40                  45

Leu Ile Tyr Gly Ala Thr Ser Arg Ala Ser Gly Val Pro Asp Arg Phe
    50                  55                  60

Ser Gly Ser Arg Ser Gly Asn Thr Ala Thr Leu Thr Ile Thr Ser Leu
65                  70                  75                  80

Gln Ala Glu Asp Glu Ala Asp Tyr Tyr Cys Ala Ser Tyr Asp Ser Ser
                85                  90                  95

Ser Tyr Thr Val Phe Gly Ser Gly Thr Arg Leu Thr Val Leu
            100                 105                 110

<210> SEQ ID NO 504
<211> LENGTH: 8
<212> TYPE: PRT
<213> ORGANISM: Artificial Sequence
<220> FEATURE:
<223> OTHER INFORMATION: Synthetic peptide

<400> SEQUENCE: 504

Tyr Arg Ser Pro Tyr Thr Gly Val
1               5

<210> SEQ ID NO 505
<211> LENGTH: 110
<212> TYPE: PRT
<213> ORGANISM: Artificial Sequence
<220> FEATURE:
<223> OTHER INFORMATION: Synthetic peptide

<400> SEQUENCE: 505

Gln Ser Ala Leu Thr Gln Pro Ala Ser Val Ser Gly Asn Pro Gly Gln
1               5                   10                  15

Thr Val Thr Ile Ser Cys Thr Gly Thr Asn Ser Asp Ile Gly Ala Ala
            20                  25                  30

Asn Tyr Ile Gly Trp Tyr Gln Gln Leu Pro Gly Ser Ala Pro Lys Thr
            35                  40                  45

Leu Ile Tyr Ala Val Asp Lys Arg Pro Ser Gly Ile Pro Ala Arg Phe
    50                  55                  60

Ser Gly Ser Lys Ser Gly Asn Thr Ala Thr Leu Thr Ile Ser Gly Leu
65                  70                  75                  80

Gln Ala Glu Asp Glu Ala Asp Tyr Tyr Cys Ser Ser Tyr Arg Ser Pro
                85                  90                  95

Tyr Thr Gly Val Phe Gly Ser Gly Thr Arg Leu Thr Val Leu
            100                 105                 110

<210> SEQ ID NO 506
<211> LENGTH: 7
<212> TYPE: PRT
<213> ORGANISM: Artificial Sequence
<220> FEATURE:
<223> OTHER INFORMATION: Synthetic peptide

<400> SEQUENCE: 506

Tyr Lys Ser Gly Gly Ile Val
1               5

<210> SEQ ID NO 507
<211> LENGTH: 109
<212> TYPE: PRT
<213> ORGANISM: Artificial Sequence
<220> FEATURE:

<223> OTHER INFORMATION: Synthetic peptide

<400> SEQUENCE: 507

Gln Ser Ala Leu Thr Gln Pro Ala Ser Val Ser Gly Asn Pro Gly Gln
1               5                   10                  15

Thr Val Thr Ile Ser Cys Thr Gly Thr Ser Ser Asp Val Gly Ile Tyr
            20                  25                  30

Lys Tyr Val Gly Trp Tyr Gln Gln Leu Pro Gly Ser Ala Pro Lys Thr
        35                  40                  45

Leu Ile Tyr His Val Asn Glu Arg Pro Ser Gly Ile Pro Ala Arg Phe
    50                  55                  60

Ser Gly Ser Lys Ser Gly Asn Thr Ala Thr Leu Thr Ile Ser Gly Leu
65                  70                  75                  80

Gln Ala Glu Asp Glu Ala Asp Tyr Tyr Cys Ser Ser Tyr Lys Ser Gly
                85                  90                  95

Gly Ile Val Phe Gly Ser Gly Thr Arg Leu Thr Val Leu
            100                 105

<210> SEQ ID NO 508
<211> LENGTH: 8
<212> TYPE: PRT
<213> ORGANISM: Artificial Sequence
<220> FEATURE:
<223> OTHER INFORMATION: Synthetic peptide

<400> SEQUENCE: 508

Tyr Asp Asn Asn Asn Ser Asn Leu
1               5

<210> SEQ ID NO 509
<211> LENGTH: 110
<212> TYPE: PRT
<213> ORGANISM: Artificial Sequence
<220> FEATURE:
<223> OTHER INFORMATION: Synthetic peptide

<400> SEQUENCE: 509

Gln Thr Val Leu Thr Gln Pro Ser Ser Val Ser Lys Ser Leu Gly Gln
1               5                   10                  15

Ala Val Ser Ile Thr Cys Ser Gly Ser Ser Asn Ile Gly Tyr Gly
            20                  25                  30

Asp Tyr Val Arg Trp Phe Gln Gln Val Pro Gly Ser Ala Pro Lys Leu
        35                  40                  45

Leu Ile Tyr Gly Ala Ser Ser Arg Ala Ser Gly Val Pro Asp Arg Phe
    50                  55                  60

Ser Gly Ser Arg Ser Gly Asn Thr Ala Thr Leu Thr Ile Ser Ser Leu
65                  70                  75                  80

Gln Ala Glu Asp Glu Ala Asp Tyr Tyr Cys Ala Thr Tyr Asp Asn Asn
                85                  90                  95

Asn Ser Asn Leu Phe Gly Ser Gly Thr Arg Leu Thr Val Leu
            100                 105                 110

<210> SEQ ID NO 510
<211> LENGTH: 8
<212> TYPE: PRT
<213> ORGANISM: Artificial Sequence
<220> FEATURE:
<223> OTHER INFORMATION: Synthetic peptide

<400> SEQUENCE: 510

Asp Asp Thr Ser Asp Ser Val Leu
1               5

<210> SEQ ID NO 511
<211> LENGTH: 110
<212> TYPE: PRT
<213> ORGANISM: Artificial Sequence
<220> FEATURE:
<223> OTHER INFORMATION: Synthetic peptide

<400> SEQUENCE: 511

Gln Ala Val Leu Thr Gln Pro Ser Ser Val Ser Lys Ser Leu Gly Gln
1               5                   10                  15

Ser Val Ser Ile Thr Cys Ser Gly Ser Ser Asn Val Gly Tyr Gly
                20                  25                  30

Asp Tyr Val Ser Trp Phe Gln Gln Val Pro Gly Ser Ala Pro Lys Leu
            35                  40                  45

Leu Ile Tyr Gly Ala Thr Arg Arg Ala Ser Gly Val Pro Asp Arg Phe
        50                  55                  60

Ser Gly Ser Arg Ser Gly Asn Thr Ala Thr Met Thr Ile Ser Ser Leu
65                  70                  75                  80

Gln Ala Glu Asp Glu Ala Asp Tyr Tyr Cys Ala Ser Asp Asp Thr Ser
                85                  90                  95

Asp Ser Val Leu Phe Gly Ser Gly Thr Arg Leu Thr Val Leu
            100                 105                 110

<210> SEQ ID NO 512
<211> LENGTH: 15
<212> TYPE: PRT
<213> ORGANISM: Artificial Sequence
<220> FEATURE:
<223> OTHER INFORMATION: Synthetic peptide

<400> SEQUENCE: 512

Asn Tyr Ala Gly His Pro Gly Tyr Gly Tyr Ala Pro Phe Asn Leu
1               5                   10                  15

<210> SEQ ID NO 513
<211> LENGTH: 15
<212> TYPE: PRT
<213> ORGANISM: Artificial Sequence
<220> FEATURE:
<223> OTHER INFORMATION: Synthetic peptide

<400> SEQUENCE: 513

Asn Tyr Ala Gly His Ser Gly Tyr Gly Tyr Ala Pro Phe Asn Leu
1               5                   10                  15

<210> SEQ ID NO 514
<211> LENGTH: 15
<212> TYPE: PRT
<213> ORGANISM: Artificial Sequence
<220> FEATURE:
<223> OTHER INFORMATION: Synthetic peptide

<400> SEQUENCE: 514

Asn Tyr Ala Gly His Pro Gly Tyr Gly Tyr Ala Pro Phe Asn Leu
1               5                   10                  15

<210> SEQ ID NO 515
<211> LENGTH: 15
<212> TYPE: PRT
<213> ORGANISM: Artificial Sequence
<220> FEATURE:

<223> OTHER INFORMATION: Synthetic peptide

<400> SEQUENCE: 515

Asn Tyr Ala Gly His Pro Gly Tyr Gly Tyr Ala Pro Phe Asn Leu
1               5                   10                  15

<210> SEQ ID NO 516
<211> LENGTH: 15
<212> TYPE: PRT
<213> ORGANISM: Artificial Sequence
<220> FEATURE:
<223> OTHER INFORMATION: Synthetic peptide

<400> SEQUENCE: 516

Asn Tyr Ala Gly His Pro Gly Tyr Gly Tyr Ala Pro Phe Asn Leu
1               5                   10                  15

<210> SEQ ID NO 517
<211> LENGTH: 15
<212> TYPE: PRT
<213> ORGANISM: Artificial Sequence
<220> FEATURE:
<223> OTHER INFORMATION: Synthetic peptide

<400> SEQUENCE: 517

Asn Tyr Ala Gly His Pro Gly Tyr Gly Tyr Ala Pro Phe Asn Leu
1               5                   10                  15

<210> SEQ ID NO 518
<211> LENGTH: 15
<212> TYPE: PRT
<213> ORGANISM: Artificial Sequence
<220> FEATURE:
<223> OTHER INFORMATION: Synthetic peptide

<400> SEQUENCE: 518

Asn Tyr Ala Asp Gly Pro Gly Tyr Gly Phe Ala Pro Phe Asn Leu
1               5                   10                  15

<210> SEQ ID NO 519
<211> LENGTH: 15
<212> TYPE: PRT
<213> ORGANISM: Artificial Sequence
<220> FEATURE:
<223> OTHER INFORMATION: Synthetic peptide

<400> SEQUENCE: 519

Asn Tyr Ala Asp Gly Pro Gly Tyr Gly Phe Ala Pro Phe Asn Leu
1               5                   10                  15

<210> SEQ ID NO 520
<211> LENGTH: 15
<212> TYPE: PRT
<213> ORGANISM: Artificial Sequence
<220> FEATURE:
<223> OTHER INFORMATION: Synthetic peptide

<400> SEQUENCE: 520

Asn Tyr Ala Asp Gly Pro Gly Tyr Gly Phe Ala Pro Phe Asn Leu
1               5                   10                  15

<210> SEQ ID NO 521
<211> LENGTH: 15
<212> TYPE: PRT
<213> ORGANISM: Artificial Sequence
<220> FEATURE:
<223> OTHER INFORMATION: Synthetic peptide

<400> SEQUENCE: 521

Asn Tyr Ala Asp Gly Pro Gly Tyr Gly Phe Ala Pro Phe Asn Leu
1               5                   10                  15

<210> SEQ ID NO 522
<211> LENGTH: 15
<212> TYPE: PRT
<213> ORGANISM: Artificial Sequence
<220> FEATURE:
<223> OTHER INFORMATION: Synthetic peptide

<400> SEQUENCE: 522

Asn Tyr Ala Asp Gly Pro Gly Tyr Gly Phe Ala Pro Phe Asn Leu
1               5                   10                  15

<210> SEQ ID NO 523
<211> LENGTH: 15
<212> TYPE: PRT
<213> ORGANISM: Artificial Sequence
<220> FEATURE:
<223> OTHER INFORMATION: Synthetic peptide

<400> SEQUENCE: 523

Asn Tyr Ala Asp Gly Pro Gly Tyr Gly Phe Ala Pro Phe Asn Leu
1               5                   10                  15

<210> SEQ ID NO 524
<211> LENGTH: 15
<212> TYPE: PRT
<213> ORGANISM: Artificial Sequence
<220> FEATURE:
<223> OTHER INFORMATION: Synthetic peptide

<400> SEQUENCE: 524

Asn Tyr Ala Asp Gly Pro Gly Tyr Gly Phe Ala Pro Phe Asn Leu
1               5                   10                  15

<210> SEQ ID NO 525
<211> LENGTH: 15
<212> TYPE: PRT
<213> ORGANISM: Artificial Sequence
<220> FEATURE:
<223> OTHER INFORMATION: Synthetic peptide

<400> SEQUENCE: 525

Asn Tyr Ala Gly Gly Pro Gly Tyr Gly Phe Ala Pro Phe Asn Leu
1               5                   10                  15

<210> SEQ ID NO 526
<211> LENGTH: 15
<212> TYPE: PRT
<213> ORGANISM: Artificial Sequence
<220> FEATURE:
<223> OTHER INFORMATION: Synthetic peptide

<400> SEQUENCE: 526

Asn Tyr Ala Gly Gly Pro Gly Tyr Gly Phe Ala Pro Phe Asn Leu
1               5                   10                  15

<210> SEQ ID NO 527
<211> LENGTH: 15
<212> TYPE: PRT
<213> ORGANISM: Artificial Sequence
<220> FEATURE:
<223> OTHER INFORMATION: Synthetic peptide

<400> SEQUENCE: 527

Asn Tyr Ala Gly Asn Pro Gly Tyr Gly Tyr Ala Pro Phe Asn Leu
1               5                   10                  15

<210> SEQ ID NO 528
<211> LENGTH: 15
<212> TYPE: PRT
<213> ORGANISM: Artificial Sequence
<220> FEATURE:
<223> OTHER INFORMATION: Synthetic peptide

<400> SEQUENCE: 528

Asn Tyr Ala Gly Asn Pro Gly Tyr Gly Tyr Ala Pro Phe Asn Leu
1               5                   10                  15

<210> SEQ ID NO 529
<211> LENGTH: 15
<212> TYPE: PRT
<213> ORGANISM: Artificial Sequence
<220> FEATURE:
<223> OTHER INFORMATION: Synthetic peptide

<400> SEQUENCE: 529

Asn Tyr Ala Gly Asn Pro Gly Tyr Gly Tyr Ala Pro Phe Asn Leu
1               5                   10                  15

<210> SEQ ID NO 530
<211> LENGTH: 15
<212> TYPE: PRT
<213> ORGANISM: Artificial Sequence
<220> FEATURE:
<223> OTHER INFORMATION: Synthetic peptide

<400> SEQUENCE: 530

Asn Tyr Ala Gly Asn Pro Gly Tyr Gly Tyr Ala Pro Phe Asn Leu
1               5                   10                  15

<210> SEQ ID NO 531
<211> LENGTH: 15
<212> TYPE: PRT
<213> ORGANISM: Artificial Sequence
<220> FEATURE:
<223> OTHER INFORMATION: Synthetic peptide

<400> SEQUENCE: 531

Asn Tyr Ala Pro Phe Pro Gly Tyr Gly Phe Ala Pro Phe Asn Leu
1               5                   10                  15

<210> SEQ ID NO 532
<211> LENGTH: 15
<212> TYPE: PRT
<213> ORGANISM: Artificial Sequence
<220> FEATURE:
<223> OTHER INFORMATION: Synthetic peptide

<400> SEQUENCE: 532

Asn Tyr Ala Gly Asp Ala Gly Tyr Gly Tyr Ala Pro Phe Asn Leu
1               5                   10                  15

<210> SEQ ID NO 533
<211> LENGTH: 15
<212> TYPE: PRT
<213> ORGANISM: Artificial Sequence
<220> FEATURE:
<223> OTHER INFORMATION: Synthetic peptide

<400> SEQUENCE: 533

Asn Tyr Ala Ala Asp Ala Gly Tyr Gly Tyr Ala Pro Phe Asn Leu
1               5                   10                  15

<210> SEQ ID NO 534
<211> LENGTH: 15
<212> TYPE: PRT
<213> ORGANISM: Artificial Sequence
<220> FEATURE:
<223> OTHER INFORMATION: Synthetic peptide

<400> SEQUENCE: 534

Asn Tyr Ala Ala Asp Ala Gly Tyr Gly Tyr Ala Pro Phe Asn Leu
1               5                   10                  15

<210> SEQ ID NO 535
<211> LENGTH: 15
<212> TYPE: PRT
<213> ORGANISM: Artificial Sequence
<220> FEATURE:
<223> OTHER INFORMATION: Synthetic peptide

<400> SEQUENCE: 535

Asn Tyr Ala Ala Asp Ala Gly Tyr Gly Tyr Ala Pro Phe Asn Leu
1               5                   10                  15

<210> SEQ ID NO 536
<211> LENGTH: 15
<212> TYPE: PRT
<213> ORGANISM: Artificial Sequence
<220> FEATURE:
<223> OTHER INFORMATION: Synthetic peptide

<400> SEQUENCE: 536

Asn Tyr Ala Gly Asp Ala Gly Tyr Gly Tyr Ala Pro Phe Asn Leu
1               5                   10                  15

<210> SEQ ID NO 537
<211> LENGTH: 15
<212> TYPE: PRT
<213> ORGANISM: Artificial Sequence
<220> FEATURE:
<223> OTHER INFORMATION: Synthetic peptide

<400> SEQUENCE: 537

Asn Tyr Ala Ala Asp Ala Gly Tyr Gly Tyr Ala Pro Phe Asn Leu
1               5                   10                  15

<210> SEQ ID NO 538
<211> LENGTH: 15
<212> TYPE: PRT
<213> ORGANISM: Artificial Sequence
<220> FEATURE:
<223> OTHER INFORMATION: Synthetic peptide

<400> SEQUENCE: 538

Asn Tyr Ala Ala Asp Ala Gly Tyr Gly Tyr Ala Pro Phe Asn Leu
1               5                   10                  15

<210> SEQ ID NO 539
<211> LENGTH: 15
<212> TYPE: PRT
<213> ORGANISM: Artificial Sequence
<220> FEATURE:
<223> OTHER INFORMATION: Synthetic peptide

<400> SEQUENCE: 539

```
Asn Tyr Ala Gly Asp Ala Gly Tyr Gly Tyr Ala Pro Phe Asn Leu
1               5                   10                  15
```

<210> SEQ ID NO 540
<211> LENGTH: 15
<212> TYPE: PRT
<213> ORGANISM: Artificial Sequence
<220> FEATURE:
<223> OTHER INFORMATION: Synthetic peptide

<400> SEQUENCE: 540

```
Asn Tyr Ala Gly Asn Ala Gly Tyr Gly Tyr Ala Pro Phe Asn Leu
1               5                   10                  15
```

<210> SEQ ID NO 541
<211> LENGTH: 14
<212> TYPE: PRT
<213> ORGANISM: Artificial Sequence
<220> FEATURE:
<223> OTHER INFORMATION: Synthetic peptide

<400> SEQUENCE: 541

```
Asn Tyr Ala Asp Ala Gly Tyr Gly Tyr Ala Pro Phe Asn Leu
1               5                   10
```

<210> SEQ ID NO 542
<211> LENGTH: 15
<212> TYPE: PRT
<213> ORGANISM: Artificial Sequence
<220> FEATURE:
<223> OTHER INFORMATION: Synthetic peptide

<400> SEQUENCE: 542

```
Asn Tyr Ala Gly Asp Ala Gly Tyr Gly Tyr Ala Pro Phe Asn Leu
1               5                   10                  15
```

<210> SEQ ID NO 543
<211> LENGTH: 15
<212> TYPE: PRT
<213> ORGANISM: Artificial Sequence
<220> FEATURE:
<223> OTHER INFORMATION: Synthetic peptide

<400> SEQUENCE: 543

```
Asn Ala Asp Gly Asn Gly Gly Tyr Arg Tyr Ala Pro Phe Asn Leu
1               5                   10                  15
```

<210> SEQ ID NO 544
<211> LENGTH: 15
<212> TYPE: PRT
<213> ORGANISM: Artificial Sequence
<220> FEATURE:
<223> OTHER INFORMATION: Synthetic peptide

<400> SEQUENCE: 544

```
Asn Tyr Ala Asp Pro Pro Gly Tyr Asn Tyr Thr Pro Phe Asn Leu
1               5                   10                  15
```

<210> SEQ ID NO 545
<211> LENGTH: 15
<212> TYPE: PRT
<213> ORGANISM: Artificial Sequence
<220> FEATURE:
<223> OTHER INFORMATION: Synthetic peptide

<400> SEQUENCE: 545

Asn Tyr Ala Asp Pro Pro Gly Tyr Asn Tyr Thr Pro Phe Asn Leu

```
1               5                  10                  15
```

<210> SEQ ID NO 546
<211> LENGTH: 10
<212> TYPE: PRT
<213> ORGANISM: Artificial Sequence
<220> FEATURE:
<223> OTHER INFORMATION: Synthetic peptide

<400> SEQUENCE: 546

```
Tyr Asp Gly Ser Ile Ala Tyr Leu Ala Leu
1               5                  10
```

<210> SEQ ID NO 547
<211> LENGTH: 16
<212> TYPE: PRT
<213> ORGANISM: Artificial Sequence
<220> FEATURE:
<223> OTHER INFORMATION: Synthetic peptide

<400> SEQUENCE: 547

```
Tyr Ser Ala Ser Ser Gly Ala Tyr Tyr Asp Gly Tyr Tyr Phe Asn Leu
1               5                  10                  15
```

<210> SEQ ID NO 548
<211> LENGTH: 16
<212> TYPE: PRT
<213> ORGANISM: Artificial Sequence
<220> FEATURE:
<223> OTHER INFORMATION: Synthetic peptide

<400> SEQUENCE: 548

```
Ala Ser Ser Ser Ser Gly His Tyr Tyr Asp Gly Tyr Tyr Phe Asn Leu
1               5                  10                  15
```

<210> SEQ ID NO 549
<211> LENGTH: 8
<212> TYPE: PRT
<213> ORGANISM: Artificial Sequence
<220> FEATURE:
<223> OTHER INFORMATION: Synthetic peptide

<400> SEQUENCE: 549

```
Asp Leu Val Met Leu Ser Tyr Leu
1               5
```

<210> SEQ ID NO 550
<211> LENGTH: 8
<212> TYPE: PRT
<213> ORGANISM: Artificial Sequence
<220> FEATURE:
<223> OTHER INFORMATION: Synthetic peptide

<400> SEQUENCE: 550

```
Gly Gly Tyr Ser Thr Phe Asp Leu
1               5
```

<210> SEQ ID NO 551
<211> LENGTH: 15
<212> TYPE: PRT
<213> ORGANISM: Artificial Sequence
<220> FEATURE:
<223> OTHER INFORMATION: Synthetic peptide

<400> SEQUENCE: 551

```
Asn Tyr Ala Gly Asn Pro Gly Tyr Gly Tyr Ala Pro Phe Asn Leu
1               5                  10                  15
```

<210> SEQ ID NO 552
<211> LENGTH: 10
<212> TYPE: PRT
<213> ORGANISM: Artificial Sequence
<220> FEATURE:
<223> OTHER INFORMATION: Synthetic peptide

<400> SEQUENCE: 552

His Arg His Gly Asp Ala Tyr Pro Asn Leu
1               5                   10

<210> SEQ ID NO 553
<211> LENGTH: 4
<212> TYPE: PRT
<213> ORGANISM: Artificial Sequence
<220> FEATURE:
<223> OTHER INFORMATION: Synthetic peptide

<400> SEQUENCE: 553

Asn Phe Lys Leu
1

<210> SEQ ID NO 554
<211> LENGTH: 11
<212> TYPE: PRT
<213> ORGANISM: Artificial Sequence
<220> FEATURE:
<223> OTHER INFORMATION: Synthetic peptide

<400> SEQUENCE: 554

Gly Asp Asp Asp Tyr Trp Tyr Tyr Leu Asn Leu
1               5                   10

<210> SEQ ID NO 555
<211> LENGTH: 17
<212> TYPE: PRT
<213> ORGANISM: Artificial Sequence
<220> FEATURE:
<223> OTHER INFORMATION: Synthetic peptide

<400> SEQUENCE: 555

Ala Asp Arg Gly Phe Tyr Ala Gly Thr Ser Asp Tyr Ser Gly Tyr Asn
1               5                   10                  15

Leu

<210> SEQ ID NO 556
<211> LENGTH: 4
<212> TYPE: PRT
<213> ORGANISM: Artificial Sequence
<220> FEATURE:
<223> OTHER INFORMATION: Synthetic peptide

<400> SEQUENCE: 556

Asp Tyr Asp Leu
1

<210> SEQ ID NO 557
<211> LENGTH: 15
<212> TYPE: PRT
<213> ORGANISM: Artificial Sequence
<220> FEATURE:
<223> OTHER INFORMATION: Synthetic peptide

<400> SEQUENCE: 557

Asn Tyr Ala Asp Gly Pro Gly Tyr Gly Phe Ala Pro Phe Asn Leu

```
<210> SEQ ID NO 558
<211> LENGTH: 15
<212> TYPE: PRT
<213> ORGANISM: Artificial Sequence
<220> FEATURE:
<223> OTHER INFORMATION: Synthetic peptide

<400> SEQUENCE: 558

Asp Ser Pro Thr Ser Gly Tyr Tyr Gly Gly Tyr Phe Asp Leu
1               5                   10                  15

<210> SEQ ID NO 559
<211> LENGTH: 10
<212> TYPE: PRT
<213> ORGANISM: Artificial Sequence
<220> FEATURE:
<223> OTHER INFORMATION: Synthetic peptide

<400> SEQUENCE: 559

Glu Ile Trp Ser Asp Gly Tyr Tyr Asp Leu
1               5                   10

<210> SEQ ID NO 560
<211> LENGTH: 13
<212> TYPE: PRT
<213> ORGANISM: Artificial Sequence
<220> FEATURE:
<223> OTHER INFORMATION: Synthetic peptide

<400> SEQUENCE: 560

Glu Ala Glu Ser Gly Asn Ser Tyr Ala Asp Phe Asn Leu
1               5                   10

<210> SEQ ID NO 561
<211> LENGTH: 15
<212> TYPE: PRT
<213> ORGANISM: Artificial Sequence
<220> FEATURE:
<223> OTHER INFORMATION: Synthetic peptide

<400> SEQUENCE: 561

Asn Tyr Ala Ala Asp Ala Gly Tyr Gly Tyr Ala Pro Phe Asn Leu
1               5                   10                  15

<210> SEQ ID NO 562
<211> LENGTH: 13
<212> TYPE: PRT
<213> ORGANISM: Artificial Sequence
<220> FEATURE:
<223> OTHER INFORMATION: Synthetic peptide

<400> SEQUENCE: 562

Gly Ile Phe Asp Tyr Asn Val Asp Gly Ala Glu Thr Leu
1               5                   10

<210> SEQ ID NO 563
<211> LENGTH: 12
<212> TYPE: PRT
<213> ORGANISM: Artificial Sequence
<220> FEATURE:
<223> OTHER INFORMATION: Synthetic peptide

<400> SEQUENCE: 563

Asp Tyr Gly Ser Ser Gly Trp Gly Gly Phe Asn Leu
1               5                   10
```

```
<210> SEQ ID NO 564
<211> LENGTH: 12
<212> TYPE: PRT
<213> ORGANISM: Artificial Sequence
<220> FEATURE:
<223> OTHER INFORMATION: Synthetic peptide

<400> SEQUENCE: 564

Asp Trp Ser Ala Asp Ile Asp Tyr Ile Leu Thr Leu
1               5                   10

<210> SEQ ID NO 565
<211> LENGTH: 15
<212> TYPE: PRT
<213> ORGANISM: Artificial Sequence
<220> FEATURE:
<223> OTHER INFORMATION: Synthetic peptide

<400> SEQUENCE: 565

Asn Tyr Ala Gly Asp Ala Gly Tyr Gly Tyr Ala Pro Phe Asn Leu
1               5                   10                  15

<210> SEQ ID NO 566
<211> LENGTH: 11
<212> TYPE: PRT
<213> ORGANISM: Artificial Sequence
<220> FEATURE:
<223> OTHER INFORMATION: Synthetic peptide

<400> SEQUENCE: 566

Asp Met Asp Gly Gly Asn Val Gly Tyr Gly Met
1               5                   10

<210> SEQ ID NO 567
<211> LENGTH: 19
<212> TYPE: PRT
<213> ORGANISM: Artificial Sequence
<220> FEATURE:
<223> OTHER INFORMATION: Synthetic peptide

<400> SEQUENCE: 567

Gly Leu Asn Ala Ala Gly Tyr Thr Thr Phe Ala Tyr Gly Thr Thr Val
1               5                   10                  15

Met Asp Leu

<210> SEQ ID NO 568
<211> LENGTH: 13
<212> TYPE: PRT
<213> ORGANISM: Artificial Sequence
<220> FEATURE:
<223> OTHER INFORMATION: Synthetic peptide

<400> SEQUENCE: 568

Phe Asp Ala Ala Tyr Ala Asp Phe Gly Val Ala Asn Leu
1               5                   10

<210> SEQ ID NO 569
<211> LENGTH: 17
<212> TYPE: PRT
<213> ORGANISM: Artificial Sequence
<220> FEATURE:
<223> OTHER INFORMATION: Synthetic peptide

<400> SEQUENCE: 569

Ala Asp Arg Gly Phe Tyr Ala Gly Thr Ser Asp Tyr Thr Gly Tyr Asn
```

```
1               5                   10                  15
Leu

<210> SEQ ID NO 570
<211> LENGTH: 17
<212> TYPE: PRT
<213> ORGANISM: Artificial Sequence
<220> FEATURE:
<223> OTHER INFORMATION: Synthetic peptide

<400> SEQUENCE: 570

Ala Asp Arg Gly Phe Tyr Ala Gly Thr Ser Asp Tyr Ser Gly Tyr Asn
1               5                   10                  15
Leu

<210> SEQ ID NO 571
<211> LENGTH: 12
<212> TYPE: PRT
<213> ORGANISM: Artificial Sequence
<220> FEATURE:
<223> OTHER INFORMATION: Synthetic peptide

<400> SEQUENCE: 571

Asp Ala Gly Gly Ser Tyr Ser Tyr Tyr Phe Asp Leu
1               5                   10

<210> SEQ ID NO 572
<211> LENGTH: 14
<212> TYPE: PRT
<213> ORGANISM: Artificial Sequence
<220> FEATURE:
<223> OTHER INFORMATION: Synthetic peptide

<400> SEQUENCE: 572

Asp Ala Gly Gly Tyr Thr Gly Asp Gly Tyr Tyr Phe Lys Leu
1               5                   10

<210> SEQ ID NO 573
<211> LENGTH: 9
<212> TYPE: PRT
<213> ORGANISM: Artificial Sequence
<220> FEATURE:
<223> OTHER INFORMATION: Synthetic peptide

<400> SEQUENCE: 573

Gly Gly Pro Ile His Tyr Ser Asn Leu
1               5

<210> SEQ ID NO 574
<211> LENGTH: 10
<212> TYPE: PRT
<213> ORGANISM: Artificial Sequence
<220> FEATURE:
<223> OTHER INFORMATION: Synthetic peptide

<400> SEQUENCE: 574

Gly Ser Gly Trp Tyr Gly Gly Leu Asn Leu
1               5                   10

<210> SEQ ID NO 575
<211> LENGTH: 15
<212> TYPE: PRT
<213> ORGANISM: Artificial Sequence
<220> FEATURE:
<223> OTHER INFORMATION: Synthetic peptide
```

-continued

```
<400> SEQUENCE: 575

Asn Tyr Ala Asp Pro Pro Gly Tyr Asn Tyr Thr Pro Phe Asn Leu
1               5                   10                  15

<210> SEQ ID NO 576
<211> LENGTH: 17
<212> TYPE: PRT
<213> ORGANISM: Artificial Sequence
<220> FEATURE:
<223> OTHER INFORMATION: Synthetic peptide

<400> SEQUENCE: 576

Leu Tyr Ala Gly Ser Ser Tyr Ser Ile Ser Pro Asp Tyr Gly Met Asp
1               5                   10                  15

Leu

<210> SEQ ID NO 577
<211> LENGTH: 26
<212> TYPE: PRT
<213> ORGANISM: Artificial Sequence
<220> FEATURE:
<223> OTHER INFORMATION: Synthetic peptide

<400> SEQUENCE: 577

Ala Arg Arg Ala Asp Gly Gly Thr Tyr Asn Leu Trp Gly Pro Gly Thr
1               5                   10                  15

Leu Val Thr Val Ser Ser Gly Gln Pro Lys
            20                  25

<210> SEQ ID NO 578
<211> LENGTH: 24
<212> TYPE: PRT
<213> ORGANISM: Artificial Sequence
<220> FEATURE:
<223> OTHER INFORMATION: Synthetic peptide

<400> SEQUENCE: 578

Arg Ala Asp Gly Gly Thr Tyr Asn Leu Trp Gly Pro Gly Thr Leu Val
1               5                   10                  15

Thr Val Ser Ser Gly Gln Pro Lys
            20

<210> SEQ ID NO 579
<211> LENGTH: 26
<212> TYPE: PRT
<213> ORGANISM: Artificial Sequence
<220> FEATURE:
<223> OTHER INFORMATION: Synthetic peptide

<400> SEQUENCE: 579

Ala Arg Leu Asn Ile Gly Gly Ala Asp Gly Leu Trp Gly Pro Gly Thr
1               5                   10                  15

Leu Val Thr Val Ser Ser Gly Gln Pro Lys
            20                  25

<210> SEQ ID NO 580
<211> LENGTH: 24
<212> TYPE: PRT
<213> ORGANISM: Artificial Sequence
<220> FEATURE:
<223> OTHER INFORMATION: Synthetic peptide

<400> SEQUENCE: 580

Leu Asn Ile Gly Gly Ala Asp Gly Leu Trp Gly Pro Gly Thr Leu Val
```

```
                1               5                   10                  15
Thr Val Ser Ser Gly Gln Pro Lys
            20

<210> SEQ ID NO 581
<211> LENGTH: 24
<212> TYPE: PRT
<213> ORGANISM: Artificial Sequence
<220> FEATURE:
<223> OTHER INFORMATION: Synthetic peptide

<400> SEQUENCE: 581

Ala Arg Gly Tyr Asn Thr Phe Asp Pro Trp Gly Pro Gly Thr Leu Val
1               5                   10                  15

Ser Val Ser Ser Gly Gln Pro Lys
            20

<210> SEQ ID NO 582
<211> LENGTH: 22
<212> TYPE: PRT
<213> ORGANISM: Artificial Sequence
<220> FEATURE:
<223> OTHER INFORMATION: Synthetic peptide

<400> SEQUENCE: 582

Gly Tyr Asn Thr Phe Asp Pro Trp Gly Pro Gly Thr Leu Val Ser Val
1               5                   10                  15

Ser Ser Gly Gln Pro Lys
            20

<210> SEQ ID NO 583
<211> LENGTH: 21
<212> TYPE: PRT
<213> ORGANISM: Artificial Sequence
<220> FEATURE:
<223> OTHER INFORMATION: Synthetic peptide

<400> SEQUENCE: 583

Ala Arg Asn Phe Lys Leu Trp Gly Pro Gly Thr Leu Val Thr Val Ser
1               5                   10                  15

Ser Gly Gln Pro Lys
            20

<210> SEQ ID NO 584
<211> LENGTH: 19
<212> TYPE: PRT
<213> ORGANISM: Artificial Sequence
<220> FEATURE:
<223> OTHER INFORMATION: Synthetic peptide

<400> SEQUENCE: 584

Asn Phe Lys Leu Trp Gly Pro Gly Thr Leu Val Thr Val Ser Ser Gly
1               5                   10                  15

Gln Pro Lys

<210> SEQ ID NO 585
<211> LENGTH: 30
<212> TYPE: PRT
<213> ORGANISM: Artificial Sequence
<220> FEATURE:
<223> OTHER INFORMATION: Synthetic peptide

<400> SEQUENCE: 585

Ala Arg Asn Val Tyr Gly Ala Ser Arg Val Cys Gly Met Asp Leu Trp
```

```
                1               5                   10                  15
Gly Pro Gly Thr Leu Val Thr Val Ser Ser Gly Gln Pro Lys
            20                  25                  30
```

<210> SEQ ID NO 586
<211> LENGTH: 21
<212> TYPE: PRT
<213> ORGANISM: Artificial Sequence
<220> FEATURE:
<223> OTHER INFORMATION: Synthetic peptide

<400> SEQUENCE: 586

```
Val Cys Gly Met Asp Leu Trp Gly Pro Gly Thr Leu Val Thr Val Ser
1               5                   10                  15
Ser Gly Gln Pro Lys
            20
```

<210> SEQ ID NO 587
<211> LENGTH: 20
<212> TYPE: PRT
<213> ORGANISM: Artificial Sequence
<220> FEATURE:
<223> OTHER INFORMATION: Synthetic peptide

<400> SEQUENCE: 587

```
Arg Arg Ser Gly Leu Trp Gly Pro Gly Thr Leu Val Ala Val Ser Ser
1               5                   10                  15
Gly Gln Pro Lys
            20
```

<210> SEQ ID NO 588
<211> LENGTH: 18
<212> TYPE: PRT
<213> ORGANISM: Artificial Sequence
<220> FEATURE:
<223> OTHER INFORMATION: Synthetic peptide

<400> SEQUENCE: 588

```
Ser Gly Leu Trp Gly Pro Gly Thr Leu Val Ala Val Ser Ser Gly Gln
1               5                   10                  15
Pro Lys
```

<210> SEQ ID NO 589
<211> LENGTH: 29
<212> TYPE: PRT
<213> ORGANISM: Artificial Sequence
<220> FEATURE:
<223> OTHER INFORMATION: Synthetic peptide

<400> SEQUENCE: 589

```
Ala Arg Ser Ser Tyr Val Asn Ser Gly Gly Ala Ala Asn Leu Trp Gly
1               5                   10                  15
Pro Gly Thr Leu Val Thr Val Ser Ser Gly Gln Pro Lys
            20                  25
```

<210> SEQ ID NO 590
<211> LENGTH: 27
<212> TYPE: PRT
<213> ORGANISM: Artificial Sequence
<220> FEATURE:
<223> OTHER INFORMATION: Synthetic peptide

<400> SEQUENCE: 590

```
Ser Ser Tyr Val Asn Ser Gly Gly Ala Ala Asn Leu Trp Gly Pro Gly
```

```
                1               5                  10                 15
Thr Leu Val Thr Val Ser Ser Gly Gln Pro Lys
            20                  25
```

<210> SEQ ID NO 591
<211> LENGTH: 31
<212> TYPE: PRT
<213> ORGANISM: Artificial Sequence
<220> FEATURE:
<223> OTHER INFORMATION: Synthetic peptide

<400> SEQUENCE: 591

```
Ala Arg Gly Gly Tyr Gly Gly Tyr Gly Tyr Asp Arg Ala Phe Asp Phe
1               5                   10                  15
Trp Gly Pro Gly Thr Leu Val Thr Val Ser Ser Gly Gln Pro Lys
            20                  25                  30
```

<210> SEQ ID NO 592
<211> LENGTH: 19
<212> TYPE: PRT
<213> ORGANISM: Artificial Sequence
<220> FEATURE:
<223> OTHER INFORMATION: Synthetic peptide

<400> SEQUENCE: 592

```
Ala Phe Asp Phe Trp Gly Pro Gly Thr Leu Val Thr Val Ser Ser Gly
1               5                   10                  15
Gln Pro Lys
```

<210> SEQ ID NO 593
<211> LENGTH: 26
<212> TYPE: PRT
<213> ORGANISM: Artificial Sequence
<220> FEATURE:
<223> OTHER INFORMATION: Synthetic peptide

<400> SEQUENCE: 593

```
Ala Arg Ser Pro Ser Ser Gly Ser Ser Asn Leu Trp Gly Pro Gly Thr
1               5                   10                  15
Leu Val Thr Val Ser Ser Gly Gln Pro Lys
            20                  25
```

<210> SEQ ID NO 594
<211> LENGTH: 24
<212> TYPE: PRT
<213> ORGANISM: Artificial Sequence
<220> FEATURE:
<223> OTHER INFORMATION: Synthetic peptide

<400> SEQUENCE: 594

```
Ser Pro Ser Ser Gly Ser Ser Asn Leu Trp Gly Pro Gly Thr Leu Val
1               5                   10                  15
Thr Val Ser Ser Gly Gln Pro Lys
            20
```

<210> SEQ ID NO 595
<211> LENGTH: 21
<212> TYPE: PRT
<213> ORGANISM: Artificial Sequence
<220> FEATURE:
<223> OTHER INFORMATION: Synthetic peptide

<400> SEQUENCE: 595

```
Ala Arg Asn Phe Gly Leu Trp Gly Gln Gly Thr Leu Val Thr Val Ser
```

```
1               5                   10                  15
Ser Gly Gln Pro Lys
            20

<210> SEQ ID NO 596
<211> LENGTH: 19
<212> TYPE: PRT
<213> ORGANISM: Artificial Sequence
<220> FEATURE:
<223> OTHER INFORMATION: Synthetic peptide

<400> SEQUENCE: 596

Asn Phe Gly Leu Trp Gly Gln Gly Thr Leu Val Thr Val Ser Ser Gly
1               5                   10                  15

Gln Pro Lys

<210> SEQ ID NO 597
<211> LENGTH: 21
<212> TYPE: PRT
<213> ORGANISM: Artificial Sequence
<220> FEATURE:
<223> OTHER INFORMATION: Synthetic peptide

<400> SEQUENCE: 597

Ala Arg Asn Phe Gly Leu Gly Gly Gln Gly Thr Leu Val Thr Val Ser
1               5                   10                  15

Ser Gly Gln Pro Lys
            20

<210> SEQ ID NO 598
<211> LENGTH: 19
<212> TYPE: PRT
<213> ORGANISM: Artificial Sequence
<220> FEATURE:
<223> OTHER INFORMATION: Synthetic peptide

<400> SEQUENCE: 598

Asn Phe Gly Leu Gly Gly Gln Gly Thr Leu Val Thr Val Ser Ser Gly
1               5                   10                  15

Gln Pro Lys

<210> SEQ ID NO 599
<211> LENGTH: 28
<212> TYPE: PRT
<213> ORGANISM: Artificial Sequence
<220> FEATURE:
<223> OTHER INFORMATION: Synthetic peptide

<400> SEQUENCE: 599

Ala Arg Gly Gly Gly Ser Asp Gly Asp Gly Tyr Asn Leu Trp Gly Pro
1               5                   10                  15

Gly Thr Leu Val Thr Val Ser Ser Gly Gln Pro Lys
            20                  25

<210> SEQ ID NO 600
<211> LENGTH: 26
<212> TYPE: PRT
<213> ORGANISM: Artificial Sequence
<220> FEATURE:
<223> OTHER INFORMATION: Synthetic peptide

<400> SEQUENCE: 600

Gly Gly Gly Ser Asp Gly Asp Gly Tyr Asn Leu Trp Gly Pro Gly Thr
1               5                   10                  15
```

Leu Val Thr Val Ser Ser Gly Gln Pro Lys
            20                  25

<210> SEQ ID NO 601
<211> LENGTH: 21
<212> TYPE: PRT
<213> ORGANISM: Artificial Sequence
<220> FEATURE:
<223> OTHER INFORMATION: Synthetic peptide

<400> SEQUENCE: 601

Ala Arg Asn Tyr Gly Leu Trp Gly Pro Gly Thr Leu Val Thr Val Ser
1               5                   10                  15

Ser Gly Gln Pro Lys
            20

<210> SEQ ID NO 602
<211> LENGTH: 19
<212> TYPE: PRT
<213> ORGANISM: Artificial Sequence
<220> FEATURE:
<223> OTHER INFORMATION: Synthetic peptide

<400> SEQUENCE: 602

Asn Tyr Gly Leu Trp Gly Pro Gly Thr Leu Val Thr Val Ser Ser Gly
1               5                   10                  15

Gln Pro Lys

<210> SEQ ID NO 603
<211> LENGTH: 21
<212> TYPE: PRT
<213> ORGANISM: Artificial Sequence
<220> FEATURE:
<223> OTHER INFORMATION: Synthetic peptide

<400> SEQUENCE: 603

Val Arg Asn Leu Tyr Leu Trp Gly Pro Gly Thr Leu Val Thr Val Ser
1               5                   10                  15

Ser Gly Gln Pro Lys
            20

<210> SEQ ID NO 604
<211> LENGTH: 19
<212> TYPE: PRT
<213> ORGANISM: Artificial Sequence
<220> FEATURE:
<223> OTHER INFORMATION: Synthetic peptide

<400> SEQUENCE: 604

Asn Leu Tyr Leu Trp Gly Pro Gly Thr Leu Val Thr Val Ser Ser Gly
1               5                   10                  15

Gln Pro Lys

<210> SEQ ID NO 605
<211> LENGTH: 27
<212> TYPE: PRT
<213> ORGANISM: Artificial Sequence
<220> FEATURE:
<223> OTHER INFORMATION: Synthetic peptide

<400> SEQUENCE: 605

Ala Arg Val Val Pro Gly Val His Ser Phe Asn Leu Trp Gly Pro Gly
1               5                   10                  15

Thr Leu Val Thr Val Ser Ser Gly Gln Pro Lys
            20                  25

<210> SEQ ID NO 606
<211> LENGTH: 25
<212> TYPE: PRT
<213> ORGANISM: Artificial Sequence
<220> FEATURE:
<223> OTHER INFORMATION: Synthetic peptide

<400> SEQUENCE: 606

Val Val Pro Gly Val His Ser Phe Asn Leu Trp Gly Pro Gly Thr Leu
1               5                   10                  15

Val Thr Val Ser Ser Gly Gln Pro Lys
            20                  25

<210> SEQ ID NO 607
<211> LENGTH: 27
<212> TYPE: PRT
<213> ORGANISM: Artificial Sequence
<220> FEATURE:
<223> OTHER INFORMATION: Synthetic peptide

<400> SEQUENCE: 607

Ala Arg Gly Gly Asn Pro Asn Tyr Asp Tyr Gly Leu Trp Gly Pro Gly
1               5                   10                  15

Thr Leu Val Thr Val Ser Ser Gly Gln Pro Lys
            20                  25

<210> SEQ ID NO 608
<211> LENGTH: 25
<212> TYPE: PRT
<213> ORGANISM: Artificial Sequence
<220> FEATURE:
<223> OTHER INFORMATION: Synthetic peptide

<400> SEQUENCE: 608

Gly Gly Asn Pro Asn Tyr Asp Tyr Gly Leu Trp Gly Pro Gly Thr Leu
1               5                   10                  15

Val Thr Val Ser Ser Gly Gln Pro Lys
            20                  25

<210> SEQ ID NO 609
<211> LENGTH: 28
<212> TYPE: PRT
<213> ORGANISM: Artificial Sequence
<220> FEATURE:
<223> OTHER INFORMATION: Synthetic peptide

<400> SEQUENCE: 609

Ala Arg Gly Leu Phe Gly Arg Ala Phe Pro Phe Lys Leu Trp Gly Pro
1               5                   10                  15

Gly Thr Leu Val Thr Val Ser Ser Gly Gln Pro Lys
            20                  25

<210> SEQ ID NO 610
<211> LENGTH: 21
<212> TYPE: PRT
<213> ORGANISM: Artificial Sequence
<220> FEATURE:
<223> OTHER INFORMATION: Synthetic peptide

<400> SEQUENCE: 610

Ala Phe Pro Phe Lys Leu Trp Gly Pro Gly Thr Leu Val Thr Val Ser
1               5                   10                  15

Ser Gly Gln Pro Lys
        20

<210> SEQ ID NO 611
<211> LENGTH: 26
<212> TYPE: PRT
<213> ORGANISM: Artificial Sequence
<220> FEATURE:
<223> OTHER INFORMATION: Synthetic peptide

<400> SEQUENCE: 611

Ala Arg Asp Leu Tyr Gly Gly Ser Ser Asp Leu Trp Gly Pro Gly Thr
1               5                   10                  15

Leu Val Thr Val Ser Ser Gly Gln Pro Lys
            20                  25

<210> SEQ ID NO 612
<211> LENGTH: 24
<212> TYPE: PRT
<213> ORGANISM: Artificial Sequence
<220> FEATURE:
<223> OTHER INFORMATION: Synthetic peptide

<400> SEQUENCE: 612

Asp Leu Tyr Gly Gly Ser Ser Asp Leu Trp Gly Pro Gly Thr Leu Val
1               5                   10                  15

Thr Val Ser Ser Gly Gln Pro Lys
            20

<210> SEQ ID NO 613
<211> LENGTH: 23
<212> TYPE: PRT
<213> ORGANISM: Artificial Sequence
<220> FEATURE:
<223> OTHER INFORMATION: Synthetic peptide

<400> SEQUENCE: 613

Ala Arg Glu Gly Leu Tyr Asn Leu Trp Gly Pro Gly Thr Leu Val Thr
1               5                   10                  15

Val Ser Ser Gly Gln Pro Lys
            20

<210> SEQ ID NO 614
<211> LENGTH: 21
<212> TYPE: PRT
<213> ORGANISM: Artificial Sequence
<220> FEATURE:
<223> OTHER INFORMATION: Synthetic peptide

<400> SEQUENCE: 614

Glu Gly Leu Tyr Asn Leu Trp Gly Pro Gly Thr Leu Val Thr Val Ser
1               5                   10                  15

Ser Gly Gln Pro Lys
            20

<210> SEQ ID NO 615
<211> LENGTH: 26
<212> TYPE: PRT
<213> ORGANISM: Artificial Sequence
<220> FEATURE:
<223> OTHER INFORMATION: Synthetic peptide

<400> SEQUENCE: 615

Ala Arg Gly Ala Gly Gly Ser Gly Tyr Asn Leu Trp Gly Pro Gly Thr

```
1               5                   10                  15
Leu Val Thr Val Ser Ser Gly Gln Pro Lys
            20                  25

<210> SEQ ID NO 616
<211> LENGTH: 24
<212> TYPE: PRT
<213> ORGANISM: Artificial Sequence
<220> FEATURE:
<223> OTHER INFORMATION: Synthetic peptide

<400> SEQUENCE: 616

Gly Ala Gly Gly Ser Gly Tyr Asn Leu Trp Gly Pro Gly Thr Leu Val
1               5                   10                  15

Thr Val Ser Ser Gly Gln Pro Lys
            20

<210> SEQ ID NO 617
<211> LENGTH: 25
<212> TYPE: PRT
<213> ORGANISM: Artificial Sequence
<220> FEATURE:
<223> OTHER INFORMATION: Synthetic peptide

<400> SEQUENCE: 617

Ser Arg Gly Gly Gly Ala Gly Tyr Gly Leu Trp Gly Pro Gly Thr Leu
1               5                   10                  15

Val Thr Val Ser Ser Gly Gln Pro Lys
            20                  25

<210> SEQ ID NO 618
<211> LENGTH: 23
<212> TYPE: PRT
<213> ORGANISM: Artificial Sequence
<220> FEATURE:
<223> OTHER INFORMATION: Synthetic peptide

<400> SEQUENCE: 618

Gly Gly Gly Ala Gly Tyr Gly Leu Trp Gly Pro Gly Thr Leu Val Thr
1               5                   10                  15

Val Ser Ser Gly Gln Pro Lys
            20

<210> SEQ ID NO 619
<211> LENGTH: 26
<212> TYPE: PRT
<213> ORGANISM: Artificial Sequence
<220> FEATURE:
<223> OTHER INFORMATION: Synthetic peptide

<400> SEQUENCE: 619

Ala Arg Lys Asp Thr Asn Pro His Trp Gly Leu Trp Gly Pro Gly Thr
1               5                   10                  15

Leu Val Thr Val Ser Ser Gly Gln Pro Lys
            20                  25

<210> SEQ ID NO 620
<211> LENGTH: 23
<212> TYPE: PRT
<213> ORGANISM: Artificial Sequence
<220> FEATURE:
<223> OTHER INFORMATION: Synthetic peptide

<400> SEQUENCE: 620
```

```
Asp Thr Asn Pro His Trp Gly Leu Trp Gly Pro Gly Thr Leu Val Thr
1               5                   10                  15

Val Ser Ser Gly Gln Pro Lys
            20
```

<210> SEQ ID NO 621
<211> LENGTH: 26
<212> TYPE: PRT
<213> ORGANISM: Artificial Sequence
<220> FEATURE:
<223> OTHER INFORMATION: Synthetic peptide

<400> SEQUENCE: 621

```
Ala Arg Lys Asp Ser Asn Pro His Trp Gly Leu Trp Gly Pro Gly Thr
1               5                   10                  15

Leu Val Thr Val Ser Ser Gly Gln Pro Lys
            20                  25
```

<210> SEQ ID NO 622
<211> LENGTH: 24
<212> TYPE: PRT
<213> ORGANISM: Artificial Sequence
<220> FEATURE:
<223> OTHER INFORMATION: Synthetic peptide

<400> SEQUENCE: 622

```
Lys Asp Ser Asn Pro His Trp Gly Leu Trp Gly Pro Gly Thr Leu Val
1               5                   10                  15

Thr Val Ser Ser Gly Gln Pro Lys
            20
```

<210> SEQ ID NO 623
<211> LENGTH: 26
<212> TYPE: PRT
<213> ORGANISM: Artificial Sequence
<220> FEATURE:
<223> OTHER INFORMATION: Synthetic peptide

<400> SEQUENCE: 623

```
Ala Arg Gly Ala Gly Gly Ser Gly Tyr Gly Leu Trp Gly Pro Gly Thr
1               5                   10                  15

Leu Val Thr Val Ser Ser Gly Gln Pro Lys
            20                  25
```

<210> SEQ ID NO 624
<211> LENGTH: 24
<212> TYPE: PRT
<213> ORGANISM: Artificial Sequence
<220> FEATURE:
<223> OTHER INFORMATION: Synthetic peptide

<400> SEQUENCE: 624

```
Gly Ala Gly Gly Ser Gly Tyr Gly Leu Trp Gly Pro Gly Thr Leu Val
1               5                   10                  15

Thr Val Ser Ser Gly Gln Pro Lys
            20
```

<210> SEQ ID NO 625
<211> LENGTH: 29
<212> TYPE: PRT
<213> ORGANISM: Artificial Sequence
<220> FEATURE:
<223> OTHER INFORMATION: Synthetic peptide

<400> SEQUENCE: 625

Ala Arg Asp Asp Val Gly Asp Gly Ala Phe Val His Asn Leu Trp Gly
1               5                   10                  15

Pro Gly Thr Leu Val Thr Val Ser Ser Gly Gln Pro Lys
            20                  25

<210> SEQ ID NO 626
<211> LENGTH: 27
<212> TYPE: PRT
<213> ORGANISM: Artificial Sequence
<220> FEATURE:
<223> OTHER INFORMATION: Synthetic peptide

<400> SEQUENCE: 626

Asp Asp Val Gly Asp Gly Ala Phe Val His Asn Leu Trp Gly Pro Gly
1               5                   10                  15

Thr Leu Val Thr Val Ser Ser Gly Gln Pro Lys
            20                  25

<210> SEQ ID NO 627
<211> LENGTH: 29
<212> TYPE: PRT
<213> ORGANISM: Artificial Sequence
<220> FEATURE:
<223> OTHER INFORMATION: Synthetic peptide

<400> SEQUENCE: 627

Ala Arg Asp His Ser Gly Asn Ser Gly Trp His Pro Asp Leu Trp Gly
1               5                   10                  15

Pro Gly Thr Leu Val Thr Val Ser Ser Gly Gln Pro Lys
            20                  25

<210> SEQ ID NO 628
<211> LENGTH: 27
<212> TYPE: PRT
<213> ORGANISM: Artificial Sequence
<220> FEATURE:
<223> OTHER INFORMATION: Synthetic peptide

<400> SEQUENCE: 628

Asp His Ser Gly Asn Ser Gly Trp His Pro Asp Leu Trp Gly Pro Gly
1               5                   10                  15

Thr Leu Val Thr Val Ser Ser Gly Gln Pro Lys
            20                  25

<210> SEQ ID NO 629
<211> LENGTH: 26
<212> TYPE: PRT
<213> ORGANISM: Artificial Sequence
<220> FEATURE:
<223> OTHER INFORMATION: Synthetic peptide

<400> SEQUENCE: 629

Ala Arg Tyr Tyr Ser Gly Thr Gly Ser Asp Leu Trp Gly Pro Gly Thr
1               5                   10                  15

Leu Val Thr Val Ser Ser Gly Gln Pro Lys
            20                  25

<210> SEQ ID NO 630
<211> LENGTH: 24
<212> TYPE: PRT
<213> ORGANISM: Artificial Sequence
<220> FEATURE:
<223> OTHER INFORMATION: Synthetic peptide

<400> SEQUENCE: 630

Tyr Tyr Ser Gly Thr Gly Ser Asp Leu Trp Gly Pro Gly Thr Leu Val
1               5                   10                  15

Thr Val Ser Ser Gly Gln Pro Lys
            20

<210> SEQ ID NO 631
<211> LENGTH: 26
<212> TYPE: PRT
<213> ORGANISM: Artificial Sequence
<220> FEATURE:
<223> OTHER INFORMATION: Synthetic peptide

<400> SEQUENCE: 631

Ala Arg Gly Val Gly Gly Tyr Gly Ser Asp Leu Trp Gly Pro Gly Thr
1               5                   10                  15

Leu Val Thr Val Ser Ser Gly Gln Pro Lys
            20                  25

<210> SEQ ID NO 632
<211> LENGTH: 24
<212> TYPE: PRT
<213> ORGANISM: Artificial Sequence
<220> FEATURE:
<223> OTHER INFORMATION: Synthetic peptide

<400> SEQUENCE: 632

Gly Val Gly Gly Tyr Gly Ser Asp Leu Trp Gly Pro Gly Thr Leu Val
1               5                   10                  15

Thr Val Ser Ser Gly Gln Pro Lys
            20

<210> SEQ ID NO 633
<211> LENGTH: 28
<212> TYPE: PRT
<213> ORGANISM: Artificial Sequence
<220> FEATURE:
<223> OTHER INFORMATION: Synthetic peptide

<400> SEQUENCE: 633

Ala Arg Gly Asn Thr Tyr Ala Val Asp Gly Tyr Asn Leu Trp Gly Pro
1               5                   10                  15

Gly Thr Leu Val Thr Val Ser Ser Gly Gln Pro Lys
            20                  25

<210> SEQ ID NO 634
<211> LENGTH: 26
<212> TYPE: PRT
<213> ORGANISM: Artificial Sequence
<220> FEATURE:
<223> OTHER INFORMATION: Synthetic peptide

<400> SEQUENCE: 634

Gly Asn Thr Tyr Ala Val Asp Gly Tyr Asn Leu Trp Gly Pro Gly Thr
1               5                   10                  15

Leu Val Thr Val Ser Ser Gly Gln Pro Lys
            20                  25

<210> SEQ ID NO 635
<211> LENGTH: 29
<212> TYPE: PRT
<213> ORGANISM: Artificial Sequence
<220> FEATURE:
<223> OTHER INFORMATION: Synthetic peptide

```
<400> SEQUENCE: 635

Ala Arg Glu Thr Ala Gly Asp Lys Asn Trp Leu Phe His Leu Trp Gly
1               5                   10                  15

Pro Gly Thr Leu Val Thr Val Ser Ser Gly Gln Pro Lys
            20                  25

<210> SEQ ID NO 636
<211> LENGTH: 21
<212> TYPE: PRT
<213> ORGANISM: Artificial Sequence
<220> FEATURE:
<223> OTHER INFORMATION: Synthetic peptide

<400> SEQUENCE: 636

Asn Trp Leu Phe His Leu Trp Gly Pro Gly Thr Leu Val Thr Val Ser
1               5                   10                  15

Ser Gly Gln Pro Lys
            20

<210> SEQ ID NO 637
<211> LENGTH: 29
<212> TYPE: PRT
<213> ORGANISM: Artificial Sequence
<220> FEATURE:
<223> OTHER INFORMATION: Synthetic peptide

<400> SEQUENCE: 637

Ala Arg Glu Gly Tyr Gly Gly Tyr Val Gly Tyr Met Gly Leu Trp Gly
1               5                   10                  15

Pro Gly Thr Leu Val Thr Val Ser Ser Gly Gln Pro Lys
            20                  25

<210> SEQ ID NO 638
<211> LENGTH: 27
<212> TYPE: PRT
<213> ORGANISM: Artificial Sequence
<220> FEATURE:
<223> OTHER INFORMATION: Synthetic peptide

<400> SEQUENCE: 638

Glu Gly Tyr Gly Gly Tyr Val Gly Tyr Met Gly Leu Trp Gly Pro Gly
1               5                   10                  15

Thr Leu Val Thr Val Ser Ser Gly Gln Pro Lys
            20                  25

<210> SEQ ID NO 639
<211> LENGTH: 27
<212> TYPE: PRT
<213> ORGANISM: Artificial Sequence
<220> FEATURE:
<223> OTHER INFORMATION: Synthetic peptide

<400> SEQUENCE: 639

Ala Arg Val Val Asp Asp Gly Asp Gly Cys Asp Leu Trp Gly Pro Gly
1               5                   10                  15

Thr Leu Val Thr Val Ser Ser Gly Gln Pro Lys
            20                  25

<210> SEQ ID NO 640
<211> LENGTH: 25
<212> TYPE: PRT
<213> ORGANISM: Artificial Sequence
<220> FEATURE:
```

<223> OTHER INFORMATION: Synthetic peptide

<400> SEQUENCE: 640

Val Val Asp Asp Gly Asp Gly Cys Asp Leu Trp Gly Pro Gly Thr Leu
1               5                   10                  15
Val Thr Val Ser Ser Gly Gln Pro Lys
            20                  25

<210> SEQ ID NO 641
<211> LENGTH: 26
<212> TYPE: PRT
<213> ORGANISM: Artificial Sequence
<220> FEATURE:
<223> OTHER INFORMATION: Synthetic peptide

<400> SEQUENCE: 641

Leu Arg Glu Arg Ser Gly Val Asn Thr Asp Leu Trp Gly Pro Gly Thr
1               5                   10                  15
Leu Val Thr Val Ser Ser Gly Gln Pro Lys
            20                  25

<210> SEQ ID NO 642
<211> LENGTH: 22
<212> TYPE: PRT
<213> ORGANISM: Artificial Sequence
<220> FEATURE:
<223> OTHER INFORMATION: Synthetic peptide

<400> SEQUENCE: 642

Ser Gly Val Asn Thr Asp Leu Trp Gly Pro Gly Thr Leu Val Thr Val
1               5                   10                  15
Ser Ser Gly Gln Pro Lys
            20

<210> SEQ ID NO 643
<211> LENGTH: 23
<212> TYPE: PRT
<213> ORGANISM: Artificial Sequence
<220> FEATURE:
<223> OTHER INFORMATION: Synthetic peptide

<400> SEQUENCE: 643

Ala Arg Glu Ala Leu Tyr Asn Leu Trp Gly Pro Gly Thr Leu Val Thr
1               5                   10                  15
Val Ala Ser Gly Gln Pro Lys
            20

<210> SEQ ID NO 644
<211> LENGTH: 21
<212> TYPE: PRT
<213> ORGANISM: Artificial Sequence
<220> FEATURE:
<223> OTHER INFORMATION: Synthetic peptide

<400> SEQUENCE: 644

Glu Ala Leu Tyr Asn Leu Trp Gly Pro Gly Thr Leu Val Thr Val Ala
1               5                   10                  15
Ser Gly Gln Pro Lys
            20

<210> SEQ ID NO 645
<211> LENGTH: 26
<212> TYPE: PRT
<213> ORGANISM: Artificial Sequence

```
<220> FEATURE:
<223> OTHER INFORMATION: Synthetic peptide

<400> SEQUENCE: 645

Ala Arg Gly Ala Gly Gly Ser Gly Tyr Asp Leu Trp Gly Pro Gly Thr
1               5                   10                  15

Leu Val Thr Val Ser Ser Gly Gln Pro Lys
            20                  25

<210> SEQ ID NO 646
<211> LENGTH: 24
<212> TYPE: PRT
<213> ORGANISM: Artificial Sequence
<220> FEATURE:
<223> OTHER INFORMATION: Synthetic peptide

<400> SEQUENCE: 646

Gly Ala Gly Gly Ser Gly Tyr Asp Leu Trp Gly Pro Gly Thr Leu Val
1               5                   10                  15

Thr Val Ser Ser Gly Gln Pro Lys
            20

<210> SEQ ID NO 647
<211> LENGTH: 29
<212> TYPE: PRT
<213> ORGANISM: Artificial Sequence
<220> FEATURE:
<223> OTHER INFORMATION: Synthetic peptide

<400> SEQUENCE: 647

Ala Arg Gly Ala Tyr Gly Asn Thr Asn Thr Tyr Tyr Asn Leu Gly Gly
1               5                   10                  15

Pro Gly Thr Leu Val Thr Val Ser Ser Gly Gln Pro Lys
            20                  25

<210> SEQ ID NO 648
<211> LENGTH: 27
<212> TYPE: PRT
<213> ORGANISM: Artificial Sequence
<220> FEATURE:
<223> OTHER INFORMATION: Synthetic peptide

<400> SEQUENCE: 648

Gly Ala Tyr Gly Asn Thr Asn Thr Tyr Tyr Asn Leu Gly Gly Pro Gly
1               5                   10                  15

Thr Leu Val Thr Val Ser Ser Gly Gln Pro Lys
            20                  25

<210> SEQ ID NO 649
<211> LENGTH: 26
<212> TYPE: PRT
<213> ORGANISM: Artificial Sequence
<220> FEATURE:
<223> OTHER INFORMATION: Synthetic peptide

<400> SEQUENCE: 649

Ala Arg Trp Ala Gly Ser Asn Gly Phe Ser Leu Trp Ser Pro Gly Thr
1               5                   10                  15

Leu Val Thr Val Ser Ser Gly Gln Pro Lys
            20                  25

<210> SEQ ID NO 650
<211> LENGTH: 24
<212> TYPE: PRT
```

<213> ORGANISM: Artificial Sequence
<220> FEATURE:
<223> OTHER INFORMATION: Synthetic peptide

<400> SEQUENCE: 650

Trp Ala Gly Ser Asn Gly Phe Ser Leu Trp Ser Pro Gly Thr Leu Val
1               5                   10                  15

Thr Val Ser Ser Gly Gln Pro Lys
            20

<210> SEQ ID NO 651
<211> LENGTH: 26
<212> TYPE: PRT
<213> ORGANISM: Artificial Sequence
<220> FEATURE:
<223> OTHER INFORMATION: Synthetic peptide

<400> SEQUENCE: 651

Leu Arg Glu Arg Ser Gly Val Asn Thr Asp Leu Gly Ala Pro Gly Thr
1               5                   10                  15

Leu Val Thr Val Ser Ser Gly Gln Pro Lys
            20                  25

<210> SEQ ID NO 652
<211> LENGTH: 22
<212> TYPE: PRT
<213> ORGANISM: Artificial Sequence
<220> FEATURE:
<223> OTHER INFORMATION: Synthetic peptide

<400> SEQUENCE: 652

Ser Gly Val Asn Thr Asp Leu Gly Ala Pro Gly Thr Leu Val Thr Val
1               5                   10                  15

Ser Ser Gly Gln Pro Lys
            20

<210> SEQ ID NO 653
<211> LENGTH: 27
<212> TYPE: PRT
<213> ORGANISM: Artificial Sequence
<220> FEATURE:
<223> OTHER INFORMATION: Synthetic peptide

<400> SEQUENCE: 653

Ala Arg Asn Leu Gly Ile Thr Asn Asp Asn Asn Leu Trp Gly Pro Gly
1               5                   10                  15

Thr Leu Val Thr Val Ser Ser Gly Gln Pro Lys
            20                  25

<210> SEQ ID NO 654
<211> LENGTH: 25
<212> TYPE: PRT
<213> ORGANISM: Artificial Sequence
<220> FEATURE:
<223> OTHER INFORMATION: Synthetic peptide

<400> SEQUENCE: 654

Asn Leu Gly Ile Thr Asn Asp Asn Asn Leu Trp Gly Pro Gly Thr Leu
1               5                   10                  15

Val Thr Val Ser Ser Gly Gln Pro Lys
            20                  25

<210> SEQ ID NO 655
<211> LENGTH: 26

<212> TYPE: PRT
<213> ORGANISM: Artificial Sequence
<220> FEATURE:
<223> OTHER INFORMATION: Synthetic peptide

<400> SEQUENCE: 655

Ala Arg Gly Ala Gly Trp Val Asp Tyr Ser Leu Trp Gly Pro Gly Thr
1               5                   10                  15

Leu Val Thr Val Ser Ser Gly Gln Pro Lys
            20                  25

<210> SEQ ID NO 656
<211> LENGTH: 24
<212> TYPE: PRT
<213> ORGANISM: Artificial Sequence
<220> FEATURE:
<223> OTHER INFORMATION: Synthetic peptide

<400> SEQUENCE: 656

Gly Ala Gly Trp Val Asp Tyr Ser Leu Trp Gly Pro Gly Thr Leu Val
1               5                   10                  15

Thr Val Ser Ser Gly Gln Pro Lys
            20

<210> SEQ ID NO 657
<211> LENGTH: 22
<212> TYPE: PRT
<213> ORGANISM: Artificial Sequence
<220> FEATURE:
<223> OTHER INFORMATION: Synthetic peptide

<400> SEQUENCE: 657

Val Arg Asp Thr Ile Gly Leu Trp Gly Pro Gly Thr Leu Val Thr Val
1               5                   10                  15

Ser Ser Gly Gln Pro Lys
            20

<210> SEQ ID NO 658
<211> LENGTH: 20
<212> TYPE: PRT
<213> ORGANISM: Artificial Sequence
<220> FEATURE:
<223> OTHER INFORMATION: Synthetic peptide

<400> SEQUENCE: 658

Asp Thr Ile Gly Leu Trp Gly Pro Gly Thr Leu Val Thr Val Ser Ser
1               5                   10                  15

Gly Gln Pro Lys
            20

<210> SEQ ID NO 659
<211> LENGTH: 27
<212> TYPE: PRT
<213> ORGANISM: Artificial Sequence
<220> FEATURE:
<223> OTHER INFORMATION: Synthetic peptide

<400> SEQUENCE: 659

Ala Arg Gly Gly Asn Pro Asn Tyr Asp Tyr Gly Leu Gly Gly Pro Gly
1               5                   10                  15

Thr Leu Val Thr Val Ser Ser Gly Gln Pro Lys
            20                  25

<210> SEQ ID NO 660

```
<211> LENGTH: 25
<212> TYPE: PRT
<213> ORGANISM: Artificial Sequence
<220> FEATURE:
<223> OTHER INFORMATION: Synthetic peptide

<400> SEQUENCE: 660

Gly Gly Asn Pro Asn Tyr Asp Tyr Gly Leu Gly Gly Pro Gly Thr Leu
1               5                   10                  15
Val Thr Val Ser Ser Gly Gln Pro Lys
            20                  25

<210> SEQ ID NO 661
<211> LENGTH: 26
<212> TYPE: PRT
<213> ORGANISM: Artificial Sequence
<220> FEATURE:
<223> OTHER INFORMATION: Synthetic peptide

<400> SEQUENCE: 661

Ala Arg Glu Phe Trp Ala Ser Thr Thr Ile Leu Trp Gly Pro Gly Thr
1               5                   10                  15
Leu Val Thr Val Ser Ser Gly Gln Pro Lys
            20                  25

<210> SEQ ID NO 662
<211> LENGTH: 24
<212> TYPE: PRT
<213> ORGANISM: Artificial Sequence
<220> FEATURE:
<223> OTHER INFORMATION: Synthetic peptide

<400> SEQUENCE: 662

Glu Phe Trp Ala Ser Thr Thr Ile Leu Trp Gly Pro Gly Thr Leu Val
1               5                   10                  15
Thr Val Ser Ser Gly Gln Pro Lys
            20

<210> SEQ ID NO 663
<211> LENGTH: 25
<212> TYPE: PRT
<213> ORGANISM: Artificial Sequence
<220> FEATURE:
<223> OTHER INFORMATION: Synthetic peptide

<400> SEQUENCE: 663

Ala Arg Glu Phe Gly Arg Ser Arg Asn Leu Trp Gly Pro Gly Thr Leu
1               5                   10                  15
Val Thr Val Ser Ser Gly Gln Pro Lys
            20                  25

<210> SEQ ID NO 664
<211> LENGTH: 23
<212> TYPE: PRT
<213> ORGANISM: Artificial Sequence
<220> FEATURE:
<223> OTHER INFORMATION: Synthetic peptide

<400> SEQUENCE: 664

Glu Phe Gly Arg Ser Arg Asn Leu Trp Gly Pro Gly Thr Leu Val Thr
1               5                   10                  15
Val Ser Ser Gly Gln Pro Lys
            20
```

-continued

```
<210> SEQ ID NO 665
<211> LENGTH: 18
<212> TYPE: PRT
<213> ORGANISM: Artificial Sequence
<220> FEATURE:
<223> OTHER INFORMATION: Synthetic peptide

<400> SEQUENCE: 665

Leu Asp Leu Trp Gly Gln Gly Thr Leu Val Thr Val Ser Ser Gly Gln
1               5                   10                  15

Pro Lys

<210> SEQ ID NO 666
<211> LENGTH: 18
<212> TYPE: PRT
<213> ORGANISM: Artificial Sequence
<220> FEATURE:
<223> OTHER INFORMATION: Synthetic peptide

<400> SEQUENCE: 666

Phe Asn Leu Trp Gly Pro Gly Thr Leu Val Thr Val Ser Ser Gly Gln
1               5                   10                  15

Pro Lys

<210> SEQ ID NO 667
<211> LENGTH: 19
<212> TYPE: PRT
<213> ORGANISM: Artificial Sequence
<220> FEATURE:
<223> OTHER INFORMATION: Synthetic peptide

<400> SEQUENCE: 667

Ala Phe Asp Pro Trp Gly Pro Gly Thr Leu Val Thr Val Ser Ser Gly
1               5                   10                  15

Gln Pro Lys

<210> SEQ ID NO 668
<211> LENGTH: 19
<212> TYPE: PRT
<213> ORGANISM: Artificial Sequence
<220> FEATURE:
<223> OTHER INFORMATION: Synthetic peptide

<400> SEQUENCE: 668

Phe Ile Asp Leu Trp Gly Pro Gly Thr Leu Val Thr Val Ser Ser Gly
1               5                   10                  15

Gln Pro Lys

<210> SEQ ID NO 669
<211> LENGTH: 17
<212> TYPE: PRT
<213> ORGANISM: Artificial Sequence
<220> FEATURE:
<223> OTHER INFORMATION: Synthetic peptide

<400> SEQUENCE: 669

Asn Leu Trp Gly Pro Gly Thr Leu Val Thr Val Ser Ser Gly Gln Pro
1               5                   10                  15

Lys

<210> SEQ ID NO 670
<211> LENGTH: 19
<212> TYPE: PRT
<213> ORGANISM: Artificial Sequence
```

<220> FEATURE:
<223> OTHER INFORMATION: Synthetic peptide

<400> SEQUENCE: 670

Ser Gln Asn Leu Trp Gly Pro Gly Thr Leu Val Thr Val Ser Ser Gly
1               5                   10                  15

Gln Pro Lys

<210> SEQ ID NO 671
<211> LENGTH: 24
<212> TYPE: PRT
<213> ORGANISM: Artificial Sequence
<220> FEATURE:
<223> OTHER INFORMATION: Synthetic peptide

<400> SEQUENCE: 671

Gly Gly Pro Ile His Tyr Ser Asn Leu Trp Gly Pro Gly Thr Leu Val
1               5                   10                  15

Thr Val Ser Ser Gly Gln Pro Lys
            20

<210> SEQ ID NO 672
<211> LENGTH: 18
<212> TYPE: PRT
<213> ORGANISM: Artificial Sequence
<220> FEATURE:
<223> OTHER INFORMATION: Synthetic peptide

<400> SEQUENCE: 672

Gly Asp Leu Trp Gly Pro Gly Thr Leu Val Thr Val Ser Ser Gly Gln
1               5                   10                  15

Pro Lys

<210> SEQ ID NO 673
<211> LENGTH: 19
<212> TYPE: PRT
<213> ORGANISM: Artificial Sequence
<220> FEATURE:
<223> OTHER INFORMATION: Synthetic peptide

<400> SEQUENCE: 673

Gly Met Asp Leu Trp Gly Pro Gly Thr Leu Val Thr Val Ser Ser Gly
1               5                   10                  15

Gln Pro Lys

<210> SEQ ID NO 674
<211> LENGTH: 19
<212> TYPE: PRT
<213> ORGANISM: Artificial Sequence
<220> FEATURE:
<223> OTHER INFORMATION: Synthetic peptide

<400> SEQUENCE: 674

Phe Phe Asn Leu Trp Gly Pro Gly Thr Leu Val Thr Val Ser Ser Gly
1               5                   10                  15

Gln Pro Lys

<210> SEQ ID NO 675
<211> LENGTH: 15
<212> TYPE: PRT
<213> ORGANISM: Artificial Sequence
<220> FEATURE:
<223> OTHER INFORMATION: Synthetic peptide -continued

<400> SEQUENCE: 675

Trp Gly Pro Gly Thr Leu Val Thr Val Ser Ser Gly Gln Pro Lys
1               5                   10                  15

<210> SEQ ID NO 676
<211> LENGTH: 19
<212> TYPE: PRT
<213> ORGANISM: Artificial Sequence
<220> FEATURE:
<223> OTHER INFORMATION: Synthetic peptide

<400> SEQUENCE: 676

Ser Phe Asn Leu Trp Gly Pro Gly Thr Leu Val Thr Val Ser Ser Gly
1               5                   10                  15

Gln Pro Lys

<210> SEQ ID NO 677
<211> LENGTH: 18
<212> TYPE: PRT
<213> ORGANISM: Artificial Sequence
<220> FEATURE:
<223> OTHER INFORMATION: Synthetic peptide

<400> SEQUENCE: 677

Phe Asp Leu Trp Gly Pro Gly Thr Leu Val Thr Val Ser Ser Gly Gln
1               5                   10                  15

Pro Lys

<210> SEQ ID NO 678
<211> LENGTH: 19
<212> TYPE: PRT
<213> ORGANISM: Artificial Sequence
<220> FEATURE:
<223> OTHER INFORMATION: Synthetic peptide

<400> SEQUENCE: 678

His Phe Asn Leu Trp Gly Pro Gly Thr Leu Val Thr Val Ser Ser Gly
1               5                   10                  15

Gln Pro Lys

<210> SEQ ID NO 679
<211> LENGTH: 19
<212> TYPE: PRT
<213> ORGANISM: Artificial Sequence
<220> FEATURE:
<223> OTHER INFORMATION: Synthetic peptide

<400> SEQUENCE: 679

Asp Tyr Phe Leu Trp Gly Pro Gly Thr Leu Val Thr Val Ser Ser Gly
1               5                   10                  15

Gln Pro Lys

<210> SEQ ID NO 680
<211> LENGTH: 19
<212> TYPE: PRT
<213> ORGANISM: Artificial Sequence
<220> FEATURE:
<223> OTHER INFORMATION: Synthetic peptide

<400> SEQUENCE: 680

Asp Trp Gly Leu Trp Gly Pro Gly Thr Leu Val Thr Val Ser Ser Gly
1               5                   10                  15

Gln Pro Lys

<210> SEQ ID NO 681
<211> LENGTH: 19
<212> TYPE: PRT
<213> ORGANISM: Artificial Sequence
<220> FEATURE:
<223> OTHER INFORMATION: Synthetic peptide

<400> SEQUENCE: 681

Gly Val Gly Leu Trp Gly Pro Gly Thr Leu Val Thr Val Ser Ser Gly
1               5                   10                  15

Gln Pro Lys

<210> SEQ ID NO 682
<211> LENGTH: 20
<212> TYPE: PRT
<213> ORGANISM: Artificial Sequence
<220> FEATURE:
<223> OTHER INFORMATION: Synthetic peptide

<400> SEQUENCE: 682

Gly Phe Phe Asn Leu Trp Gly Pro Gly Thr Leu Val Thr Val Ser Ser
1               5                   10                  15

Gly Gln Pro Lys
            20

<210> SEQ ID NO 683
<211> LENGTH: 19
<212> TYPE: PRT
<213> ORGANISM: Artificial Sequence
<220> FEATURE:
<223> OTHER INFORMATION: Synthetic peptide

<400> SEQUENCE: 683

Ser Ser Leu Leu Trp Gly Pro Gly Thr Leu Val Thr Val Ser Ser Gly
1               5                   10                  15

Gln Pro Lys

<210> SEQ ID NO 684
<211> LENGTH: 17
<212> TYPE: PRT
<213> ORGANISM: Artificial Sequence
<220> FEATURE:
<223> OTHER INFORMATION: Synthetic peptide

<400> SEQUENCE: 684

Tyr Leu Trp Gly Pro Gly Thr Leu Val Thr Val Ser Ser Gly Gln Pro
1               5                   10                  15

Lys

<210> SEQ ID NO 685
<211> LENGTH: 19
<212> TYPE: PRT
<213> ORGANISM: Artificial Sequence
<220> FEATURE:
<223> OTHER INFORMATION: Synthetic peptide

<400> SEQUENCE: 685

Tyr Phe Ser Leu Trp Gly Pro Gly Thr Leu Val Thr Val Ser Ser Gly
1               5                   10                  15

Gln Pro Lys

<210> SEQ ID NO 686

<211> LENGTH: 21
<212> TYPE: PRT
<213> ORGANISM: Artificial Sequence
<220> FEATURE:
<223> OTHER INFORMATION: Synthetic peptide

<400> SEQUENCE: 686

Tyr Ala Pro Phe Asn Leu Trp Gly Pro Gly Thr Leu Val Thr Val Ser
1               5                   10                  15

Ser Gly Gln Pro Lys
            20

<210> SEQ ID NO 687
<211> LENGTH: 18
<212> TYPE: PRT
<213> ORGANISM: Artificial Sequence
<220> FEATURE:
<223> OTHER INFORMATION: Synthetic peptide

<400> SEQUENCE: 687

Phe Asn Phe Trp Gly Pro Gly Thr Leu Val Thr Val Ser Ser Gly Gln
1               5                   10                  15

Pro Lys

<210> SEQ ID NO 688
<211> LENGTH: 19
<212> TYPE: PRT
<213> ORGANISM: Artificial Sequence
<220> FEATURE:
<223> OTHER INFORMATION: Synthetic peptide

<400> SEQUENCE: 688

Ser Tyr Ile Leu Trp Gly Pro Gly Thr Leu Val Thr Val Ser Ser Gly
1               5                   10                  15

Gln Pro Lys

<210> SEQ ID NO 689
<211> LENGTH: 19
<212> TYPE: PRT
<213> ORGANISM: Artificial Sequence
<220> FEATURE:
<223> OTHER INFORMATION: Synthetic peptide

<400> SEQUENCE: 689

Gly Phe Asn Leu Trp Gly Pro Gly Thr Leu Val Thr Val Ser Ser Gly
1               5                   10                  15

Gln Pro Lys

<210> SEQ ID NO 690
<211> LENGTH: 18
<212> TYPE: PRT
<213> ORGANISM: Artificial Sequence
<220> FEATURE:
<223> OTHER INFORMATION: Synthetic peptide

<400> SEQUENCE: 690

Phe Asp Phe Trp Gly Pro Gly Thr Leu Val Thr Val Ser Ser Gly Gln
1               5                   10                  15

Pro Lys

<210> SEQ ID NO 691
<211> LENGTH: 19
<212> TYPE: PRT
<213> ORGANISM: Artificial Sequence
<220> FEATURE:
<223> OTHER INFORMATION: Synthetic peptide

<400> SEQUENCE: 691

Asp Leu Gly Leu Trp Gly Pro Gly Thr Leu Val Thr Val Ser Ser Gly
1               5                   10                  15

Gln Pro Lys

<210> SEQ ID NO 692
<211> LENGTH: 16
<212> TYPE: PRT
<213> ORGANISM: Artificial Sequence
<220> FEATURE:
<223> OTHER INFORMATION: Synthetic peptide

<400> SEQUENCE: 692

Leu Trp Gly Pro Gly Thr Val Val Thr Val Ser Ser Gly Gln Pro Lys
1               5                   10                  15

<210> SEQ ID NO 693
<211> LENGTH: 16
<212> TYPE: PRT
<213> ORGANISM: Artificial Sequence
<220> FEATURE:
<223> OTHER INFORMATION: Synthetic peptide

<400> SEQUENCE: 693

Leu Trp Gly Pro Gly Thr Leu Val Thr Val Ser Ala Gly Gln Pro Lys
1               5                   10                  15

<210> SEQ ID NO 694
<211> LENGTH: 19
<212> TYPE: PRT
<213> ORGANISM: Artificial Sequence
<220> FEATURE:
<223> OTHER INFORMATION: Synthetic peptide

<400> SEQUENCE: 694

Tyr Phe Thr Leu Trp Gly Pro Gly Thr Leu Val Thr Val Ser Ser Gly
1               5                   10                  15

Gln Pro Lys

<210> SEQ ID NO 695
<211> LENGTH: 17
<212> TYPE: PRT
<213> ORGANISM: Artificial Sequence
<220> FEATURE:
<223> OTHER INFORMATION: Synthetic peptide

<400> SEQUENCE: 695

Asp Leu Trp Gly Pro Gly Thr Leu Val Thr Val Ser Ser Gly Gln Pro
1               5                   10                  15

Lys

<210> SEQ ID NO 696
<211> LENGTH: 19
<212> TYPE: PRT
<213> ORGANISM: Artificial Sequence
<220> FEATURE:
<223> OTHER INFORMATION: Synthetic peptide

<400> SEQUENCE: 696

Leu Phe Asn Leu Trp Gly Pro Gly Thr Leu Val Thr Val Ser Ser Gly
1               5                   10                  15

Gln Pro Lys

<210> SEQ ID NO 697
<211> LENGTH: 19
<212> TYPE: PRT
<213> ORGANISM: Artificial Sequence
<220> FEATURE:
<223> OTHER INFORMATION: Synthetic peptide

<400> SEQUENCE: 697

Glu Cys Gly Leu Trp Gly Pro Gly Thr Leu Val Thr Val Ser Ser Gly
1               5                   10                  15

Gln Pro Lys

<210> SEQ ID NO 698
<211> LENGTH: 19
<212> TYPE: PRT
<213> ORGANISM: Artificial Sequence
<220> FEATURE:
<223> OTHER INFORMATION: Synthetic peptide

<400> SEQUENCE: 698

Asp Tyr Asp Leu Trp Gly Pro Gly Thr Leu Val Thr Val Ser Ser Gly
1               5                   10                  15

Gln Pro Lys

<210> SEQ ID NO 699
<211> LENGTH: 23
<212> TYPE: PRT
<213> ORGANISM: Artificial Sequence
<220> FEATURE:
<223> OTHER INFORMATION: Synthetic peptide

<400> SEQUENCE: 699

Ala Asp Gly Gly Thr Tyr Asn Leu Trp Gly Pro Gly Thr Leu Val Thr
1               5                   10                  15

Val Ser Ser Gly Gln Pro Lys
            20

<210> SEQ ID NO 700
<211> LENGTH: 19
<212> TYPE: PRT
<213> ORGANISM: Artificial Sequence
<220> FEATURE:
<223> OTHER INFORMATION: Synthetic peptide

<400> SEQUENCE: 700

Ala Phe Asn Leu Trp Gly Pro Gly Thr Leu Val Thr Val Ser Ser Gly
1               5                   10                  15

Gln Pro Lys

<210> SEQ ID NO 701
<211> LENGTH: 19
<212> TYPE: PRT
<213> ORGANISM: Artificial Sequence
<220> FEATURE:
<223> OTHER INFORMATION: Synthetic peptide

<400> SEQUENCE: 701

Val Phe Asn Leu Trp Gly Pro Gly Thr Leu Val Thr Val Ser Ser Gly
1               5                   10                  15

Gln Pro Lys

```
<210> SEQ ID NO 702
<211> LENGTH: 27
<212> TYPE: PRT
<213> ORGANISM: Artificial Sequence
<220> FEATURE:
<223> OTHER INFORMATION: Synthetic peptide

<400> SEQUENCE: 702

Thr Gly Tyr Ile Gly Asp Gly Tyr Pro Phe Asn Leu Trp Gly Pro Gly
1               5                   10                  15

Thr Leu Val Thr Val Ser Ser Gly Gln Pro Lys
            20                  25

<210> SEQ ID NO 703
<211> LENGTH: 22
<212> TYPE: PRT
<213> ORGANISM: Artificial Sequence
<220> FEATURE:
<223> OTHER INFORMATION: Synthetic peptide

<400> SEQUENCE: 703

Glu Gly Ile Tyr Phe Asp Leu Trp Gly Pro Gly Thr Leu Val Thr Val
1               5                   10                  15

Ser Ser Gly Gln Pro Lys
            20

<210> SEQ ID NO 704
<211> LENGTH: 22
<212> TYPE: PRT
<213> ORGANISM: Artificial Sequence
<220> FEATURE:
<223> OTHER INFORMATION: Synthetic peptide

<400> SEQUENCE: 704

Ser Tyr Gly Ala Ser Asp Leu Trp Gly Pro Gly Thr Leu Val Thr Val
1               5                   10                  15

Ser Ser Gly Gln Pro Lys
            20

<210> SEQ ID NO 705
<211> LENGTH: 20
<212> TYPE: PRT
<213> ORGANISM: Artificial Sequence
<220> FEATURE:
<223> OTHER INFORMATION: Synthetic peptide

<400> SEQUENCE: 705

Tyr Ala Phe Asp Pro Trp Gly Pro Gly Thr Leu Val Thr Val Ser Ser
1               5                   10                  15

Gly Gln Pro Lys
            20

<210> SEQ ID NO 706
<211> LENGTH: 19
<212> TYPE: PRT
<213> ORGANISM: Artificial Sequence
<220> FEATURE:
<223> OTHER INFORMATION: Synthetic peptide

<400> SEQUENCE: 706

Asn Tyr Asn Leu Trp Gly Pro Gly Thr Leu Val Thr Val Ser Ser Gly
1               5                   10                  15

Gln Pro Lys
```

```
<210> SEQ ID NO 707
<211> LENGTH: 19
<212> TYPE: PRT
<213> ORGANISM: Artificial Sequence
<220> FEATURE:
<223> OTHER INFORMATION: Synthetic peptide

<400> SEQUENCE: 707

Asn Phe Gly Leu Trp Gly Pro Gly Thr Leu Val Thr Val Ser Ser Gly
1               5                   10                  15

Gln Pro Lys

<210> SEQ ID NO 708
<211> LENGTH: 17
<212> TYPE: PRT
<213> ORGANISM: Artificial Sequence
<220> FEATURE:
<223> OTHER INFORMATION: Synthetic peptide

<400> SEQUENCE: 708

Asp Leu Trp Gly Gln Gly Thr Leu Val Thr Val Ser Ser Gly Gln Pro
1               5                   10                  15

Lys

<210> SEQ ID NO 709
<211> LENGTH: 20
<212> TYPE: PRT
<213> ORGANISM: Artificial Sequence
<220> FEATURE:
<223> OTHER INFORMATION: Synthetic peptide

<400> SEQUENCE: 709

Asp Ser Gly Tyr Leu Trp Gly Pro Gly Thr Leu Val Thr Val Ser Ser
1               5                   10                  15

Gly Gln Pro Lys
            20

<210> SEQ ID NO 710
<211> LENGTH: 23
<212> TYPE: PRT
<213> ORGANISM: Artificial Sequence
<220> FEATURE:
<223> OTHER INFORMATION: Synthetic peptide

<400> SEQUENCE: 710

Asp Gly Ser Val Asp Tyr Asp Leu Trp Gly Pro Gly Thr Leu Val Thr
1               5                   10                  15

Val Ser Ser Gly Gln Pro Lys
            20

<210> SEQ ID NO 711
<211> LENGTH: 27
<212> TYPE: PRT
<213> ORGANISM: Artificial Sequence
<220> FEATURE:
<223> OTHER INFORMATION: Synthetic peptide

<400> SEQUENCE: 711

Ser Ala Asp Gly Ser Ser Ala Ser Gly Met His Leu Trp Gly Pro Gly
1               5                   10                  15

Thr Leu Val Thr Val Ser Ser Gly Gln Pro Lys
            20                  25

<210> SEQ ID NO 712
```

-continued

```
<211> LENGTH: 25
<212> TYPE: PRT
<213> ORGANISM: Artificial Sequence
<220> FEATURE:
<223> OTHER INFORMATION: Synthetic peptide

<400> SEQUENCE: 712

Asn Ile Cys Pro Ser Thr Asp Ile Asn Leu Trp Gly Pro Gly Thr Leu
1               5                   10                  15

Val Thr Val Ser Ser Gly Gln Pro Lys
            20                  25

<210> SEQ ID NO 713
<211> LENGTH: 21
<212> TYPE: PRT
<213> ORGANISM: Artificial Sequence
<220> FEATURE:
<223> OTHER INFORMATION: Synthetic peptide

<400> SEQUENCE: 713

Ser Tyr Ala Pro Thr Leu Trp Gly Pro Gly Thr Leu Val Thr Val Ser
1               5                   10                  15

Ser Gly Gln Pro Lys
            20

<210> SEQ ID NO 714
<211> LENGTH: 19
<212> TYPE: PRT
<213> ORGANISM: Artificial Sequence
<220> FEATURE:
<223> OTHER INFORMATION: Synthetic peptide

<400> SEQUENCE: 714

Gln Tyr Leu Leu Trp Gly Pro Gly Thr Leu Val Thr Val Ser Ser Gly
1               5                   10                  15

Gln Pro Lys

<210> SEQ ID NO 715
<211> LENGTH: 19
<212> TYPE: PRT
<213> ORGANISM: Artificial Sequence
<220> FEATURE:
<223> OTHER INFORMATION: Synthetic peptide

<400> SEQUENCE: 715

Asp Phe Asn Leu Trp Gly Pro Gly Thr Leu Val Thr Val Ser Ser Gly
1               5                   10                  15

Gln Pro Lys

<210> SEQ ID NO 716
<211> LENGTH: 20
<212> TYPE: PRT
<213> ORGANISM: Artificial Sequence
<220> FEATURE:
<223> OTHER INFORMATION: Synthetic peptide

<400> SEQUENCE: 716

Tyr Phe Met Asp Leu Trp Gly Pro Gly Thr Leu Val Thr Val Ser Ser
1               5                   10                  15

Gly Gln Pro Lys
            20

<210> SEQ ID NO 717
<211> LENGTH: 19
```

```
<212> TYPE: PRT
<213> ORGANISM: Artificial Sequence
<220> FEATURE:
<223> OTHER INFORMATION: Synthetic peptide

<400> SEQUENCE: 717

Asn Gly Gly Leu Trp Gly Pro Gly Thr Leu Val Thr Val Ser Ser Gly
1               5                   10                  15

Gln Pro Lys

<210> SEQ ID NO 718
<211> LENGTH: 7
<212> TYPE: PRT
<213> ORGANISM: Artificial Sequence
<220> FEATURE:
<223> OTHER INFORMATION: Synthetic peptide

<400> SEQUENCE: 718

Leu Tyr Asp Tyr Asp His Tyr
1               5

<210> SEQ ID NO 719
<211> LENGTH: 10
<212> TYPE: PRT
<213> ORGANISM: Artificial Sequence
<220> FEATURE:
<223> OTHER INFORMATION: Synthetic peptide

<400> SEQUENCE: 719

Ala Gly Asp Tyr Tyr Ser Met Asp Tyr
1               5                   10

<210> SEQ ID NO 720
<211> LENGTH: 13
<212> TYPE: PRT
<213> ORGANISM: Artificial Sequence
<220> FEATURE:
<223> OTHER INFORMATION: Synthetic peptide

<400> SEQUENCE: 720

Asp Pro Leu Tyr Tyr Gly Gly Arg Tyr Ala Met Asp Tyr
1               5                   10

<210> SEQ ID NO 721
<211> LENGTH: 7
<212> TYPE: PRT
<213> ORGANISM: Artificial Sequence
<220> FEATURE:
<223> OTHER INFORMATION: Synthetic peptide

<400> SEQUENCE: 721

Tyr Asp Tyr Tyr Phe Asp Tyr
1               5

<210> SEQ ID NO 722
<211> LENGTH: 9
<212> TYPE: PRT
<213> ORGANISM: Artificial Sequence
<220> FEATURE:
<223> OTHER INFORMATION: Synthetic peptide

<400> SEQUENCE: 722

Tyr Gly Ser Arg Tyr Tyr Phe Asp Tyr
1               5

<210> SEQ ID NO 723
```

```
<211> LENGTH: 5
<212> TYPE: PRT
<213> ORGANISM: Artificial Sequence
<220> FEATURE:
<223> OTHER INFORMATION: Synthetic peptide

<400> SEQUENCE: 723

Asp Gly Phe Ala Tyr
1               5

<210> SEQ ID NO 724
<211> LENGTH: 10
<212> TYPE: PRT
<213> ORGANISM: Artificial Sequence
<220> FEATURE:
<223> OTHER INFORMATION: Synthetic peptide

<400> SEQUENCE: 724

Asp Gly Ser Ser Tyr Trp Tyr Phe Asp Tyr
1               5                   10

<210> SEQ ID NO 725
<211> LENGTH: 11
<212> TYPE: PRT
<213> ORGANISM: Artificial Sequence
<220> FEATURE:
<223> OTHER INFORMATION: Synthetic peptide

<400> SEQUENCE: 725

Leu Leu Tyr Asp Phe Arg Asp Tyr Phe Asp Tyr
1               5                   10

<210> SEQ ID NO 726
<211> LENGTH: 12
<212> TYPE: PRT
<213> ORGANISM: Artificial Sequence
<220> FEATURE:
<223> OTHER INFORMATION: Synthetic peptide

<400> SEQUENCE: 726

Asp Tyr Tyr Gly Ser Ser Tyr Trp Tyr Phe Asp Val
1               5                   10

<210> SEQ ID NO 727
<211> LENGTH: 9
<212> TYPE: PRT
<213> ORGANISM: Artificial Sequence
<220> FEATURE:
<223> OTHER INFORMATION: Synthetic peptide

<400> SEQUENCE: 727

Gln Asp Tyr Gly Asn Tyr Phe Asp Tyr
1               5

<210> SEQ ID NO 728
<211> LENGTH: 12
<212> TYPE: PRT
<213> ORGANISM: Artificial Sequence
<220> FEATURE:
<223> OTHER INFORMATION: Synthetic peptide

<400> SEQUENCE: 728

Gln Gly Tyr Asp Tyr Asp Pro Tyr Ala Met Asp Tyr
1               5                   10

<210> SEQ ID NO 729
<211> LENGTH: 11
```

```
<212> TYPE: PRT
<213> ORGANISM: Artificial Sequence
<220> FEATURE:
<223> OTHER INFORMATION: Synthetic peptide

<400> SEQUENCE: 729

Glu Asp Tyr Gly Asn Tyr Trp Tyr Phe Asp Val
1               5                   10

<210> SEQ ID NO 730
<211> LENGTH: 9
<212> TYPE: PRT
<213> ORGANISM: Artificial Sequence
<220> FEATURE:
<223> OTHER INFORMATION: Synthetic peptide

<400> SEQUENCE: 730

Glu Gly Asn Tyr Gly Ala Met Asp Tyr
1               5

<210> SEQ ID NO 731
<211> LENGTH: 6
<212> TYPE: PRT
<213> ORGANISM: Artificial Sequence
<220> FEATURE:
<223> OTHER INFORMATION: Synthetic peptide

<400> SEQUENCE: 731

Tyr Arg Thr Met Asp Tyr
1               5

<210> SEQ ID NO 732
<211> LENGTH: 8
<212> TYPE: PRT
<213> ORGANISM: Artificial Sequence
<220> FEATURE:
<223> OTHER INFORMATION: Synthetic peptide

<400> SEQUENCE: 732

Tyr Gly Asn Tyr Tyr Phe Asp Tyr
1               5

<210> SEQ ID NO 733
<211> LENGTH: 12
<212> TYPE: PRT
<213> ORGANISM: Artificial Sequence
<220> FEATURE:
<223> OTHER INFORMATION: Synthetic peptide

<400> SEQUENCE: 733

Gly Thr Pro Phe Glu Gly Leu Arg Arg Ala Asp Tyr
1               5                   10

<210> SEQ ID NO 734
<211> LENGTH: 11
<212> TYPE: PRT
<213> ORGANISM: Artificial Sequence
<220> FEATURE:
<223> OTHER INFORMATION: Synthetic peptide

<400> SEQUENCE: 734

Ala Tyr Tyr Tyr Gly Ser Ser Ser Phe Ala Tyr
1               5                   10

<210> SEQ ID NO 735
<211> LENGTH: 9
<212> TYPE: PRT
```

<210> SEQ ID NO 735
<211> LENGTH: 8
<212> TYPE: PRT
<213> ORGANISM: Artificial Sequence
<220> FEATURE:
<223> OTHER INFORMATION: Synthetic peptide

<400> SEQUENCE: 735

Thr Ser Tyr Glu Asn Tyr Phe Asp Tyr
1               5

<210> SEQ ID NO 736
<211> LENGTH: 10
<212> TYPE: PRT
<213> ORGANISM: Artificial Sequence
<220> FEATURE:
<223> OTHER INFORMATION: Synthetic peptide

<400> SEQUENCE: 736

Ala Gly Asp Tyr Tyr Tyr Ala Met Asp Tyr
1               5                   10

<210> SEQ ID NO 737
<211> LENGTH: 11
<212> TYPE: PRT
<213> ORGANISM: Artificial Sequence
<220> FEATURE:
<223> OTHER INFORMATION: Synthetic peptide

<400> SEQUENCE: 737

His Tyr Tyr Gly Ser Ser Trp Tyr Phe Asp Val
1               5                   10

<210> SEQ ID NO 738
<211> LENGTH: 21
<212> TYPE: DNA
<213> ORGANISM: Artificial Sequence
<220> FEATURE:
<223> OTHER INFORMATION: Synthetic primer

<400> SEQUENCE: 738
ctttatgatt acgaccacta c                                            21

<210> SEQ ID NO 739
<211> LENGTH: 30
<212> TYPE: DNA
<213> ORGANISM: Artificial Sequence
<220> FEATURE:
<223> OTHER INFORMATION: Synthetic primer

<400> SEQUENCE: 739
gcgggggatt attactattc tatggactac                                   30

<210> SEQ ID NO 740
<211> LENGTH: 30
<212> TYPE: DNA
<213> ORGANISM: Artificial Sequence
<220> FEATURE:
<223> OTHER INFORMATION: Synthetic primer

<400> SEQUENCE: 740
gatccccttt actacggtgg taggtatgct                                   30

<210> SEQ ID NO 741
<211> LENGTH: 21
<212> TYPE: DNA
<213> ORGANISM: Artificial Sequence
<220> FEATURE:
<223> OTHER INFORMATION: Synthetic primer

```
<400> SEQUENCE: 741
tatgattact actttgacta c                                           21

<210> SEQ ID NO 742
<211> LENGTH: 27
<212> TYPE: DNA
<213> ORGANISM: Artificial Sequence
<220> FEATURE:
<223> OTHER INFORMATION: Synthetic primer

<400> SEQUENCE: 742
tacggtagta ggtactactt tgactac                                     27

<210> SEQ ID NO 743
<211> LENGTH: 15
<212> TYPE: DNA
<213> ORGANISM: Artificial Sequence
<220> FEATURE:
<223> OTHER INFORMATION: Synthetic primer

<400> SEQUENCE: 743
gatgggtttg cttac                                                  15

<210> SEQ ID NO 744
<211> LENGTH: 30
<212> TYPE: DNA
<213> ORGANISM: Artificial Sequence
<220> FEATURE:
<223> OTHER INFORMATION: Synthetic primer

<400> SEQUENCE: 744
gacggtagta gctactggta cttcgatgtc                                  30

<210> SEQ ID NO 745
<211> LENGTH: 31
<212> TYPE: DNA
<213> ORGANISM: Artificial Sequence
<220> FEATURE:
<223> OTHER INFORMATION: Synthetic primer

<400> SEQUENCE: 745
cttctctatg atttcaggga ctactttgac t                                31

<210> SEQ ID NO 746
<211> LENGTH: 30
<212> TYPE: DNA
<213> ORGANISM: Artificial Sequence
<220> FEATURE:
<223> OTHER INFORMATION: Synthetic primer

<400> SEQUENCE: 746
gattactacg gtagtagcta ctggtacttc                                  30

<210> SEQ ID NO 747
<211> LENGTH: 27
<212> TYPE: DNA
<213> ORGANISM: Artificial Sequence
<220> FEATURE:
<223> OTHER INFORMATION: Synthetic primer

<400> SEQUENCE: 747
caggactacg gaaactactt tgactac                                     27

<210> SEQ ID NO 748
<211> LENGTH: 30
```

```
<212> TYPE: DNA
<213> ORGANISM: Artificial Sequence
<220> FEATURE:
<223> OTHER INFORMATION: Synthetic primer

<400> SEQUENCE: 748
cagggctatg attacgatcc ttatgctatg                              30

<210> SEQ ID NO 749
<211> LENGTH: 30
<212> TYPE: DNA
<213> ORGANISM: Artificial Sequence
<220> FEATURE:
<223> OTHER INFORMATION: Synthetic primer

<400> SEQUENCE: 749
gaggactatg gtaactactg gtacttcgat                              30

<210> SEQ ID NO 750
<211> LENGTH: 27
<212> TYPE: DNA
<213> ORGANISM: Artificial Sequence
<220> FEATURE:
<223> OTHER INFORMATION: Synthetic primer

<400> SEQUENCE: 750
gaaggtaact acggggctat ggactac                                 27

<210> SEQ ID NO 751
<211> LENGTH: 18
<212> TYPE: DNA
<213> ORGANISM: Artificial Sequence
<220> FEATURE:
<223> OTHER INFORMATION: Synthetic primer

<400> SEQUENCE: 751
tacaggacta tggactac                                           18

<210> SEQ ID NO 752
<211> LENGTH: 24
<212> TYPE: DNA
<213> ORGANISM: Artificial Sequence
<220> FEATURE:
<223> OTHER INFORMATION: Synthetic primer

<400> SEQUENCE: 752
tatggtaact actactttga ctac                                    24

<210> SEQ ID NO 753
<211> LENGTH: 29
<212> TYPE: DNA
<213> ORGANISM: Artificial Sequence
<220> FEATURE:
<223> OTHER INFORMATION: Synthetic primer

<400> SEQUENCE: 753
gggacccctt tcgagggggtt acgacgtgc                              29

<210> SEQ ID NO 754
<211> LENGTH: 31
<212> TYPE: DNA
<213> ORGANISM: Artificial Sequence
<220> FEATURE:
<223> OTHER INFORMATION: Synthetic primer

<400> SEQUENCE: 754
```

-continued gcttattact acggtagtag ctcctttgct t    31

<210> SEQ ID NO 755
<211> LENGTH: 27
<212> TYPE: DNA
<213> ORGANISM: Artificial Sequence
<220> FEATURE:
<223> OTHER INFORMATION: Synthetic primer

<400> SEQUENCE: 755
acgagctatg agaactactt tgactac    27

<210> SEQ ID NO 756
<211> LENGTH: 30
<212> TYPE: DNA
<213> ORGANISM: Artificial Sequence
<220> FEATURE:
<223> OTHER INFORMATION: Synthetic primer

<400> SEQUENCE: 756
gcgggggatt attactatgc tatggactac    30

<210> SEQ ID NO 757
<211> LENGTH: 30
<212> TYPE: DNA
<213> ORGANISM: Artificial Sequence
<220> FEATURE:
<223> OTHER INFORMATION: Synthetic primer

<400> SEQUENCE: 757
cattactacg gtagtagctg gtacttcgat    30

<210> SEQ ID NO 758
<211> LENGTH: 111
<212> TYPE: PRT
<213> ORGANISM: Artificial Sequence
<220> FEATURE:
<223> OTHER INFORMATION: Synthetic peptide

<400> SEQUENCE: 758

Glu Val Lys Leu Val Glu Ser Gly Gly Gly Phe Val Lys Pro Gly Gly
1               5                   10                  15

Ser Leu Lys Leu Ser Cys Ala Ala Ser Gly Phe Thr Phe Ser Thr Tyr
            20                  25                  30

Gly Met Ser Trp Val Arg Gln Thr Pro Glu Lys Arg Leu Glu Trp Val
        35                  40                  45

Ala Ser Ile Ser Ala Gly Gly Thr Thr Tyr Tyr Ser Asp Ser Val Lys
    50                  55                  60

Gly Arg Phe Thr Ile Ser Arg Asp Asn Ala Arg Asn Ile Leu Tyr Leu
65                  70                  75                  80

Gln Met Ser Ser Leu Arg Ser Glu Asp Thr Ala Met Tyr Tyr Cys Ala
                85                  90                  95

Arg Trp Leu Leu Leu Ala Tyr Trp Gly Gln Gly Thr Leu Val Thr
            100                 105                 110

<210> SEQ ID NO 759
<211> LENGTH: 111
<212> TYPE: PRT
<213> ORGANISM: Artificial Sequence
<220> FEATURE:
<223> OTHER INFORMATION: Synthetic peptide

<400> SEQUENCE: 759

Asp Val Lys Leu Val Glu Ser Gly Gly Gly Leu Val Lys Pro Gly Gly
1               5                   10                  15

Ser Leu Lys Ile Ser Cys Ala Ala Ser Gly Phe Thr Phe Ser Thr Tyr
            20                  25                  30

Gly Met Ser Trp Val Arg Gln Thr Pro Glu Lys Arg Leu Glu Trp Val
        35                  40                  45

Ala Ser Ile Ser Ser Gly Gly Ser Thr Tyr Tyr Pro Asp Ser Val Lys
50                  55                  60

Gly Arg Phe Thr Ile Ser Arg Asp Asn Ala Arg Asn Ile Leu Tyr Leu
65                  70                  75                  80

Gln Met Ser Ser Leu Arg Ser Glu Asp Thr Ala Met Tyr Tyr Cys Ala
            85                  90                  95

Arg Trp Leu Leu Leu Ala Tyr Trp Gly Gln Gly Thr Leu Val Thr
            100                 105                 110

<210> SEQ ID NO 760
<211> LENGTH: 111
<212> TYPE: PRT
<213> ORGANISM: Artificial Sequence
<220> FEATURE:
<223> OTHER INFORMATION: Synthetic peptide

<400> SEQUENCE: 760

Glu Val Lys Leu Val Glu Ser Gly Gly Gly Leu Val Lys Ser Gly Gly
1               5                   10                  15

Ser Leu Lys Ile Ser Cys Ala Ala Ser Gly Phe Thr Phe Ser Thr Tyr
            20                  25                  30

Gly Met Ser Trp Val Arg Gln Thr Pro Glu Lys Arg Leu Glu Trp Val
        35                  40                  45

Ala Ser Ile Ser Ser Gly Gly Ser Thr Tyr Tyr Pro Asp Ser Val Lys
50                  55                  60

Gly Arg Phe Thr Ile Ser Arg Asp Asn Ala Arg Asn Ile Leu Tyr Leu
65                  70                  75                  80

Gln Met Ser Ser Leu Arg Ser Glu Asp Thr Ala Met Tyr Tyr Cys Ala
            85                  90                  95

Arg Trp Leu Leu Leu Ala Tyr Trp Gly Gln Gly Thr Leu Val Thr
            100                 105                 110

<210> SEQ ID NO 761
<211> LENGTH: 96
<212> TYPE: PRT
<213> ORGANISM: Artificial Sequence
<220> FEATURE:
<223> OTHER INFORMATION: Synthetic peptide

<400> SEQUENCE: 761

Ala Val Thr Leu Asp Glu Ser Gly Gly Gly Leu Gln Thr Pro Gly Arg
1               5                   10                  15

Ala Leu Ser Leu Val Cys Lys Ala Ser Gly Phe Thr Phe Ser Ser Tyr
            20                  25                  30

Asn Met Gly Trp Val Arg Gln Ala Pro Gly Lys Gly Leu Glu Phe Val
        35                  40                  45

Ala Gly Ile Asp Asn Thr Gly Arg Tyr Thr Gly Tyr Gly Ser Ala Val
50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Tyr Cys
            85                  90                  95

<210> SEQ ID NO 762
<211> LENGTH: 96
<212> TYPE: PRT
<213> ORGANISM: Artificial Sequence
<220> FEATURE:
<223> OTHER INFORMATION: Synthetic peptide

<400> SEQUENCE: 762

```
Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Leu Ser Ser Tyr
            20                  25                  30

His Met Leu Trp Val Arg Gln Ala Pro Gly Lys Gly Leu Glu Phe Val
        35                  40                  45

Ala Gln Ile Thr Ser Ser Gly Ser Thr Tyr Tyr Gly Ala Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Tyr Cys
                85                  90                  95
```

<210> SEQ ID NO 763
<211> LENGTH: 95
<212> TYPE: PRT
<213> ORGANISM: Artificial Sequence
<220> FEATURE:
<223> OTHER INFORMATION: Synthetic peptide

<400> SEQUENCE: 763

```
Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Ser Ile Ser Ser Tyr
            20                  25                  30

Asp Met Gly Trp Met Arg Gln Ala Pro Gly Lys Gly Leu Glu Phe Val
        35                  40                  45

Ala Val Ile Asn Ala Ala Gly Ser Gly Thr Asn Tyr Gly Ser Ala Val
    50                  55                  60

Lys Arg Ala Thr Ile Ser Arg Asp Asn Gly Gln Ser Thr Val Arg Leu
65                  70                  75                  80

Gln Leu Asn Asn Leu Arg Ala Glu Asp Thr Ala Thr Tyr Tyr Cys
                85                  90                  95
```

<210> SEQ ID NO 764
<211> LENGTH: 77
<212> TYPE: PRT
<213> ORGANISM: Artificial Sequence
<220> FEATURE:
<223> OTHER INFORMATION: Synthetic peptide

<400> SEQUENCE: 764

```
Ser Leu Asn Gly Phe Ser Gly Phe Thr Phe Asn Asp Tyr Tyr Met Gly
1               5                   10                  15

Trp Met His Arg Ala Leu Gly Lys Gly Leu Glu Tyr Val Gly Val Ile
            20                  25                  30

Ser Pro Asp Gly Ser Thr Pro Tyr Tyr Gly Ala Ala Val Lys Gly Arg
        35                  40                  45

Ala Thr Ile Ser Arg Asp Asn Gly Gln Ser Thr Val Arg Leu Gln Leu
    50                  55                  60
```

Asn Asn Leu Arg Ala Glu Asp Thr Gly Thr Tyr Tyr Cys
65                  70                  75

<210> SEQ ID NO 765
<211> LENGTH: 81
<212> TYPE: PRT
<213> ORGANISM: Artificial Sequence
<220> FEATURE:
<223> OTHER INFORMATION: Synthetic peptide

<400> SEQUENCE: 765

Gly Ala Gly Leu Ser Leu Ile Cys Lys Ala Ser Gly Phe Thr Phe Ser
1               5                   10                  15

Tyr Ala Met Asn Trp Val Arg Gln Ala Pro Gly Lys Gly Leu Glu Tyr
            20                  25                  30

Val Gly Leu Ile Ser Ser Ser Gly Thr Thr Thr Lys Tyr Gly Ala Ala
        35                  40                  45

Val Lys Gly Arg Ala Thr Ile Ser Arg Asp Asn Gly Gln Ser Thr Val
    50                  55                  60

Arg Leu Gln Leu Asn Asn Leu Arg Ala Glu Asp Thr Ala Thr Tyr Tyr
65                  70                  75                  80

Cys

<210> SEQ ID NO 766
<211> LENGTH: 96
<212> TYPE: PRT
<213> ORGANISM: Artificial Sequence
<220> FEATURE:
<223> OTHER INFORMATION: Synthetic peptide

<400> SEQUENCE: 766

Ala Val Thr Leu Asp Glu Ser Gly Gly Gly Leu Gln Thr Pro Gly Gly
1               5                   10                  15

Gly Leu Ser Leu Ile Cys Lys Ala Ser Gly Tyr Ser Phe Ile His Phe
            20                  25                  30

Trp Met Asn Trp Val Arg Gln Ala Pro Gly Lys Gly Leu Glu Phe Ile
        35                  40                  45

Ala Ser Ile Ser Asn Thr Gly Ser Tyr Thr Ala Tyr Gly Ala Ala Val
    50                  55                  60

Lys Gly Arg Ala Thr Ile Ser Arg Asp Asp Gly Gln Ser Thr Val Arg
65                  70                  75                  80

Leu Gln Leu Asn Asn Leu Arg Ala Glu Asp Thr Gly Thr Tyr Leu Cys
                85                  90                  95

<210> SEQ ID NO 767
<211> LENGTH: 95
<212> TYPE: PRT
<213> ORGANISM: Artificial Sequence
<220> FEATURE:
<223> OTHER INFORMATION: Synthetic peptide

<400> SEQUENCE: 767

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Phe
            20                  25                  30

Asn Met Phe Trp Val Arg Gln Ala Pro Gly Lys Leu Glu Tyr Val Ala
        35                  40                  45

Glu Ile Ser Gly Thr Gly Ser Ser Thr Tyr Tyr Ala Pro Ala Val Lys
    50                  55                  60

Gly Arg Ala Thr Ile Ser Arg Asp Asn Gly Gln Ser Thr Val Arg Leu
65                  70                  75                  80

Gln Leu Asn Asn Leu Arg Ala Glu Asp Thr Gly Thr Tyr Tyr Cys
            85                  90                  95

<210> SEQ ID NO 768
<211> LENGTH: 95
<212> TYPE: PRT
<213> ORGANISM: Artificial Sequence
<220> FEATURE:
<223> OTHER INFORMATION: Synthetic peptide

<400> SEQUENCE: 768

Ala Val Arg Leu Asp Lys Ser Gly Gly Gly Leu Gln Thr Pro Gly Gly
1               5                   10                  15

Gly Leu Ser Leu Ile Cys Lys Ala Ser Gly Phe Thr Phe Ser Ser Tyr
            20                  25                  30

Ser Met Glu Trp Val Arg Gln Ala Pro Gly Lys Gly Leu Glu Trp Val
        35                  40                  45

Ala Gly Ile Glu Asn Asp Gly Ser Thr Thr Phe Tyr Gly Pro Ala Val
    50                  55                  60

Asp Arg Ala Thr Ile Ser Lys Asp Asn Gly Gln Ser Thr Val Arg Leu
65                  70                  75                  80

Leu Leu Asn Asn Leu Arg Ala Glu Asp Thr Ala Thr Tyr Tyr Cys
            85                  90                  95

<210> SEQ ID NO 769
<211> LENGTH: 95
<212> TYPE: PRT
<213> ORGANISM: Artificial Sequence
<220> FEATURE:
<223> OTHER INFORMATION: Synthetic peptide

<400> SEQUENCE: 769

Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Thr Phe Ser Ser Tyr
            20                  25                  30

Thr Met Gln Trp Val Arg Gln Ala Pro Gly Lys Gly Leu Glu Trp Val
        35                  40                  45

Ala Gly Ile Tyr Ser Gly Ser Ser Thr Tyr Tyr Gly Ala Ala Val Lys
    50                  55                  60

Gly Arg Ala Thr Ile Ser Arg Asp Asn Gly Gln Ser Thr Val Arg Leu
65                  70                  75                  80

Gln Leu Asn Asn Leu Arg Ala Glu Asp Thr Ala Thr Tyr Phe Cys
            85                  90                  95

<210> SEQ ID NO 770
<211> LENGTH: 90
<212> TYPE: PRT
<213> ORGANISM: Artificial Sequence
<220> FEATURE:
<223> OTHER INFORMATION: Synthetic peptide

<400> SEQUENCE: 770

Phe Met Arg Ser Leu Leu Met Pro Gly Gly Leu Ser Leu Val Cys
1               5                   10                  15

Lys Ala Ser Gly Phe Thr Phe Ser Ser His Met Gly Trp Val Arg
            20                  25                  30

Gln Ala Pro Gly Lys Gly Leu Glu Tyr Val Gly Val Ile Ser Ser Ser
            35                  40                  45

Gly Ser Thr Thr Lys Tyr Gly Val Ala Val Gln Gly Arg Ala Thr Ile
 50                  55                  60

Ser Lys Asp Asn Gly Gln Ser Thr Val Arg Leu Gln Leu Asn Asn Leu
 65                  70                  75                  80

Arg Ala Glu Asp Thr Ala Thr Tyr Tyr Cys
                85                  90

<210> SEQ ID NO 771
<211> LENGTH: 93
<212> TYPE: PRT
<213> ORGANISM: Artificial Sequence
<220> FEATURE:
<223> OTHER INFORMATION: Synthetic peptide

<400> SEQUENCE: 771

Leu Asp Glu Ser Gly Gly Gly Leu Gln Thr Pro Gly Gly Ala Leu Ser
 1               5                  10                  15

Leu Val Cys Lys Ala Ser Gly Phe Thr Phe Ser Ser Val Asn Met Phe
                20                  25                  30

Trp Val Arg Gln Ala Pro Gly Lys Gly Leu Glu Phe Val Ala Gly Ile
            35                  40                  45

Tyr Ser Thr Gly Ser Gly Thr Gly Tyr Ala Pro Ala Val Lys Gly Arg
 50                  55                  60

Ala Thr Ile Ser Arg Asp Asn Gly Gln Ser Thr Val Arg Leu Gln Leu
 65                  70                  75                  80

Asn Asn Leu Arg Ala Glu Asp Thr Gly Thr Tyr Tyr Cys
                85                  90

<210> SEQ ID NO 772
<211> LENGTH: 21
<212> TYPE: PRT
<213> ORGANISM: Artificial Sequence
<220> FEATURE:
<223> OTHER INFORMATION: Synthetic peptide

<400> SEQUENCE: 772

Leu Arg Arg Ala Ser Pro Ser Met Asn Asn Leu Arg Ala Glu Asp Thr
 1               5                  10                  15

Ala Thr Ser Tyr Cys
            20

<210> SEQ ID NO 773
<211> LENGTH: 91
<212> TYPE: PRT
<213> ORGANISM: Artificial Sequence
<220> FEATURE:
<223> OTHER INFORMATION: Synthetic peptide

<400> SEQUENCE: 773

Leu Gly Glu Pro Cys Arg His Pro Glu Glu Gly Ser Ala Ser Ser Ala
 1               5                  10                  15

Arg Ser Pro Gly Ser Pro Ser Ala Val Ile Arg Cys Ser Gly Cys Asp
                20                  25                  30

Arg Arg Leu Ala Arg Ser Trp Asn Trp Glu Ala Asn Ile Ser Tyr Ser
            35                  40                  45

Gly Gly Ser Asn Thr Tyr Tyr Ala Pro Ala Val Gln Gly Arg Ala Thr
 50                  55                  60

Ile Ser Arg Asp Asn Gly Gln Ser Thr Val Arg Leu Gln Leu Asn Asn

```
                65                  70                  75                  80
Leu Arg Ala Glu Asp Thr Ala Thr Tyr Tyr Cys
                85                  90

<210> SEQ ID NO 774
<211> LENGTH: 96
<212> TYPE: PRT
<213> ORGANISM: Artificial Sequence
<220> FEATURE:
<223> OTHER INFORMATION: Synthetic peptide

<400> SEQUENCE: 774

Ala Val Thr Leu Asp Glu Ser Gly Gly Gly Leu Gln Thr Pro Gly Arg
1               5                   10                  15

Ala Leu Ser Leu Val Cys Lys Gly Ser Gly Phe Thr Phe Ser Ser Phe
                20                  25                  30

Tyr Met Phe Trp Val Arg Gln Ala Pro Gly Lys Gly Leu Glu Tyr Val
            35                  40                  45

Ala Gly Ile Ser Ser Thr Gly Ser Ser Thr Tyr Tyr Ala Pro Ala Val
        50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Ala Thr Tyr Tyr Cys
                85                  90                  95

<210> SEQ ID NO 775
<211> LENGTH: 96
<212> TYPE: PRT
<213> ORGANISM: Artificial Sequence
<220> FEATURE:
<223> OTHER INFORMATION: Synthetic peptide

<400> SEQUENCE: 775

Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Thr Phe Ser Asp Tyr
                20                  25                  30

Gly Met Gly Trp Met Arg Gln Ala Pro Gly Lys Gly Leu Glu Tyr Val
            35                  40                  45

Thr Ala Ile Asn Asn Phe Gly Asn Ser Thr Gly Tyr Ala Ala Ala Val
        50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Ala Thr Tyr Tyr Cys
                85                  90                  95

<210> SEQ ID NO 776
<211> LENGTH: 96
<212> TYPE: PRT
<213> ORGANISM: Artificial Sequence
<220> FEATURE:
<223> OTHER INFORMATION: Synthetic peptide

<400> SEQUENCE: 776

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Phe Phe Ser Ser
                20                  25                  30

Tyr Ala Met Met Trp Val Arg Gln Thr Pro Ser Lys Ser Leu Trp Ile
            35                  40                  45
```

```
Ala Gly Ile Arg Gly Ala Gly Ser Ser Thr Trp Tyr Ala Thr Ala Val
            50                  55                  60

Lys Gly Arg Ala Thr Ile Ser Arg Asp Asn Gly Gln Ser Thr Val Arg
 65                  70                  75                  80

Leu Gln Leu Asn Asn Leu Arg Ala Glu Asp Thr Gly Tyr Tyr Cys
                85                  90                  95

<210> SEQ ID NO 777
<211> LENGTH: 94
<212> TYPE: PRT
<213> ORGANISM: Artificial Sequence
<220> FEATURE:
<223> OTHER INFORMATION: Synthetic peptide

<400> SEQUENCE: 777

Ala Val Thr Leu Asp Glu Ser Gly Gly Gly Leu Gln Thr Pro Gly Gly
  1               5                  10                  15

Gly Leu Ser Leu Val Cys Lys Ala Ser Gly Phe Thr Phe Ser Ser Phe
                20                  25                  30

Tyr Met Tyr Trp Val Arg Gln Ala Pro Gly Lys Gly Leu Glu Phe Val
            35                  40                  45

Ala Gln Ile Thr Ser Ser Gly Ser Thr Tyr Tyr Gly Ser Ala Val Lys
        50                  55                  60

Gly Arg Ala Thr Ile Ser Arg Asp Asn Gln Ser Thr Val Arg Leu Gln
 65                  70                  75                  80

Leu Asn Asn Leu Arg Ala Glu Asp Thr Ser Thr Tyr Phe Cys
                85                  90

<210> SEQ ID NO 778
<211> LENGTH: 97
<212> TYPE: PRT
<213> ORGANISM: Artificial Sequence
<220> FEATURE:
<223> OTHER INFORMATION: Synthetic peptide

<400> SEQUENCE: 778

Ala Val Thr Leu Asp Glu Ser Gly Gly Gly Leu Gln Thr Pro Gly Gly
  1               5                  10                  15

Ala Leu Ser Leu Val Cys Lys Val Ser Gly Phe Asp Gly Phe Ser Ser
                20                  25                  30

Tyr Asp Met Tyr Trp Val Gln Gln Glu Pro Ser Lys Gly Leu Glu Tyr
            35                  40                  45

Val Ala Gln Ile Ser Ser Thr Gly Ser Ser Thr Tyr Tyr Ala Pro Ala
        50                  55                  60

Val Lys Gly Arg Ala Thr Ile Ser Arg Asp Asn Gly Gln Ser Thr Val
 65                  70                  75                  80

Arg Leu Gln Leu Asn Asn Leu Arg Ala Glu Asp Thr Ala Thr Tyr Tyr
                85                  90                  95

Cys

<210> SEQ ID NO 779
<211> LENGTH: 60
<212> TYPE: DNA
<213> ORGANISM: Artificial Sequence
<220> FEATURE:
<223> OTHER INFORMATION: Synthetic primer

<400> SEQUENCE: 779
maggtgcrgc tgcaggagtc gggacccagc ctggtgaagc cctcacagac cctctccctc    60
```

<210> SEQ ID NO 780
<211> LENGTH: 60
<212> TYPE: DNA
<213> ORGANISM: Artificial Sequence
<220> FEATURE:
<223> OTHER INFORMATION: Synthetic primer

<400> SEQUENCE: 780
caggtgcggc tgcaggagtc gggacccagc ctggtgaagc cctcacagac cctctccctc     60

<210> SEQ ID NO 781
<211> LENGTH: 60
<212> TYPE: DNA
<213> ORGANISM: Artificial Sequence
<220> FEATURE:
<223> OTHER INFORMATION: Synthetic primer

<400> SEQUENCE: 781
caggtgcggc tgcaggagtc gggacccagc ctggtgaagc cctcacagac cctctccctc     60

<210> SEQ ID NO 782
<211> LENGTH: 60
<212> TYPE: DNA
<213> ORGANISM: Artificial Sequence
<220> FEATURE:
<223> OTHER INFORMATION: Synthetic primer

<400> SEQUENCE: 782
caggtgcggc tgcaggagtc gggacccagc ctggtgaagc cctcacagac cctctccctc     60

<210> SEQ ID NO 783
<211> LENGTH: 60
<212> TYPE: DNA
<213> ORGANISM: Artificial Sequence
<220> FEATURE:
<223> OTHER INFORMATION: Synthetic primer

<400> SEQUENCE: 783
caggtgcggc tgcaggagtc gggacccagc ctggtgaagc cctcacagac cctctccctc     60

<210> SEQ ID NO 784
<211> LENGTH: 60
<212> TYPE: DNA
<213> ORGANISM: Artificial Sequence
<220> FEATURE:
<223> OTHER INFORMATION: Synthetic primer

<400> SEQUENCE: 784
caggtgcagc tgcaggagtc gggacccagc ctggtgaagc cctcacagac cctctccctc     60

<210> SEQ ID NO 785
<211> LENGTH: 60
<212> TYPE: DNA
<213> ORGANISM: Artificial Sequence
<220> FEATURE:
<223> OTHER INFORMATION: Synthetic primer

<400> SEQUENCE: 785
caggtgcagc tgcaggagtc gggacccagc ctggtgaagc cctcacagac cctctccctc     60

<210> SEQ ID NO 786
<211> LENGTH: 60
<212> TYPE: DNA
<213> ORGANISM: Artificial Sequence
<220> FEATURE:

<223> OTHER INFORMATION: Synthetic primer

<400> SEQUENCE: 786
caggtgcggc tgcaggagtc gggacccagc ctggtgaagc cctcacagac cctctccctc    60

<210> SEQ ID NO 787
<211> LENGTH: 60
<212> TYPE: DNA
<213> ORGANISM: Artificial Sequence
<220> FEATURE:
<223> OTHER INFORMATION: Synthetic primer

<400> SEQUENCE: 787
caggtgcagc tgcaggagtc gggacccagc ctggtgaagc cctcacagac cctctccctc    60

<210> SEQ ID NO 788
<211> LENGTH: 60
<212> TYPE: DNA
<213> ORGANISM: Artificial Sequence
<220> FEATURE:
<223> OTHER INFORMATION: Synthetic primer

<400> SEQUENCE: 788
caggtgcagc tgcaggagtc gggacccagc ctggtgaagc cctcacagac cctctccctc    60

<210> SEQ ID NO 789
<211> LENGTH: 60
<212> TYPE: DNA
<213> ORGANISM: Artificial Sequence
<220> FEATURE:
<223> OTHER INFORMATION: Synthetic primer

<400> SEQUENCE: 789
aaggtgcggc tgcaggagtc gggacccagc ctggtgaagc cctcacagac cctctccctc    60

<210> SEQ ID NO 790
<211> LENGTH: 20
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid

<400> SEQUENCE: 790

Xaa Val Xaa Leu Gln Glu Ser Gly Pro Ser Leu Val Lys Pro Ser Gln
1               5                   10                  15

Thr Leu Ser Leu
            20

<210> SEQ ID NO 791
<211> LENGTH: 20
<212> TYPE: PRT
<213> ORGANISM: Artificial sequence
<220> FEATURE:
<223> OTHER INFORMATION: Synthetic peptide

<400> SEQUENCE: 791

Gln Val Arg Leu Gln Glu Ser Gly Pro Ser Leu Val Lys Pro Ser Gln
1               5                   10                  15

-continued

Thr Leu Ser Leu
        20

<210> SEQ ID NO 792
<211> LENGTH: 20
<212> TYPE: PRT
<213> ORGANISM: Artificial sequence
<220> FEATURE:
<223> OTHER INFORMATION: Synthetic peptide

<400> SEQUENCE: 792

Gln Val Arg Leu Gln Glu Ser Gly Pro Ser Leu Val Lys Pro Ser Gln
1               5                   10                  15

Thr Leu Ser Leu
        20

<210> SEQ ID NO 793
<211> LENGTH: 20
<212> TYPE: PRT
<213> ORGANISM: Artificial sequence
<220> FEATURE:
<223> OTHER INFORMATION: Synthetic peptide

<400> SEQUENCE: 793

Gln Val Arg Leu Gln Glu Ser Gly Pro Ser Leu Val Lys Pro Ser Gln
1               5                   10                  15

Thr Leu Ser Leu
        20

<210> SEQ ID NO 794
<211> LENGTH: 20
<212> TYPE: PRT
<213> ORGANISM: Artificial sequence
<220> FEATURE:
<223> OTHER INFORMATION: Synthetic peptide

<400> SEQUENCE: 794

Gln Val Gln Leu Gln Glu Ser Gly Pro Ser Leu Val Lys Pro Ser Gln
1               5                   10                  15

Thr Leu Ser Leu
        20

<210> SEQ ID NO 795
<211> LENGTH: 20
<212> TYPE: PRT
<213> ORGANISM: Artificial sequence
<220> FEATURE:
<223> OTHER INFORMATION: Synthetic peptide

<400> SEQUENCE: 795

Gln Val Gln Leu Gln Glu Ser Gly Pro Ser Leu Val Lys Pro Ser Gln
1               5                   10                  15

Thr Leu Ser Leu
        20

<210> SEQ ID NO 796
<211> LENGTH: 20
<212> TYPE: PRT
<213> ORGANISM: Artificial sequence
<220> FEATURE:
<223> OTHER INFORMATION: Synthetic peptide

<400> SEQUENCE: 796

Gln Val Arg Leu Gln Glu Ser Gly Pro Ser Leu Val Lys Pro Ser Gln
1               5                   10                  15

Thr Leu Ser Leu
         20

<210> SEQ ID NO 797
<211> LENGTH: 20
<212> TYPE: PRT
<213> ORGANISM: Artificial sequence
<220> FEATURE:
<223> OTHER INFORMATION: Synthetic peptide

<400> SEQUENCE: 797

Gln Val Gln Leu Gln Glu Ser Gly Pro Ser Leu Val Lys Pro Ser Gln
1               5                   10                  15

Thr Leu Ser Leu
         20

<210> SEQ ID NO 798
<211> LENGTH: 20
<212> TYPE: PRT
<213> ORGANISM: Artificial sequence
<220> FEATURE:
<223> OTHER INFORMATION: Synthetic peptide

<400> SEQUENCE: 798

Gln Val Gln Leu Gln Glu Ser Gly Pro Ser Leu Val Lys Pro Ser Gln
1               5                   10                  15

Thr Leu Ser Leu
         20

<210> SEQ ID NO 799
<211> LENGTH: 20
<212> TYPE: PRT
<213> ORGANISM: Artificial sequence
<220> FEATURE:
<223> OTHER INFORMATION: Synthetic peptide

<400> SEQUENCE: 799

Gln Val Arg Leu Gln Glu Ser Gly Pro Ser Leu Val Lys Pro Ser Gln
1               5                   10                  15

Thr Leu Ser Leu
         20

<210> SEQ ID NO 800
<211> LENGTH: 20
<212> TYPE: PRT
<213> ORGANISM: Artificial sequence
<220> FEATURE:
<223> OTHER INFORMATION: Synthetic peptide

<400> SEQUENCE: 800

Lys Val Arg Leu Gln Glu Ser Gly Pro Ser Leu Val Lys Pro Ser Gln
1               5                   10                  15

Thr Leu Ser Leu
         20

<210> SEQ ID NO 801
<211> LENGTH: 60
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: n = c or a

```
<220> FEATURE:
<221> NAME/KEY: misc_feature
<222> LOCATION: (8)..(8)
<223> OTHER INFORMATION: n = g or a

<400> SEQUENCE: 801
naggtgcngc tgcaggagtc gggacccagc ctggtgaagc cctcacagac cctctccctc    60

<210> SEQ ID NO 802
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: X = Y or F

<400> SEQUENCE: 802

Asp Xaa Xaa Xaa Xaa Xaa Cys
1               5

<210> SEQ ID NO 803
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: X = T or S

<400> SEQUENCE: 803

Trp Gly Xaa Gly Xaa
1               5

<210> SEQ ID NO 804
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: X = F or Y

<400> SEQUENCE: 804

Asp Xaa Xaa Xaa Tyr Xaa Cys
1               5

<210> SEQ ID NO 805
<211> LENGTH: 5
<212> TYPE: PRT
<213> ORGANISM: Artificial sequence
<220> FEATURE:
<223> OTHER INFORMATION: Synthetic peptide
```

```
<220> FEATURE:
<221> NAME/KEY: misc_feature
<222> LOCATION: (3)..(3)
<223> OTHER INFORMATION: Xaa can be any naturally occurring amino acid

<400> SEQUENCE: 805

Phe Gly Xaa Gly Thr
1               5

<210> SEQ ID NO 806
<211> LENGTH: 20
<212> TYPE: PRT
<213> ORGANISM: Artificial sequence
<220> FEATURE:
<223> OTHER INFORMATION: Synthetic linker

<400> SEQUENCE: 806

Gly Gly Gly Gly Ser Gly Gly Gly Gly Ser Gly Gly Gly Gly Ser Gly
1               5                   10                  15

Gly Gly Gly Ser
            20
```

RAPID ISOLATION OF MONOCLONAL ANTIBODIES FROM ANIMALS

CROSS-REFERENCE TO RELATED APPLICATIONS

This application claims the benefit of U.S. Provisional Patent Application Nos. 61/345,538 and 61/377,816, filed May 17, 2010 and Aug. 27, 2010, respectively, the entirety of which are incorporated herein by reference.

This invention was made with government support under HR0011-10-1-0052 awarded by Defense Advanced Research Projects Agency. The government has certain rights in the invention.

BACKGROUND OF THE INVENTION

1. Field of the Invention

The present invention relates generally to the field of antibody analysis and generation, such as antibody discovery from immunized animals. More particularly, it concerns novel methods and compositions for identification and/or production of desired antibodies or antigen-binding fragments. It also concerns identification of monoclonal antibodies from any mammal and more generally any animal that has an adaptive immune response that leads to the expression of soluble immunoglobulin and for which genomic information on its immunoglobulin locus is available.

2. Description of Related Art

Over the last 12 years, the development of cancer therapeutic antibodies, such as Herceptin (Trastuzumab, anti-Her2), Rituxan (Rituximab, anti-CD20), Eribitux/Vectibix (Cetuximab/Panitumumab, anti-EGFR), Avastin (anti-VEGF) and others have saved many tens of thousands of lives world-wide. Antibody therapeutics offer distinct advantages relative to small molecule drugs, namely: (i) better understood mechanisms of action; (ii) higher specificity and fewer-off target effects; (iii) predictable safety and toxicological profiles. Currently, there are more than 200 antibody therapeutics in clinical trials in the U.S., many of them for cancer treatment.

The discovery of monoclonal antibodies is an immensely important aspect in therapeutic antibody development. Additionally, monoclonal antibodies are widely used for numerous diagnostic and analytical purposes. Since the development of the hybridoma technology by Kohler and Milstein 35 years ago (Kohler and Milstein, 1975), a variety of methods for the generation of MAbs have been developed. Such methods include B cell immortalization by genetic reprogramming via Epstein-Barr Virus (Traggiai et al., 2004) or retrovirus-mediated gene transfer (Kwakkenbos et al., 2010), cloning of V genes by single cell PCR (Wrammert et al., 2008; Meijer et al., 2008), and methods for in vitro discovery via the display and screening of recombinant antibody libraries (Clackson et al., 1991; Feldhaus et al., 2003; Harvey et al., 2004; Schaffitzel et al., 1999; Hosse et al., 2006; Mazor et al., 2007; Zahnd et al., 2007; Kretzschmar and von Ruden, 2002). Both in vitro and in vivo methods for antibody discovery are critically dependent on high-throughput screening to determine antigen specificity. Recently, B cell analysis has been expedited by microengraving techniques that utilize soft lithography for the high-throughput identification of antigen-specific B cells, however, this is at the cost of considerable technical complexity due to the need for antibody V gene amplification and cell expansion (Jin et al., 2009; Love et al., 2006).

Similarly, the success of in vitro antibody discovery techniques is dependent on screening parameters including the nature of the display platform, antigen concentration, binding avidity during enrichment, multiple rounds of screening (e.g., panning or sorting), and importantly, on the design and diversity of synthetic antibody libraries (Hoogenboom, 2005; Cobaugh et al., 2008; Persson et al., 2006).

Current use of display technologies coupled with library screening systems such as a phage display where antibodies are isolated by panning has a number of significant problems—in particular, some antibodies produced by a library may cause the death of the organism expressing them and therefore they simply cannot be detected. There is a particular problem when one is searching for antibodies specific to an antigen from a pathogen which might be homologous to one produced by the host expression system (e.g., *E. coli*) then important antibodies cannot be expressed. The use of *E. coli* to express libraries of human antibodies also suffers from the problem of codon usage—codons used by humans for specific amino acids can frequently not be the optimum ones for the same amino acid in *E. coli* or other host systems. This means that an important antibody might not be expressed (or at least not in sufficient quantities) since the codons in its sequence are highly inefficient in *E. Coli*, resulting in the *E. coli* being unable to read through and express it in full. Codon optimization of antibody libraries is obviously not an option since the libraries would first have to be sequenced, which defeats the main advantages of using libraries.

There is a pressing need to identify biologically relevant antibodies that exhibit a beneficial effect in controlling diseases. Mammals mount antibody (humoral) immune responses against infectious agents, toxins or cancer cells. Diseased individuals produce circulating antibodies that recognize the disease agent and in many cases (e.g., in patients that recover from an infection or in cancer patients in remission); these antibodies play a key role in recovery and therapy. Currently there are no methods available to identify the circulating antibodies in blood and to produce the antibodies that are specific to the disease agent and have a therapeutic effect.

On the other hand, the isolation of monoclonal antibodies from different animal species is of great value for the development of therapeutics and diagnostics. A major limitation of the existing methods for isolation of monoclonal antibodies is that their application is limited to a very small number of species. Different animals have evolved distinct ways of diversifying their antibody repertoire and thus can produce antibodies that recognize distinct epitopes on an antigen or display very high affinity for a particular antigen, compared to mice and humans. For example, it is well known in the art that antibodies from rabbits generally display much higher affinity than those produced from mice.

Current production of monoclonal antibodies from a particular species using the hybridoma technology necessitates that B cell are immortalized by fusion to a myeloma from that species. Such myeloma cell lines are difficult and time consuming to develop and therefore exist only for mice, primates, rabbits and sheep. Alternatively, researchers have attempted to generate interspecies hybridomas, by fusing a mouse myeloma cell line with B cells from an animal for which autologous myeloma cell lines are not available. However, interspecies hybrids are generated with very low efficiency and are unstable, ceasing to produce monoclonal antibodies after a few passages. Thus at present the production of monoclonal antibodies from the vast majority of animals that have an adaptive immunoglobulin system is a major challenge. Moreover, even for species for which stable B cell fusions can be generated (rabbits, mice, sheep and primates) the isolation of monoclonal antibodies using the hybridoma technology is a lengthy process requiring 2-6 months after animal sacrifice.

Alternatively monoclonal antibodies can be isolated in vitro from large libraries of the variable (V) chains of the immunoglobulin repertoire from an immunized animal and then screening such libraries by a variety of display methods such as phage display, yeast display or bacterial display. Once again the utility of these methods is limited to the few species for which extensive information on their immunoglobulin repertoire is available, namely mice, primates and rabbits. This is because, the cloning of the immunoglobulin repertoire requires the availability of sets of oligonucleotide primers capable of amplifying the majority, preferably all, of the immunoglobulin variable regions that are generated in that animal via somatic recombination mechanisms. This in turn requires extensive information on the sequences of immunoglobulins expressed in a particular species and it is not available for the vast majority of animals that have an antibody-encoding, humoral immunity system. Additionally it is not known whether the antibodies isolated by combinatorial library screening correspond to those that have been expanded by the immune system and produced in large amounts in animals.

Obviously all of these techniques are somewhat complex, inconvenient, and time consuming. Therefore, there remains a need to develop a more efficient and accurate method for identifying antigen-specific antibodies or monoclonal antibodies directly from a patient or any animal.

SUMMARY OF THE INVENTION

Aspects of the present invention overcome a major deficiency in the art by providing novel methods for determining serum antibody sequences or identifying abundant antibody sequences from serum, B cells, or directly from lymphoid tissues or from isolated B cells. Accordingly, in a first embodiment there is provided a method for identifying abundant antibody sequences in circulation, comprising: a) determining amino acid sequences of at least the complementarity determining region 3 (CDR3) of the VH and VL regions of antibodies in a serum-containing sample of a subject, to provide serum antibody sequences; and b) identifying the antibody sequences that exhibit a threshold level of abundancy relative to other serum antibody sequences. A "serum-containing sample" is intended to include any blood-related sample, such as a serum-containing sample, a plasma sample, or a blood sample with an additive. In certain aspects, the amino acid sequences so determined comprises sequences of whole VH and VL regions.

In a second embodiment, there may be provided a method for generating one or more antibodies or antigen-binding fragments, comprising: a) obtaining sequence and abundancy information of antibody amino acid sequences of at least the CDR3 of VH and VL regions of antibodies present in the serum of a subject; b) identifying those sequences that exhibit at least a threshold level of abundancy; and c) generating one or more antibodies or antigen-binding fragments that comprise one or more of the abundant amino acid sequences so determined. For example, generation of such antibodies or antigen-binding fragments may comprise expression in a heterologous system or the use of in vitro protein synthesis.

In a further embodiment, there may be provided a method for determining antibody sequences in circulation, comprising: a) obtaining nucleic acid sequences, and the corresponding amino acid, sequence information of one or more VH and VL genes in mature B cells of a subject and the corresponding amino acid sequences; b) obtaining mass spectra of peptides derived from serum antibodies of the subject; and c) using the sequence information and the mass spectra to determine the amino acid sequence of VH and VL regions of one or more antibodies in circulation.

In an additional embodiment, there may be provided a method for generating antibodies, comprising: a) obtaining sequence and abundancy information of amino acid sequences of VH and VL regions of antibodies in a serum-containing sample of a subject; and b) generating one or more antibodies that comprise VH and VL regions of the serum antibodies based on the sequence and abundancy information.

In a certain embodiment, there may also be provided a method for preparing CDR3-containing peptide fragments from serum antibodies of a subject, comprising: a) obtaining nucleic acid, and corresponding amino acid, sequence information of at least the CDR3 of VH and VL genes in mature B cells of a subject; b) using the sequence information to select a protease; and c) preparing CDR3-containing peptide fragments from serum antibodies of the subject with the protease. Such a protease may predominantly do not cleave CDR3 of the VH and VL peptides. For example, the protease may cleave at sites adjacent to the CDR3 regions, leaving the CDR3 regions substantially intact.

In other aspects, there may also be provided methods related to nucleic acid information in B cells. For example, there may be provided a method for generating one or more antibodies or antigen-binding fragments, comprising: a) obtaining sequence and abundancy information of nucleic acid sequences of at least the CDR3 of VH and VL genes in a plasma cell population of a subject; and b) identifying those sequences that exhibit at least a threshold level of abundancy; and c) generating one or more antibodies or antigen-binding fragments comprising one or more of the amino acid sequences corresponding to identified nucleic acid sequences.

The inventors found that abundant antibody sequences present in the serum may be correlated with abundant antibody genes in B cells, especially B cells from a selected organ, such as bone marrow. In a further embodiment, there may be provided a method for identifying abundant antibody sequences in circulation, comprising: a) determining sequence and abundancy information of nucleic acid sequences of at least the CDR3 of the VH and VL genes in plasma cells of a subject; and b) identifying those antibody amino acid sequences that correspond to antibody nucleic acid sequences that exhibit at least a threshold level of abundancy, thereby identifying abundant antibody sequences in circulation. For example, the identified antibody amino acid sequences may be sequences of a selected class of antibodies, such as IgG, IgM, or IgA.

In certain aspects, determining or obtaining abundance information for vV gene sequences (e.g., a VH, VL) comprises obtaining the abundance information for a cluster of high homologous sequences derived from the same VDJ lineage. For example, multiple sequences can be aligned to identify clusters of highly homologous sequences (e.g., sequence that differ by the results of somatic hypermutation) and then the clusters can be ranked to determine the prevalence of the clusters. Accordingly, in aspects wherein VH and VL domains are paired to form a complete antibody V domain VH and VL domains belonging to similarly ranked clusters can be paired.

In further embodiments, there may be provided methods for monoclonal antibody generation in any animal are provided. The methods may overcome prior limitations by capitalizing on high throughput DNA sequencing of immunoglobulin DNA from a subject such as an immunized animal followed by bioinformatic analysis of the antibody nucleic acid sequence repertoire for the identification of monoclonal antibodies with specificity to the immunization antigen. The antibodies thus identified may be class-switched and somatic hypermutated or may be of a selected antibody class, such as IgG or IgA in humans and mice or their equivalents in other animals.

In certain embodiments, there may be provided a method for identifying candidate antigen-specific antibody variable region nucleic acid sequences. The method may comprise obtaining a pool of antibody variable region nucleic acids from a population of nucleic acids of a lymphoid tissue of a subject, preferably without separation of B cells from the lymphoid tissue. The subject may have been exposed to an antigen, such as an infectious agent, an immunization agent, or a toxin. The variable region may at least contain a CDR3 region or a full length region containing CDR1-3, and may be a variable heavy chain or a variable light chain or both.

The method may comprise immunizing the subject. The method may further comprise isolation of a lymphoid tissue. The lymphoid tissue isolation may at least or about 1, 2, 3, 4, 5, 6, 6, 8, 9, days or any intermediate ranges after immunization. The method may further comprising obtaining a population of nucleic acids of lymphoid tissue, preferably without separation B cells from the lymphoid tissue. The lymphoid tissue may be a primary, secondary or tertiary lymphoid tissue, such as bone marrow, spleen, or lymph nodes. The subject may be any animal, such as mammal, fish, amphibian, or bird. The mammal may be human, mouse, primate, rabbit, sheep, or pig.

The nucleic acid pool of antibody variable regions may be a cDNA pool. Obtaining the nucleic acid pool may comprise the use of reverse transcriptase. The method for obtaining the nucleic acid pool, for example, may comprise rapid cDNA end amplification (RACE), PCR amplification, or nucleic acid hybridization. Without separation of B cells from the lymphoid tissue, the nucleic acid population of the lymphoid tissue may contain other non-B cell nucleic acids as well as non-antibody nucleic acids. For the antibody sequence separation, antibody-specific primer or probes may be used, such as primer or probes based on known antibody constant region cDNA sequences. In alternative aspects, the nucleic acid pool may be a genomic nucleic acid pool.

The method may further comprise determining sequences and occurrence frequency of antibody variable region nucleic acids in the pool. In a further embodiment, the method may comprise identifying abundant variable region sequences. In specific embodiments, the method may further comprise identifying CDR3 sequences of the antibody variable region nucleic acid sequences, such as by homolog searching. Since CDR3 is the most variable region, variable region sequence frequency is preferably based on corresponding CDR3 frequency. Particularly, the occurrence frequency of a selected variable region sequence may be further defined as the sum of the occurrence frequency of any variable region sequences having the same or similar CDR3 sequences as that of the selected variable region sequence. The similar CDR3 sequences may be at least about 90, 91, 92, 93, 94, 95, 96, 97, 98, 99% or any intermediate ranges. For example, variable region sequences may be grouped based on the same or similar CDR3 sequences and each group has the same frequency as defined by the sum of the frequency of all the sequences in the same group. In other aspects, the frequency of variable region sequences may be the frequency of each different variable region sequence or based on similarity of full length variable regions, which contains CDR1, CDR2, and CDR3.

In certain aspects, identification of abundant CDR3 sequences may be performed followed by identification of full length variable regions containing the identified abundant CDR3 sequences. For example, primer or probes may be generated based on the abundant CDR3 sequences and used to enrich or amplify antibody variable region sequences encoding the abundant CDR3 sequences.

In exemplary aspects, such abundant sequences may occur in total at a frequency of at least 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10% or any intermediate ranges in the sequences so determined. The abundant variable region sequences so identified may be candidate antigen-specific sequences.

For generation of antigen-specific antibody or antibody fragments, the method may further comprise selecting a pair comprising nucleic acid sequences of a $V_H$ and a $V_L$ at similar abundancy levels or a pair comprising nucleic acid sequences that belong to a cluster of nucleic acid sequences comprising similar abundancy. For example, the $V_H$ nucleic acid sequence in the pair is the most abundant $V_H$ sequence and the $V_L$ nucleic acid sequence in the pair is the most abundant $V_L$ sequence. Alternatively, the $V_H$ and a $V_L$ at similar abundancy levels may be any $V_H$ and a $V_L$ have the same relative rank order in the $V_H$ or $V_L$ subpopulation, respectively, or similar concentration levels. For example, the third most abundant $V_H$ may be paired with the third most abundant $V_L$. In still further aspects, a $V_H$ and/or $V_L$ may be aligned with other identified $V_H$ or $V_L$ sequences to identify clusters of highly homologous sequences (e.g., sequences differing by the results of hypermutation) the clusters are then ranked and the $V_H$ can be paired with a $V_L$ which belongs to a cluster of similar rank.

The method may further comprise generating antibody or antibody fragments comprising amino acid sequences encoded by the paired nucleic acid sequences of $V_H$ and $V_L$. At least one of the generated antibody or antibody fragments may bind the antigen that the subject has been exposed to, such as the immunization agent used to immunize the subject. For example, the abundant variable region sequences may be directly chemical synthesized, such as an automatic synthesis method. The method may further comprise expressing the abundant variable region sequences (e.g., synthesized) in an in vitro expression system or a heterologous cell expression system.

The subject may be any animal, preferably a mammal or a human. The subject may have a disease or a condition including a tumor, an infectious disease, or an autoimmune disease, or have been immunized. In certain aspects, the subject may recover or survive from a disease or a condition such as a tumor, an infectious disease, or an autoimmune disease. In further aspects, the subject may be under or after prevention and treatment for a disease or a condition, such as cancer therapy or infection disease therapy, or vaccination. For example, the subject has or has been exposed to an antigen which is an infectious agent, a tumor antigen, a tumor cell, an allergen or a self-antigen. Such an infectious agent may be any pathogenic viruses, pathogenic bacteria, fungi, protozoa, multicellular parasites, and aberrant proteins such as prions, as wells as nucleic acids or antigens derived therefrom. An allergen could be any nonparasitic antigen capable of stimulating a type-I hypersensitivity reaction in individuals, such as many common environmental antigens.

Tumor antigen could be any substance produced in tumor cells that triggers an immune response in the host. Any protein produced in a tumor cell that has an abnormal structure due to mutation can act as a tumor antigen. Such abnormal proteins are produced due to mutation of the concerned gene.

Mutation of protooncogenes and tumor suppressors which lead to abnormal protein production are the cause of the tumor and thus such abnormal proteins are called tumor-specific antigens. Examples of tumor-specific antigens include the abnormal products of ras and p53 genes.

In certain aspects, there may be provided methods comprising obtaining sequence information of nucleic acid sequences of at least the CDR3-coding sequence of VH and VL genes in B cells of the subject. For example, the nucleic acid sequences so determined may comprise VH and VL genes. The B cells may be preferably mature B cells. For example, the mature B cells may comprise memory B cells, plasma cells, or a combination thereof. The plasma cells may comprise bone marrow plasma cells, lymph node plasma cells or spleen plasma cells. In a particular example, bone marrow plasma cells may be used. The plasma cells may be selected or enriched based on differential expression of cell markers, particularly cell surface markers, such as Blimp-1, CD138, CXCR4, and/or CD45.

Obtaining the nucleic acid sequence information may comprise determining the nucleic acid sequences and optionally the corresponding amino acid sequences in the B cells or in lymphoid tissues, or in other aspects, obtaining such information from a service provider or a data storage device. In further aspects, such nucleic acid sequence information may be used for determining the amino acid sequences of the serum antibodies.

For determining the nucleic acid sequences in the B cells or in lymphoid tissues, any nucleic acid sequencing methods known in the art may be used, including high throughput DNA sequencing. Non-limiting examples of high-throughput sequencing methods comprise sequencing-by-synthesis (e.g., 454 sequencing), sequencing-by-ligation, sequencing-by-hybridization, single molecule DNA sequencing, multiplex polony sequencing, nanopore sequencing, or a combination thereof.

In certain aspects, there may be provided methods for obtaining sequence information of amino acid sequences of at least the CDR3 of the VH and VL regions of antibodies in a serum-containing sample of a subject. Obtaining sequence information may comprise determining amino acid or nucleic acid sequences or obtaining such information from a service provider or a data storage device.

Such amino acid sequence determination methods may comprise obtaining mass spectra of peptides derived from serum antibodies of the subject. To separate peptides derived from serum antibodies, any chromatography methods may be used, such as high performance liquid chromatography (HPLC).

For determining amino acid sequences, there may be provided methods comprising isolating or enriching a selected class of serum antibodies such as IgG, IgM, IgA, IgE, or other major Ig classes, isolating or enriching serum antibodies that bind to a predetermined antigen, and/or isolating or enriching CDR3-containing fragments of serum antibodies.

In further aspects, the methods may comprise preparing CDR3-containing peptide fragments from serum antibodies using a protease that is identified based on the sequence information of nucleic acid sequences and corresponding amino acid sequences of at least the CDR3 of VH and VL regions in mature B cells of the subject. For example, the protease cleaves VH and VL peptides at the site outside or adjacent to CDR3, thus leaving CDR3 regions substantially intact.

In certain aspects, there may also be provided method comprising enriching or purifying CDR3-containing peptide fragments. For example, such methods may comprise conjugating CDR3-containing peptide fragments with a labeled thiol-specific conjugating agent for specific conjugation of the unique cysteine at the end of the CDR3 sequences. Methods of enriching or purifying conjugated CDR3-containing peptide fragments may be based on the label on the conjugated CDR3-containing peptide fragments. Examples of the label include biotin.

Certain aspects of the invention is based, in part, on the discovery that highly abundant antibody cDNAs in plasma cells or in a lymphoid tissue are correlated with antibody specificity toward an antigen related to a disease or a condition in the subject, such as a tumor. In additional aspects, there may be provided methods comprising determining the abundancy level of the amino acid sequences of the serum antibodies or of the nucleic acid sequences of VH and VL genes in the B cells or in a lymphoid tissue, for example, by an automated method. For the determination of abundancy level of the amino acid sequences of serum antibodies, a quantitative method for mass spectrometry may be used.

In certain methods, there may be provided methods comprising identifying antibody amino acid sequences that exhibit at least a threshold level of abundancy. For example, the threshold level of abundancy is a concentration of about, at least, or at most 5, 10, 20, 30, 40, 50, 100, 200, 300, 400, 500 μg/ml (or any range derivable therein) or a level of any one of the about 20, 30, 40, 50, 60, 70, 80, 90, 100, 200 (or any numerical range derivable therein) most abundant CDR3-containing amino acid sequences of the serum antibodies.

In certain methods, there may be provided methods comprising identifying antibody nucleic acid sequences that exhibit at least a threshold level of abundancy. Such threshold level of abundancy may be at least 0.5, 1, 2, 3, 4, 5, 6, 7, 8, 9, 10, 15% of frequency in an antibody gene pool of the subject, for example, antibody genes in a B cell population or a lymphoid tissue. Such a B cell population may be a specific mature B cell population, such as a population of mature B cells from a selected lymphoid tissue like bone marrow, spleen or lymph nodes.

In certain further aspects, there may be provided methods comprising reporting any of the determination or identification described above. For example, such report may be in a computer-accessible format.

In certain aspects, there may also be provided methods comprising generating one or more antibodies or antigen-binding fragments comprising one or more of the abundant amino acid sequences as described above. Generation of antibodies or antigen-binding fragments may comprise chemical synthesis of $V_H$ and $V_L$ coding regions corresponding to abundant VH and VL amino acid sequences of serum antibodies that exhibit at least a threshold level of abundancy, or comprise, in other aspects, chemical synthesis of abundant nucleic acid sequences of VH and VL genes in B cells or in a lymphoid tissue.

The B cells may be mature B cells, particularly, plasma cells, more particularly, bone marrow plasma B cells. The generation methods may further comprise incorporating the abundant sequences into one or more expression vectors. Further aspects may comprise expressing the abundant sequences such as synthesized VH and VL sequences in any host cells, such as bacteria cells, yeast cells, insect cells, or mammalian cells.

For example, the antibodies or antigen-binding fragments so generated may bind an antigen the subject has or has been exposed to. The antigen may be an infectious agent, a tumor antigen, a tumor cell or a self-antigen. Such binding may have a monovalent affinity of at least or about 100, 200, $10^3$, $10^4$, $10^5$ pM, or 1, 2, 3, 4, 5 μM or any range derivable therein.

There may be further provided methods comprising evaluating the generated antibody or antigen-binding fragments for binding affinity or specificity to a predetermined antigen such as an infectious agent, a tumor antigen, a tumor cell or a self-antigen.

In a preferable aspect, each of the antibodies or antigen-binding fragments so generated comprises similarly abundant amino acid or nucleic acid sequences of $V_H$ and $V_L$. For example, a $V_H$ sequence may have a level of abundancy ranked as the $3^{rd}$ most abundant VH sequence in a serum-containing sample, which may be paired with a $V_L$ sequence that have a similar rank level of abundancy (for example, $3^{rd}$, $4^{th}$, or $5^{th}$)) in the same sample. The inventors determined that pairing $V_H$ genes with $V_L$ genes having a rank-order abundancy within +/−3 (e.g., the $3^{th}$ most abundant $V_H$ with any of the $1^{st}$-$6^{th}$ most abundant $V_L$) results in antigen specific antibodies at a frequency greater than 50%.

Embodiments discussed in the context of methods and/or compositions of the invention may be employed with respect to any other method or composition described herein. Thus, an embodiment pertaining to one method or composition may be applied to other methods and compositions of the invention as well.

As used herein the terms "encode" or "encoding" with reference to a nucleic acid are used to make the invention readily understandable by the skilled artisan; however, these terms may be used interchangeably with "comprise" or "comprising" respectively.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 13A) Anti-C1s 2.1L-2.1HB was injected onto a chip with immobilized C1s at 25 nM, 50 nM, 100 nM or 200 nM and (FIG. 13B) As above for anti-C1s 2.3L-2.2H injected at 2.625 nM, 5.25 nM, 10.5 nM or 21 nM.

DESCRIPTION OF ILLUSTRATIVE EMBODIMENTS

I. Introduction

Figure 1:
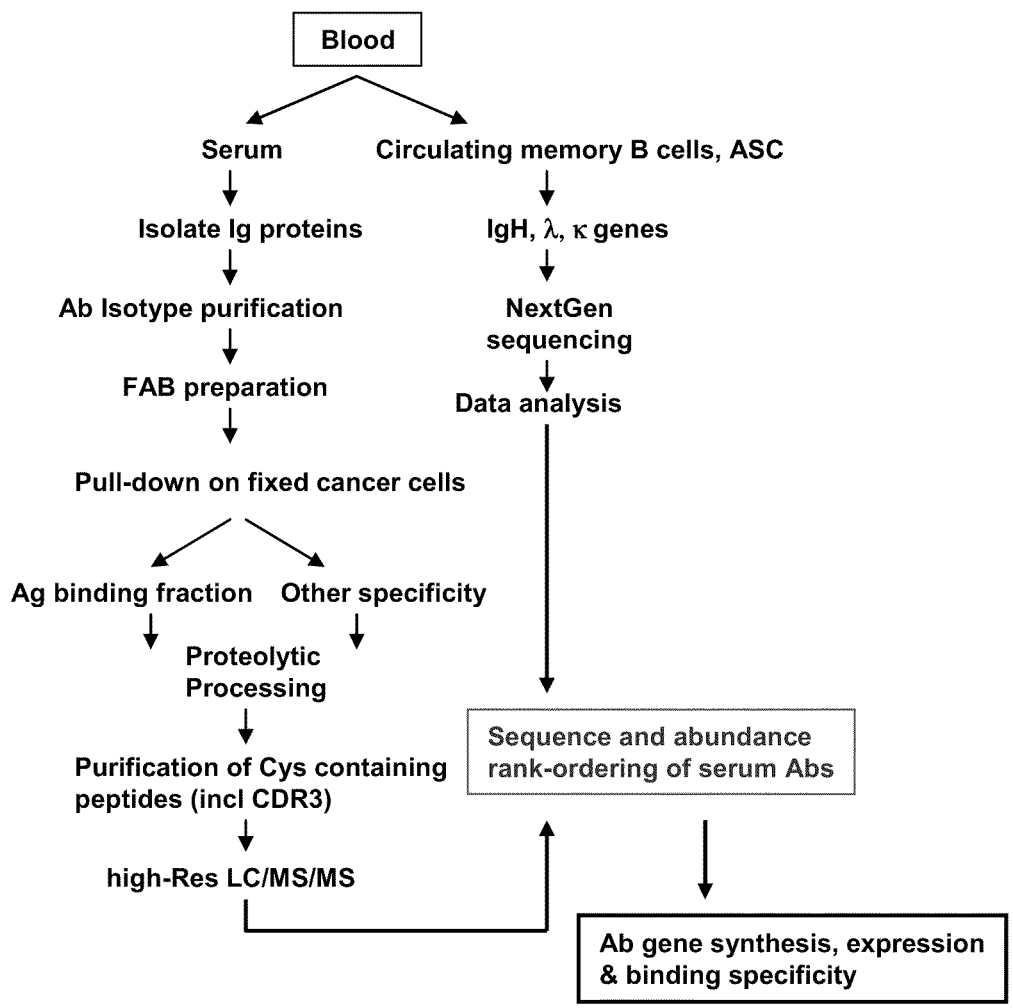
FIG. 1: Flow diagram of an exemplary embodiment of the experimental methodology for the quantitative analysis of serum Ig.

It is remarkable to ponder how biological research has failed to address certain key issues that lie at the heart of understanding living systems. One such issue is the analysis of the composition of the polyclonal immune response in mammals. Serum antibodies play an indispensable role in protecting jawed vertebrates against challenges from environmental agents, pathogens and aberrant self cells. Yet despite immense progress in understanding the origin of immune responses and B cell development, it has not been possible to resolve at a molecular level, the ultimate outcome of humoral immunity which is to populate the serum with a protective polyclonal antibody population. For technical reasons, serum antibody responses have only been characterized with respect to titers for specific antigens with little or no information on the relative amounts and affinities and specificities of the immunoglobulins that bind to the antigen. The ability of certain aspects of the present invention to deconvolute the serum immune response by characterizing the relative abundancy and amino acid sequences of its antibody components and then to individually evaluate them for therapeutic function can revolutionize protein therapeutics.

B-cell maturation and homing are hallmarks of adaptive immunity and the production of protective immunoglobulin responses. Extensive studies in molecular immunology and genetics have led to a great appreciation of the temporal stages of B cell differentiation and many of the functions of various B cell subpopulations in mammals. The terminal- and irreversible-stage of B cell development is the formation of plasma cells that populate the bone marrow, spleen and other lymphoid tissues and serve as immunoglobulin (Ig) production factories. Fully differentiated plasma cells together with immature plasma cells (plasmablasts) that secrete lower amounts of antibody, collectively represent less than 1% of the lymphoid cells and yet are responsible for all the antibodies in circulation. From a functional standpoint, circulating antibodies are comprised of three pools: a low affinity, non-specific pool (produced primarily by ASC of B1 and marginal zone B cell origin), a more abundant pool of polyclonal and progressively higher affinity/specificity antibodies generated in response to challenge, and a third pool of high affinity antibodies with diverse specificities towards antigens from earlier exposure. Antibodies comprising the third pool are produced throughout most of the organism's life time (as long as 50 yrs in man) without an apparent need for antigen re-stimulation. These long lasting responses play an important protective role to-reinfection and constitute the "humoral memory." The non-specific antibody pool constitutes the "natural antibody" or "innate" component of the humoral immune response that confers early protection against pathogens. The second population of antibodies comprise the adaptive immune response and declines rapidly in intensity within weeks after challenge (Rajewsky, 1996; Manz et al., 2005; Shapiro-Shelef and Calame, 2005; Lanzavecchia and Sallusto, 2009).

Plasma cells represent less than 1% of the lymphoid cells and yet they are responsible for all the antibodies in circulation (Rajewsky, 1996; Manz et al., 2005; Shapiro-Shelef and Calame, 2005; Lanzavecchia and Sallusto, 2009). In mice and humans, antibodies are present in serum at concentrations between 10-20 mg/ml, of which 85% is IgG, about 7% is IgM and another 7-10% monomeric IgA (Manz et al., 2005). Analysis of the antibody secreting cell (ASC) populations in the mouse indicates that serum may contain as many as 500 different antibodies of which multiple may be of the same antigen specificity. However, low abundancy antibodies present at concentrations <20 µg/ml (about 1 nM) are not likely to play a significant role, at least individually, in cancer surveillance and killing.

Remarkably, given the immense importance of serum antibodies in mammalian immunity, there is still no way to quantitatively characterize the relative concentrations and determine the sequence and affinity/specificity of the various antibodies that comprise the serum Ig pool. For technical reasons, serum antibody responses have only been characterized with respect to titers for specific antigens. Proteomic analysis of serum Igs has not been possible, first because the junctionally diverse and somatically mutated amino acid sequences of fully assembled V regions in Igs are essential for the interpretation of MS spectra but are not known a priori. In other words MS analysis of serum IgG requires knowledge of the amino acid sequences of the proteins but these sequences are not known. Second, because serum is a highly complex mixture of numerous proteins shot gun proteomic methods are extremely difficult to implement. Third, proteomic methods cannot inform on antibody specificities and biological function.

Immunologists have relied on the isolation of antibodies with desired specificity by immortalization using techniques such as the hybridoma technology or B-cell immortalization by viral (EBV) infection or alternatively, by B-cell screening and cloning. However, these approaches cannot capture the repertoire of antibodies in circulation. Plasma cells which produce antibodies cannot proliferate and cannot be fused or immortalized. It is not possible to know whether an antibody isolated from immortalizing/cloning memory B-cells is represented in the serum and at what level relative to other antibodies. For these reasons the art does not contain any information on how to isolate the antibodies that are present in circulation, especially those antibodies that are present in higher abundance or are specific for binding to a disease causing antigen.

In addition, these approaches cannot be generally applied to any animal other than a small set of mammals, mice, primates and in some cases rabbits for which suitable tools for B cell immortalization have been developed. Moreover, these methods are very time consuming and as a result it can take many months between the sacrifice of an animal and the isolation of an antigen specific antibody.

This invention seeks to overcome the prior art disadvantages and develops methods for the quantitative molecular deconvolution of antibody responses in humans and animals. For example, high-throughput sequencing, proteomic and/or bioinformatic analyses could be combined to identify the sequence and relative abundance of highly represented immunoglobulins (Igs) in circulation or in lymphoid tissues. In certain further embodiments, the genes for the variable domains of these antibodies could then be synthesized, the respective IgGs or antibody fragments such as scFvs expressed and purified and then the antibodies or antibody fragments could be analyzed for binding to an antigen in the source of the subject, such as infectious agents or cancer cells of interest.

For quantitative molecular deconvolution of antibody response from serum, there may be provided a method with exemplary embodiments illustrated in FIG. 1. In certain embodiments one or more of the steps may be optional and variations of the steps may be used to carry out the same purpose. First, high-throughput sequencing like NextGen sequencing of V gene cDNAs from mature B-cells (memory and plasmablasts) in peripheral blood, or from plasma cells in the bone marrow and spleen (when available) is used to create a database of the amino acid sequences of the patient's antibodies. In certain aspects, DNA sequencing could be used to build a sequence database of all the antibodies that are made by an individual. Second, for proteomic analysis the immunoglobulin fraction from patient's serum is isolated, and antibodies are fractionated by various affinity methods for Ig class separation, and also by affinity binding on various antigens of interest. Third, the Ig polypeptides in the various fractions are fragmented using proteases that preserve the integrity of the CDR3 regions. The CDR3 regions are unique or near unique identifiers of the different antibodies. The CDR3 peptides are also enriched from unrelated peptide by virtue of methods that capitalize on the presence of a Cys residue in the peptide. For example, reagents that react with thiols to introduce a biotin are used. Fourth, the CDR3 peptides are then resolved and sequenced by shotgun proteomics LC-MS/MS methods that provide absolute quantitation of the various CDR3 sequences in the pool. Fifth, the MS data is interpreted with reference to the amino acid sequence database generated in the first step above. Sixth, the most abundant $V_H$ and $V_L$ genes identified in the serum are synthesized by total gene synthesis. Seventh, $V_H$ and $V_L$ genes of the same abundancy are paired into IgG which is expressed and characterized for antigen binding affinity.

In further embodiments antigen specific antibodies are isolated by affinity chromatography with immobilized antigen. Then, peptides that are unique or otherwise can identify sequences encoded by V gene families are identified as in the paragraph above. Subsequently VH and VL genes corresponding to peptides having the same abundance (frequency) or rank-order abundance are synthesized and paired into IgG which is expressed and characterized for antigen binding affinity.

In further embodiments, the relative abundance of VH and VL cDNA in B cells from lymphoid tissues after immunization is used to identify antigen-specific antibodies. Following immunization, adaptive immune responses result in the production of antigen-specific antibodies by newly differentiated B cells. The inventors have found that V gene cDNAs that encode antigen specific antibodies are expressed at very high level in lymphoid tissues. Thus, the inventors have employed high throughput DNA sequencing to determine the V genes expressed by B cells in a particular lymphoid compartment and then deduce the abundance or frequency of these V genes. The inventors synthesized highly abundant V genes and paired VH and VL genes according to their abundance or to their rank-order abundance in that tissue. The inventors have found that between 40% and >80% of the paired V genes give rise to antigen specific antibodies. The percentage of antigen specific antibodies thus produced correlates to the serum titer of antibodies as determined by dilution series of ELISA assays on plated coated with immobilized antigen.

Pairing of $V_H$ and $V_L$ chains can also be guided by grouping the identified $V_H$ and $V_L$ sequences into clusters of related sequences (e.g., clusters representing sequences that differ only by somatic hypermutation). Such clustering can be accomplished by producing multiple sequence alignments of the identified $V_H$ and $V_L$ sequences and thereby clusters of related sequences. Clustering information can then be used to guide $V_H$ and $V_L$ chaining pairing. Alternatively or additionally, $V_H$ and $V_L$ chains identified by the instant methods can be screened by a combinatorial affinity assay (e.g., ELISA) to identified paired chains. These methods may be of particular use in situations where an antibody repertoire is not highly polarized, such as often occurs in samples from sheep, goats and rabbits.

In further embodiments there may be provided methods to identify antigen-specific variable gene sequences directly from lymphoid tissues without separation of B cells. An exemplary embodiment may be illustrated in FIG. 2. One or more of the steps may be optional and variations of the steps may be used to carry out the same purpose. First the process may begin with the sacrifice of an immunized animal and the collection of primary, secondary or tertiary lymphoid organs or tissue sample. Second, high-throughput sequencing like NextGen sequencing of V gene cDNAs may be carried out. Third, bioinformatic analysis may be employed to determine the frequency of occurrence of the various V genes. Fourth, V genes expressed at high abundance or frequency could be identified. For example, each of these high abundance (i.e., frequency) genes comprises at least 0.5% of the entire V gene population obtained or analyzed from the corresponding tissue. Fifth, synthetic DNA encoding the abundant genes from above may be prepared. Sixth, the genes encoding the $V_H$ and $V_L$ chains may be paired based on their ranked-ordered abundance. Seventh, the respective $V_H$-$V_L$ gene combinations may be expressed in a host cell to produce antibodies specific to the antigen used for animal immunization.

II. Definitions

Unless defined otherwise, all technical and scientific terms used herein have the meaning commonly understood by one of ordinary skill in the art relevant to the invention. The definitions below supplement those in the art and are directed to the embodiments described in the current application.

The term "antibody" is used herein in the broadest sense and specifically encompasses at least monoclonal antibodies, polyclonal antibodies, multi-specific antibodies (e.g. bispecific antibodies), naturally polyspecific antibodies, chimeric antibodies, humanized antibodies, human antibodies, and antibody fragments. An antibody is a protein comprising one or more polypeptides substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes.

"Antibody fragments" comprise a portion of an intact antibody, for example, one or more portions of the antigen-binding region thereof. Examples of antibody fragments include Fab, Fab', F(ab')2, and Fv fragments, diabodies, linear antibodies, single-chain antibodies, and multi-specific antibodies formed from intact antibodies and antibody fragments.

An "intact antibody" is one comprising full-length heavy- and light-chains and an Fc region. An intact antibody is also referred to as a "full-length, heterodimeric" antibody or immunoglobulin.

The term "variable" refers to the portions of the immunoglobulin domains that exhibit variability in their sequence and that are involved in determining the specificity and binding affinity of a particular antibody.

As used herein, "antibody variable domain," refers to a portion of the light and heavy chains of antibody molecules that include amino acid sequences of Complementary Determining Regions (CDRs; i.e., CDR1, CDR2, and CDR3), and Framework Regions (FRs; i.e., FR1, FR2, FR3, and FR4). FR include those amino acid positions in an antibody variable domain other than CDR positions as defined herein. VH refers to the variable domain of the heavy chain. VL refers to the variable domain of the light chain.

As used herein, the term "complementary nucleotide sequence" refers to a sequence of nucleotides in a single-stranded molecule of DNA or RNA that is sufficiently complementary to that on another single strand to specifically hybridize to it with consequent hydrogen bonding.

An "expression vector" is intended to be any nucleotide molecule used to transport genetic information.

III. Antibody Variable Domains

Certain aspects of the invention provide methods for identifying antibody variable domains or variable domain-coding sequences that are over-represented in serum or B cells. Such skewed representation of antibody variable domains is useful to identify novel antigen binding molecules having high affinity or specificity. Generating antibody or antibody fragments having variable domains with a high level of abundancy allows for the isolation of high affinity binders. The present invention is based, in part, on the discovery that abundancy levels of regions of an antibody variable domain that form the antigen binding pocket, for example CDR3 regions, could correlate with the desired affinity or specificity.

For identifying desired antibody variable domains, certain aspects of the present invention provide methods of determining sequences and distribution of antibody complementarity determining regions (CDRs). Specifically, the sequences of one to six of the complementary determining regions (CDRs) on VH and/or VL could be determined by protein sequencing or nucleic acid sequencing methods. The level of abundancy of variable domains or CDRs could be determined as an absolute level like a concentration or relative level like a rank-order.

Antibodies are globular plasma proteins (~150 kDa) that are also known as immunoglobulins. They have sugar chains added to some of their amino acid residues. In other words, antibodies are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds. Each chain is composed of structural domains called Ig domains. These domains contain about 70-110 amino acids and are classified into different categories (for example, variable or IgV, and constant or IgC) according to their size and function. They have a characteristic immunoglobulin fold in which two beta sheets create a "sandwich" shape, held together by interactions between conserved cysteines and other charged amino acids.

There are five types of human Ig heavy chain denoted by the Greek letters: α, δ, ε, γ, and μ. The type of heavy chain present defines the class of antibody; these chains are found in IgA, IgD, IgE, IgG, and IgM antibodies, respectively. Distinct heavy chains differ in size and composition; Ig heavy chains α and γ contain approximately 450 amino acids, while μ and ε have approximately 550 amino acids. Other animals encode analogous immunoglobulin heavy chain classes.

Each heavy chain has two regions, the constant region and the variable region. The constant region is identical in all antibodies of the same isotype, but differs in antibodies of different isotypes. Heavy chains γ, α and δ have a constant region composed of three tandem (in a line) Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In humans (and mice) there are two types of Immunoglobulin light chain, which are called lambda (λ) and kappa (κ). A light chain has two successive domains: one constant domain and one variable domain. The approximate length of a light chain is 211 to 217 amino acids. Each antibody contains two light chains that are always identical; only one type of light chain, κ or λ, is present per antibody in these species.

The fragment antigen-binding (Fab fragment) is a region on an antibody that binds to antigens. It is composed of one constant and one variable domain of each of the heavy and the light chain. These domains shape the paratope—the antigen-binding site—at the amino terminal end of the monomer.

The two variable domains bind the epitope on their specific antigens. The variable domain is also referred to as the $F_V$ region and is the most important region for binding to antigens. More specifically variable loops, three each on the light ($V_L$) and heavy ($V_H$) chains are responsible for binding to the antigen. These loops are referred to as the Complementarity Determining Regions (CDRs).

A complementarity determining region (CDR) is a short amino acid sequence found in the variable domains of antigen receptor (e.g. immunoglobulin and T cell receptor) proteins that complements an antigen and therefore provides the receptor with its specificity for that particular antigen. CDRs are supported within the variable domains by conserved framework regions (FRs).

Each polypeptide chain of an antigen receptor contains three CDRs (CDR1, CDR2 and CDR3). Since the antigen receptors are typically composed of two polypeptide chains, there are six CDRs for each antigen receptor that can come into contact with the antigen (each heavy and light chain contains three CDRs), twelve CDRs on a single antibody molecule and sixty CDRs on a pentameric IgM molecule. Since most sequence variation associated with immunoglobulins and T cell receptors are found in the CDRs, these regions are sometimes referred to as hypervariable domains. Among these, CDR3 shows the greatest variability as it is encoded by a recombination of the VJ (VDJ in the case of heavy chain) regions.

IV. Antibody Variable Region Analysis

In certain aspects of the invention, antibody variable gene (V gene) sequences derived from cDNA may be analyzed. For example, information from such analysis may be used to generate a database of the V genes (V gene database) that give rise to circulating antibodies so that mass spectrometry (MS) spectra of peptides derived from serum antibodies can be assigned and in turn used to identify the respective full length V genes in the database encoding those peptides. In another embodiment, the sequence information may be used to identify abundant variable gene nucleic acids such as mRNA transcripts and generate antibody or antibody fragments based on the abundant variable genes. The abundant variable genes so identified may correspond to antibodies or antibody fragments that have desired specificity or affinity.

From the nucleotide sequences determined by the initial sequencing, putative amino acid sequences for the VH and VL regions can be determined using standard algorithms and software packages (e.g. see the world wide web at mrc-lmb.cam.ac.uk/pubseq/, the Staden package and Gap4 programs). These can be further characterized to determine the CDR (Complementarity Determining Region) parts of the VH and VL sequences, particularly CDR1, CDR2 and CDR3. Methods for determining the putative amino acid sequences and identifying CDR regions are well known in the art. In one particular embodiment, CDR3 sequences are identified by searching for highly conserved sequence motif at the N-terminal region preceding the CDR3. This method could correctly identified >90% of the CDR3 sequences in antibodies. The putative amino acid sequence derived based on the nucleic acid sequencing of B cell cDNA could be used for the shot gun proteomic analysis of serum antibodies in some embodiments.

A variety of methods have been developed for the immortalization or cloning of antibodies from individual B cells. These techniques include hybridoma technology, memory B cell immortalization by viral (EBV) infection, the engineering of memory B cells that express both surface and secreted antibodies, and the cloning of antigen-specific, antibody genes from transient ASC populations, from memory B cells or from splenic plasma cells. Recently microfluidic and nano-patterning devices have been used to increase the throughput of B cells interrogated for antigen binding and for the subsequent cloning of the $V_H$ and $V_L$ genes.

While invaluable for the isolation of monoclonal antibodies, these techniques have several drawbacks: First, most have focused on and, in some cases, are only compatible with certain stages of the B cell life cycle. Thus, extensive studies on terminally differentiated mature plasma ASC have not been done. This leaves unresolved the central issue of whether a particular antibody isolated from B cells is represented at a significant amount in the serum of that individual. Also, there is evidence that plasma cells in the bone marrow are the main compartment for antibody synthesis and are selected on the basis of their affinity and perhaps protective function. Second, single B cell cloning methods are still not efficient enough to provide complete information on the diversity of antibodies in serum, especially with respect to serum concentration and abundancy of specific antibody clones. Third, current attempts to pool recombinant mAbs in order to reconstitute a polyclonal antibody that displays higher therapeutic efficacy cannot possibly capture the true protective effect of sera since the mixing of cloned antibodies is completely ad hoc. The present invention could avoid one or more of these problems by the methods described herein.

In certain embodiments, the mRNA from B cells or directly from one or more lymphoid tissues could be isolated and converted to cDNA. In further embodiments, the cDNA may be subject to $V_H$ and $V_L$ gene isolation. For example, the genes encoding for the variable heavy and the variable light ($V_H$ and Vκ,λ) genes could be amplified using specific primers that hybridize to the 5' and 3' ends of the cDNA. Depending on the primers used for cDNA construction, V genes of different Ig classes could be distinguished. For example, the $V_H$ and $V_L$ gene isolation may be based on Ig classes either by using known primer sets of variable gene amplification or, preferably by 3' RACE (rapid amplification of cDNA ends) using a class-specific 3' primer. For example, the class-specific 3' primer may hybridize to the $C_{H2}$ domain.

V. Lymphoid Tissues

In certain embodiments, there may be provided methods of identifying antigen-specific variable region sequences by obtaining nucleic acid sequences directly from lymphoid tissues. In optional aspects, B cells may not be separated from the lymphoid tissue where the B cells reside. The method may comprise isolation of primary, secondary, or tertiary lymphoid tissues. Any methods known for isolation of lymphoid tissues may be used.

Lymphoid tissue associated with the lymphatic system is concerned with immune functions in defending the body against the infections and spread of tumors. It consists of connective tissue with various types of white blood cells enmeshed in it, most numerous being the lymphocytes.

The lymphoid tissue may be primary, secondary, or tertiary depending upon the stage of lymphocyte development and maturation it is involved in. (The tertiary lymphoid tissue typically contains far fewer lymphocytes, and assumes an immune role only when challenged with antigens that result in inflammation. It achieves this by importing the lymphocytes from blood and lymph.

The central or primary lymphoid organs generate lymphocytes from immature progenitor cells. The thymus and the bone marrow constitute the primary lymphoid tissues involved in the production and early selection of lymphocytes.

Secondary or peripheral lymphoid organs maintain mature naive lymphocytes and initiate an adaptive immune response. The peripheral lymphoid organs are the sites of lymphocyte activation by antigen. Activation leads to clonal expansion and affinity maturation. Mature Lymphocytes recirculate between the blood and the peripheral lymphoid organs until they encounter their specific antigen.

Secondary lymphoid tissue provides the environment for the foreign or altered native molecules (antigens) to interact with the lymphocytes. It is exemplified by the lymph nodes, and the lymphoid follicles in tonsils, Peyer's patches, spleen, adenoids, skin, etc. that are associated with the mucosa-associated lymphoid tissue (MALT).

A lymph node is an organized collection of lymphoid tissue, through which the lymph passes on its way to returning to the blood. Lymph nodes are located at intervals along the lymphatic system. Several afferent lymph vessels bring in lymph, which percolates through the substance of the lymph node, and is drained out by an efferent lymph vessel.

The substance of a lymph node consists of lymphoid follicles in the outer portion called the "cortex", which contains the lymphoid follicles, and an inner portion called "medulla", which is surrounded by the cortex on all sides except for a portion known as the "hilum". The hilum presents as a depression on the surface of the lymph node, which makes the otherwise spherical or ovoid lymph node bean-shaped. The efferent lymph vessel directly emerges from the lymph node here. The arteries and veins supplying the lymph node with blood enter and exit through the hilum.

Lymph follicles are a dense collection of lymphocytes, the number, size and configuration of which change in accordance with the functional state of the lymph node. For example, the follicles expand significantly upon encountering a foreign antigen. The selection of B cells occurs in the germinal center of the lymph nodes.

Lymph nodes are particularly numerous in the mediastinum in the chest, neck, pelvis, axilla (armpit), inguinal (groin) region, and in association with the blood vessels of the intestines.

VI. B Cell Sample Preparation

In certain embodiments, B cells may be extracted for isolation of variable region nucleic acid sequences. In other embodiments, B cells may not need to be separated from a lymphoid tissue, thus saving cost and time for B cell isolation. Without B cell separation, lymphoid tissues may be directed used to obtain a pool of antibody variable gene sequences, for example, by using antibody-specific primers or probes, such as primer or probes based on antibody constant region sequences.

In one embodiment, mature, circulating B-cells (memory cells and/or antigen secreting cells (ASCs)) in peripheral blood (for example, about or at least or up to 3, 4, 5, 6, 7, 8, 9, 10, 15, 20 ml or any ranges derivable therefrom) may be used. The circulating B cells may be separated by magnetic sorting protocols (Jackson et al., 2008; Scheid et al., 2009; Smith et al., 2009; Kwakkenbos et al., 2010) as described in the Examples. Alternatively, plasma cells which are terminally differentiated B cells that reside in the bone marrow, spleen or in secondary lymphoid organs could be isolated and used for the determination of the B cell repertoire in an individual animal or human. In particular aspects, plasma cells could be mobilized from the bone marrow into circulation, e.g., by administration of G-CSF (granulocyte colony-stimulating factor) and isolated.

ASC are terminally or near terminally differentiated B cells (including plasma cells and plasmablasts) that are demarcated by the surface markers (for example, syndecan-1). They lack surface IgM and IgD, other typical B cell surface markers (e.g., CD19) and importantly, they express the repressor Blimp-1, the transcription factor Xbp-1 and down-regulate Pax-5. Antibody secreting cells can be generated from: (i) B1 cells which produce low specificity "innate-like" IgM, (ii) from B cells that do not reside in the follicles of lymphoid organs (extrafollicular) and include marginal zone (MZ, $IgM^+$, $IgD^+$, $CD27^{+)}$ cells which generally produce lower affinity antibodies (the latter mostly in the absence T-cell help), and finally, (iii) cells of the B2 lineage that have circulated through the lymphoid follicles. B2 cells progress to the plasma stage either directly from the germinal centers where they undergo selection for higher antigen affinity (following somatic hypermutation) or after they have first entered the memory compartment. Regardless of their precise origin, these cells express high affinity antibodies predominantly of the IgG isotype and constitute the major component of the protective immune response following challenge.

Plasma cells are typically unable to proliferate or de-differentiate back to earlier B cell lineages. Most plasma cells are short-lived and die within a few days. In contrast, a fraction of the plasma cells occupy "niches' (primarily in bone marrow) that provide an appropriate cytokine microenvironment for survival and continued antibody secretion that may last from months to years; i.e., these are the cells that produce antibodies primarily involved with protection to re-challenge and constitute the "humoral memory" immune response.

A particularly preferred site for ASC isolation is the bone marrow where a large number of plasma cells that express antibodies specific for the antigen are found. It should be noted that B cells that mature to become plasma cells and to reside in the bone marrow predominantly express high affinity IgG antibodies. Mature plasma cells in the bone marrow are selected using based on cell surface markers well known in the field, e.g., $CD138^{++}$, $CXCR4^+$ and $CD45^{-/weak}$. Mature plasma cells can also be isolated based on the high expression level of the transcription factor Blimp-1; methods for the isolation of Blimp-$1^{high}$ cells, especially from transgenic animals carrying reporter proteins linked to Blimp-1 are known in the art.

On the other hand, memory B cells are formed from activated B cells that are specific to the antigen encountered during the primary immune response. These cells are able to live for a long time, and can respond quickly following a second exposure to the same antigen. In wake of first (primary response) infection involving a particular antigen, the responding naïve (ones which have never been exposed to the antigen) cells proliferate to produce a colony of cells, most of which differentiate into the plasma cells, also called effector B cells (which produce the antibodies) and clear away with the resolution of infection, and the rest persist as the memory cells that can survive for years, or even a lifetime.

VII. Nucleic Acid Sequencing

Any sequencing methods, particularly high-throughput sequencing methods, may be used to determine one or more of the VH and VL nucleotide sequences in the B cell repertoire. For example, the nucleotide sequence of the VH and VL could be determined by 454 sequencing (Fox et al., 2009) with a universal primer and without amplification to allow accurate quantitation of the respective mRNAs. Reads longer than 300 bp may be processed for further analysis (Weinstein et al., 2009). Non-limiting examples of high-throughput sequencing technologies are described below.

High-throughput sequencing technologies are intended to lower the cost of DNA sequencing beyond what is possible with standard dye-terminator methods. Most of such sequencing approaches use an in vitro cloning step to amplify individual DNA molecules, because their molecular detection methods are not sensitive enough for single molecule sequencing. Emulsion PCR isolates individual DNA molecules along with primer-coated beads in aqueous droplets within an oil phase. Polymerase chain reaction (PCR) then coats each bead with clonal copies of the DNA molecule followed by immobilization for later sequencing. Emulsion PCR is used in the methods by Marguilis et al. (commercialized by 454 Life Sciences), Shendure and Porreca et al. (also known as "Polony sequencing") and SOLiD sequencing, (developed by Agencourt, now Applied Biosystems). Another method for in vitro clonal amplification is bridge PCR, where fragments are amplified upon primers attached to a solid surface, used in the Illumina Genome Analyzer. The single-molecule method developed by Stephen Quake's laboratory (later commercialized by Helicos) is an exception: it uses bright fluorophores and laser excitation to detect pyrose-quencing events from individual DNA molecules fixed to a surface, eliminating the need for molecular amplification.

In parallelized sequencing, DNA molecules are physically bound to a surface, and sequenced in parallel. Sequencing by synthesis, like dye-termination electrophoretic sequencing, uses a DNA polymerase to determine the base sequence. Reversible terminator methods (used by Illumina and Helicos) use reversible versions of dye-terminators, adding one nucleotide at a time, detect fluorescence at each position in real time, by repeated removal of the blocking group to allow polymerization of another nucleotide. Pyrosequencing (used by 454) also uses DNA polymerization, adding one nucleotide species at a time and detecting and quantifying the number of nucleotides added to a given location through the light emitted by the release of attached pyrophosphates.

Sequencing by ligation uses a DNA ligase to determine the target sequence. Used in the polony method and in the SOLiD technology, it uses a pool of all possible oligonucleotides of a fixed length, labeled according to the sequenced position. Oligonucleotides are annealed and ligated; the preferential ligation by DNA ligase for matching sequences results in a signal informative of the nucleotide at that position.

In microfluidic Sanger sequencing the entire thermocycling amplification of DNA fragments as well as their separation by electrophoresis is done on a single glass wafer (approximately 10 cm in diameter) thus reducing the reagent usage as well as cost.

Sequencing by hybridization is a non-enzymatic method that uses a DNA microarray. A single pool of DNA whose sequence is to be determined is fluorescently labeled and hybridized to an array containing known sequences. Strong hybridization signals from a given spot on the array identifies its sequence in the DNA being sequenced. Mass spectrometry may be used to determine mass differences between DNA fragments produced in chain-termination reactions.

DNA sequencing methods currently under development include labeling the DNA polymerase (Scheid et al., 2009), reading the sequence as a DNA strand transits through nanopores, and microscopy-based techniques, such as atomic force microscopy (AFM) or electron microscopy that are used to identify the positions of individual nucleotides within long DNA fragments (>5,000 bp) by nucleotide labeling with heavier elements (e.g., halogens) for visual detection and recording.

The inventors found that less than $10^5$ reads for each of the VH and VL pools could be sufficient to provide information on the variable gene sequences that correspond to the most abundant antibodies found in serum.

VIII. Sequence Abundancy Determination

Bioinformatic methods for the automated analysis of sequencing results such as 454 reads, statistical sequencing error analysis and finally identification and classification of CDRs, especially of CDR3, the most hypervariable region in antibodies have been developed by the inventors.

In certain embodiments, for example to account for sequencing/PCR uncertainties, antibody sequences, particularly CDR3 sequences, could be grouped into families, with each family consisting of all the CDR3 sequences differing by one or two nucleotides or amino acids.

For example, the abundancy level of antibody variable region sequences may be based on the CDR3 sequences as identifiers. The sequences for determination of a level of abundancy may be a family including an identical CDR3 sequence (amino acid sequence or nucleic acid sequence) and a CDR3 sequence having at least 80% homology, for example 85, 90, 95, 96, 97, 98 or 99% homology therewith. Sequence homology is as determined using the BLAST2 program (Tatusova et al., 1999) at the National Center for Biotechnology Information, USA (world wide web at.ncbi.nlm.nih.gov) with default parameters. For example, the sequences occurring in total at a relative level of abundancy represented by a frequency at least 1 percent in the set of sequences may be a combination of the CDR3 sequences or a sequence having 1 or 2 amino acid changes therefrom. For example, a first sequence may occur at a frequency of 0.7 percent, and second, third and fourth sequences each having a single amino acid change therefrom each occur at a frequency of 0.1%—the total occurrence in abundancy is therefore 1.1% and the dominant antibody sequence (occurring at a frequency of 0.7%) is therefore a candidate CDR3 sequence that could be used for antibody generation/characterization.

IX. Use of Antibody Variable Sequence Information

In addition to providing a reference database for interpreting mass spectra data of serum antibody analysis, the nucleic acid information through analysis of the variable region especially CDR sequence and abundancy could also be used to provide potential antigen-specific antibody or antibody fragments. In certain aspects, the resulting $V_H$ and Vκ, λ libraries based on the abundant variable region especially CDR information could be inserted into an appropriate expression vector suitable for the production of either full length IgG proteins or of antibody fragments (scFv or Fab or single domain antibodies comprising of only the $V_H$ or the Vκ, λ chain). Libraries comprising of $V_H$ and Vκ, λ could result in combinatorial pairing of the heavy and light chains.

Some of the randomly paired $V_H$ and Vκ, λ chains may be active while others will not give rise to functional antibodies. However the inventors have found that because of the very high representation of antigen specific plasma cells in bone marrow, a very large fraction of the resulting clones express functional and high affinity recombinant antibodies. In one example a scFv library constructed from $V_H$ and Vκ, λ genes isolated from bone marrow plasma cells >5% of the clones contained antigen specific antibodies.

For example, the inventors analyzed $V_H$ and $V_L$ transcript levels in bone marrow plasma cells isolated 5 days after booster immunization (incomplete Freund's adjuvant) with 4 different protein antigens in two mice each. Patterns of V-D-J usage and somatic hypermutation were determined and correlated with representation within the bone marrow plasma cell population. Consistent with the pivotal role of bone marrow plasma cells on antibody secretion, antigen specific $V_H$ and $V_L$ cDNAs were found to be highly enriched to levels between 1-20% of the total Ig RNA. For each of the four antigens tested, 2-4 $V_H$ and $V_L$ cDNAs were represented at frequencies >4% of the total $V_H$ cDNA pool. The four most abundant $V_H$ and $V_L$ genes for each antigen and from each mouse were synthesized, the heavy and light chains paired as discussed below, and the resulting antibody fragments were expressed in bacteria. Importantly, on average, >80% of the antibody fragments corresponding to the most highly expressed $V_H$ and $V_L$ genes in the immunized animals were found to be antigen specific by ELISA (enzyme-linked immunosorbent assay) and BIACore analysis.

Thus, the inventors have found that manual ELISA screening of a few hundred clones from such libraries is sufficient to allow the generation of antibodies with high affinity and specificity. Manual ELISA screening of additional clones can be used to reveal different combinations of $V_H$ and Vκ, λ genes that give rise to a diverse set of antibodies. This method is simple and fast and the inventors believe that is likely to replace the hybridoma technology for the isolation of antibodies from animals.

X. Quantitative Serum Antibody Analysis

To identify a pool of abundant amino acid sequences of CDR regions, especially CDR3 regions of circulating antibodies, MS shotgun proteomics or protein sequencing methods may be used to determine the amino acid sequences.

Any protein sequencing methods determining the amino acid sequences of its constituent peptides may be used. The two major direct methods of protein sequencing are mass spectrometry and the Edman degradation reaction. It is also possible to generate an amino acid sequence from the DNA or mRNA sequence encoding the protein, if this is known. However, there are also a number of other reactions which can be used to gain more limited information about protein sequences and can be used as preliminaries to the aforementioned methods of sequencing or to overcome specific inadequacies within them.

For example, shotgun proteomic strategy based on digesting proteins into peptides and sequencing them using tandem mass spectrometry and automated database searching could be the method of choice for identifying serum antibody sequences. "Shotgun proteomics" refers to the direct analysis of complex protein mixtures to rapidly generate a global profile of the protein complement within the mixture. This approach has been facilitated by the use of multidimensional protein identification technology (MudPIT), which incorporates multidimensional high-pressure liquid chromatography (LC/LC), tandem mass spectrometry (MS/MS) and database-searching algorithms.

A. IgG Fractionation

Ig proteins of a particular class could be isolated, for example, by affinity chromatography using protein A (or anti-IgA and anti-IgM antibodies for affinity purification of the other major Ig classes).

In certain aspects, antibodies or antibody fragments such as FAB fraction from digestion of purified Igs with papain and FAB purification, could be affinity enriched for binding to desired antigen or pathogen (e.g., a cancer cell, a tumor antigen, or an infection agent), or host tissue for the isolation of antibodies suspected to have a role in autoimmunity. Antibodies may be eluted under denaturing conditions. In further embodiments, several fractions or pools of serum-derived FABs could be generated, including those that are: (a) enriched for antigen, (b) enriched for host tissue and (c) antibodies with unrelated or unknown specificities.

B. Proteolytic Fragmentation

For quantitative shotgun proteomics mass spectrometry analysis, antibodies or antibody fragments such as FAB could be digested using proteases that cleave after amino acids/amino acid pairs that are under-represented in CDR3 but present in the adjacent framework regions. The appropriate proteases for proteomic processing may be identified by bioinformatics analysis of the V gene sequence database.

In one example the FAB fractions are subjected to proteolysis with sequencing grade trypsin (Sigma) at 37° C. for 4 hr. As an alternate method, a combination of the proteases GluC (NEB) and LysC (Sigma) could be used in place of trypsin to generate a distinct set of proteolytic peptides that in computational tests provide better coverage of the CDR3s (i.e. so that cleavage occurs at positions flanking the CDR3s and therefore peptides with intact CDR3s are produced).

In certain embodiments, CDR3 peptides could be enriched from unrelated peptides via specific conjugation of the unique Cys at the end of the CDR3 sequence with a thiol specific reagent that allows the purification of such peptides.

The inventors have developed protocols that deploy a combination of appropriate proteases for peptide generation and Cys specific pull down of thiol containing CDR3 peptides which result in a peptide mixture comprising of at least 30% CDR3 peptide sequences. In one example, CDR3 peptides are enriched via reversible thiol specific biotinylation. In another example, CDR3 peptides are reacted with special chromophores that allow their specific excitation and detection during MS analysis. As the CDR3 peptides almost universally (>99%) contain cysteine, a biotinylated thiol-specific cross-linking agent is used to affinity isolate these peptides for mass spectral analysis thus greatly simplifying the complexity of the spectra.

C. Shotgun MS (Mass Spectrometry) Proteomics

In certain exemplary aspects, the peptides of antibody molecules could be resolved by reverse phase chromatography and in-line nanoelectrospray ionization/high-resolution tandem mass spectrometry, using well-established protocols (Ong and Mann, 2005; Pandey and Mann, 2000; Shevchenko et al., 1996; Hunt et al., 1986; Link et al., 1999; Washburn et al., 2001; Lu et al., 2007) and Fourier-transform LTQ-Orbitrap mass spectrometry (Hu et al., 2005) to collect hundreds of thousands of tandem mass spectra from CDR3 and other FAB-derived peptides.

For example, peptides are separated on a reverse phase Zorbax C-18 column (Agilent) running an elution gradient from 5% to 38% acetonitrile, 0.1% formic acid. Peptides were eluted directly into an LTQ-Orbitrap mass spectrometer (Thermo Scientific) by nano-electrospray ionization. Data-dependant ion selection could be enabled, with parent ion mass spectra (MS1) collected at 100k resolution. Ions with known charge >+1 may be selected for CID fragmentation spectral analysis (MS2) in order to decrease intensity, with a maximum of 12 parent ions selected per MS1 cycle. Dynamic exclusion is activated, with ions selected for MS2 twice within 30 sec. Ions identified in an LC-MS/MS run as corresponding to peptides from the constant regions of the heavy and light chains may be excluded from data-dependent selection in subsequent experiments in order to increase selection of peptides from the variable region.

D. MS Proteomic Data Analysis

The variable gene sequencing data from B cells of the same subject are employed to supplement the protein sequence database for interpreting peptide mass spectra in shotgun proteolysis (Marcotte, 2007). With the aid of the sample-specific sequence database, we identify CDR3 peptides from the tandem mass spectra (controlling for false discovery rate using standard methods (Keller et al., 2002; Nesvizhskii et al., 2009).

Several recent advances in shotgun proteomics enable protein quantification to ~2-fold absolute accuracy without introducing additional requirements for isotope labels or internal calibrant peptides (Lu et al., 2007; Malmstrom et al., 2009; Silva et al., 2006a; Vogel and Marcotte, 2008; Ishihama et al., 2005; Liu et al., 2004). Among these approaches, two are well-suited to quantification of individual IgGs: the APEX approach is based upon weighted counts of tandem mass spectra affiliated with a protein (the weighting incorporates machine learning estimates of peptide observability (Lu et al., 2007; Vogel, 2008), and the average ion intensity approach, based on mass spectrometry ion chromatogram peak volumes (Silva et al., 2006a). For example, both methods could be employed to measure abundances of each of the identified antigen-specific IgGs in the serum-containing sample. Combinations (Malmstrom et al., 2009) and single peptide quantitation methods could also be used as alternatives. Algorithms for subtraction of non-CDR3 peptides could be used. On the basis of these measured abundances, at least the 50 or 100 most highly abundant $V_H$ and $V_L$ proteins in the sample could be rank-ordered.

For example, sample-specific protein sequence databases are created from high-throughput V region cDNA transcript data. $V_H$ and $V_L$ gene represented by >8 reads by 454 sequencing are compiled into a database which in turn is added to a concatenated forward/reversed-sequence protein-coding database. The LC-MS/MS data is searched against this database using the Sequest search algorithm as part of the Bioworks software package (Thermo Scientific). Filters are applied to ensure high confidence peptide identifications as follows: $\Delta CN \geq 0.250$; XCorr=2.0, 2.5, and 3.0 for +2, +3, and $\geq$+4 charge; and accuracy $\leq 10.0$ ppm.

In certain embodiments the amino acid sequence analysis coupled with the information various V gene pools of different B cell source (e.g., the particular organ-specific ASC population that expresses $V_H$ and $V_L$ genes whose products are found in serum) could be employed to identify whether a particular serum antibody originated preferentially in the bone marrow, in secondary lymphoid tissues (as is likely to be the case early in the immune response), or in the case of persistent infection, possibly in tertiary lymphoid tissues. The possibility that a particular antibody is secreted by plasma cells that have migrated to different tissues could also be addressed. At a systems level the inventors could employ this information to estimate the contribution of different compartments to humoral immunity in a quantitative fashion and could generate antibody or antibody fragments involved in different stage of immune response.

XI. Antibody Generation and Characterization

Certain embodiments described above lead to the identification and quantitation of abundant serum antibodies of interest or the most abundant variable region sequences in B cells or in a selected lymphoid tissue. Such information may be used to develop antibody or antibody fragments that have desired binding affinity or antigen response. In certain aspects, their binding specificities or therapeutic utility could be evaluated. For example, antibody or antibody fragments which are cytotoxic towards cancer cells could be generated from the abundant serum polyclonal antibody pool. In further embodiments, antibody or antibody specific fragments that are specific for the antigen used to immunize any animal may be provided by analyzing sequence and abundance information of variable region nucleic acids in B cells or directly from lymphoid tissues.

A. Gene Synthesis for Antibody Generation

To generate antibody or antibody fragments with desired binding specificity or property, the V genes could be synthesized, assembled into FAB or IgG and expressed. $V_H$ and $V_L$ genes may be generated by high throughout gene synthesis based on the sequence information obtained by the methods described above.

For example, automated gene synthesis could be used. Briefly, gene fragments (lengths from 200 to 500 nucleotides) are generated using inside-out nucleation PCR reactions under carefully controlled conditions to ensure construction of the desired final fragment. Subsequently stitch-overlap extension PCR is used to synthesize the gene of interest. The design of these fragments and relevant overlaps is automated, with oligonucleotide synthesizer worklists and robot operation scripts for synthesis and assembly. With the current configuration, a throughput of 48 kilobases is attained per robotic assembly run (4 hours). Alignment of sequences so as to maintain maximal conservation and subsequent "padding" of the sequences at either end to maintain identical length permits the use of a generic overlapping oligonucleotide assembly strategy and also ensures the most oligonucleotide re-use. Currently throughput stands at 50 $V_H$ and 50 $V_L$ genes (i.e. >38,000 bp of DNA) synthesized and validated for correct ORF by one researcher within a week and at a reagent cost <$2,000.

B. Pairing of $V_H$ and $V_L$

For expression, a particular $V_H$ has to be paired with cognate $V_L$. The pairing problem could be addressed as follows: First the inventors have empirically found that the correct pairings of $V_H$ and $V_L$s in a sample correlate well with the rank-ordered abundancy of the proteins in the sample. For example the fifth most abundant $V_H$ pairs with the fifth most abundant $V_L$. So far with this approach, using $V_H$ and $V_L$ bioinformatic rank-ordering information for pairing, the inventors have achieved 75% success in pairing $V_H$ and $V_L$ genes to produce high affinity antigen specific antibodies from four different mice. Further, the inventors have found that even if the optimal VL for pairing is not the one having similar abundancy based on proteomic analysis and because antigen recognition is dominated by the $V_H$ sequence, antigen binding could be still observed, albeit with lower affinity.

In certain aspects, VH and VL chains can be identified by grouping together related VH and VL sequences. For example, identified VH and/or VL sequence can be aligned and clustered base on the relatedness of the sequences. For example, each group may comprise antibody sequences that differ from each other only by the result of somatic hypermutation. In some cases, clusters of sequences can be ranked and the rank of the clusters used guide paring between VH and VL sequences.

In still further aspects, VH and VL chains can be paired based combinatorial affinity assays. In this case, VH and VL pairs for testing can be guided by abundance ranking and/or by clustering of related sequences as outlined above.

The pairing could also be addressed or confirmed by other approaches. For example, in situ hybridization (ISH) of fixed plasma cells with $V_H$ and candidate $V_L$ probes, for example, identified from the abundancy analysis. ISH can easily be applied in a high throughput manner using appropriate robotic automation. Alternatively, ESI-MS (electrospray ionization mass spectrometry) of the FAB pool, coupled with matching of these spectra to the expected molecular weight can in certain cases determine $V_H$ and $V_L$ pairing.

C. Antibody Expression

In further aspects, the synthesized $V_H$ and $V_L$ genes may be inserted into appropriate vectors for expression, for example, as FABs in *E. coli* or as full length IgGs by transient transfection of HEK293 cells.

Binding between candidate antibody or antibody fragments and antigen could be then evaluated by any methods for binding detection and quantification, particularly ELISA. For example, cancer specific antibodies or antibody fragments could be characterized by cancer and host cell binding by fluorescence-activated cell sorting (FACS) following fluorescent labeling of antibodies.

Antibodies according to certain aspects of the invention may be labeled with a detectable label or may be conjugated with an effector molecule, for example a drug e.g., an antibacterial agent or a toxin or an enzyme, using conventional procedures and the invention extends to such labeled antibodies or antibody conjugates.

Antibodies usable or produced in the present invention, may be a whole antibody or an antigen binding fragment thereof and may in general belong to any immunoglobulin class. Thus, for example, it may be an IgM or an IgG antibody. The antibody or fragment may be of animal, for example, mammalian origin and may be for example of murine, rat, sheep or human origin. Preferably, it may be a recombinant antibody fragment, i.e., an antibody or antibody fragment which has been produced using recombinant DNA techniques. Such recombination antibody fragment may comprise prevalent CDR or variable domain sequences identified as above.

Particular recombinant antibodies or antibody fragments include, (1) those having an antigen binding site at least part of which is derived from a different antibody, for example those in which the hypervariable or complementarity determining regions of one antibody have been grafted into the variable framework regions of a second, different antibody (as described in, for example, EP 239400); (2) recombinant antibodies or fragments wherein non-Fv sequences have been substituted by non-Fv sequences from other, different antibodies (as described in, for example, EP 171496, EP 173494 and EP 194276); or (3) recombinant antibodies or fragments possessing substantially the structure of a natural immunoglobulin but wherein the hinge region has a different number of cysteine residues from that found in the natural immunoglobulin but wherein one or more cysteine residues in a surface pocket of the recombinant antibody or fragment is in the place of another amino acid residue present in the natural immunoglobulin (as described in, for example, WO 89/01782 and WO 89/01974).

Teachings of texts such as Harlow and Lane (1998) further details antibodies, antibody fragments, their preparation and use.

The antibody or antibody fragment may be of polyclonal or monoclonal origin. It may be specific for at least one epitope.

Antigen binding antibody fragments include, for example, fragments derived by proteolytic cleavage of a whole antibody, such as F(ab')2, Fab' or Fab fragments, or fragments obtained by recombinant DNA techniques, for example Fv fragments (as described, for example, in WO 89/02465).

XII. Therapeutic Applications

The present invention may involve methods that have a wide range of therapeutic applications, such as cancer therapy, enhancing immune response, vaccination, or treatment of infectious disease or autoimmune diseases.

In some embodiments, the present methods may be used for the quantitative molecular deconvolution of antibody response in cancer patients in remission to identify the sequence and abundancy of the highly represented antibodies in circulation that may contribute to the eradication of the tumor in the patient. Such antibodies could be very useful as therapeutic agents on their own or for the identification new antigens on cancer cells that can serve as therapeutic targets. Similarly in some embodiments the present methods can be used to identify antibodies that can protect patients from a particular infectious agent. Such antibodies may be identified either from patients that had been infected and then recovered from the infection or alternatively, from vaccinated patients. These antibodies or antibody fragments could be produced and their specificity and cytotoxicity toward cancer cells or neutralization pitency towards infectious agents could be evaluated. The ability to deconvolute the serum polyclonal response by characterizing the relative abundancy and amino acid sequences of its antibody components and then to individually evaluate cancer cell binding and cytotoxicity could provide an unprecedented wealth of information on the nature of adaptive immune responses to malignancies. Such identified antibodies could lead to discovery of potent cytotoxic cancer therapeutics and the identification of novel tumor antigens used for cancer detection and therapy.

For example, therapeutic antibodies for leukemia via the deconvolution of antibody responses in patients in remission, following allogeneic hematopoietic stem cell (HSC) transplantation could be identified by the methods described above. Promising antibodies could then be taken through pharmacological engineering and animal evaluation.

Certain aspects of the present invention may involve the passive transfer of antibody or antibody fragments generated by certain aspects of the present invention to non-immune individuals (e.g. patients undergoing chemo/radio therapy, immunosuppression for organ transplantation, immunocompromised due to underlying conditions such as diabetes, trauma etc, also the very young or very old). For example, the sequences of antibodies conferring immunity can be determined by looking for over-represented VH and VL sequences in patients who have overcome infection. These protective antibodies can be re-synthesised at the genetic level, over-expressed in *E. coli* (or other expression systems) and purified. The resultant purified recombinant antibody can then be administered to patients as a passive immunotherapy. Antibodies can also be ordered from commercial suppliers such as Operon Technologies Inc., USA (on the world wide web at operon.com) by simply supplying them with the sequence of the antibody to be manufactured.

Vaccination protects against infection by priming the immune system with pathogen-derived antigen(s). Vaccination is effected by a single or repeated exposures to the pathogen-derived antigen(s) and allows antibody maturation and B cell clonal expansion without the deleterious effects of the full-blown infectious process. T cell involvement is also of great importance in effecting vaccination of patients. Certain aspects of the present invention can also be used to monitor the immunisation process with experimental vaccines along with qualitative and quantitative assessment of antibody response. For example, one or more subjects are given the experimental vaccine and VH and VL sequences are amplified from the subjects and the antibody repertoire analyzed as described above. An increased abundancy of a given antibody variable domain or CDR sequence with vaccination could lead to the identification of a protective antibody candidate pool. After validation, such protective antibodies could be used for treatment of patients in need of such protection, such as patients infected by a microorganism, such as a virus.

XIII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Immunization Protocol

Protein antigens (e.g., purified human complement protein C1s (CalBiochem), purified chicken egg ovalbumin (OVA, Sigma), or recombinant bacterially-expressed human B cell regulator of IgH transcription (BRIGHT) were resuspended in sterile-filtered phosphate buffered saline (PBS) at 1.0 mg/ml. On the day of primary immunization, 25 µl of antigen solution was thoroughly mixed with 25 µl of Complete Freund's Adjuvant (CFA, Pierce Biotechnology) and 50 µl of sterile PBS and stored on ice. Female Balb/c mice (Charles Rivers Laboratories) 6-8 weeks old were housed in conventional barrier space and were maintained on a normal chow diet. Prior to injections, mice were bled from the tail vein and approximately 25 µl of blood was collected and stored at −20° C. for later analysis. Day 1 was designated as the day primary immunizations were performed. 100 µl of the antigen-CFA mixture per mouse was injected with a 26-gauge needle subcutaneously into the backpad. Mice were monitored daily by animal housing staff and cages were changed twice per week.

For secondary immunization, 25 µl of antigen solution was thoroughly mixed with 25 µl of Incomplete Freund's Adjuvant (IFA, Pierce Biotechnology) and 50 µl of sterile PBS and stored on ice. On day 21 mice were given the secondary immunization intraperitoneally at 100 µl of antigen-IFA mixture per mouse. On day 26 mice were sacrificed by $CO_2$ asphyxiation and blood, lymph nodes, spleen, femurs and tibia were collected. For $3^{rd}$ and subsequent immunizations as needed, 25 µl of antigen solution was thoroughly mixed with 25 µl of Incomplete Freund's Adjuvant (IFA, Pierce Biotechnology) in 50 µl of sterile PBS were injected into animals two weeks after secondary immunization and every 2 weeks for subsequent immunizations, as needed.

Example 2

Isolation of the Plasma Cell ($CD138^+CD45R$ $(B220)^-CD49b^-$) Population from Murine Bone Marrow The muscle and fat tissue was removed from tibias and femurs harvested from immunized mice. The ends of both tibia and femurs were clipped with surgical scissors and bone marrow was flushed out with a 26-gauge insulin syringe (Becton Dickinson, BD). Bone marrow tissue was collected in sterile-filtered Buffer#1 (PBS/0.1% bovine serum albumin (BSA)/2 mM ethylenediaminetetracetic acid (EDTA)). Bone marrow cells were collected by filtration through a 70-um cell strainer (BD) with mechanical disruption and washed with 20 ml of PBS and collected in a 50 ml tube (Falcon, BD). Bone marrow cells were then centrifuged at 1200 RPM for 10 min at 4° C. Supernatant was decanted and cell pellet was resuspended with 3.0 ml of RBC lysis buffer (eBioscience) and shaken gently at 25° C. for 5 minutes. Cell suspension was then diluted with 20 ml of PBS and centrifuged at 1200 RPM for 10 minutes at 4° C. Supernatant was decanted and cell pellet was resuspended in 1.0 ml of Buffer#1.

Each isolated bone marrow cell suspension was incubated with 7.5 ug and 10 ug of biotinylated rat anti-mouse CD45R (B220) and biotinylated rat anti-mouse CD49b (eBioscience), respectively. In Example 9, each isolated bone marrow cell suspension was incubated with 2.5 ug and 1.5 ug of biotinylated rat anti-mouse CD45R (B220) and biotinylated rat anti-mouse CD49b (eBioscience), respectively. Cell suspension was rotated at 4° C. for 20 minutes. Cell suspensions were then centrifuged at 2,000 RPM for 6 minutes at 4° C., supernatant was removed and the cell pellet was resuspended in 1.5 ml of Buffer#1. Streptavidin conjugated M280 magnetic beads (Invitrogen) were washed and resuspended according to manufacturer's protocol. 50 µl of magnetic beads were added to each cell suspension and the mixture was rotated at 4° C. for 20 min. Cell suspension was then placed on Dynabead magnet (Invitrogen) and the supernatant (negative fraction, cells unconjugated to beads) was collected, cells conjugated to beads were discarded (alternatively, bead bound cells could be saved for later analysis).

Optionally, the negative fraction cells were then incubated with 2.5 µg of both biotinylated rat anti-mouse CD45R (B220) and biotinylated rat anti-mouse CD49b and rotated at 4° C. for 20 min. Cells were then centrifuged at 2,000 RPM at 4° C. for 6 min, supernatant was removed and cell pellet was resuspended in 1.0 ml of Buffer#1. 50 µl of magnetic beads were added to each cell suspension and the mixture was rotated at 4° C. for 20 min. Cell suspension was then placed on Dynabead magnet (Invitrogen) and the supernatant (negative fraction, cells unconjugated to beads) was collected, cells conjugated to beads were discarded (alternatively, bead bound cells could be saved for only analysis).

Pre-washed streptavidin M280 magnetic beads were incubated for 30 min at 4° C. with biotinylated rat anti-mouse CD138 (BD Pharmingen) with 0.75 µg antibody per 25 µl of magnetic beads. Beads were then washed with magnet according to manufacturer's protocol and resuspended in Buffer#1. The negative cell fraction (double-depleted of CD45R/B220$^+$ and CD49b$^+$ cells) collected previously was incubated with 50 µl of CD138 conjugated magnetic beads and rotated at 4° C. for 30 min. Cells were then placed on magnet and washed 3 times with Buffer#1, the negative (CD138$^-$) cells unbound to beads were discarded (or saved only for analysis). The positive CD138$^+$ bead-bound cells were collected and stored at 4° C. until further processed.

Figure 3:
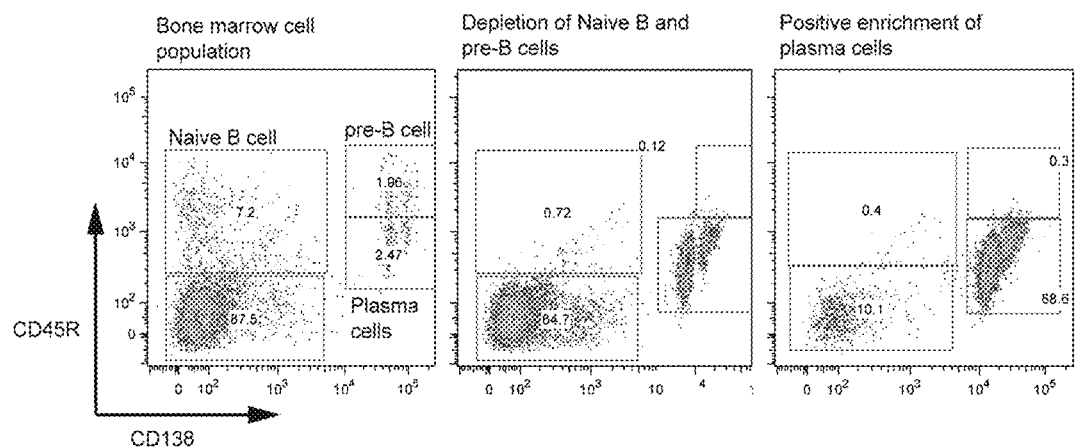
FIG. 3: Isolation of plasma cells from bone marrow. Left Panel: Flow cytometry plot of the total mouse bone marrow cell population labeled with anti-CD45R-APC and anti-CD138-PE antibodies. Middle panel: Bone marrow cells remaining following depletion of CD45R⁺ cells. Right Panel. Cell population isolated following magnetic sorting with anti-CD138⁺ conjugated magnetic beads.

Flow cytometry analysis of the plasma cell purification process is shown in FIG. 3.

Example 3

Isolation of Antibody Secreting Cells (ASCs) and Memory B Cells

Murine memory B cells. Secondary lymphoid organs (spleen and lymph nodes) are harvested from immunized mice following euthanization. Tissue was collected in sterile-filtered Buffer#1 (PBS/0.1% bovine serum albumin (BSA)/2 mM EDTA). Splenic and lymph node cells were collected by filtration through a 70-um cell strainer (BD) with mechanical disruption and washed with 20 ml of PBS and collected in a 50 ml tube (Falcon, BD). Splenic and lymph node cells were then centrifuged at 1200 RPM for 10 min at 4° C. Supernatant was decanted and cell pellet was resuspended with 3.0 ml of RBC lysis buffer (eBioscience) and shaken gently at 25° C. for 5 minutes. Cell suspension was then diluted with 20 ml of PBS and centrifuged at 1200 RPM for 10 minutes at 4° C. Supernatant was decanted and cell pellet was resuspended in 1.0 ml of Buffer#1.

Additionally whole blood is extracted by cardiac puncture. Whole Blood is added to histopaque solution (Sigma) at 1:1 volume, avoiding mixing of the contents. The blood-histopaque solution is centrifuged at 1,600 RPM for 30 minutes at 23° C. without centrifugation braking. The peripheral blood mononuclear cell (PBMC) layer is isolated following gradient centrifugation, and washed twice through centrifugation with wash buffer (PBS, 2.5% Fetal Bovine Serum (FBS), 1 mM ethylenediaminetetraacetic acid (EDTA)). Cells were then resuspended in Buffer#1.

Splenic or lymph node germinal center cells are labeled with peanut agglutinnan biotin and germinal center memory B cells are then isolated with streptavidin magnetic beads (Invitrogen).

Human ASC and memory B cells. PBMCs from human volunteers are isolated and then stained with fluorescent antibodies. PBMC's are isolated using FACS by gating on CD19high/CD20low/CD3neg and then a second sort on CD27high/CD38high to obtain a pure population of ASC and memory B cells (Wrammert et al., 2008).

Example 4

Preparation of Variable Light (VL) and Variable Heavy (VH) Genes for High-Throughput DNA Sequencing RNA isolation CD138$^+$CD45R$^-$ bone marrow plasma cells or peripheral ASC and B cells isolated as described in Examples 2 and 3 above were centrifuged at 2,000 RPM at 4° C. for 5 min. Cells were then lysed with TRI reagent and total RNA was isolated according to the manufacturer's protocol in the Ribopure RNA isolation kit (Ambion). mRNA was isolated from total RNA through with oligodT resin and the Poly(A) purist kit (Ambion) according to the manufacturer's protocol. mRNA concentration was measured with an ND-1000 spectrophotometer (Nanodrop).

PCR amplification The isolated mRNA was used for first strand cDNA synthesis by reverse transcription with the Maloney murine leukemia virus reverse transcriptase (MMLV-RT, Ambion). For cDNA synthesis, 50 ng of mRNA was used as a template and oligo(dT) primers were used RT-PCR was performed according to manufacturer protocol of Retroscript kit (Ambion). Following cDNA construction, PCR amplification was performed to amplify the VL and VH genes using 2 ul of unpurified cDNA product and established VL and VH degenerate primer mixes (Krebber et al., 1997; Mazor et al., 2007). A complete list of primers can be found in Table 1.

TABLE 1

Primer mixes for PCR amplification of $V_L$ and $V_H$ genes

| Primers | Sequence | SEQ ID NO: |
|---|---|---|
| $V_L$-Forward | | |
| YarivL-FOR 1 | AGC CGG CCA TGG CGG AYA TCC AGC TGA CTC AGC C | 67 |
| YarivL-FOR 2 | AGC CGG CCA TGG CGG AYA TTG TTC TCW CCC AGT C | 68 |
| YarivL-FOR 3 | AGC CGG CCA TGG CGG AYA TTG TGM TMA CTC AGT C | 69 |
| YarivL-FOR 4 | AGC CGG CCA TGG CGG AYA TTG TGY TRA CAC AGT C | 70 |
| YarivL-FOR 5 | AGC CGG CCA TGG CGG AYA TTG TRA TGA CMC AGT C | 71 |
| YarivL-FOR 6 | AGC CGG CCA TGG CGG AYA TTM AGA TRA MCC AGT C | 72 |
| YarivL-FOR 7 | AGC CGG CCA TGG CGG AYA TTC AGA TGA YDC AGT C | 73 |
| YarivL-FOR 8 | AGC CGG CCA TGG CGG AYA TYC AGA TGA CAC AGA C | 74 |
| YarivL-FOR 9 | AGC CGG CCA TGG CGG AYA TTG TTC TCA WCC AGT C | 75 |
| YarivL-FOR 10 | AGC CGG CCA TGG CGG AYA TTG WGC TSA CCC AAT C | 76 |
| YarivL-FOR 11 | AGC CGG CCA TGG CGG AYA TTS TRA TGA CCC ART C | 77 |
| YarivL-FOR 12 | AGC CGG CCA TGG CGG AYR TTK TGA TGA CCC ARA C | 78 |
| YarivL-FOR 13 | AGC CGG CCA TGG CGG AYA TTG TGA TGA CBC AGK C | 79 |
| YarivL-FOR 14 | AGC CGG CCA TGG CGG AYA TTG TGA TAA CYC AGG A | 80 |
| YarivL-FOR 15 | AGC CGG CCA TGG CGG AYA TTG TGA TGA CCC AGW T | 81 |
| YarivL-FOR 16 | AGC CGG CCA TGG CGG AYA TTG TGA TGA CAC AAC C | 82 |
| YarivL-FOR 17 | AGC CGG CCA TGG CGG AYA TTT GCT GA CTC AGT C | 83 |
| YarivL-FOR 1 Lambda | AGC CGG CCA TGG CGG ARG CTG TTG TGA CTC AGG AAT C | 84 |

TABLE 1-continued

Primer mixes for PCR amplification of $V_L$ and $V_H$ genes

| Primers | Sequence | SEQ ID NO: |
|---|---|---|
| $V_L$-Reverse | | |
| YarivL-REV 1 | GAT GGT GCG GCC GCA GTA CGT TTG ATT TCC AGC TTG G | 85 |
| YarivL-REV 2 | GAT GGT GCG GCC GCA GTA CGT TTT ATT TCC AGC TTG G | 86 |
| YarivL-REV 4 | GAT GGT GCG GCC GCA GTA CGT TTT ATT TCC AAC TTT G | 87 |
| YarivL-REV 5 | GAT GGT GCG GCC GCA GTA CGT TTC AGC TCC AGC TTG G | 88 |
| YarivL-REV 1 Lambda | GAT GGT GCG GCC GCA GTA CCT AGG ACA GTC AGT TTG G | 89 |
| YarivL-REV Lambda 2 | GAT GGT GCG GCC GCA GTA CCT AGG ACA GTG ACC TTG G | 90 |
| $V_H$-Forward | | |
| YarivH-FOR 1 | GTT ATT GCT AGC GGC TCA GCC GGC AAT GGC GGA KGT RMA GCT TCA GGA GTC | 91 |
| YarivH-FOR 2 | GTT ATT GCT AGC GGC TCA GCC GGC AAT GGC GGA GGT BCA GCT BCA GCA GTC | 92 |
| YarivH-FOR 3 | GTT ATT GCT AGC GGC TCA GCC GGC AAT GGC GCA GGT GCA GCT GAA GSA STC | 93 |
| YarivH-FOR 4 | GTT ATT GCT AGC GGC TCA GCC GGC AAT GGC GGA GGT CCA RCT GCA ACA RTC | 94 |
| YarivH-FOR 5 | GTT ATT GCT AGC GGC TCA GCC GGC AAT GGC GCA GGT YCA GCT BCA GCA RTC | 95 |
| YarivH-FOR 6 | GTT ATT GCT AGC GGC TCA GCC GGC AAT GGC GCA GGT YCA RCT GCA GCA GTC | 96 |
| YarivH-FOR 7 | GTT ATT GCT AGC GGC TCA GCC GGC AAT GGC GCA GGT CCA CGT GAA GCA GTC | 97 |
| YarivH-FOR 8 | GTT ATT GCT AGC GGC TCA GCC GGC AAT GGC GGA GGT GAA SST GGT GGA ATC | 98 |
| YarivH-FOR 9 | GTT ATT GCT AGC GGC TCA GCC GGC AAT GGC GGA VGT GAW GYT GGT GGA GTC | 99 |
| YarivH-FOR 10 | GTT ATT GCT AGC GGC TCA GCC GGC AAT GGC GGA GGT GCA GSK GGT GGA GTC | 100 |
| YarivH-FOR 11 | GTT ATT GCT AGC GGC TCA GCC GGC AAT GGC GGA KGT GCA MCT GGT GGA GTC | 101 |
| YarivH-FOR 12 | GTT ATT GCT AGC GGC TCA GCC GGC AAT GGC GGA GGT GAA GCT GAT GGA RTC | 102 |
| YarivH-FOR 13 | GTT ATT GCT AGC GGC TCA GCC GGC AAT GGC GGA GGT GCA RCT TGT TGA GTC | 103 |
| YarivH-FOR 14 | GTT ATT GCT AGC GGC TCA GCC GGC AAT GGC GGA RGT RAA GCT TCT CGA GTC | 104 |
| YarivH-FOR 15 | GTT ATT GCT AGC GGC TCA GCC GGC AAT GGC GGA AGT GAA RST TGA GGA GTC | 105 |
| YarivH-FOR 16 | GTT ATT GCT AGC GGC TCA GCC GGC AAT GGC GCA GGT TAC TCT RAA AGW GTS TG | 106 |
| YarivH-FOR 17 | GTT ATT GCT AGC GGC TCA GCC GGC AAT GGC GCA GGT CCA ACT VCA GCA RCC | 107 |
| YarivH-FOR 18 | GTT ATT GCT AGC GGC TCA GCC GGC AAT GGC GGA TGT GAA CTT GGA AGT GTC | 108 |
| YarivH-FOR 19 | GTT ATT GCT AGC GGC TCA GCC GGC AAT GGC GGA GGT GAA GGT CAT CGA GTC | 109 |
| $V_H$-Reverse | | |
| YarivH-REV 1 | CCC TTG AAG CTT GCT GAG GAA ACG GTG ACC GTG GT | 110 |
| YarivH-REV 2 | CCC TTG AAG CTT GCT GAG GAG ACT GTG AGA GTG GT | 111 |
| YarivH-REV 3 | CCC TTG AAG CTT GCT GCA GAG ACA GTG ACC AGA GT | 112 |
| YarivH-REV 4 | CCC TTG AAG CTT GCT GAG GAG ACG GTG ACT GAG GT | 113 |

A 50 ul PCR reaction consisted of 0.2 mM of forward and reverse primer mixes, 5 ul of Thermopol buffer (NEB), 2 ul of unpurified cDNA, 1 ul of Taq DNA polymerase (NEB), and 39 ul of double distilled H2O. The PCR thermocycle program was: 92° C. for 3 min; 4 cycles (92° C. for 1 min, 50° C. for 1 min, 72° C. for 1 min); 4 cycles (92° C. for 1 min, 55° C. for 1 min, 72° C. for 1 min); 20 cycles (92° C. for 1 min, 63° C. for 1 min, 72° C. for 1 min); 72° C. for 7 min; 4° C. storage. PCR gene products were gel purified and submitted to SeqWright (Houston, Tex.) and Genomic Sequencing and Analysis Center at the University of Texas Austin for Roche GS-FLX 454 DNA sequencing.

PCR products of the VL and VH genes were gel purified and submitted to Genomic Sequencing and Analysis Center at the University of Texas Austin for 454 DNA sequencing.

Rapid cDNA end (RACE) amplification. Alternatively, a cDNA amplicon library specific for the variable light (VL) and variable heavy (VH) was constructed from the isolated mRNA. To start, first strand cDNA was synthesized from mRNA using the SMARTScribe Maloney murine leukemia virus reverse transcriptase (MMLV-RT, Clonetech). The cDNA synthesis utilized 25 ng mRNA, template switching specific 5' primers and 3' gene specific primers. Buffers and reaction conditions were used according to manufacturer's protocol. Primers were used that already incorporated 454 sequencing primers (Roche) on both 5' and 3' ends along with multiplex identifiers (MID) so that the cDNA synthesized and amplified could be directly used in the 454 emPCR step. The 5' forward primer utilized MMLV-RT template switching by the addition of three cytosine residues at the 3' end of first strand cDNA along with a portion of the 5' sequencing Primer B of 454 Titanium (SRp#1). For the reverse primer, primers were used to amplify the VL gene and a small portion of the 3' terminal of the light chain constant region Cκ along with the Primer A of 454 Titanium including 3 unique MIDs (SRp#2,3,4). Similarly, VH genes were amplified along with a small portion of the 3' terminal of the heavy chain constant 1 (CH1) region along with the Primer A of 454 Titatnium including 3 unique MIDs (SRp#5,6,7). All primers were synthesized and HPLC purified from Integrated DNA Technologies (IDT) and are listed in Table 2.

TABLE 2

Primers used for VL and VH cDNA amplicon Library

| Primer Name | Sequence 5' to 3' |
|---|---|
| SRp#1 | TGTGCCTTGGCAGTCTCAGGGG (SEQ ID NO: 1) |
| SRp#2 | CCATCTCATCCCTGCGTGTCTCCGACTCAGACGAGTGCGTAC AGTTGGTGCAGCATCAGC (SEQ ID NO: 2) |
| SRp#3 | CCATCTCATCCCTGCGTGTCTCCGACTCAGACGCTCGACAAC AGTTGGTGCAGCATCAGC (SEQ ID NO: 3) |
| SRp#4 | CCATCTCATCCCTGCGTGTCTCCGACTCAGAGACGCACTCAC AGTTGGTGCAGCATCAGC (SEQ ID NO: 4) |
| SRp#5 | CCATCTCATCCCTGCGTGTCTCCGACTCAGACGAGTGCGTGA TAGACCGATGGGGCTGTTG (SEQ ID NO: 5) |
| SRp#6 | CCATCTCATCCCTGCGTGTCTCCGACTCAGACGCTCGACAGA TAGACCGATGGGGCTGTTG (SEQ ID NO: 6) |
| SRp#7 | CCATCTCATCCCTGCGTGTCTCCGACTCAGAGACGCACTCGA TAGACCGATGGGGCTGTTG (SEQ ID NO: 7) |
| SRp#8 | /5BioTEG/CCTATCCCCTGTGTGCCTTGGCAGTCTCAG (SEQ ID NO: 8) |
| SRp#9 | GAGACACGCAGGGATGAGATGG (SEQ ID NO: 9) |

Following first strand cDNA synthesis, PCR was performed to amplify cDNA with primers based on the 5' and 3' ends of the added 454 sequencing primers (SRp#8 and 9, respectively; note that 5' forward primer SRp#8 was biotinylated on the 5' end). Standard PCR conditions were used according to the Advantage 2 PCR kit (Clontech). The cDNA samples were then run on a 1% agarose gel and the bands corresponding to VL or VH at ~450 and ~500 bp, respectively were extracted and further purified (Zymogen). cDNA concentration was measured using a nanodrop spectrophotometer. 500 ng of cDNA per sample was then used for 454 sequencing.

High-throughput sequencing of $V_L$ and $V_H$ repertoires. V gene repertoires isolated from BM-PC of eight mice were sequenced using high-throughput 454 GS-FLX sequencing (University of Texas, Austin, Tex.; SeqWright, Houston, Tex.). In total, 415,018 sequences were generated, and 454 data quality control filtered and grouped >97% of the sequences into datasets for each mouse according to their Multiplex Identifiers (MID) usages.

Example 5

Analysis of Antibody Variable Heavy and Variable Light Sequences

454 GS-FLX was used to obtain full-length reads of antibody variable regions VL and VH from the bone marrow plasma cells or ACS or memory B cells or directly from isolated bone marrow, lymph nodes or spleen. A full-length read was considered a sequence with coverage of all 3 CDRs.

CDR3s were identified by homology searching of highly conserved four amino acid motifs at N- and C-terminal of CDR3. Table 3 lists the motifs used to identify CDR-L3 and CDR-H3 and their occurrence frequency in KabatMan database (world wide web at bioinf.org.uk).

Reverse complementary sequences were also generated for motif search, and only in-frame CDR3 were considered for the following analysis. The identified CDR3 sequences were used as the VL and VH unique signature identifiers and their relative abundancy was calculated and used to represent corresponding variable gene abundancy (Tables 4-5). The full-length VL and VH sequences carrying the highly abundant CDR3 were then identified by an alignment similarity search and standard BLAST against the dataset (Table 6).

TABLE 3

Conserved motifs used to identify CDR3s

| | | | | | |
|---|---|---|---|---|---|
| N-CDR3H | Kabat # | 86 | 90 | 91 | 92 |
| | Residue | Asp | Tyr/Phe | Tyr/Phe | Cys |
| | Frequency | 98.3% | 99.4% | 98.8% | 99.5% |
| C-CDR3L | Kabat # | 103 | 104 | 106 | 107 |
| | Residue | Trp | Gly | Gly | Ser/Thr |
| | Frequency | 99.4% | 98.6% | 99.7% | 98.7% |
| N-CDR3H | Kabat # | 82 | 86 | 87 | 88 |
| | Residue | Asp | Tyr | Tyr/Phe | Cys |
| | Frequency | 98.5% | 98.2% | 97.7% | 99.1% |
| C-CDR3L | Kabat # | 98 | 99 | 101 | 102 |
| | Residue | Phe | Gly | Gly | Thr |
| | Frequency | 99.5% | 99.4% | 98.5% | 98.1% |

TABLE 4

Consensus CDR3H sequences from Bright-1 sample and their occurrence frequency (%)

| | SEQ ID NO: | control-1 | control-2 | C1s-1 | C1s-2 | Bright-1 | Bright-2 |
|---|---|---|---|---|---|---|---|
| HDYGNYVDY | 10 | 0 | 0 | 0 | 0 | 7.21 | 0.02 |
| DGNYQEDYFDY | 11 | 0 | 0 | 0.02 | 0 | 5.62 | 0 |

TABLE 4-continued

Consensus CDR3H sequences from Bright-1 sample and their occurrence frequency (%)

| | SEQ ID NO: | control-1 | control-2 | C1s-1 | C1s-2 | Bright-1 | Bright-2 |
|---|---|---|---|---|---|---|---|
| EGYAYDVDY | 12 | 0 | 0 | 0 | 0 | 1.91 | 0.01 |
| DDYDWYFDV | 13 | 0.09 | 2.11 | 1.97 | 0.03 | 1.54 | 0.01 |
| DNWDWYFDV | 14 | 0.27 | 0 | 1.11 | 0.72 | 1.48 | 0.01 |
| DDGYYWYFDV | 15 | 0 | 2.54 | 0.01 | 0 | 1.26 | 0 |
| YDYGKDFDY | 16 | 0 | 0 | 0 | 0 | 1.21 | 0 |
| CADGNY | 17 | 0 | 0 | 0 | 0 | 1.07 | 0 |
| VLGQGDYYAMDY | 18 | 0 | 0 | 0 | 0 | 0.97 | 0 |

20

TABLE 5

Consensus CDR3H sequences from C1s-2 sample and their occurrence frequency (%)

| | SEQ ID NO: | Control-1 | control-2 | C1s-1 | C1s-2 | Bright-1 | Bright-2 |
|---|---|---|---|---|---|---|---|
| SDRYDGYFDY | 19 | 0 | 0 | 0.09 | 10.98 | 0.04 | 0.01 |
| SDRFDGYFDY | 20 | 0 | 0 | 0.05 | 9.93 | 0.05 | 0.03 |
| WLLLAY | 21 | 0 | 0 | 0 | 3.33 | 0.01 | 0.02 |
| YGNYFDY | 22 | 0.01 | 0.94 | 0.35 | 2.47 | 0.14 | 0.58 |
| SDGYYYFDY | 23 | 0 | 0 | 0.02 | 1.66 | 0 | 0 |
| SGGNYDAMDY 24 | 24 | 0 | 0 | 0 | 1.17 | 0.02 | 0 |
| YYDYDKAYYFDY | 25 | 0 | 0 | 0.03 | 1.15 | 0 | 0 |

TABLE 6

Full-length amino acid sequence of consensus VL and VH

| | SEQ ID NO: | Full-length amino acid sequence of consensus VL and VH |
|---|---|---|
| C1s-2.1L | 26 | DVLMTQTPLSLPVSLGDQASISCRSSQSIVHSNGDTYLEWYLQKPG QSPKLLVYKLSNRFSGVPDRFSGSGSGTDFTLKISRVEAEDLGVYYC FQGSHVPLTFGAGTKLEIK |
| C1s-2.2L | 27 | DIVMTQSPASLAVSLGQRATISCRASESVDSYGNSFMHWYQQKPG QPPKLLIYRASNLESGIPARFSGSGSRTDFTLTINPVEADDVTTYYCQ QSNEDPWTFGGGTKLEIK |
| C1s-2.3L | 28 | DIVMTQSPLTLTVTIGQPASISCKSSQSLLDSDGKTYLNWLLQRPGQ SPKRLIYLVSKLDSGVPDRFTGSGSGTEFTLKTSRVEAEDLGVYYC WQGTHFPHFGGGTKLEIK |
| C1s-2.1H | 29 | QVQLQQSGAELARPGASVKMSCKASGYTFTSYTMHWVKQRPGQG LEWIGYINPSSGYTNYNQKFKDKATLTADKSSSTANMQLSSLTSED SAVYYCARSDRYDGYFDYWGQGTTLTVSSA |
| C1s-2.2H | 30 | EVKLVESGGGFVKPGGSLKLSCAASGFTFSTYGMSWVRQTPEKRL EWVASISAGGTTYYSDSVKGRFTISRDNARNILYLQMSSLRSEDTA MYYCARWLLLAYWGQGTLVTSSA |
| C1s-2.3H | 31 | QVQLQQSGTVLARPGASVKMSCKASGYTFTSYWMHWVKQRPGQ GLEWIGAIYPGNSDTSYNQKFKGKAKLTAVTSTSTAYMELSSLTNE DSAVYYCTRSDGYYFDYWGQGTTLTVSSA |

TABLE 6-continued

Full-length amino acid sequence of consensus VL and VH

| | SEQ ID NO: | Full-length amino acid sequence of consensus VL and VH |
|---|---|---|
| Bright-1.1L | 32 | DIVMTQSPSSLSASLGERVSLTCRASQDIGSSLNWLQQEPDGTIKRLI YATSSLDSGVPKRFSGSRSGSDYSLTISSLESVDFVDYYCLQYASSPF TFGSGTKLEIK |
| Bright-1.2L | 33 | DIVMTQSPLTLSVTIGQPASISCKSSQSLLDSDGKTYLNWLLQRPGQ SPKRLIYLVSKLDSGVPDRFTGSGSGTDFTLKISRVEAGDLGVYYC WQGTHFPRTFGGGTKLEIK |
| Bright-1.3L | 34 | DIVMTQSPASLAVSLGQRATISCRASESVDSYGNSFMHWYQQKPG QPPKLLIYLASNLESGVPARFSGSGSRTDFTLTIDPVEADDAVTYYC QQNNEDPRTFGGGTKLEIK |
| Bright-1.4L | 35 | DIVMTQSPAIMSASPGEKVTITCSASSSVSYMHWFQQKPGTSPKLWI YSTSNLASGVPARFSGSGSGTSYSLTISRVEAEDAATYYCQQRSSYP LTFGAGTKLEIK |
| Bright-1.1H | 36 | EVKLVESGGDLVKPGGSLKLSCAASGFTFSSYGMSWVRQTPDKRL EWVATISSGGSYTYYPDSVKGRFTISRDNAKNTLYLQMSSLKSEDT AMYYCARHDYGNYVDYWGQGTTLTVSSA |
| Bright-1.2H | 37 | EVQLVESGGDLVKPGGSLKLSCAASGFTFSSYGMSWVRQTPDKRL EWVATISSGGSYTYYPDSVKGRFTISRDNAKNTLYLQMSSLKSEDT AMYYCARDGNYQEDYFDYWGQGTTLTVSS |
| Bright-1.3H | 38 | EVQLVESGGGLVQPGGSRKLSCAASGFTFSSFGMHWVRQAPEKGL EWVAYISSGSRTIYYADSVKGRFTISRDNPKNTLFLQMTSLRSEDTA IYYCAREGYAYDVDYWGQGTTLTVSS |
| Bright-1.4H | 39 | EVQGVESGGGLVQPGGSRKLSCAASGFTFSSFGMHWVRQAPEKGL EWVAYISSGSSNIFYSDTVKGRFTISRDNPKNTLFLQMTSLRSEDTA MYYCARYDYGKDFDYWGQGTTLTVSS |

Example 6

Proteomic Quantization of V Genes in IgG of Serum

Serum Ig proteins were isolated by affinity chromatography using protein A or G chromatography with elution using acetate buffer, pH 3.0 (or anti-IgA and anti-IgM antibodies for affinity purification of the other major Ig classes). Additionally, antigen-specific IgGs were further purified by affinity chromatography on an immobilized antigen column and elution with either 6 M urea or acetate buffer pH 3.0. Eluted samples were dialyzed in PBS for further processing.

Purified IgG proteins or FAB fragments as appropriate were denatured in 50% 2,2,2-trifluoroethanol (TFE). 15 mM dithiothreitol was added to reduce proteins, and samples were incubated at 55° C. for 45 min., followed by alkylation with 55 mM iodoacetamide for 30 min. at room temperature. Samples were diluted 10-fold to 5% TFE concentration and subjected to protease digestion by appropriate proteases that preserve the CDR3 domains largely intact. The selection of the proper proteases is based on the bionformatic analysis of the V domain protein sequences so that protease cleavage generates peptides that cleave N- and C-terminal of the CDR3, leaving the CDR3 sequence largely intact in most sequences on the data base. In one embodiment proteolytic cleavage was accomplished using sequencing grade trypsin (Sigma) at 37° C. for 4 hr. In a separate embodiment a combination of the GluC (NEB) and LysC (Sigma) proteases were used to generate a distinct set of proteolytic peptides that in computational tests provide better coverage of the CDR3. In yet a third embodiment, proteolytic cleavage was accomplished using engineered variants of trypsin or of the bacterial outer membrane protease OmpT selected again so that cleavage preserves the integrity of CDR3. Digestions were quenched with 1% formic acid. Sample volume was reduced by speedvac centrifugation. To remove contaminants, peptides were bound and washed on C-18 Hypersep SpinTips (Thermo Scientific) and filtered through 10 kDa Microcon YM-10 centrifugal filters (Amicon) prior to LC-MS/MS analysis.

In certain embodiments, CDR3 peptides were enriched by affinity purification of Cys containing immunoglobulin peptides. An invariant Cys residue is localized at the N-terminus of the CDR3 domain. VL-Cκ, λ and VH-CH1 polypeptides in FAB proteins each contain 4 Cys. Thus, isolation of Cys containing peptides from either the heavy or light chain results in significant enrichment of CDR3 peptides to approximately 25% of the pool. Enrichment of Cys containing peptides therefore significantly reduces the number of redundant peptides interrogated by MS and increases the depth of coverage. For purification of Cys-containing CDR3 peptides, the peptide fragments generated above are reacted with a 3-fold molar excess of thiol specific biotinylation reagents such as isodoacetyl-LC-biotin (ProtecoChem) according to the manufacturers instructions. Following biotinylation, Cys-containing peptide fragments are separated by affinity chromatography on neutravidin and elution with a large excess (5 mM) free biotin.

Peptides are then separated on a reverse phase Zorbax C-18 column (Agilent) running a 230 min elution gradient from 5% to 38% acetonitrile, 0.1% formic acid. Peptides are eluted directly into an LTQ-Orbitrap mass spectrometer (Thermo Scientific) by nano-electrospray ionization. Data-dependant ion selection was enabled, with parent ion mass spectra (MS1) collected at 100K resolution. Ions with known charge >+1 were selected for CID fragmentation spectral analysis (MS2) in order of decreasing intensity, with a maximum of 12 parent ions selected per MS1 cycle. Dynamic exclusion was activated, with ions selected for MS2 twice within 30 sec. excluded from MS2 selection for 30 sec.

Ions identified in an LC-MS/MS run as corresponding to peptides from the constant regions of the heavy and light chains are excluded from data-dependant selection in subsequent experiments in order to increase selection of peptides from the variable region. As an alternate method, predicted protease-specific peptides overlapping the hyper-variable regions of heavy and light chains are compiled into an inclusion list for which corresponding parent ions are preferentially selected for MS2 fragmentation analysis.

Sample-specific protein sequence databases are created from the high-throughput V gene cDNA sequencing data. LC-MS/MS data are searched against this database using the Sequest search algorithm as part of the Bioworks software package (Thermo Scientific). Filters are applied to ensure high confidence peptide identifications as follows: ΔCN≥0.250; XCorr=2.0, 2.5, and 3.0 for +2, +3, and ≥+4 charge; and accuracy ≤10.0 ppm. Alternatively, other label-free (Silva et al., 2006b; Gygi et al., 1999; Ross et al., 2004) or isotope label-based quantitative methods for mass spectrometry can be used to determine the abundancy of specific CDR3 families at the protein level.

It should be noted that for plasma cell transcript abundancy and protein levels based on CDR3 peptide counting are often not correlated. There are three reasons for this discrepancy. First and foremost, the V gene abundancy profile provides a snapshot of antibody transcription and protein synthesis. However, antibodies persist in circulation with a $t_{1/2}$ of approx 14 days for IgGs. The plasma cell population is dynamic and is renewed continuously. Thus well transcribed Ig that are not as highly abundant in the serum may be the product of new plasma cells that have only recently populated the plasma compartment. The presence of "declining" plasma cells that show low transcription rates but are highly represented supports this hypothesis (shown in red and underlined in Table 7). Second, the sequencing data comprised all V genes irrespective of isotype where the proteomic data reflects only the IgG pool. Therefore, some CDR3 not represented or poorly represented may correspond to IgA and would not be detected by the present analysis. Third, because trypsinization was used for fragmentation, some CDR3s may have been partially cleaved and hence underrepresented as intact peptides (CDR3 sequences containing putative trypsin cleavage sites are highlighted in gray in Table 7).

In Table 7, Frequency of VL transcripts in bone marrow plasma cells (CD138+, CD45R(B220)−/CD49b−) isolated by MACS/FACS and analyzed by Roche 454 sequencing (aprx 15-35K complete reads). The CDR3 peptide counts determined by shotgun proteomic analysis of the purified IgG from the serum from the same mouse are also shown. CDR3 sequences containing putative proteolytic sites and therefore underrepresented during fragmentation are shown. CDR3 peptides that show relatively high counts but low transcript levels are in red and underlined.

TABLE 7

Example of CDR3 VL gene mRNA sequence abundancy in plasma cells and the corresponding relative abundancy of the respective antibodies in serum as determined by counting the CDR3 peptide identified by MS.

| VL CDR3 sequence | SEQ ID NO: | mRNA sequence Count | CDR3 Peptide Count |
|---|---|---|---|
| CFQGSHVPLTF | 40 | 2404 | 261 |
| CWQGTHFPHF | 41 | 296 | 9 |
| CWQGTHFPTF | 42 | 284 | 10 |
| CWQGIHFPTF | 43 | 219 | 3 |
| CLQGSHVPLTF | 44 | 196 | 38 |
| CWQGTHFPQTF | 45 | 188 | 9 |
| CSQSTHVPWTF | 46 | 159 | 10 |
| CFQGSHVPWTF | 47 | 109 | 6 |
| CFQGSHVPRTF | 48 | 151 | 14 |
| CWQGTHFPRTF | 49 | 145 | 13 |
| CFQGSHFPYTF | 50 | 143 | 14 |
| CFQGSHVPYTF | 51 | 95 | 19 |
| CSQSTHVPYTF | 52 | 92 | 4 |
| CQQSNEDPRTF | 53 | 47 | 2 |
| CQQSKEVPWTF | 54 | 46 | 2 |
| CQHHYGIPRTF | 55 | 43 | 35 |
| CSQSTHVPFTF | 56 | 39 | 8 |
| CQHSRELPFTF | 57 | 28 | 52 |
| CFQGSHVPFTF | 58 | 19 | 9 |
| CQQSRKVPWTF | 59 | 14 | 10 |

In some embodiments, grouping of V genes based on CDR3 families substantially improves quantitation of the peptide dataset. This introduced a number of additional steps into the bioinformatics analysis pipeline: (1) After performing the shotgun proteomics experiments and identifying peptides based on the standard mass spectrometry analysis pipeline and the sample-specific sequence database, peptides that overlap CDR3 regions are identified. (2) These observed peptides are mapped to V gene cDNA-defined CDR3 families, and (3) Spectral counts attributable to each CDR3 family are defined. A comparison of the rank-order abundancy of the CDR3 peptides identified by the MS proteomic analysis with the DNA sequence analysis is shown in Table 7. Comparison of the VL transcript abundancy with protein abundancy as determined from the CDR3 analysis indicates that the most highly represented antibody (expressed at 17% of all the VL transcripts in the bone marrow plasma cell population!) is also most highly represented among the CDR3 peptides.

In several cases, plasma cell transcription does not correlate with the concentration of antibodies in serum. This finding has many important implications for disease detection and therapeutic antibody discovery and is related to three factors: First, transcript analysis provides only a snapshot of transcription and protein synthesis. However, antibodies persist in circulation with a $t_{1/2}$ of approx 14 days for IgGs. The plasma cell population is dynamic and is renewed continuously. Thus well transcribed Ig that are not as highly abundant in the serum may be the product of new plasma cells that have only recently populated the plasma compartment. The presence of "declining" plasma cells that show low transcription rates but are highly represented supports this hypothesis. Second, the sequencing data comprised all V genes irrespective of isotype where the proteomic data reflects only the IgG pool. Therefore, some CDR3 not represented or poorly represented may correspond to IgA and would not be detected by the present analysis. Third, the proteolytic fragmentation used to generate this data led to some CDR3s that were partially cleaved and hence underrepresented as intact peptides (CDR3 sequences containing putative trypsin cleavage sites are highlighted in green). As discussed above this issue is successfully dealt with by judicious selection of fragmentation conditions.

Example 7

Construction of Synthetic Antibody Genes

The most abundant VL and VH protein sequences identified by the proteomic analysis and those from the gene sequencing analyses are then synthesized by automated gene construction adapting a previously developed process that exploits sequence data basing software and liquid handling robots for the rapid and efficient production of high-fidelity synthetic genes (Cox et al., 2007). Briefly, gene fragments are generated from synthetic oligonucleotides using inside-out nucleation PCR reactions, subsequent stitch-overlap extension PCR reactions are used and thus obviated the need for purification steps, making the process amenable for automation. Fragment design and relevant overlaps were automated through software, which further generated oligonucleotide synthesizer worklists and robot operation scripts for construction and assembly.

For IgG production the VH and VL genes are paired based on the data from the proteomic and gene sequence frequency distributions. VH and VL genes occurring at the similar frequencies are paired. The inventors find that this strategy results in a high rate of success (>75%) of correctly paired antibodies exhibiting high antigen affinity (Tables 8). In Table 8, VL and VH have CDR3 sequences paired based on abundancy rank order shown in Table 2 and affinities of the respective antibodies were measured by ELISA.

TABLE 8

Examples of synthetic antibodies identified in serum via the technology disclosed herein and their antigen binding affinities.

| VL-VH CDRL3 pair/ Antigen | CDRL3 | CDRH3 | $IC_{50}$ by ELISA |
|---|---|---|---|
| C1s | | | |
| 2.1L-2.1H | FQGSHVPLT (SEQ ID NO: 60) | SDRYDGYFDY (SEQ ID NO: 19) | 50 nM |
| 2.3L-2.2H | WQGTHFPH (SEQ ID NO: 61) | WLLLAY (SEQ ID NO: 21) | 0.43 nM |
| 2.3L-2.3H | WQGTHFPH (SEQ ID NO: 61) | SDGYYYFDY (SEQ ID NO: 23) | 100 nM |
| BRIGHT | | | |
| 1.1L-1.1H | LQYASSPFT (SEQ ID NO: 63) | HDYGNYVDY (SEQ ID NO: 10) | ~100 (ND) |
| 1.2L-1.4H | WQGTHFPRT (SEQ ID NO: 64) | YDYGKDFDY (SEQ ID NO: 16) | NA |
| 1.4L-1.4H | QQRSSYPLT (SEQ ID NO: 65) | YDYGKDFDY (SEQ ID NO: 16) | ~10 (ND) |

TABLE 8-continued

Examples of synthetic antibodies identified in serum via the technology disclosed herein and their antigen binding affinities.

| VL-VH CDRL3 pair/ Antigen | CDRL3 | CDRH3 | $IC_{50}$ by ELISA |
|---|---|---|---|
| 1.2L-1.1H | WQGTHFPRT (SEQ ID NO: 64) | HDYGNYVDY (SEQ ID NO: 10) | 1 µM |

Example 8

IgG expression and binding analysis

Synthetic VL and VH genes are assembled for full-length IgG expression. Synthetic gene products are purified by gel extraction following digestion with the restriction enzymes BssHII/BsiWI and BssHII/NheI for VL and VH, respectively. Digested VL and VH genes are ligated into the vectors pMAZ-IgL and pMAZ-IgH1, respectively. pMAZ-IgL carries the constant human kappa light chain antibody region and pMAZ-IgH carries the constant human heavy chain antibody region of IgG1. Vectors are transformed into E. coli Jude 1 cells and plated on Luria Broth (LB, Miller) agar plates supplemented with 100 ug/ml ampicillin. Single colonies are selected and verified for correct V gene sequence. E. coli cells carrying pMAZ-IgL and pMAZ-IgH vectors are then grown in 10 ml TB supplemented with 100 ug/ml ampicillin isolated and DNA is purified. 20 µg each of purified pMAZ-IgL and pMAZ-IgH are used for co-transfection and transient expression from HEK293-F cells following the Freestyle MAX expression system protocol (Invitrogen). HEK293-F cells are grown for 96 h following transfection and media was harvested and IgG is purified by a protein-A agarose chromatography column.

To determine antigen affinity, a standard ELISA is performed with a 96 well plate coated with either purified antigen at 2 ug/ml in PBS and blocked with 0.5% BSA. Purified IgGs were added to the plate at various concentrations for 1.5 h and washed with PBS/0.05% Tween-20. A polyclonal antibody of goat anti-human Fc region conjugated HRP was used for detection and developed with TMB substrate and stopped with 2N $H_2SO_4$. The absorbance was measured at 450 nm with a 96 well spectrophotometer. A titration curve of purified IgGs was used to determine an approximate IC50 for binding (Table 8).

Alternatively, a whole cell ELISA can be performed to estimate binding affinity. Tumor cells at $2 \times 10^5$ cells/ml are added to a 96 well cell culture cluster plate in 100 ul of PBS. Cells were then exposed to purified IgGs at various concentrations for 1.5. The plate was then centrifuged at 2000 RPM for 1 min to pellet cells and resuspended and washed with PBS and repeated 3 times. For detection, a polyclonal antibody of goat anti-human Fc region conjugated HRP was and developed with TMB substrate and stopped with 2N $H_2SO_4$. The absorbance was measured at 450 nm with a 96 well spectrophotometer.

Example 9

Figure 2:
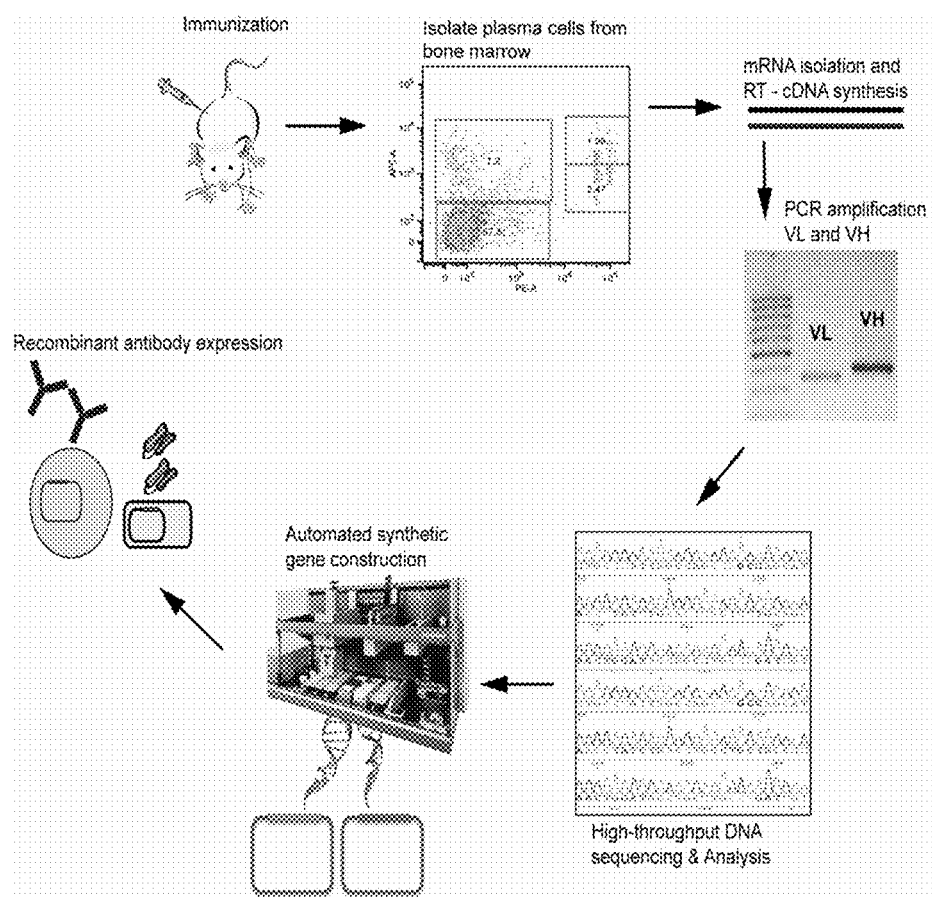
FIG. 2: Schematic for isolation of monoclonal antibodies without screening by mining the antibody variable (V) gene repertoires of bone marrow plasma cells. Following immunization, mice are sacrificed and CD45R⁻CD138⁺ plasma cells are isolated. Following mRNA isolation and first-strand cDNA synthesis, variable light ($V_L$) and variable heavy ($V_H$) gene DNA is generated. High-throughput 454 DNA sequencing and bioinformatic analysis is performed to determine the $V_L$ and $V_H$ repertoire. The most abundant $V_L$ and $V_H$ genes are identified and pairing is determined by a simple relative frequency rule. The respective antibody genes are synthesized using automated robotically assisted gene synthesis. Finally, antigen-specific antibody single chain variable fragments or full-length IgGs are expressed in bacteria or mammalian cells, respectively

Isolation of Monoclonal Antibodies by Mining the Variable Gene Repertoire of Plasma Cells A simple and rapid method has been developed for antibody isolation without the need for any laborious screening steps. High-throughput DNA sequencing was exploited to analyze the $V_L$ and $V_H$ antibody gene repertoires derived from the mRNA transcripts of fully differentiated mature B cells—antibody secreting plasma cells—found within the bone marrow of immunized mice. Following bioinformatic analysis, several abundant antibody $V_L$ and $V_H$ gene sequences could be identified within the repertoire of each immunized mouse. $V_L$ and $V_H$ genes were paired according to their relative frequencies within the repertoire. Antibody genes were rapidly synthesized by oligonucleotide and PCR assembly by utilizing automated liquid handling robots. Antibodies were recombinantly expressed in bacterial and mammalian systems as single-chain variable fragments (scFv) and full-length IgG, respectively (FIG. 2). Finally, it was confirmed that the resulting antibodies were overwhelmingly antigen-specific (21/27 or 78%), thus providing a method for rapid and direct isolation of MAbs without screening.

B cell maturation culminates in the terminal, non-proliferative stage of B cell development—the formation of plasma cells that serve as immunoglobulin production factories. Plasma cells represent less than 1% of all lymphoid cells and yet are responsible for the overwhelming majority of antibodies in circulation (Manz et al., 2005; Shapiro-Shelef and Calame, 2005). The bone marrow constitutes the major compartment where plasma cells take residency and produce antibodies for prolonged periods of time. In mice, a stable and highly-enriched antigen-specific BM-PC population of ~$10^5$ cells (10-20% of all BM-PCs) appears 6 days following secondary immunization and persists for prolonged periods (Manz et al., 1997). In contrast, the splenic plasma cell population is highly transient, as it peaks at day 6 and rapidly declines to <$10^4$ cells by day 11. Importantly, BM-PCs are responsible for the synthesis of the most abundant circulating antibodies, which in turn are likely to play a dominant role in pathogen neutralization and other protective humoral immune responses (Manz et al., 2005).

Figure 4:
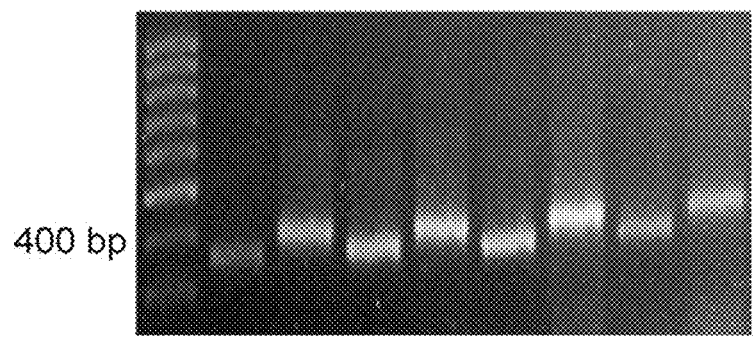
FIG. 4: Variable light ($V_L$) and variable heavy ($V_H$) chain genes from bone marrow plasma cells. Agarose gel electrophoresis of $V_L$ and $V_H$ genes amplified by PCR from cDNA derived from bone marrow plasma cells of mice immunized with different antigens. From left: $1^{st}$ lane is DNA Ladder; $2^{nd}$, $4^{th}$, $6^{th}$, $8^{th}$ lanes are $V_L$ (~370 bp); $3^{rd}$, $5^{th}$, $7^{th}$, $9^{th}$ lanes are $V_H$ (~400 bp).

To examine the dynamics of the antibody V gene repertoires in BM-PCs, especially early after challenge (i.e., to mimic situations where mice exhibit weak immune responses), pairs of mice were immunized with chicken egg ovalbumin (OVA), human complement serine protease (C is), human B cell regulator of IgH transcription (Bright), or adjuvant only. Antigen was co-injected with complete Freund's adjuvant followed by a secondary booster immunization in incomplete Freund's adjuvant. Mice were sacrificed 6 days post-secondary immunization and BM-PCs (CD45R⁻ CD138⁺) were isolated to high purity (FIG. 3). Total RNA was extracted and reverse transcribed for synthesis of first strand cDNA. Well characterized (Mazor et al., 2007), degenerate V gene primer mixes were utilized for second strand amplifications, resulting in $V_L$ and $V_H$ PCR products of high purity (FIG. 4), which were then submitted for high-throughput DNA sequencing of long reads using 454-GS FLX technology (Roche).

Unlike recent high-throughput sequencing analyses that explored V gene repertoire diversity in zebrafish (Weinstein et al., 2009), humans (Boyd et al., 2009; Glanville et al., 2009), or synthetic libraries (Ge et al., 2010), the goals were to: (1) identify highly expressed V genes likely to be antigen-specific and (2) to determine the relative V gene transcript abundance in the BM-PC repertoires of immunized mice. These tasks do not require exhaustive coverage of the V gene repertoire; it has been found that obtaining >5K V gene sequences per BM-PC sample is sufficient to provide the information needed for antibody discovery, minimizing DNA sequencing costs.

Figure 5:
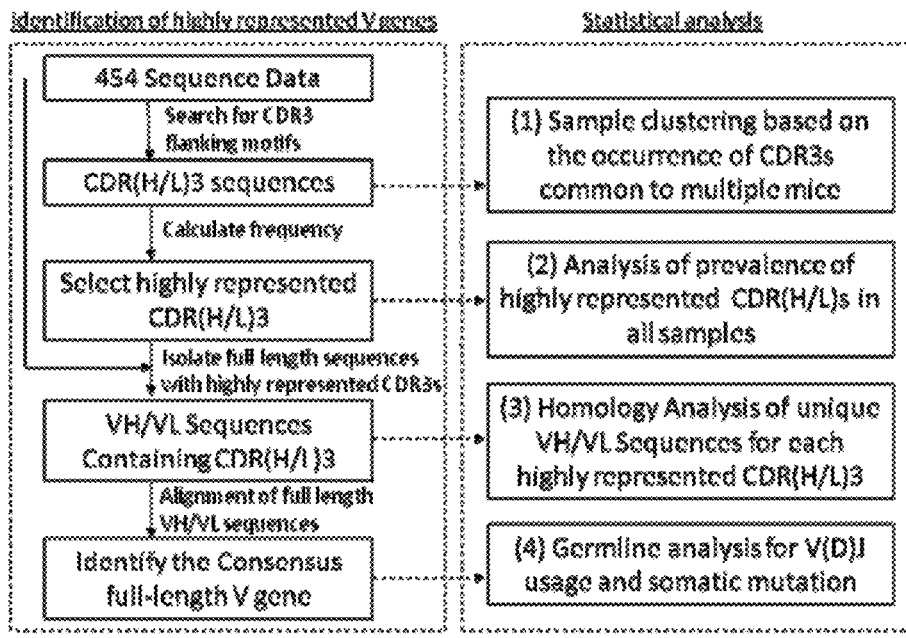
FIG. 5: Flow chart of an exemplary embodiment of the bioinformatics pipeline for V gene analysis. First, CDR3s were identified by homology to conserved flanking amino acid sequences motifs. CDR3s found at the highest frequency (typically with frequency >1%) were used to group the V gene sequences of interest. Homology analysis of V genes containing highly represented CDR3s was performed by multiple sequence alignment and calculation of pairwise identity. Finally, germline analysis of highly represented full-length V genes was performed to determine somatic mutations and V(D)J and V-J gene usage.

454 reads were first processed by multiple sequence and signal filters, and then subjected to a simple and rapid bioinformatic analysis that relied on homologies to conserved framework regions within V genes in order to identify the most common complementarity determining region 3 (CDR3) sequences (FIG. 5).

This approach correctly identified ~94% of $V_H$ and ~92% of $V_L$ sequences in the Kabat database (Table 3). Out of a total of 415,018 reads, 23.2% contained CDR3 of $V_H$ (CDRH3) and 26.6% contained CDR3 of $V_L$ (CDRL3) sequences (Table 9), representing 6,681-16,743 and 7,112-21,241 CDRH3 and CDRL3 sequences reads per mouse, respectively.

TABLE 9

Number of CDR3 containing sequences identified from 454 GS-FLX DNA sequencing using CDR3 flanking consensus motifs.

| | | Sequences Containing CDR-H3 motif | | | Sequences Containing CDR-L3 motif | | |
|---|---|---|---|---|---|---|---|
| Sample | 454 GS-FLX Sequencing Size | Total Number | Number of Unique CDR-H3 | Number of CDR-H3 as Single Copy | Total Number | Number of Unique CDR-L3 | Number of CDR-L3 as Single Copy |
| Adjuvant -1 | 32066 | 6681 | 2706 | 1811 | 7112 | 1638 | 1053 |
| Adjuvant -2 | 86720 | 16743 | 4640 | 2890 | 21241 | 3136 | 1888 |
| Ova-1 | 63872 | 15350 | 4789 | 3010 | 13355 | 2251 | 1355 |
| Ova-2 | 72257 | 15751 | 3821 | 2401 | 17200 | 2786 | 1700 |
| C1s-1 | 43753 | 11595 | 2440 | 1443 | 13972 | 1706 | 1045 |
| C1s-2 | 39961 | 9071 | 1799 | 999 | 14664 | 1477 | 847 |
| Bright-1 | 36599 | 9453 | 2025 | 1178 | 12209 | 1383 | 632 |
| Bright-2 | 39790 | 11769 | 2530 | 1210 | 10441 | 1422 | 578 |
| Total | 415018 | 96413 | 24750 | 14942 | 110194 | 15799 | 9098 |
| Unique Sequences Across All Samples | | | 21271 | | | 8690 | |

Figure 6:
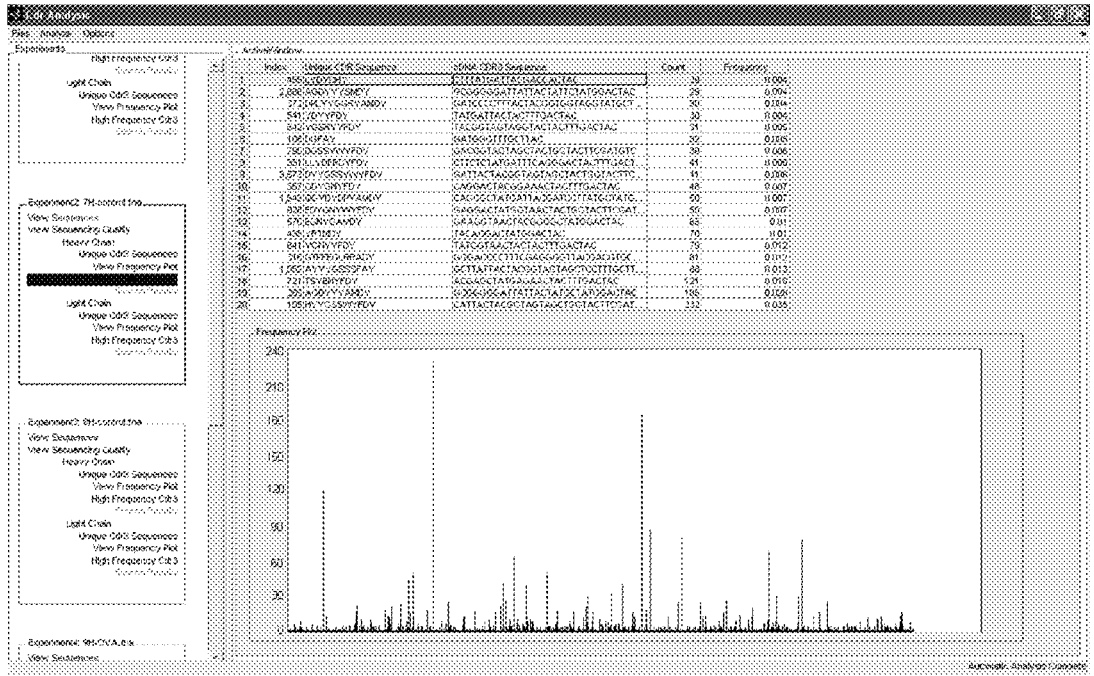
FIG. 6: Example of graphical user interface (GUI) for V gene repertoire analysis. A GUI application was developed for organization and graphical representation of high-throughput sequencing results of V genes. The program imports and organizes data sets from different samples, identifies CDRH3 and CDRL3 using the described CDR flanking motifs, and extracts CDR3 frequency distributions (SEQ ID NOS: 718-737 PRT and SEQ ID NOS: 738-747 DNA).

For each mouse, frequency distributions of the CDR3s were calculated. Sequencing of the same samples, from separate cDNA library preparations by different facilities gave quantitatively similarrankings of CDR3. As shown in Table 10 the same rank order frequencies are observed for all the highly expressed CDR3s. This is important because as discussed below our approach for antibody discovery exploits the rank-order frequency of V genes and specifically on the identification of the most highly expressed clones. V gene sequences containing a particular CDR3 were accepted as full-length if they covered all 3 CDRs. Pairwise identities and frequencies were calculated by multiple sequence alignments followed by germline analysis (FIG. 5 and bioinfomatic methods described below). A graphical user interface application was developed to enhance data analysis and visualization of the results (FIG. 6).

TABLE 10

Comparison of 454 DNA sequencing results generated by two different facilities from two different cDNA library preparations (SeqWright and UT-Austin Genome Sequencing Center).

| Sample | | Adjuvant-1 | | OVA-2 | |
|---|---|---|---|---|---|
| Facility | | SeqWright | UT-Austin | SeqWright | UT-Austin |
| Total seq reads | SEQ ID | 7112 | 20850 | 17200 | 17291 |
| CDR-L3 seq | NO: | % | % | % | % |
| WQGTHFPLT | 114 | 7.02 | 10.9 | 5.32 | 6.80 |
| QQYNSYPLT | 115 | 5.28 | 4.97 | 4.05 | 3.70 |
| QQYSSYPLT | 116 | 4.91 | 3.88 | 3.46 | 2.82 |
| QQSNSWYT | 117 | 2.00 | 2.20 | 1.41 | 1.45 |
| QNGHSFPLT | 118 | 1.27 | 0.98 | 1.12 | 0.98 |
| WQGTHFPRT | 64 | 1.18 | 1.71 | 1.23 | 1.64 |
| QHHYGTPPWT | 119 | 1.52 | 1.48 | 0.77 | 0.87 |
| QQHYSTPWT | 120 | 1.42 | 1.35 | 2.01 | 2.01 |
| HQWSSYPT | 121 | 0.48 | 0.47 | 1.87 | 0.43 |
| SQTTHVPPT | 122 | 1.15 | 1.06 | 0.74 | 0.64 |
| WQGTHFPQT | 123 | 1.69 | 1.92 | 1.63 | 1.83 |
| AQFYSYPLT | 124 | 1.45 | 1.22 | 1.69 | 1.19 |
| MQHLEYPYT | 125 | 0.65 | 0.72 | 0.72 | 0.45 |
| QQGQSYPWT | 126 | 0.65 | 0.77 | 1.07 | 1.31 |
| QQWNYPLIT | 127 | 0.84 | 0.77 | 0.78 | 0.87 |
| QQGNTLPWT | 128 | 0.58 | 0.68 | 0.59 | 0.59 |

Figure 7:
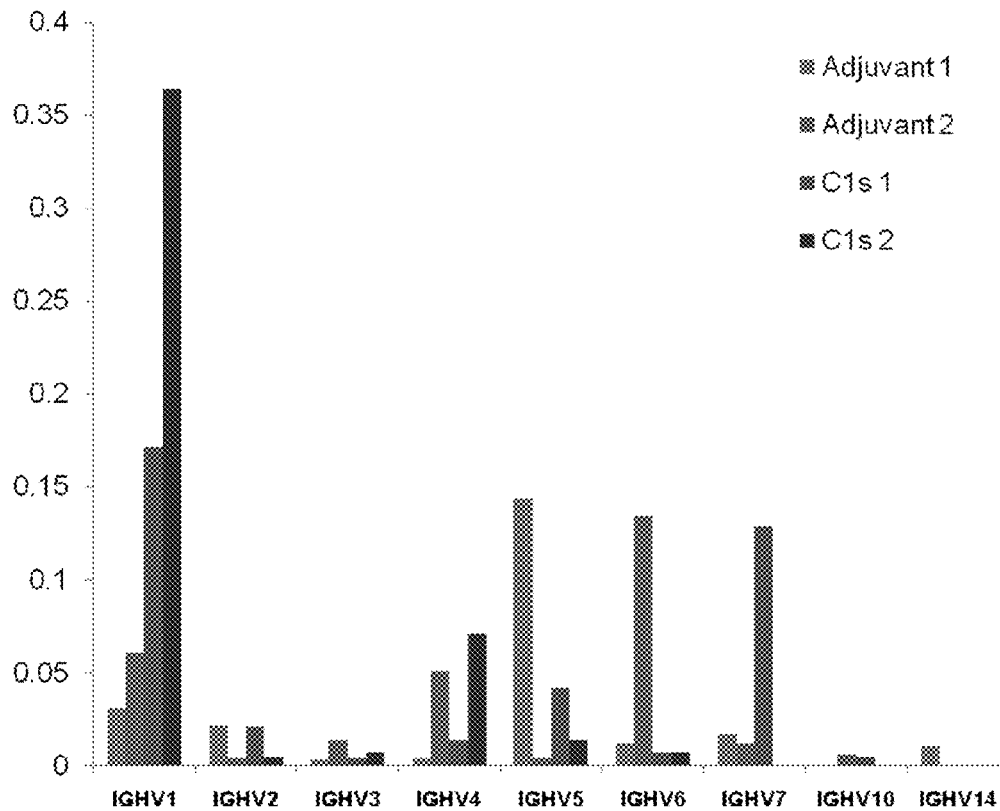
FIG. 7: $V_H$ germline family representation in adjuvant and C1s immunized repertoires. Bar graph represents the frequency of $V_H$ gene families among the top 30 $V_H$ sequences in each repertoire (representing 24-47% of the total $V_H$ repertoire). A clear skewing towards IGHV1 is demonstrated in immunized mice.

Analysis of the BM-PC repertoires led to several interesting observations. First, ~10-20% of the total repertoire of all immunized mice were on average comprised of only 4 CDRH3 sequences (Table 11). For example, in the two mice immunized with C1s, the frequencies of the most abundant CDRH3s were 7.93% and 10.99% of the total repertoire. Second, as expected for early responses, the most highly abundant CDR3s were assembled from a diverse array of germline V gene segments, with an average somatic mutation rate of only 2 and 5 amino acid substitutions for $V_L$ and $V_H$, respectively (Tables 12-13). Not surprisingly, certain germline V gene families were represented preferentially in mice responding to particular antigens. For example in mice immunized with C1s, between 15-30% of the entire $V_H$ gene repertoire utilized IGHV1 family whereas the adjuvant only immunized mice were dominated by IGHV5 or IGHV6 families (FIG. 7).

TABLE 11

Frequencies (%) of the most highly represented CDRL3 and CDRH3[a] sequences

| Clone | Percent | CDRL3 | Clone | Percent | CDRH3 |
|---|---|---|---|---|---|
| Ovalbumin | | | Ovalbumin | | |
| 1.1L | 11.69 | WQGTHFPLT SEQ ID 114 | 1.1H | 7.17 | TYGSSYYAMDY SEQ ID 137 |
| 1.2L | 4.44 | QQYNSYPLT SEQ ID 115 | 1.2H | 1.13 | TRLLWLYAMDY SEQ ID 138 |
| 1.3L | 3.38 | QQSNSWYT SEQ ID 117 | 1.3H | 0.57 | DVYDGYAMDY SEQ ID 139 |
| 1.4L | 2.20 | QHHYGTPPWT SEQ ID 119 | 1.4H | 0.54 | NPYAMDY SEQ ID 140 |
| 2.1L | 5.32 | WQGTHFPLT SEQ ID 114 | 2.1H | 7.59 | RTTVSRDWYFDV SEQ ID 141 |

TABLE 11-continued

Frequencies (%) of the most highly represented CDRL3 and CDRH3[a] sequences

| Clone | Percent | CDRL3 | Clone | Percent | CDRH3 |
|---|---|---|---|---|---|
| 2.2L | 4.05 | QQYNSYPLT SEQ ID 115 | 2.2H | 3.22 | YYYGSSAMDY SEQ ID 142 |
| 2.3L | 3.46 | QQYSSYPLT SEQ ID 116 | 2.3H | 2.22 | DGWYYFDY SEQ ID 143 |
| 2.4L | 2.01 | QQHYSTPWT SEQ ID 120 | 2.4H | 2.11 | EDDYDLFAY SEQ ID 144 |
| 2.5L | 1.87 | HQWSSYPT SEEQ ID 121 | 2.5H | 1.25 | DTTVVEGDYFDY SEQ ID 183 |
| C1s | | | C1s | | |
| 1.1L | 12.95 | WQGTHFPQT SEQ ID 123 | 1.1H | 7.93 | GNYYYAMDY SEQ ID 145 |
| 1.2L | 6.94 | QQWSSYPQLT SEQ ID 129 | 1.2H | 2.64 | DMISYWYFDV SEQ ID 146 |
| 1.3L | 3.81 | QNDHSYPLT SEQ ID 130 | 1.3H | 1.67 | EDYGNYWYFDV SEQ ID 147 |
| 1.4L | 3.16 | QQGQSYPFT SEQ ID 131 | 1.4H | 1.17 | EGYYYGSSYFDY SEQ ID 148 |
| 2.1L | 17.10 | FQGSHVPLT SEQ ID 60 | 2.1H-A | 10.99 | SDRYDGFDY SEQ ID 19 |
| 2.2L | 2.62 | QQSNEDPWT SEQ ID 132 | 2.1H-B | 9.93 | SDRFDGYFDY SEQ ID 20 |
| 2.3L | 2.20 | WQGTHFPH SEQ ID 61 | 2.2H | 3.30 | WLLLAY SEQ ID 21 |
| 2.4L | 1.64 | QQHYSTPFT SEQ ID 133 | 2.3H | 1.65 | SDGYYYFDY SEQ ID 23 |
| Bright | | | Bright | | |
| 1.1L | 6.63 | LQYASSPFT SEQ ID 63 | 1.1H | 7.19 | HDYGNYVDY SEQ ID 10 |
| 1.2L | 4.73 | WQGTHFPRT SEQ ID 64 | 1.2H | 5.62 | DGNYQEDYFDY SEQ ID 11 |
| 1.3L | 4.51 | QQNNEDPRT SEQ ID 134 | 1.3H | 1.91 | EGYAYDVDY SEQ ID 12 |
| 1.4L | 3.59 | QQRSSYPLT SEQ ID 65 | 1.4H | 1.21 | YDYGKDFDY SEEQ ID 16 |
| 2.1L | 7.25 | WQGTHFPQT SEQ ID 123 | 2.1H | 2.56 | RGDGNYFFDY SEQ ID 149 |
| 2.2L | 4.51 | QQGQSYPWT SEQ ID 126 | 2.2H | 2.27 | GDEAWFAY SEQ ID 150 |
| 2.3L | 3.12 | LQYASSPYT SEQ ID 135 | 2.3H | 2.04 | EGDFDY SEQ ID 151 |
| 2.4L | 2.59 | FQGSHVPWT SEQ ID 136 | 2.4H | 1.63 | GGNYDYAMDY SEQ ID 152 |

[a] CDRH3 sequences present at high frequency in both immunized mice and adjuvant only mice were considered background and thus excluded from the list.

TABLE 12

Germline identity and the number of amino acid somatic mutations (SM) of the most highly represented $V_L$ and $V_H{}^a$ genes.

| Clone | Germline $V_L$ | #SM $V_L$ | Clone | Germline $V_H$ | #SM $V_H$ |
|---|---|---|---|---|---|
| Ovalbumin | | | Ovalbumin | | |
| 1.1 L | V1-135*01-J5*01 | 2 | 1.1 | V1-5*01-J4*01-D1-1*01 | 5 |
| 1.2 L | V6-23*01-J5*01 | 4 | | | |
| 1.3 L | N/A - low alignment score | N/A | 1.2 | V6-6*02-J4*01-D2-2*01 | 2 |
| 1.4 L | V12-44*01-J1*01 | 1 | 1.3 | V1S132*01-J4*01-D2-3*01 | 14 |
| 2.1 L | V1-135*01-J5*01 | 2 | | | |
| 2.2 L | V6-15*01-J5*01 | 1 | 1.4 | V5-6*01-J4*01-D6-1*01 | 7 |
| 2.3 L | N/A - low alignment score | 3 | 2.1 | V5-17*02-J1*01-D2-1*01 | 5 |
| 2.4 L | V6-23*01-J5*01 | 2 | 2.2 | N/A - low alignment score | N/A |
| | | | 2.3 | V5-17*02-J2*01-D2-3*01 | 5 |
| | | | 2.4 | V1-67*01-J3*01-D2-4*01 | 8 |
| | | | 2.5 | V3-2*02-J2*01-D1-1*01 | 3 |
| C1s | | | C1s | | |
| 1.1 L | V1-135*01-J1*01 | 2 | 1.1 | V1-5*01-J4*01-D2-1*01 | 2 |
| 1.2 L | V4-55*01-J5*01 | 3 | | | |
| 1.3 L | V8-28*01-J5*01 | 1 | 1.2 | V7-3*02-J1*01-D2-4*01 | 0 |
| 1.4 L | V15-103*01-J1*01 | 2 | 1.3 | V2-9*02-J1*02-D2-1*01 | 3 |
| 2.1 L | V1-117*01-J5*01 | 4 | | | |
| 2.2 L | V3-5*01-J1*01 | 1 | 1.4 | V1-14*01-J2*01-D1-1*01 | 4 |
| 2.3 L | V1-135*01-J2*01 | 4 | | | |
| 2.4 L | V6-25*01-J4*01 | 0 | 2.1 (A, B) | V1-4*01-J2*01-D2-14*01 | 3 |
| | | | 2.2 | V5-9-1*01-J3*01-D2-3*01 | 8 |
| | | | 2.3 | V1-5*01-J2*01-D2-3*01 | 3 |
| | | | 2.4 | V1-7*01-J2*01-D2-4*01 | 5 |
| Bright | | | Bright | | |
| 1.1 L | V9-120*01-J4*01 | 1 | 1.1 | V5-6*01-J2*01-D2-1*01 | 1 |
| 1.2 L | V1-135*01-J1*01 | 3 | | | |
| 1.3 L | V3-10*01-J1*01 | 2 | 1.2 | V5-6*01-J2*01-D2-1*01 | 2 |
| 1.4 L | V4-57*01-J1*01 | 3 | | | |
| 2.1 L | V1-135*01-J1*01 | 3 | 1.3 | V5-17*02-J2*01-D1-3*01 | 5 |
| 2.2 L | V15-103*01-J1*01 | 2 | 1.4 | V5-17*02-J2*01-D1-1*01 | 6 |
| 2.3 L | V9-120*01-J2*01 | 1 | 2.1 | V5-6*01-J2*01-D2-1*01 | 3 |
| 2.4 L | V1-117*01-J1*01 | 0 | 2.2 | V5-6*01-J3*01-D4-1*01 | 4 |
| | | | 2.3 | V5-6-4*01-J2*01-D3-2*02 | 4 |
| | | | 2.4 | V14-3*02-J4*01-D1-1*02 | 9 |

$^a V_H$ sequences present at high frequency in both immunized mice and adjuvant only mice were considered background and thus excluded from the list.

TABLE 13

Average somatic mutations in nucleotides (nt) and amino acids (AA) of the top 30 $V_H$ sequences in each BM-PC repertoire.

| Mouse | # of nt | # of AA |
|---|---|---|
| Adjuvant - 1 | 5.3 | 2.9 |
| Adjuvant - 2 | 5.2 | 2.7 |
| OVA - 1 | 5.5 | 3.3 |
| OVA - 2 | 7.0 | 3.8 |
| C1s - 1 | 5.0 | 2.6 |
| C1s - 2 | 6.7 | 3.9 |
| Bright - 1 | 4.9 | 2.8 |
| Bright - 2 | 7.5 | 4.6 |

In most instances the V genes encoding a highly abundant CDR3 were dominated by one sequence with the second most abundant V gene sequence (somatic variant) being present at >10-fold lower level and differing from the dominant sequence by 1-2 amino acids.

Figure 8:
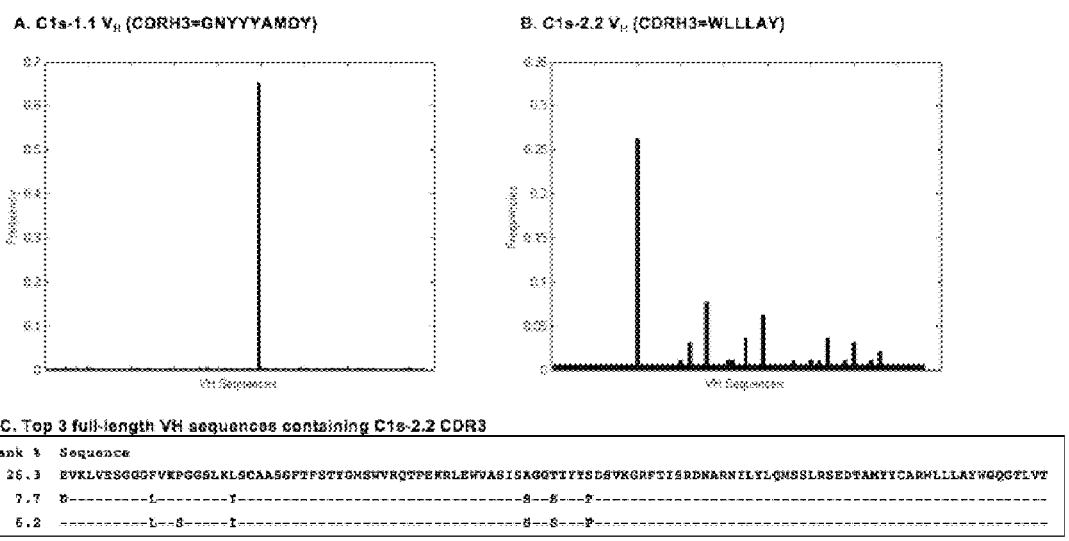
FIG. 8: Homology analysis of full-length V genes containing the same CDR3. (A) The dataset of full-length C1s-1.1 $V_H$ genes (CDRH3=GNYYYAMDY (SEQ ID NO:145)) is dominated by a single sequence (65%), as all the other sequences occur at a frequency <0.8%. (B) Frequency distribution of full-length C1s-2.2 $V_H$ genes (CDRH3=WLLLAY (SEQ ID NO:21) shows multiple sequences with high frequency. (C) Top three full-length $V_H$ sequences containing C1s-2.2 CDR3 and their respective frequencies (%) (SEQ ID NOS:758-760).
Figure 9:
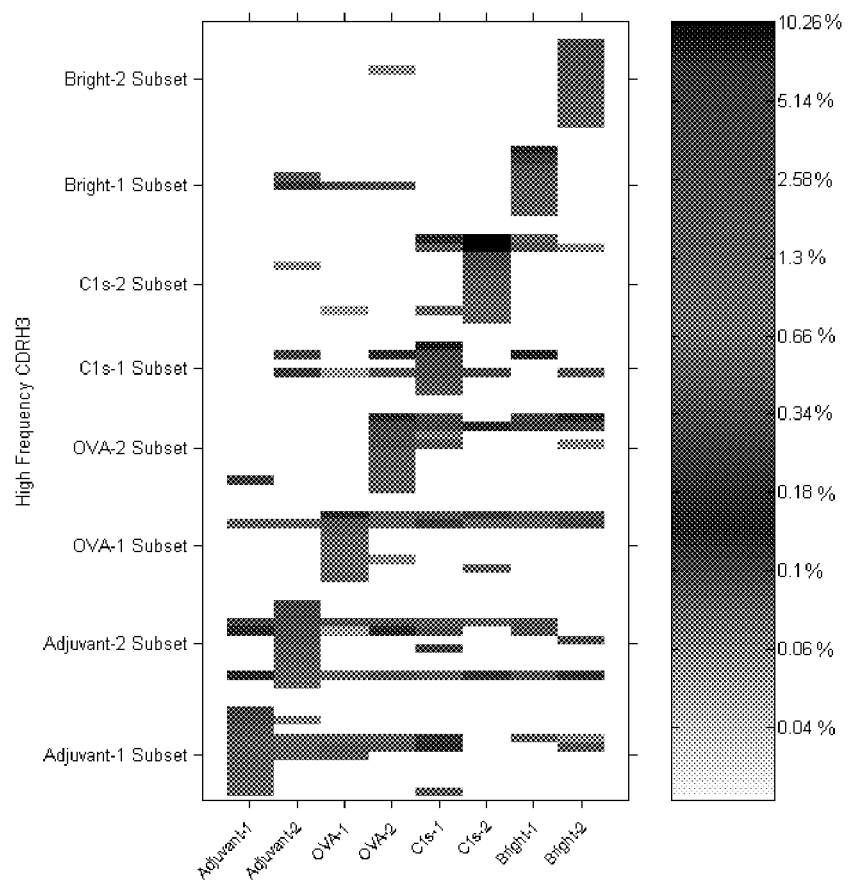
FIG. 9: Comparison of high frequency CDRH3s reveals unique $V_H$ genes in each mouse. Heat map showing the distribution of highly represented CDRH3s in mice injected with Adjuvant (Adv), ovalbumin (OVA), C1s, and Bright (BR). The Y-axis represents the 10 highest frequency CDRH3 sequences identified in each mouse. The X-axis compares the frequency of these prevalent CDRH3 sequences across all other mice. White: sequences found at frequencies that are not statistically significant (0.00-0.03%). Black: sequences found at a frequency of >10%.

The following test and tables provide further information regarding the antibody repertoires that were studied using the techniques detailed herein. There were some instances in which abundant CDRH3s were encoded by several V genes that were represented at comparable frequencies (FIG. 8 and Table 14). Notably, the $V_H$ repertoires were quite distinct even among genetically identical littermates immunized with the same antigen on the same day. For mice immunized with C1s or Bright, each mouse developed a distinct and diverse set of abundant CDRH3 sequences (FIG. 9 and Table 15). This suggests that each mouse generates its own unique and highly expressed $V_H$ gene repertoire, which may allow for the discovery of a panel of diverse antibodies. One exception however was that in the cohort of OVA-immunized mice we observed that a few abundant CDRH3 sequences were also present at high frequency in other mice, suggesting that the corresponding antibodies may be poly-specific. Not surprisingly, some moderately represented CDRH3 sequences from animals that received adjuvant only, were also present in immunized mice (FIG. 9). Antibodies encoding these sequences were probably specific to adjuvant or to common natural antigens. CDRL3 diversity was lower with several promiscuous sequences represented at high frequency in several mice (Table 16). Fourth, even though the BM-PC $V_H$ repertoires were largely comprised of sequences unique to each mouse, principal component analysis of CDRH3s shared between mice revealed distinct clustering of the data for each cohort (i.e., same cage and litter) immunized at the same time but with different antigens (FIG. 10). This signature likely reflects environmental factors, such as the antigenic history of the animal groups, and suggests that V gene repertoire analysis may provide valuable diagnostic information.

TABLE 14

The most highly represented CDR3 groups and their full-length variable heavy ($V_H$) and variable light ($V_L$) gene frequencies and homologies.

| Antigen | CDR3 | SEQ ID NO: | CDR3 Freq (%) | 1st $V_H$ Freq (%)[a] | 2nd $V_H$ Freq (%)[a] | $V_H$ Homology[b] |
|---|---|---|---|---|---|---|
| OVA-1.1 | GSSYYAMDY | 153 | 7.11 | 60.0 | 1.7 | 96.1 |
| OVA-1.2 | DYYGSSYWYFDV | 154 | 1.10 | 47.1 | 5.8 | 89.9 |
| OVA-1.3 | DNWDWYFDV | 14 | 0.57 | 49.0 | 4.0 | 95.0 |
| OVA-1.4 | LLWLYAMDY | 155 | 0.54 | 54.7 | 4.7 | 97.3 |
| OVA-2.1 | RTTVSRDWYFDV | 141 | 7.61 | 15.3 | 5.6 | 92.3 |
| OVA-2.2 | YYYGSSAMDY | 142 | 3.23 | 26.0 | 10.8 | 96.0 |
| OVA-2.3 | DGWYYFDY | 143 | 2.22 | 22.7 | 4.1 | 89.1 |
| OVA-2.4 | EDDYDLFAY | 144 | 2.10 | 9.4 | 8.7 | 94.9 |
| C1s-1.1 | GNYYYAMDY | 145 | 7.93 | 68.8 | 1.1 | 97.9 |
| C1s-1.2 | DDGYWYFDV | 156 | 5.14 | 60.9 | 5.3 | 90.0 |
| C1s-1.3 | YYYGSSAMDY | 142 | 4.37 | 58.5 | 3.7 | 94.5 |
| C1s-1.4 | DMISYWYFDV | 146 | 2.64 | 70.9 | 1.1 | 90.0 |
| C1s-2.1 | SDRYDGYFDY | 19 | 10.99 | 11.1 | 9.4 | 95.7 |
| C1s-2.2 | SDRFDGYFDY | 20 | 9.93 | 12.5 | 4.2 | 94.7 |
| C1s-2.3 | WLLLAY | 21 | 3.30 | 26.3 | 7.7 | 88.8 |
| C1s-2.4 | YGNYFDY | 22 | 2.47 | 72.1 | 1.4 | 96.8 |
| Bright-1.1 | HDYGNYVDY | 10 | 7.20 | 66.2 | 2.6 | 98.7 |
| Bright-1.2 | DGNYQEDYFDY | 11 | 5.62 | 63.1 | 5.9 | 98.6 |
| Bright-1.3 | EGYAYDVDY | 12 | 1.91 | 27.4 | 23.9 | 95.6 |
| Bright-1.4 | DDYDWYFDV | 13 | 1.54 | 59.3 | 2.8 | 97.5 |
| Bright-2.1 | RGDGNYFFDY | 149 | 2.57 | 16.1 | 14.0 | 95.0 |
| Bright-2.2 | GDEAWFAY | 150 | 2.27 | 43.3 | 6.7 | 97.1 |

TABLE 14-continued

The most highly represented CDR3 groups and their full-length variable heavy ($V_H$) and variable light ($V_L$) gene frequencies and homologies.

| | | | | | |
|---|---|---|---|---|---|
| Bright-2.3 | EGDFDY | 151 | 2.03 | 14.9 | 8.1 | 95.3 |
| Bright-2.4 | YYYGSSYFDV | 157 | 1.84 | 77.8 | 0.7 | 99.2 |

| Antigen | CDRL3 | | CDR3 Freq (%) | 1st $V_L$ Freq (%)[a] | 2nd $V_L$ Freq (%)[a] | $V_L$ Homology[b] |
|---|---|---|---|---|---|---|
| OVA-1.1 | WQGTHFPLT | 114 | 11.70 | 41.4 | 1.8 | 92.1 |
| OVA-1.2 | QQSNSWYT | 117 | 4.40 | 54.5 | 2.4 | 94.0 |
| OVA-1.3 | QQYSSYPLT | 116 | 3.38 | 46.2 | 1.9 | 93.9 |
| OVA-1.4 | QHHYGTPPWT | 119 | 2.20 | 49.7 | 2.1 | 93.7 |
| OVA-2.1 | WQGTHFPLT | 114 | 5.32 | 33.3 | 2.3 | 93.7 |
| OVA-2.2 | QQYSSYPLT | 116 | 4.05 | 43.6 | 1.1 | 94.3 |
| OVA-2.3 | QQYNSYPLT | 115 | 3.46 | 20.1 | 4.5 | 92.3 |
| OVA-2.4 | QQHYSTPWT | 120 | 2.01 | 50.2 | 2.6 | 95.3 |
| C1s-1.1 | WQGTHFPQT | 123 | 12.95 | 68.8 | 1.1 | 97.9 |
| C1s-1.2 | QQWSSYPQLT | 129 | 6.94 | 60.9 | 5.3 | 90.0 |
| C1s-1.3 | QNDHSYPLT | 130 | 3.81 | 58.5 | 3.7 | 94.5 |
| C1s-1.4 | QQGQSYPWT | 126 | 3.16 | 70.8 | 1.1 | 98.5 |
| C1s-2.1 | FQGSHVPLT | 60 | 17.10 | 5.7 | 4.7 | 90.4 |
| C1s-2.2 | QQSNEDPWT | 132 | 2.62 | 65.7 | 2.8 | 97.4 |
| C1s-2.3 | WQGTHFPH | 61 | 2.20 | 36.1 | 18.5 | 96.5 |
| C1s-2.4 | WQGTHFPT | 158 | 2.15 | 39.2 | 15.6 | 96.9 |
| Bright-1.1 | LQYASSPFT | 63 | 6.64 | 74.0 | 1.0 | 98.3 |
| Bright-1.2 | WQGTHFPRT | 64 | 4.73 | 60.8 | 1.5 | 97.9 |
| Bright-1.3 | QQNNEDPRT | 134 | 4.51 | 61.8 | 3.7 | 97.8 |
| Bright-1.4 | QQRSSYPLT | 65 | 3.59 | 68.4 | 0.8 | 96.5 |
| Bright-2.1 | WQGTHFPQT | 123 | 7.24 | 44.5 | 5.7 | 95.8 |
| Bright-2.2 | QQGQSYPWT | 126 | 4.50 | 71.3 | 1.0 | 98.8 |
| Bright-2.3 | LQYASSPYT | 135 | 3.12 | 70.7 | 2.0 | 98.6 |
| Bright-2.4 | FQGSHVPWT | 136 | 2.58 | 47.3 | 3.8 | 95.0 |

[a] The frequencies of the top two $V_H$ and $V_L$ full-length sequences of a particular CDR3 group.
[b] The $V_H$ and $V_L$ homologies were determined by calculating the pairwise identity by multiple sequence alignment of all V genes that shared the same CDR3.

TABLE 15

Occurrence of the highest frequency CDRH3s from the bone marrow plasma cell repertoire of mice immunized with C1s, and their relative frequency in mice immunized with adjuvant or different antigens.

| Antigen<br>Total Seq Reads<br>CDRH3 | C1s-1<br>11,595<br>% | C1s-2<br>9,071<br>% | Br-1<br>9,453<br>% | Br-2<br>11,769<br>% | OVA-1<br>15,350<br>% | OVA-2<br>15,751<br>% | Adjuv-1<br>6,681<br>% | Adjuv-2<br>16,743<br>% |
|---|---|---|---|---|---|---|---|---|
| GNYYYAMDY SEQ ID NO: 145 | 7.93 | 0.01 | 0.01 | 0.01 | 0.00 | 0.00 | 0.04 | 0.01 |
| DDGYWYFDV SEQ ID NO: 156 | 3.00 | 0.00 | 0.12 | 0.00 | 0.01 | 0.16 | 0.00 | 0.28 |
| YYYGSSAMDY SEQ ID NO: 142 | 2.68 | 0.15 | 0.24 | 0.29 | 0.00 | 3.22 | 0.00 | 0.00 |
| DMISYWYFDV SEQ ID NO: 146 | 2.64 | 0.00 | 0.00 | 0.00 | 0.00 | 0.00 | 0.00 | 0.00 |
| DGYDWYFDV SEQ ID NO: 159 | 2.26 | 0.06 | 0.00 | 0.05 | 0.02 | 0.46 | 0.00 | 0.07 |
| DDYDWYFDV SEQ ID NO: 13 | 1.97 | 0.03 | 1.53 | 0.01 | 0.02 | 0.10 | 0.09 | 2.11 |
| GSSYYAMDY SEQ ID NO: 153 | 1.67 | 0.00 | 0.00 | 0.00 | 0.00 | 0.00 | 0.00 | 0.00 |
| EDYGNYWYFDV SEQ ID NO: 147 | 1.67 | 0.21 | 0.41 | 0.40 | 7.17 | 0.53 | 0.00 | 0.01 |
| QGYDYDPYAMDY SEQ ID NO: 160 | 1.22 | 0.00 | 0.00 | 0.00 | 0.00 | 0.00 | 0.75 | 0.00 |
| EGYYYGSSYFDY SEQ ID NO: 148 | 1.17 | 0.00 | 0.00 | 0.00 | 0.00 | 0.00 | 0.00 | 0.00 |
| TGFDY SEQ ID NO: 161 | 1.11 | 0.00 | 0.00 | 0.02 | 0.01 | 0.01 | 0.00 | 0.01 |
| KGSTTATYFDY SEQ ID NO: 162 | 1.06 | 0.00 | 0.00 | 0.00 | 0.00 | 0.00 | 0.00 | 0.00 |

| Antigen<br>Total Seq Reads<br>CDRH3 | C1s-1<br>11,595<br>% | C1s-2<br>9,071<br>% | Br-1<br>9,453<br>% | Br-2<br>11,769<br>% | OVA-1<br>15,350<br>% | OVA-2<br>15,751<br>% | Adjuv-1<br>6,681<br>% | Adjuv-2<br>16,743<br>% |
|---|---|---|---|---|---|---|---|---|
| SDRYDGYFDY SEQ ID NO: 19 | 0.09 | 10.99 | 0.04 | 0.01 | 0.00 | 0.00 | 0.00 | 0.00 |
| SDRFDGYFDY SEQ ID NO: 20 | 0.05 | 9.93 | 0.05 | 0.03 | 0.00 | 0.00 | 0.00 | 0.00 |
| WLLLAY SEQ ID NO: 21 | 0.00 | 3.30 | 0.01 | 0.02 | 0.00 | 0.00 | 0.00 | 0.00 |
| YGNYFDY SEQ ID NO: 22 | 0.02 | 2.39 | 0.01 | 0.01 | 0.00 | 0.02 | 0.00 | 0.02 |
| SDGYYYFDY SEQ ID NO: 23 | 0.02 | 1.65 | 0.00 | 0.00 | 0.00 | 0.00 | 0.00 | 0.00 |
| SGGNYDAMDY SEQ ID NO: 24 | 0.00 | 1.17 | 0.02 | 0.00 | 0.00 | 0.00 | 0.00 | 0.00 |
| YYDYDKAYYFDY SEQ ID NO: 25 | 0.03 | 1.15 | 0.00 | 0.00 | 0.00 | 0.00 | 0.00 | 0.00 |

TABLE 16

Occurrence of the highest frequency CDRL3s from the bone marrow plasma cell repertoire of mice immunized with C1s, and their relative frequency in mice immunized with adjuvant or different antigens.

| Antigen<br>Total Seq Reads<br>CDRL3 | C1s-1<br>13,972<br>% | C1s-2<br>14,664<br>% | Br-1<br>12,228<br>% | Br-2<br>10,452<br>% | OVA-1<br>13,355<br>% | OVA-2<br>17,200<br>% | Adjuv-1<br>7,112<br>% | Adjuv-2<br>21,241<br>% |
|---|---|---|---|---|---|---|---|---|
| WQGTHFPQT<br>SEQ ID NO: 123 | 12.95 | 1.56 | 2.33 | 7.25 | 1.66 | 1.63 | 1.69 | 1.54 |
| QQWSSYPQLT<br>SEQ ID NO: 129 | 6.94 | 0.01 | 0.00 | 0.00 | 0.00 | 0.00 | 0.00 | 0.00 |
| QNDHSYPLT<br>SEQ ID NO: 130 | 3.81 | 0.04 | 0.13 | 0.04 | 0.11 | 0.12 | 0.18 | 0.10 |
| QQGQSYPWT<br>SEQ ID NO: 126 | 3.16 | 0.48 | 3.21 | 4.50 | 0.67 | 1.07 | 0.65 | 1.42 |
| FQGSHVPWT<br>SEQ ID NO: 136 | 2.76 | 0.83 | 1.04 | 2.59 | 0.37 | 0.28 | 0.44 | 0.30 |
| QQGQSYPFT<br>SEQ ID NO: 131 | 2.64 | 0.10 | 0.39 | 0.12 | 0.01 | 0.00 | 0.00 | 0.01 |
| LQHGESPFT<br>SEQ ID NO: 163 | 2.43 | 1.55 | 2.59 | 2.41 | 0.00 | 0.02 | 0.01 | 0.01 |
| QQGQSYPLT<br>SEQ ID NO: 164 | 2.07 | 1.05 | 2.97 | 0.11 | 0.25 | 0.26 | 0.17 | 0.58 |
| QQSKEVPPT<br>SEQ ID NO: 165 | 1.74 | 0.53 | 0.08 | 0.11 | 0.07 | 0.04 | 0.13 | 0.07 |
| QQHYSTPWT<br>SEQ ID NO: 120 | 1.47 | 1.41 | 0.36 | 0.82 | 0.88 | 2.01 | 1.42 | 1.13 |
| QNDYSFT<br>SEQ ID NO: 166 | 1.46 | 0.04 | 0.01 | 0.05 | 0.00 | 0.00 | 0.00 | 0.00 |
| WQGTHFPWT<br>SEQ ID NO: 167 | 1.17 | 0.68 | 1.55 | 0.99 | 0.54 | 0.83 | 0.93 | 0.95 |
| WQGTHFPRT<br>SEQ ID NO: 64 | 1.12 | 1.15 | 4.73 | 0.94 | 1.27 | 1.23 | 1.18 | 2.70 |
| FQGSHVPFT<br>SEQ ID NO: 168 | 0.97 | 0.14 | 0.47 | 0.47 | 0.01 | 0.00 | 0.00 | 0.00 |
| WQGTHFPT<br>SEQ ID NO: 158 | 0.95 | 0.04 | 0.03 | 0.00 | 0.00 | 0.01 | 0.00 | 0.00 |
| FQGSHVPLT<br>SEQ ID NO: 60 | 0.19 | 17.10 | 2.29 | 0.23 | 0.16 | 0.23 | 0.24 | 0.19 |
| QQSNEDPWT<br>SEQ ID NO: 132 | 0.23 | 2.62 | 0.50 | 1.00 | 0.28 | 0.32 | 0.24 | 0.23 |
| WQGTHFPH<br>SEQ ID NO: 61 | 0.01 | 2.20 | 0.00 | 0.00 | 0.00 | 0.00 | 0.00 | 0.00 |
| WQGTHFPT<br>SEQ ID NO: 158 | 0.00 | 2.11 | 0.00 | 0.07 | 0.02 | 0.02 | 0.04 | 0.00 |
| QQHYSTPFT<br>SEQ ID NO: 133 | 0.19 | 1.64 | 0.17 | 0.15 | 0.00 | 0.00 | 0.00 | 0.01 |
| WQGTHFPQT<br>SEQ ID NO: 123 | 12.95 | 1.56 | 2.33 | 7.25 | 1.66 | 1.63 | 1.69 | 1.54 |
| LQHGESPFT<br>SEQ ID NO: 163 | 2.43 | 1.55 | 2.59 | 2.41 | 0.00 | 0.02 | 0.01 | 0.01 |
| LQGSHVPLT<br>SEQ ID NO: 169 | 0.01 | 1.50 | 0.01 | 0.00 | 0.01 | 0.00 | 0.00 | 0.00 |
| QQHYSTPWT<br>SEQ ID NO: 120 | 1.47 | 1.41 | 0.36 | 0.82 | 0.88 | 2.01 | 1.42 | 1.13 |

TABLE 16-continued

Occurrence of the highest frequency CDRL3s from the bone marrow plasma cell repertoire of mice immunized with C1s, and their relative frequency in mice immunized with adjuvant or different antigens.

| Antigen<br>Total Seq Reads<br>CDRL3 | C1s-1<br>13,972<br>% | C1s-2<br>14,664<br>% | Br-1<br>12,228<br>% | Br-2<br>10,452<br>% | OVA-1<br>13,355<br>% | OVA-2<br>17,200<br>% | Adjuv-1<br>7,112<br>% | Adjuv-2<br>21,241<br>% |
|---|---|---|---|---|---|---|---|---|
| LQHGESPYT<br>SEQ ID NO: 170 | 0.44 | 1.23 | 0.84 | 0.66 | 0.25 | 0.44 | 0.76 | 0.61 |
| SQSTHVPWT<br>SEQ ID NO: 171 | 0.89 | 1.21 | 1.68 | 1.30 | 0.50 | 0.51 | 0.32 | 0.28 |
| WQGTHFPRT<br>SEQ ID NO: 64 | 1.12 | 1.15 | 4.73 | 0.94 | 1.27 | 1.23 | 1.18 | 2.70 |

Figure 11:
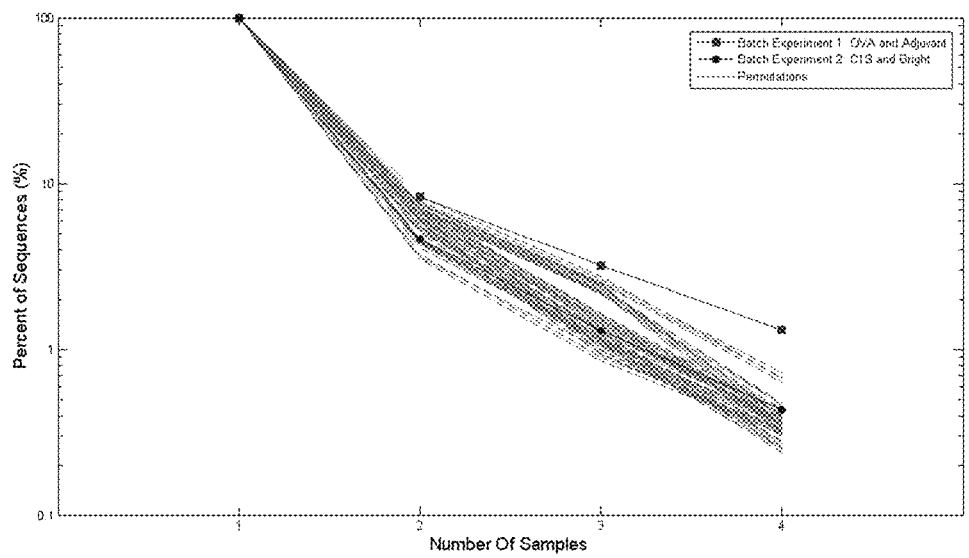
FIG. 11: Percentage of CDRH3s distributed across subsets of four mouse populations. The percentage of common CDRH3 sequences between all combinations of four mice chosen from a set of eight. The percent similarity between mice immunized on the same day with either ovalbumin (OVA) or adjuvant is shown in red; percent similarity between mice immunized on the same day with either Bright or C1s is shown in blue; gray represents the similarity for every other possible combination.

It should be noted that a few copies (typically <5) of the most abundant CDRH3 sequences raised to a given antigen were observed at very low levels (typically <0.1%) in the CDRH3 repertoires of mice receiving other antigens. Since several of the respective V genes were shown to encode antigen-specific antibodies (see below), the inventors believe that the presence of these sequences in mice immunized with other antigens might originate from low levels of cross-sample contamination, a conclusion supported by the biased distributions of common CDRH3 sequences within the same cohort (FIG. 11). Because of the high sensitivity of 454 DNA sequencing, even with the utmost care it is not possible to completely rule out low-level contamination (sequence noise) during library preparation/multiplex sequencing. Although an important consideration for studies aiming to compare unbiased repertoires (Weinstein et al., 2009; Boyd et al., 2009), sequence noise does not impact the methodology described herein, since the most abundant V genes in the BM-PC repertoire are represented at levels 20- to >100-fold higher than the sequence noise level.

Manual screening of small combinatorial libraries of scFvs in *E. coli* using the entire BM-PC V genes pool (i.e. not of the most abundant V genes as determined by the NextGen sequencing analysis) led to a low yield of antigen-specific clones (<4 positive clones per 96 well plate, data not shown). Upon further analysis, most of these scFvs displayed low apparent affinity by ELISA and/or poor expression and aggregation. The inventors reasoned that this was a consequence of combinatorial pairing: even if a $V_L$ and a $V_H$ gene are represented at 5% of the cDNA pool, assuming no PCR biases in scFv assembly, the probability of correct pairing is only 0.25%, and therefore discovery of positive clones would require an extensive amount of screening.

To overcome these problems, and to avoid screening altogether, it was contemplated that $V_L$ and $V_H$ genes represented at approximately the same frequency likely arise from the same plasma cell and hence, are naturally paired. To test this hypothesis, the top 4-5 most abundant full-length $V_L$ and $V_H$ genes from each mouse (excluding $V_H$ sequences that were cross-represented in adjuvant-only mice), which accounted for a minimum of 0.5% of the repertoire, were gene synthesized as pairs, recombinantly expressed, and tested for antigen binding.

Figure 12:
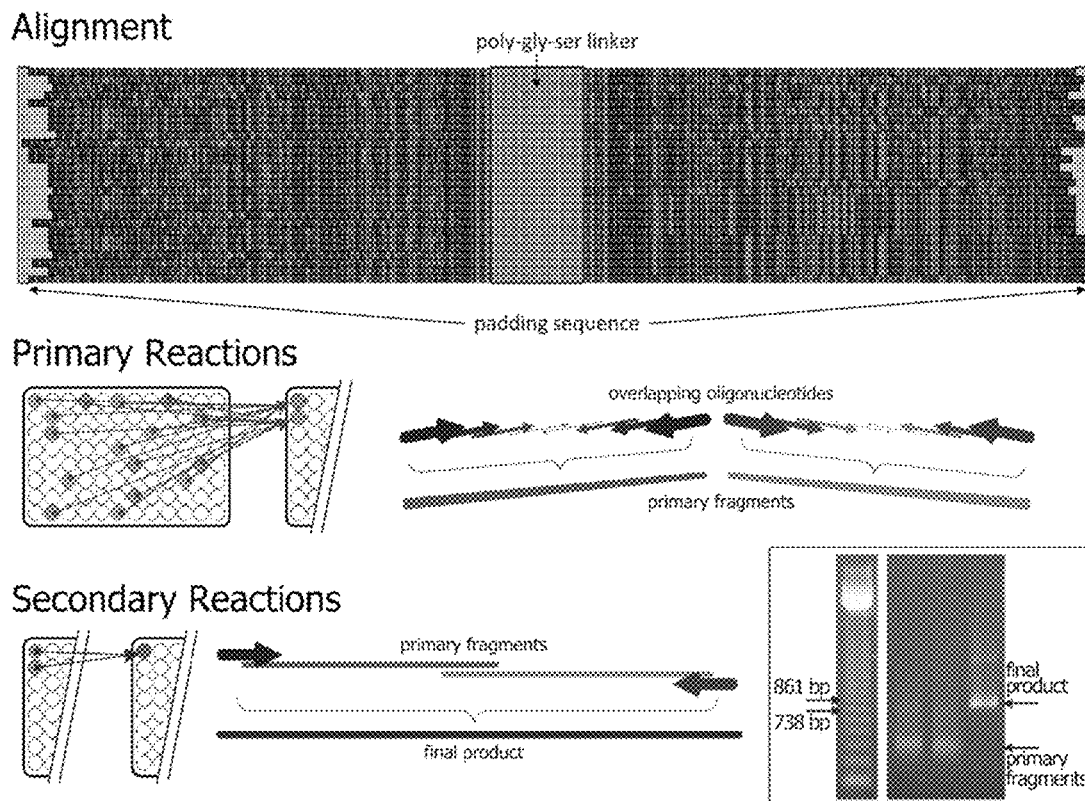
FIG. 12: Construction of synthetic antibody genes. Highly represented $V_H$ and $V_L$ genes from bone marrow plasma cell repertoires were synthesized as single chain variable fragments (scFvs) by joining V genes with a poly-gly-ser linker. Alignment. The poly-gly-ser linker serves as the anchor point for aligning the set of desired genes. Appropriate restriction sites are added to facilitate cloning and the sequences are padded to uniform length to enable a single overlapping oligonucleotide assembly scheme for building all genes. Primary assembly. Primary fragments are generated from overlapping sets of oligonucleotides using inside-out nucleation PCR (scheme right). Secondary assembly. The second step of the assembly is a conventional overlap-extension PCR joining the primary fragments together to form the final product (scheme right). The primary PCR products are diluted with water by the liquid-handling robot and a portion of each diluted primary reaction is added to the secondary reaction (example left). Gel image. Agarose gel of typical scFv assembly products. First lane: DNA ladder; second and third lanes: primary products at ~400 bp; fourth lane: final product at ~810 bp.

Synthetic genes were constructed by robotically assisted, high-throughput DNA synthesis as shown in detail above. Briefly, gene fragments (lengths from 200 to 500 nucleotides) were generated using inside-out nucleation PCR reactions. The design of these fragments and relevant overlaps was automated using customized software to facilitate robotic synthesis and assembly. Alignment and "padding" of the sequences at either end yielded genes of identical length and permitted the use of a generic overlapping assembly strategy that ensured the greatest oligonucleotide re-use (FIG. 12). In this manner, up to 48 $V_L$ and 48 $V_H$ genes could be synthesized and validated for correct ORF by one researcher within one week, at a reagent cost <$2,000.

In most cases, $V_L$ and $V_H$ pairing was determined by rank ordering of CDR3 frequency within the repertoire. In cases where two $V_L$ or $V_H$ genes were found at very similar frequencies, multiple $V_L$-$V_H$ combinations were constructed. Paired V genes were then expressed as scFv fragments in *E. coli*.

*E. coli* whole cell lysates were prepared to express antibody single chain variable fragments (scFvs) that were constructed by pairing the most abundant V genes (as shown above). VL and VH gene pairing was determined by relative frequency (%) of the respective V genes in the bone marrow plasma cell repertoires. ELISA analysis was performed to determine antigen binding (see Online Methods). (+): >3-fold ELISA signal on antigen-coated wells relative to wells coated with unrelated antigen (bovine serum albumin and/or gelatin).

ELISA analysis of bacterial lysates indicated that the resulting antibodies were overwhelmingly antigen-specific (~78%): 21/27 antigen specific antibodies were obtained from six mice immunized with three different protein antigens (Table 17). To further evaluate the utility of this simple pairing strategy, there was constructed a combinatorial library of scFvs comprising the 4 most abundant $V_L$ and $V_H$ genes from each of the two mice immunized with C1s. scFv antibodies were expressed in *E. coli*; binding analysis by ELISA revealed that all of the highest antigen-binding clones possessed the same $V_L$-$V_H$ gene combinations predicted by the pairing strategy (Table 18).

TABLE 17

Antigen binding of antibody single chain variable fragments (scFvs) from high frequency $V_L$ and $V_H$ genes.

| $V_L$-$V_H$ pair | % $V_L$ | CDRL3 | % $V_H$ | CDRH3 | scFv binding |
|---|---|---|---|---|---|
| α̃-OVA | | | | | |
| 1.1L-1.1H | 11.70 | WQGTHFPLT SEQ ID NO: 114 | 7.11 | GSSYYAMDY SEQ ID NO: 153 | + |
| 1.2L-1.2H | 4.40 | QQYNSYPLT SEQ ID NO: 115 | 1.10 | LLWLYAMDY SEQ ID NO: 155 | + |
| 1.3L-1.3H | 3.38 | QQSNSWYT SEQ ID NO: 117 | 0.57 | DVYDGYAMDY SEQ ID NO: 139 | + |
| 1.4L-1.4H | 2.20 | QHHYGTPPWT SEQ ID NO: 119 | 0.54 | NPYAMDY SEQ ID NO: 140 | − |
| 2.1L-2.1H | 5.32 | WQGTHFPLT SEQ ID NO: 114 | 7.61 | RTTVSRDWYFDV SEQ ID NO: 141 | + |
| 2.2L-2.2H | 4.05 | QQYNSYPLT SEQ ID NO: 115 | 3.23 | YYYGSSAMDY SEQ ID NO: 142 | + |
| 2.3L-2.3H | 3.46 | QQYSSYPLT SEQ ID NO: 116 | 2.22 | DGWYYFDY SEQ ID NO: 143 | + |
| 2.4L-2.4H | 2.01 | QQHYSTPWT SEQ ID NO: 120 | 2.10 | EDDYDLFAY SEQ ID NO: 144 | + |
| α̃-C1s | | | | | |
| 1.1L-1.1H | 12.95 | WQGTHFPQT SEQ ID NO: 123 | 7.93 | GNYYYAMDY SEQ ID NO: 145 | + |
| 1.2L-1.1H | 6.94 | QQWSSYPQLT SEQ ID NO: 129 | 7.93 | GNYYYAMDY SEQ ID NO: 145 | + |
| 1.3L-1.2H | 3.81 | QNDHSYPLT SEQ ID NO: 130 | 2.64 | DMISYWYFDV SEQ ID NO: 146 | + |
| 1.4L-1.3H | 3.16 | QQGQSYPFT SEQ ID NO: 131 | 1.67 | EDYGNYWYFDV SEQ ID NO: 147 | + |
| 1.4L-1.4H | 3.16 | QQGQSYPFT SEQ ID NO: 131 | 1.67 | EGYYYGSSYFDY SEQ ID NO: 148 | − |
| 2.1L-2.1HA | 17.10 | FQGSHVPLT SEQ ID NO: 60 | 10.99 | SDRYDGYFDY SEQ ID NO: 19 | + |
| 2.1L-2.1HB | 17.10 | FQGSHVPLT SEQ ID NO: 60 | 9.93 | SDRFDGYFDY SEQ ID NO: 20 | + |
| 2.2L-2.2H | 2.62 | QQSNEDPWT SEQ ID NO: 132 | 3.30 | WLLAY SEQ ID NO: 21 | + |
| 2.3L-2.2H | 2.20 | WQGTHFPH SEQ ID NO: 61 | 3.30 | WLLAY SEQ ID NO: 21 | + |
| 2.3L-2.3H | 2.20 | WQGTHFPH SEQ ID NO: 61 | 1.65 | SDGYYYFDY SEQ ID NO: 23 | + |
| 2.4L-2.4H | 1.64 | QQHYSTPFT SEQ ID NO: 133 | 1.15 | YYDYDKAYYFDY SEQ ID NO: 25 | − |
| α̃-Br | | | | | |
| 1.1L-1.1H | 6.64 | LQYASSPFT SEQ ID NO: 63 | 7.20 | HDYGNYVDY SEQ ID NO: 10 | + |
| 1.2L-1.2H | 4.73 | WQGTHFPRT SEQ ID NO: 64 | 5.62 | DGNYQEDYFDY SEQ ID NO: 11 | − |
| 1.3L-1.3H | 4.51 | QQNNEDPRT SEQ ID NO: 134 | 1.91 | EGYAYDVDY SEQ ID NO: 12 | + |
| 1.4L-1.4H | 3.59 | QQRSSYPLT SEQ ID NO: 65 | 1.20 | YDYGKDFDY SEQ ID NO: 16 | + |

TABLE 17-continued

Antigen binding of antibody single chain variable fragments (scFvs) from high frequency $V_L$ and $V_H$ genes.

| $V_L$-$V_H$ pair | % $V_L$ | CDRL3 | % $V_H$ | CDRH3 | scFv binding |
|---|---|---|---|---|---|
| 2.1L-2.1H | 7.24 | WQGTHFPQT SEQ ID NO: 123 | 2.57 | RGDGNYFFDY SEQ ID NO: 149 | + |
| 2.2L-2.2H | 4.50 | QQGQSYPWT SEQ ID NO: 126 | 2.27 | GDEAWFAY SEQ ID NO: 150 | − |
| 2.3L-2.3H | 3.12 | LQYASSPYT SEQ ID NO: 135 | 2.03 | EGDFDY SEQ ID NO: 151 | − |
| 2.4L-2.4H | 2.58 | FQGSHVPWT SEQ ID NO: 136 | 1.63 | GGNYDYAMDY SEQ ID NO: 152 | + |

TABLE 18

Antibody single chain variable fragments (scFvs) identified by by combinatorial pairing of top four $V_L$ and $V_H$ genes.

| $V_L$-$V_H$ Pairing | ELISA Signal[a] |
|---|---|
| C1s-1 | — |
| 1L-1H | 4.36 |
| 2L-1H | 19.92 |
| 3L-2H | 4.36 |
| 4L-3H | 6.8 |
| 4L-4H | 3.7 |
| C1s-2 | — |
| 1L-1HB | 63.3 |
| 3L-1HB | 4.65 |
| 2L-2H | 3.1 |
| 3L-2H | 4.22 |
| 3L-3H | 8.8 |

[a]ELISA signal correlates to *E. coli* whole cell lysates expressing scFvs, measured as the OD$_{450}$ signal of scFvs binding to antigen-coated wells relative to wells coated with unrelated antigen (bovine serum albumin).

Figure 13A:
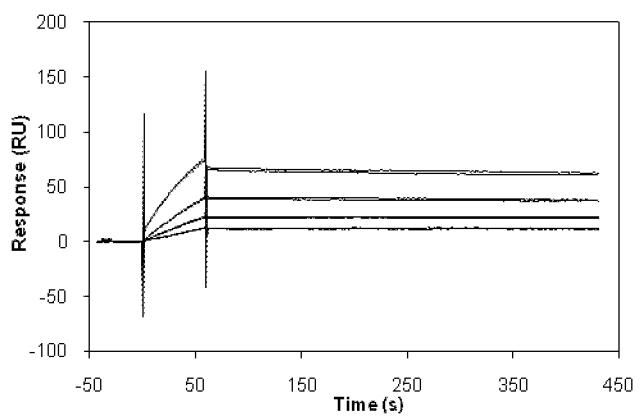
FIGS. 13A-13B. Kinetic binding analysis of purified anti-C1s IgGs by Surface Plasmon Resonance (Biacore).
Figure 13B:
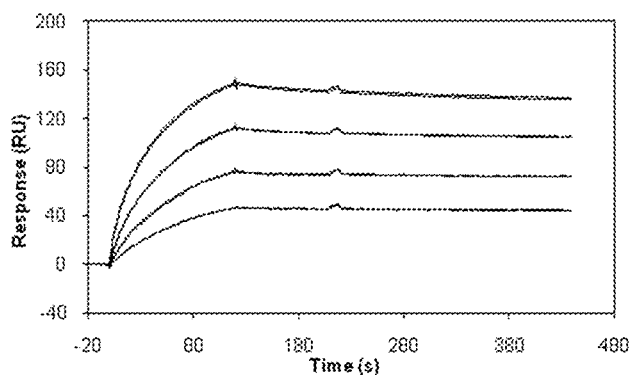
Figure 14:
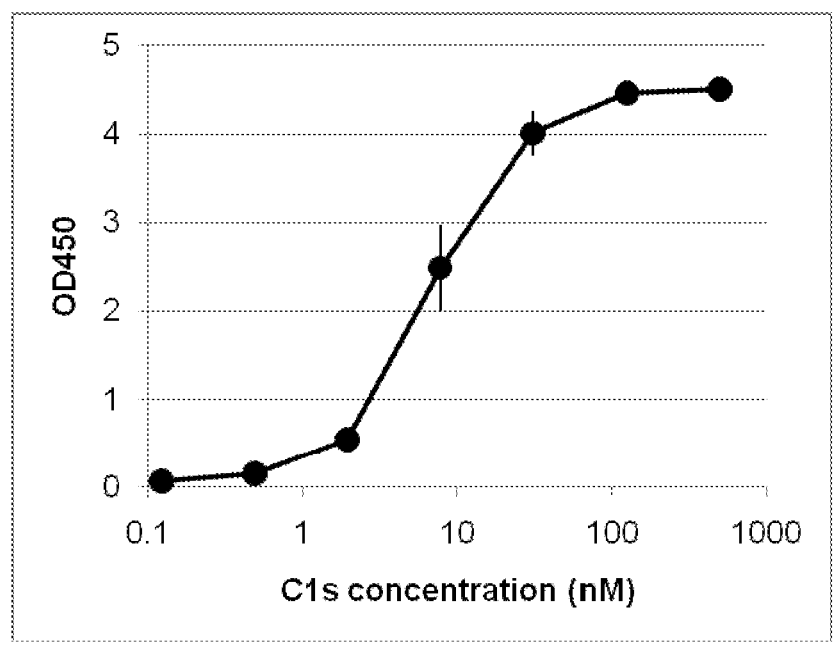
FIG. 14: Detection of C1s by sandwich ELISA using antibodies derived by mining bone marrow plasma cell repertoires. Anti-C1s scFv 2.1L-2.1HB was coated on the plate and used as the capture antibody and anti-C1s IgG 2.3L-2.2H was used as a detection antibody.
Figure 15:
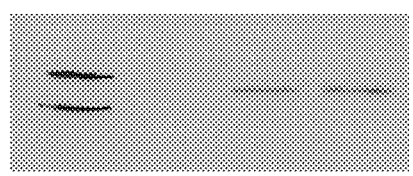
FIG. 15. Immunoprecipitation of C1s from human serum by using antibodies derived by mining bone marrow plasma cell repertoires. Anti-C1s IgG 2.3L-2.2H was used to capture C1s in human serum, following binding on Protein-A agarose beads. Western blot analysis was performed with anti-C1s scFv 2.1L-2.1HB as the primary antibody following by detection with anti-polyHis-HRP. Lane 1: 100 kDa and 70 kDa M.W. markers; lane 2: no capture antibody; lanes 3 and 4: capture with 1.5 µg/ml and 3 µg/ml 2.3L-2.2H antibody, respectively.

Mouse C1s-2 displayed the highest serum titers (Table 19) and therefore, antibodies from this mouse were selected for biophysical characterization of antigen binding affinity by surface plasmon resonance (Biacore). Antibodies were recombinantly expressed and purified as monomeric scFv fragments in *E. coli* and as full-length IgG antibodies in HEK 293F cells. Pairing of the most abundant light (2.1L) and heavy (2.1H-B) V genes (17.10% and 9.93% CDRL3 and CDRH3 frequencies, respectively) from mouse C1s-2 yielded an antibody with a $K_D$ of 20 nM as a scFv ($k_{on}$=2.3× $10^4$ M$^{-1}$ sec$^{-1}$; $k_{off}$=5.0×10$^{-4}$ sec$^{-1}$) and unexpectedly, a slightly lower monovalent $K_D$ of 50 nM ($k_{on}$=2.4×10$^4$ M$^{-1}$ sec$^{-1}$; $k_{off}$=1.2×10$^{-3}$ sec$^{-1}$) as an IgG. From the same mouse, pairing of C1s 2.2L with 2.2H (2.62% and 3.30% CDRL3 and CDRH3 frequencies, respectively) resulted in an IgG that displayed low binding affinity ($K_D$ of ~500 nM, data not shown). However, the pairing of C1s 2.3L with 2.2H (2.20% and 3.30% CDRL3 and CDRH3 frequency, respectively) yielded an IgG with sub-nanomolar binding affinity ($K_D$=0.43 nM, $k_{on}$=4.5×10$^5$ M$^{-1}$ sec$^{-1}$; $k_{off}$=1.9×10$^{-4}$ sec$^{-1}$, FIG. 13 and Table 20), indicating that the natural pairing is likely 2.3L-2.2H. Furthermore, the antibodies were suitable for functional assays, such as sandwich ELISA and immunoprecipitation of C1s from human serum (FIGS. 14-15).

TABLE 19

Serum IgG titers in mice immunized with different antigens.

| Antigen | IgG Titer (serum dilution) |
|---|---|
| Ovalbumin-1 | 1:5,000 |
| Ovalbumin-2 | 1:5,000 |
| C1s-1 | 1:10,000 |
| C1s-2 | 1:50,000 |
| Bright-1 | 1:10,000 |
| Bright-2 | 1:10,000 |

*IgG titer was determined by maximum mouse serum dilution that gave an ELISA signal above background (binding with pre-immunized mouse serum).

TABLE 20

Biophysical characterization of antibody single chain variable fragments (scFv) and IgGs derived by mining the bone marrow plasma cell repertoire of mouse C1s-2, which displayed the highest serum IgG titer.

| $V_L$-$V_H$ pair | 2.1L-2.1HB (scFv) | 2.1L-2.1HB (IgG) | 2.3L-2.2H (IgG) |
|---|---|---|---|
| % $V_L$ | 17.10 | 17.10 | 2.20 |
| % $V_H$ | 9.93 | 9.93 | 3.30 |
| CDRL3 | FQGSHVPLT SEQ ID NO: 60 | FQGSHVPLT SEQ ID NO: 60 | WQGTHFPH SEQ ID NO: 61 |
| CDRH3 | SDRFDGYFDY SEQ ID NO: 20 | SDRFDGYFDY SEQ ID NO: 20 | WLLLAY SEQ ID NO: 21 |

TABLE 20-continued

Biophysical characterization of antibody single chain variable fragments (scFv) and IgGs derived by mining the bone marrow plasma cell repertoire of mouse C1s-2, which displayed the highest serum IgG titer.

| $V_L$-$V_H$ pair | 2.1L-2.1HB (scFv) | 2.1L-2.1HB (IgG) | 2.3L-2.2H (IgG) |
|---|---|---|---|
| $k_{on}$ (M$^{-1}$ sec$^{-1}$) | 2.3 × 10$^4$ | 2.4 × 10$^4$ | 4.5 × 10$^5$ |
| $k_{off}$ (sec$^{-1}$) | 5.0 × 10$^{-4}$ | 1.2 × 10$^{-3}$ | 1.9 × 10$^{-4}$ |
| $K_D$ (nM) | 20 | 50 | 0.43 |

Methods of immunization, isolation of bone marrow plasma cells, preparation of variable light (VL) and variable heavy (VH) genes, and high-throughput sequencing of VL and VH repertoires were essentially the same as described in Examples 1-4 unless otherwise stated.

Bioinformatic Analysis:

(1) CDR3 identification A search method was developed based on conserved flanking sequence motifs found upstream and downstream of CDR3. Searching motifs for CDRH3 and CDRL3 were determined based on amino acids that occur with an average frequency of 99% at specific positions in V genes from the Kabat database (Table 3). $V_H$ sequences were searched for the motif DXXX(Y/F)(Y/F)C (Kabat # 86-92; SEQ ID NO: 802) and WGXG(T/S) (Kabat # 103-107; SEQ ID NO: 803) at N- and C-termini of CDRH3, respectively. Analogously, $V_L$ genes were found by searching for the motifs DXXXY[F/Y]C (Kabat # 82-88; SEQ ID NO: 804) and FGXGT (Kabat # 98-102; SEQ ID NO: 805). This approach correctly identifies over 94% of $V_H$ and 92% of $V_L$ full-length sequences in the Kabat database. Any sequences or reverse complements containing these motifs were extracted as either $V_H$ or $V_L$ genes, respectively. Only the sequences with in-frame CDR3 and without stop codons were further analyzed. For each sample, the most highly represented CDR3 sequences (typically represented at frequencies >1%) were discovered, and their relative abundances in all other the 7 samples were calculated. To find a consensus full-length $V_H$/$V_L$ gene sequence, sequences containing high frequency CDR3s of interest were analyzed for pairwise homology by BLAST, and the sequence with the highest score was chosen. FIG. 5 summarizes the bioinformatics analysis of the V gene sequences. Analysis was performed using Perl scripts in a Unix environment, which were converted into a graphical user interface using the Matlab 7.1 gui builder for enhanced visualization of results.

Figure 10A:
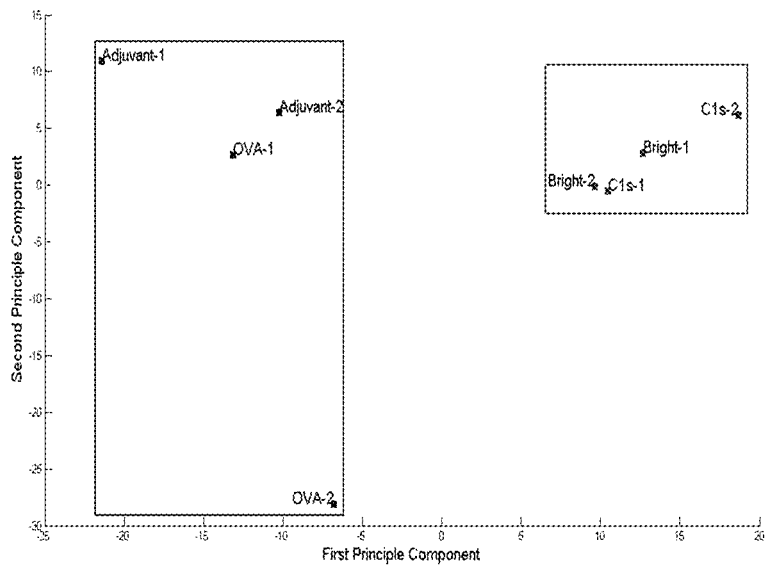
FIGS. 10A-10B: Principal component analysis (PCA) of CDRH3 sequences from bone marrow plasma cell repertoires of different mouse groups. Ovalbumin (OVA) and Adjuvant only mice were one immunization group (derived from the same cage and same litter) while C1s and Bright mice were another immunization group. First principal component analysis identified two main cluster groups, blue and red, which represent different experiments (i.e. immunizations carried out on different dates).
Figure 10B:
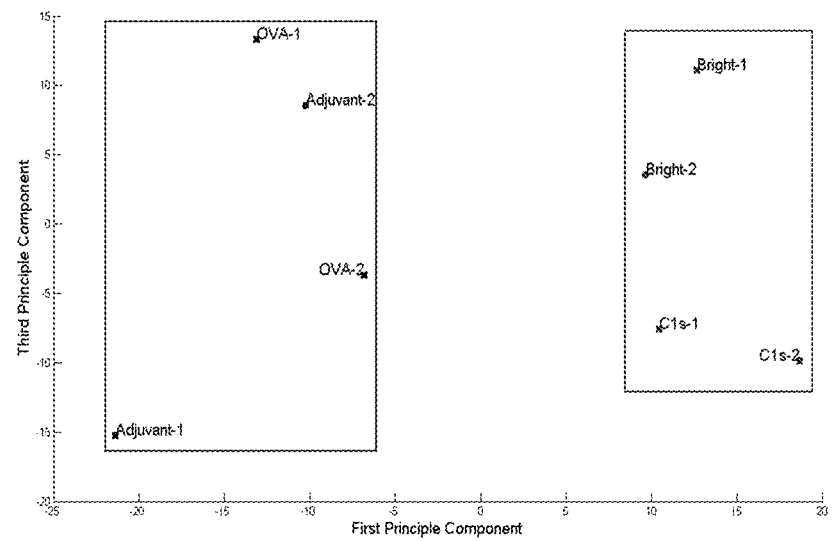

(2) Analysis of CDR3 expression across samples from different mice. CDR3 sequences found in multiple samples were extracted and analyzed for their prevalence in all mice. First, Principle Component Analysis (PCA) was performed using Matab to analyze the variance of CDR3 expression in different mice (FIGS. 10A-10B). The majority of the variance between mouse samples was categorized into seven principle components. Second, the percent of CDRH3 sequences found in multiple samples were calculated. Since, it could not be determined whether replicate sequences were due to contamination or a true biological effect, a permutation test was performed to determine whether the percentage of sequences shared across four samples was biased by samples analyzed on a specific day. The percent of shared sequences was calculated for all 70 possible combinations of the eight samples selected four times, subsequently ranked by percentage overlap. The top three ranked combinations were considered significant and not attributed to random combinations.

(3) Frequency distribution of abundant CDRH3. A heat map was generated to illustrate the prevalence of highly abundant CDRH3s from each sample in mice receiving different antigen. Only CDRH3 sequences with statistically significant frequencies in the top 5% of the distribution (frequency cutoff ~0.03%) were represented (FIG. 9).

(4) Homology analysis of full-length V genes. Full-length V genes were found for sequences containing identical CDR3s. First, sequences were placed in-frame by docking CDR3 motifs. Second, full-length V gene sequences were accepted if they did not contain stop codons and covered all three CDR regions. Non-identical, full-length V genes (containing at least one amino acid difference) were aligned to determine pairwise homology using the multiple sequence alignment tool in Geneious Software (Biomatters Ltd., FIG. 8 and Table 14).

(5) Germline analysis. The top 4 full-length consensus $V_L$ and $V_H$ genes were analyzed by the IMGT/V-Quest Tool (Brochet et al., 2008). Additionally, the top 30 ranked CDRH3 sequences, of four mice (adjuvant-1, adjuvant-2, C1 s-1, and C1s-2) were further analyzed for V(D)J recombination using IMGT/V-QUEST tool. The V segment germline usage and $V_H$ gene somatic mutations were identified after the IMGT/V-QUEST analysis. These data are reported in FIG. 7 and Table 13.

Construction of Synthetic Antibody Genes.

Synthetic antibodies can be constructed in accordance with the methods described in the Example 8 above.

Surface Plasmon Resonance (Biacore) C1s was covalently immobilized on a CM5 chip (GE healthcare, NJ) at a level of approximately 200 response units via standard amine coupling chemistry as described in the manufacturer's protocol. BSA was similarly coupled for baseline correction. All kinetic analyses were performed at 25° C. in HBS-EP (10 mM HEPES, 150 mM NaCl, 50 µM EDTA, 0.005% P-20, pH 7.4) on a BIAcore 3000 (GE healthcare, NJ). Antibodies were injected over immobilized antigen at a flow rate of 50 µl/min or 100 µl/min and the chip was regenerated with a single 10s injection of 20 mM NaOH. Each sensogram was run in duplicate. Kinetic and equilibrium constants were determined by global fitting to a bivalent model using BIAevaluation software (GE healthcare, NJ).

Example 10

Rapid Generation of Monoclonal Antibodies Directly from Lymphoid Tissues without B Cell Isolation Immunization Protocol Protein antigens (e.g., purified hen egg lysozyme or keyhole limpet hemocyanin)) were resuspended in sterile-filtered phosphate buffered saline (PBS) at 1.0 mg/ml. On the day of primary immunization, 200 ul of antigen solution was thoroughly mixed with 200 ul of Complete Freund's Adjuvant (CFA, Pierce Biotechnology) and 600 ul of sterile PBS and stored on ice. Animal species (rabbits, sheep, goats, pigs) mice were bled approximately 20 ml of blood was collected and stored at −20° C. for later analysis. Day 1 was designated as the day primary immunizations were performed. 1.0 ml of the antigen-CFA mixture per animal was injected with a 21-gauge needle subcutaneously.

For subsequent booster immunizations, 200 ul of antigen solution was thoroughly mixed with 200 ul of Incomplete Freund's Adjuvant (IFA, Pierce Biotechnology) and 600 ul of sterile PBS and stored on ice. Animals were given booster immunizations every 14 days, injections were given intraperitoneally at 1.0 ml of antigen-IFA mixture per animal. Animals were bled 7 days following the booster immunization and antigen-specific antibody titers were measured to monitor immune responses. When immune responses reached high titers (>1/100,000 serum dilution), animals were sacrificed and blood and tissue was harvested.

Isolation Bone Marrow, Lymph Nodes, and Spleen

Bone Marrow: The muscle and fat tissue was removed from femurs harvested from immunized animals. Using an electric drill and sterilized drill bit, holes were drilled into the ends of both tibia and femurs to provide enough space for a 22-gauge needle to enter the bone. Bone marrow was flushed out using this procedure. Bone marrow tissue was collected in sterile-filtered Buffer#1 (PBS/0.1% bovine serum albumin (BSA)/2 mM ethylenediaminetetracetic acid (EDTA)). Bone marrow cells were collected by filtration through a 70-um cell strainer (BD) with mechanical disruption, washed with 40 ml of PBS and collected in a 50 ml tube (Falcon, BD). Bone marrow cells were then centrifuged at 1200 RPM for 10 min at 4° C. Supernatant was decanted and cell pellet was resuspended with 5.0 ml of RBC lysis buffer (eBioscience) and shaken gently at 25° C. for 5 minutes. Cell suspension was then diluted with 40 ml of PBS and centrifuged at 1200 RPM for 10 minutes at 4° C. Supernatant was decanted and cell pellet was resuspended in 2.0 ml of Buffer#1.

Lymph Nodes: Lymph nodes were harvested from animals, placed in Buffer#1 and stored on ice. Using two 22-gauge needles, lymph node tissue was teased apart into small 1-2 mm fractions. Fractions were then placed in a petri dish, with 5 ml of Buffer#1. Next, 0.5 ml of 10× collagenase D (R&D Systems) was added to each lymph node tissue fraction and incubated at 37 C for 30 minutes. Following incubation, 100 ul of 100 mM EDTA is added to the lymph node fractions (to quench collagenase). Lymph node fragments were then transferred to a 70-um cell strainer and with mechanical disruption were washed with 40 ml of PBS. Lymph node cells were then centrifuged at 1200 RPM for 10 min at 4 C. Supernatant was decanted and cell pellet was resuspended in 20 ml of PBS and centrifuged at 1200 RPM for 10 min at 4 C. Supernatent was decanted and cell pellet was resuspended in 2.0 ml of Buffer#1.

Spleen: Spleens were harvested from animals and placed in Buffer#1 and stored on ice. Using two 22-gauge needles, spleen tissue was teased apart into small 1-2 mm fractions. Fractions were then placed in a petri dish, with 5 ml of Buffer#1. Next, 0.5 ml of 10× collagenase D (R&D Systems) was added to each spleen tissue fraction and incubated at 37 C for 30 minutes. Following incubation, 100 ul of 100 mM EDTA is added to the spleen fractions (to quench collagenase). Spleen fragments were then transferred to a 70-um cell strainer and with mechanical disruption were washed with 40 ml of PBS. Spleen cells were then centrifuged at 1200 RPM for 10 min at 4 C. Supernatant was decanted and cell pellet was resuspended with 5.0 ml of RBC lysis buffer (eBioscience) and shaken gently at 25° C. for 5 minutes. Cell suspension was then diluted with 40 ml of PBS and centrifuged at 1200 RPM for 10 minutes at 4° C. Supernatent was decanted and cell pellet was resuspended in 2.0 ml of Buffer#1.

Preparation of mRNA.

Cell isolated as described herein were centrifuged at 2,000 RPM at 4° C. for 5 min. Supernatant was decanted, and cell pellets were then resuspended and lysed with TRI reagent and total RNA was isolated according to the manufacturer's protocol in the Ribopure RNA isolation kit (Ambion). mRNA was isolated from total RNA through with oligodT resin and the Poly(A) purist kit (Ambion) according to the manufacturer's protocol. mRNA concentration was measured with an ND-1000 spectrophotometer (Nanodrop).

Preparation of Antibody VL and VH Genes Using 5' RACE.

cDNA libraries of the VL and VH genes from antibodies of a desired class (IgA, IgG, IgM or IgE) were constructed from the isolated mRNA. To start first strand cDNA was synthesized from mRNA using the SMARTscribe Maloney Murine leukemia virus cDNA was prepared from mRNA using reverse transcriptase (MMLV-RT, Clonetech). The cDNA synthesis utilized 300 ng mRNA template switching 5' adaptor primers and oligo(dT) 3' primers. Subsequently, 5' RACE was performed by using RNA ligation according to the RLM-RACE First Choice kit (Ambion), according to the manufacturer's instructions. 2 µl of unpurified cDNA was used as a template. 5' Primers, buffers, polymerase, and reaction conditions were provided by manufacturer (Clontech and Ambion). 3' primers were designed based upon Ig µ or γ or constant region sequences of other species, which are publicly available from the IMGT database. 3' constant region specific primers for various species are shown in Table 21. PCR products were purified with a 1% agarose gel, bands at ~400-450 bp correlated to VL and VH and were isolated and submitted for 454 high-throughput DNA sequencing.

V Gene Amplification by PCR Using Primer Mixes.

Isolated mRNA was used for first strand cDNA synthesis by reverse transcription with the Maloney murine leukemia virus reverse transcriptase (MMLV-RT, Ambion). For cDNA synthesis, 50 ng of mRNA was used as a template and oligo (dT) primers were used; RT-PCR was performed according to manufacturer protocol of Retroscript kit (Ambion). Following cDNA synthesis VH and VL genes were amplified by PCR using 2 ul of unpurified cDNA product. 5' primer mixes for VL and VH were generated based on germline repertoire sequences available on the IMGT database. An example of 5' regions of VH genes in sheep is provided in FIG. 16. 3' primers were used based on constant regions, as described in Table 21. PCR products of the VL and VH genes were gel purified and submitted for 454 DNA sequencing.

TABLE 21

Constant region 3' primers

| | 3' primer sequence | CH1 region | Tm (° C.) |
|---|---|---|---|
| Rabbit | | | |
| IGHG*01 | GGG AAG ACT GAC GGA GCC TTA GGT TGC C (SEQ ID NO: 172) | 1 to 28 | 65.6 |
| IGHG*02 | GGA AGA CTG ATG GAG CCT TAG GTT GCC C (SEQ ID NO: 173) | 1 to 28 | 64 |
| IGHG*05 | GGG TAC AGA GTT GGA GAT GAC AGG CTC A (SEQ ID NO: 174) | 1 to 28 | 62.8 |
| IGHM | GGG TAC AGA GTT GGA GAT GAC AGG CTC AC (SEQ ID NO: 175) | 1 to 29 | 63.1 |
| Sheep | | | |
| IGHG1 | GGT AGA CTT TCG GGG GTG TTG TTG AGG C (SEQ ID NO: 176) | 1 to 28 | 64.3 |
| IGHG2 | CTT TCG GGG CTG TGG TGG AGG C (SEQ ID NO: 177) | 1 to 22 | 65 |
| IGHM | GGA AGA CTT TCG GGT GAG ATT CAC TTT C (SEQ ID NO: 178) | 1 to 28 | 59.1 |
| Pig | | | |
| IGHG1, 2A, 3, 5 | GAT GGG GCC GTC TTG GGG GC (SEQ ID NO: 179) | 1 to 20 | 66.1 |
| IGHG2B | AAT GGG GCC GTC TTG GGG GC (SEQ ID NO: 180) | 1 to 20 | 65.7 |
| IGHM*01 | GTA GAG ATT CGG GGC AGA CTG GCT CT (SEQ ID NO: 181) | 1 to 26 | 63.3 |
| IGHM*02 | GGA CGG GAA GTC CTG GAT GTT CTG GC (SEQ ID NO: 182) | 1 to 26 | 64.6 |

Isolation of VH and VL cDNA by Hybridization.

Isolated mRNA was used for first strand cDNA synthesis by reverse transcription with MMLV-RT (Ambion). For cDNA synthesis, 200 ng of mRNA was used as a template and 3' specific primers for $V_L$ and $V_H$ constant regions (Table 21) were used in the RT reaction; RT-PCR was performed at 55 C for 90 min followed by 90 C for 10 min. Following RT-PCR, RNase was added to the reaction to deplete remaining mRNA. Next, 10 µM of biotinylated primers were added to the cDNA. Biotinylated primers were based on the reverse complement of primers described in Table 21 and contained an overhang on the 3' end of 454 sequencing Primer B. 25 ul of streptavidin coated Dynabeads (Invitrogen) were added to the cDNA and rotated for 5 min at room temperature. The tube was then placed on the magnet and supernatant was removed and discarded, the cDNA-bead complex was then washed twice with 200 ul of PBS. cDNA was then eluted from the beads with 20 ul of 10 mM Tris-HCl, pH 7.5, mixture was heated at 70 C for 2 min and then placed on the magnet. The eluted cDNA in the supernatant and transferred to a new tube, then gel purified by a 1% agarose gel, and bands ~600-700 nt corresponding in size to IgL and IgH cDNAs were excised and processed for 454 DNA sequencing.

Bioinformatic Analysis for CDR3 Identification.

CDR3 is the most diversified region of antibody and dominates antigen recognition. The inventors realized that the sequences flanking CDR3 are highly conserved in all the species that have an immunoglobulin-encoding adaptive immune response system (fish, frog, birds, mammals, etc). These conserved motifs are believed to be essential to provide a rigid conformation context for properly presenting the ultra-variable CDR3 loop while keeping the overall structure of variable domain undisturbed. The inventors develop a fast algorithm for identifying the CDR3 based on probabilistic homology analysis. Three strategies can be used to design searching motifs for individual specie—using antibody database (rearranged genes), germline genes, or genomic sequences of immunoglobulins. This bioinformatics analysis method could be therefore applied for antibody sequences of nearly all the species carrying adapted immune systems, even without large antibody databases. The inventors developed a fast algorithm for identifying the CDR3 based on probabilistic homology analysis. Three strategies were used to design searching motifs for individual specie—using antibody database (rearranged genes), germline genes, or the genomic sequences of germline immunoglobulin segments from the genome sequence of the animal. This bioinformatics analysis method could be therefore applied for antibody sequences of nearly all the species carrying adapted immune systems, even without large antibody databases.

Design of Rabbit CDR-H3 Homology Search Motifs. A Perl script was written to calculate amino acid occurrence frequency at each residue position alone antibody variable domain by alignment of 506 rabbit VH genes in KabatMan database. Calculation result revealed the existence of highly conserved sequences flanking CDR-H3 regions (Kabat numbering residues #95-102). For example 99% of rabbit VH genes have cysteine and glycine at the position of 92 and 106, respectively. 10 highly conserved positions flanking CDR3 (>90%) were identified. Tables 22-23 list the calculated amino acid occupancy probabilities at these positions. To efficiently identify antibody sequences with somatic hypermutation located at motif regions, a possibility weight is evenly given to any non-dominant amino acids. For example, at position 86, possibility for aspartic acid is 0.97, possibility for alanine is 0.03, and possibility for any one out of the other 18 amino acids is 0.03/18=0.00167.

Analysis of antibody variable heavy and variable light chain sequences was performed essentially as described in Example 5. The conserved motifs as exemplified above were used to search for CDR3 regions. Construction of synthetic antibody genes based on identified abundant variable region sequences was essentially as described in Example 7. Antibody expression and binding analysis was essentially as described in Example 8.

Example 11

Rapid of V Gene Repertoires from Total Lymphoid Tissues without B Cell Isolation Following Immunization of Different Animals Protein antigens (purified hen egg lysozyme or *Concholepas concholepas* hemocyanin)) were resuspended in sterile-filtered phosphate buffered saline (PBS) at 10 mg/ml. On the day of primary immunization, 100 µg of antigen diluted in 1

TABLE 22

5' searching motif for rabbit CDR-H3 and associated probability matrix

| Kabat # | 85 | 86 | 90 | 91 | 92 | 93 | 94 |
|---|---|---|---|---|---|---|---|
| Residue (possibility) | A 0.83 | D 0.97 | Y 0.94 | F 0.83 | C 0.99 | A 0.93 | R 0.92 |
| | E 0.07 | A 0.03 | A 0.05 | Y 0.09 | X 0.01 | G 0.02 | S 0.04 |
| | T 0.05 | X 0.03 | X 0.01 | M 0.03 | | V 0.02 | X 0.04 |
| | X 0.05 | | | X 0.05 | | X 0.03 | |

TABLE 23

3' searching motif for rabbit CDR-H3 and associated probability matrix

| Kabat # | 103 | 104 | 105 | 106 | 107 | 108 |
|---|---|---|---|---|---|---|
| Residue (possibility) | W 0.97 | G 0.94 | P 0.90 | G 0.99 | T 0.92 | L 0.98 |
| | X 0.03 | I 0.04 | W 0.05 | X 0.01 | P 0.07 | X 0.02 |
| | | X 0.02 | Q 0.03 | | X 0.01 | |
| | | | X 0.02 | | | |

Figures 16, 17:
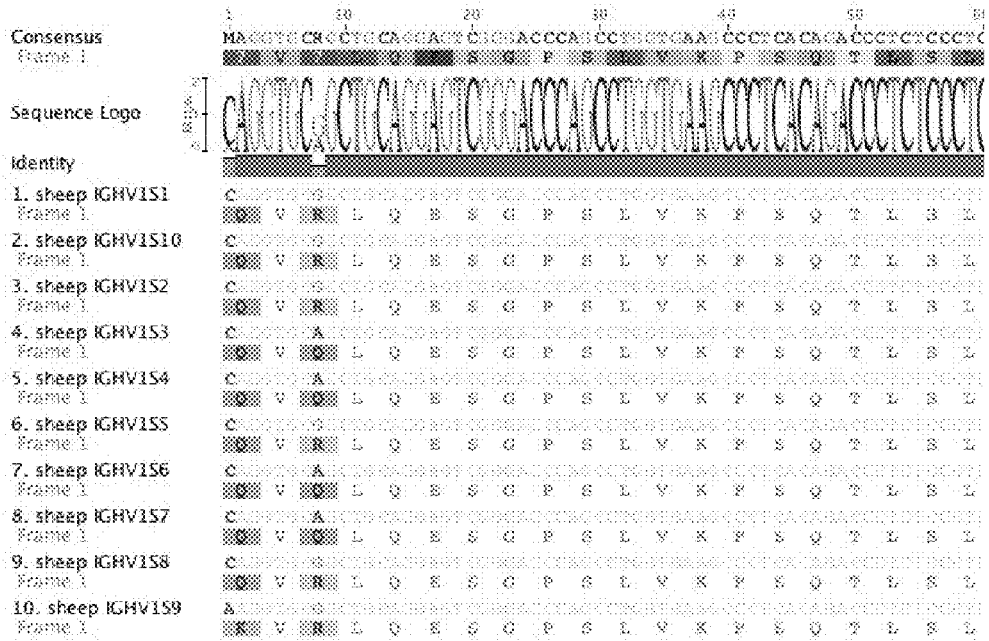
FIG. 16. Sequence alignment displays the 5' regions of all known sheep germline VH genes (IGHV). 5' degenerate primer mixes can be designed based on these sequences and used for PCR amplification from sheep first-strand cDNA (SEQ ID NOS:779-789). (Frame 1sequences correspond to SEQ ID NOS: 790-800; Sequence Logo=SEQ ID NO: 801)
FIG. 17: Amino acid sequences of chicken germline IGHV region genes (SEQ ID NOS:761-778).

Chicken CDR-H3 Search Motif Derived from Germline Sequence Analysis using Genomic Data. When an antibody sequence database is not available, search motifs can be identified from the germline sequences available from genomic information. As an illustrative example, the search motif for the 5' of VDR3 in chicken was identified and the respective probability Table 24 was constructed. All 18 chicken germline IGHV genes, including both functional and pseudogenes, were extracted from the database. FIG. 17 displays the aligned protein sequences of all chicken heavy chain v-segment genes. A conserved motif flanking the 5' of the CDR3 was then calculated as above.

mL saline was mixed with 1 ml of Complete Freund's Adjuvant (CFA) and stored on ice. Animal species (rabbits, sheep, or goats) were bled on day 0 (pre-immunization bleed) into two heparin tubes to obtain approximately 15 mL blood for subsequent RNA isolation and serum titers. Day 1 was designated as the day primary immunizations were performed. 2.0 ml of the antigen-CFA mixture per animal was injected.

For subsequent booster immunizations, 100 µg of antigen diluted in 1 mL saline was mixed with 1 ml of Incomplete Freund's Adjuvant (IFA) and stored on ice. Animals were given booster immunizations every 14 days, injections were given at 2.0 ml of antigen-IFA mixture per animal. Animals were bled 6 days following the booster immunization and antigen-specific antibody titers were measured to monitor immune responses. When immune responses reached high titers (>1/25,000 serum dilution, see Table 25), animals were sacrificed and blood and tissue was harvested.

TABLE 24

5' searching motif for chicken CDR-H3 and associated possibility matrix

| Kabat # | 85 | 86 | 87 | 90 | 91 | 92 | 93 | 94 |
|---|---|---|---|---|---|---|---|---|
| Residue (probability) | E 0.98 | D 0.98 | T 0.98 | Y 0.93 | Y 0.83 | C 0.99 | A 0.55 | K 0.58 |
| | X 0.02 | X 0.02 | X 0.02 | S 0.05 | F 0.09 | X 0.01 | T 0.44 | R 0.41 |
| | | | | X 0.02 | L 0.03 | | X 0.01 | X 0.01 |
| | | | | | X 0.02 | | | |

TABLE 25

Serum titers against HEL and CCH in all eight injected animals

| Animal | Titer[a] |
|---|---|
| Rabbit CCH1 | 1:3,125,000 |
| Rabbit CCH2 | 1:625,000 |
| Rabbit HEL1 | 1:5,000 |
| Rabbit HEL2 | 1:25,000 |
| Goat 52 | 1:625,000 |
| Goat 53 | 1:125,000 |
| Sheep 54 | 1:625,000 |
| Sheep 55 | 1:25,000 |

[a]Titer was against injected antigen (HEL except for the two CCH rabbits) as determined by ELISA using a secondary antibody against species-specific IgG + IgM Isolation of Bone Marrow, Spleen, and PBMCs Bone Marrow: The muscle and fat tissue was removed from femurs and humeri harvested from immunized animals. Using a Dremel saw, bones were cross-sectioned directly adjacent to the joints. Bone marrow was flushed out with sterile PBS with the aid of a small spatula to break up cellular masses of the red marrow. Bone marrow cells were collected by filtration through a 70-μm cell strainer (BD) with mechanical disruption, washed with 40 ml of PBS and collected in a 50 ml tube (Falcon, BD). Bone marrow cells were then centrifuged at 1200 RPM for 10 min at 4° C. Supernatant was decanted and cell pellet was resuspended with 5.0 ml of RBC lysis buffer (eBioscience) and shaken gently at 25° C. for 5 minutes. Cell suspension was then diluted with 40 ml of PBS and centrifuged at 1200 RPM for 10 minutes at 4° C. Supernatant was decanted and cell pellet was resuspended in 1.0-2.0 ml of Buffer#1.

Spleen: Spleens were harvested from animals and placed in sterile PBS and stored on ice. Using two razor blades, spleen tissue was diced and then teased apart into small 1-2 mm fractions. Fractions were then placed in a petri dish, with 5 ml of Buffer#1. Spleen fragments were then transferred to a 70-um cell strainer and with mechanical disruption were washed with 40 ml of PBS. Spleen cells were then centrifuged at 1,200 RPM for 10 min at 4° C. Supernatant was decanted and cell pellet was resuspended with 5.0 ml of RBC lysis buffer (eBioscience) and shaken gently at 25° C. for 5 minutes. Cell suspension was then diluted with 40 ml of PBS and centrifuged at 1200 RPM for 10 minutes at 4° C. Supernatant was decanted and cell pellet was resuspended in 1.0-2.0 ml of Buffer#1.

Blood: Blood was collected from animals into sealed heparin tubes and stored on ice. Blood was collected at day 0, six days after every booster injection, and at sacrifice of each animal. Blood at various time points (day 0, day 20, day 34 for all animals, as well as at sacrifice for each animal) was processed to isolate PBMCs for subsequent isolation of RNA. PBMC purification was accomplished by layering each bleed (16-20 mL for each animal) on top of histopaque solution (Sigma) at 1:1 volume, avoiding mixing of the contents. The blood-histopaque solution is centrifuged at 1,600 RPM for 30 minutes at 23° C. without centrifugation braking. The peripheral blood mononuclear cell (PBMC) layer is isolated following gradient centrifugation, and washed through centrifugation with wash buffer (PBS). Cells were then resuspended in 1.0-2.0 Buffer#1. The top layer containing 10-12 mL serum was collected for analysis of serum titers against the respective antigen. Cardiac punctures at the time of sacrifice for each animal yielded approximately double the volume of blood. Serum volumes from these bleeds contained 30-50 mL.

Cells isolated as described herein were centrifuged at 2,000 RPM at 4° C. for 5 min. Supernatant was decanted, and cell pellets were then resuspended by vigorous pipetting and vortexing in 1 mL TRI reagent and total RNA was isolated according to the manufacturer's protocol in the Ribopure RNA isolation kit (Ambion). RNA concentration was measured with an ND-1000 spectrophotometer (Nanodrop).

200-700 ng of total RNA in a volume of 2.75 ul was used for first strand cDNA synthesis with the SMARTer RACE cDNA amplification kit (Clontech). 1.0 ul of CDS Primer A was added to the RNA, followed by incubation in a thermal cycler at 72° C. for 3 minutes, then to 42° C. for 2 minutes. 1 ul of the SMARTer IIA oligo was added, followed by 5.25 ul of a master mix including 2.0 ul 5× First-Strand Buffer, 1.0 ul 20 mM DTT, 1.0 ul of 10 mM dNTP mix, 0.25 ul RNase inhibitor (40 U/ul), and 1.0 ul SMARTScribe Reverse Transcriptase (100 U). The first strand synthesis reaction mixture was then incubated at 42° C. for 90 minutes, followed by 70° C. for 10 minutes. The first strand cDNA product was diluted with 100 ul of Tricine-EDTA Buffer. The 5' RACE amplification was setup with a master mix including 70.5 ul RNase-free water, 10 ul 10× Advantage 2 PCR Buffer (Clontech), 2.0 ul 10 mM dNTP mix, 10 ul 10× Universal Primer A Mix (Clontech), and 1.5 ul Advantage 2 Polymerase Mix (Clontech). 94 ul of master mix was added to a PCR tube containing 2.0 ul of first strand cDNA product and 1.0 ul of a 3' primer (10 μM). For VH amplification, 3' primers were designed based upon Ig mu or gamma CH1 gene sequences of rabbit, sheep, or goat, which are publicly available from the IMGT database (rabbit and sheep) or Genbank (goat). For VL amplification, 3' primers were designed based upon Ig kappa or lambda gene sequences of rabbit, sheep, or goat, which are publicly available from the IMGT database (rabbit kappa) or Genbank (rabbit lambda, sheep and goat). 3' constant region specific primers for each species are shown in Table 26. PCR products were purified with a 1% agarose gel, bands at ~500-550 bp correlated to VL and VH and were isolated and submitted for 454 high-throughput DNA sequencing.

TABLE 26

Constant region 3' primers

| | 3' primer sequence | SEQ ID NO: | CH1/Cκ/Cλ region |
|---|---|---|---|
| Rabbit | | | |
| IGHG1 | CAGTGGGAAGACTGACGGAGCCTTAG | 184 | 5 to 30 |
| IGHG2 | CAGTGGGAAGACTGATGGAGCCTTAG | 185 | 5 to 30 |
| IGHM | GGAGACGAGCGGGTACAGAGTTGGAG | 186 | 13 to 38 |

TABLE 26-continued

Constant region 3' primers

| | 3' primer sequence | SEQ ID NO: | CH1/Cκ/Cλ region |
|---|---|---|---|
| IGκ | TGGTGGGAAGAKGAGGACAGTAGG | 187 | 15 to 38 |
| IGλ1 | CAAGGGGGCGACCACAGGCTGAC | 188 | 2 to 24 |
| IGλ2 | GTGAAGGAGTGACTACGGGTTGACC | 189 | 1 to 25 |
| IGλ3 | GAGGGGGTCACCGCGGGCTGAC | 190 | 2 to 23 |
| Sheep | | | |
| IGHG1 | GACTTTCGGGGGTGTTGTTGAGG | 191 | 1 to 23 |
| IGHG2 | GACTTTCGGGGCTGTGGTGGAGG | 192 | 1 to 23 |
| IGHM | CCAGGGGGAAGACTTTCGGGTGAGATTC | 193 | 6 to 33 |
| IGκ | GATGGTTTGAAGAGGGAGACGGATGGCTGAGC | 194 | 9 to 40 |
| IGλ | ACAGGGTGACCGAGGGTGCGGACTTGG | 195 | 8 to 34 |
| Goat | | | |
| IGHG | GACTTTCGGGGGTGTGGTGGAGG | 196 | 1 to 23 |
| IGHM | CCAGGGGGAAGACTTTCGGGTGAGATTC | 197 | 6 to 33 |
| IGκ | GATGGTTTGAAGAGGGAGACGGATGGCTGAGC | 198 | 9 to 40 |
| IGλ | ACAGGGTGACTGAGGGTGCGGACTTGG | 199 | 8 to 34 |

The V gene repertoire prepared by 5' RACE of unfractionated lymphoid tissues described above was compared with the V gene repertoire obtained by first sorting antigen secreting B cells (CD138+ plasma cells and plasmablasts) followed by 5' RACE amplification of the V gene mRNAs as described above. CD138+ cells were purified by magnetic sorting using rat α-murine CD138 antibody clone 281-2 (BD Pharmingen) as described in Example 2. The V gene DNA obtained from unfractionated lymphoid tissue was designated total lymphoid tissue V gene (tLT-V). DNA obtained from isolated antibody secreting CD138+B cells was designated as Plasma cell V gene (PC-V). The tLT-V and the PC-V DNA was sequenced using NExtGEn sequencing as described in Example 4 and the data was processed as described in Example 5. The inventors established that more than 95% of the abundant CDRH3 sequences (minimum of 10 reads or ≥0.04%) in the PC-V pool are also detected in the tLT-V pool when comparing rabbit HEL1 tLT-V and PC-V, which both approximately the same number of aligned reads. Table 27 shows a comparison of the most abundant VH sequences detected in the tLT-V sample and in the PC-V sample obtained from bone marrow plasma cells for four rabbits immunized with CCH (CCH1 and CCH2) or with HEL (HEL1 and HEL2).

TABLE 27

Comparison of most abundant VH genes identified from the sequencing of the repertoire from V gene cDNA prepared from total lymphoid tissue (tLT-V) or from purified CD138+ B cells (PC-V)

| top 10 PC-V CDRH3 | tLT-V[a] | SEQ ID NO: |
|---|---|---|
| Rabbit CCH1 | | |
| ARGLNAAGYTTFAYGTTVMDL | + | 200 |
| ARDMDGGNVGYGM | + | 201 |

TABLE 27-continued

Comparison of most abundant VH genes identified from the sequencing of the repertoire from V gene cDNA prepared from total lymphoid tissue (tLT-V) or from purified CD138+ B cells (PC-V)

| top 10 PC-V CDRH3 | tLT-V[a] | SEQ ID NO: |
|---|---|---|
| ARFDAAYADFGVANL | + | 202 |
| ARADRGFYAGTSDYTGYNL | + | 203 |
| ARADRGFYAGTSDYSGYNL | − | 204 |
| ARDAGGSYSYYFDL | − | 205 |
| ARDAGGYTGDGYYFKL | − | 206 |
| ARGGPIHYSNL | + | 207 |
| ARGSGWYGGLNL | + | 208 |
| ASNYADPPGYNYTPFNL | + | 209 |
| Rabbit CCH2 | | |
| ATDRGPSGSGPLDL | + | 210 |
| SRDGKYAGIAGYGSTYFDL | + | 211 |
| AGDGRSYYADYAFVDL | + | 212 |
| ARDPVTRLVAGADYFDL | + | 213 |
| ARDVYTYDADGDYRHFNL | + | 214 |
| ARAPVYYNGGYAGFREFNL | + | 215 |

TABLE 27-continued

Comparison of most abundant VH genes identified from the sequencing of the repertoire from V gene cDNA prepared from total lymphoid tissue (tLT-V) or from purified CD138+ B cells (PC-V)

| top 10 PC-V CDRH3 | tLT-V[a] | SEQ ID NO: |
|---|---|---|
| ARDGGWGYNL | + | 216 |
| ARDSFDGYGDFNL | – | 217 |
| ARVGNHYGMDL | – | 218 |
| ARGAAGYAGYAYAYYYFDF | – | 219 |
| Rabbit HEL1 | | |
| ARDWNYGMDL | + | 220 |
| ARNFAL | + | 221 |
| ARDLNAAHRTNSPKL | + | 222 |
| WITNL | + | 223 |
| ARGFSLLGYLTL | + | 224 |
| ARDPYGRSGDDFVL | + | 225 |
| ARGYDDYGDYLDL | + | 226 |
| ARSAYNDFGDYVSPLTL | – | 227 |
| ARQYLL | + | 228 |
| ARGSVIYVGEL | + | 229 |
| Rabbit HEL2 | | |
| ARGRSDTNYRLNL | + | 230 |
| GRSVEAVQGASNWYFDI | + | 231 |
| GKTSTIDSDYYNL | + | 232 |
| ARGGFTDRTYANI | – | 233 |
| ARNAGGNDYFRL | – | 234 |
| GRYGGNVGAFDM | + | 235 |
| ARGNSVTDTYLIDSGMDL | + | 236 |
| AKSAYNTAGYSPL | + | 237 |
| ARDLSYDPYGDLGTRLDL | – | 238 |
| ARRNPNYDTGHFNI | + | 239 |

[a]Present (+) or absent (–) in the top 15 most abundant CDRH3 of tLT-V repertoire.

Example 12

Isolation of Monoclonal Antibodies by Mining the IgG Variable Gene Repertoire of Bone Marrow, Spleen, and PBMC Cell Populations—Application to Rabbit, Sheep, and Goat V gene cDNAs from different lymphoid organs or from peripheral blood were sequenced, as described in Examples 4 and 9, and 454 reads were processed by rapid bioinformatic analysis that relied on homologies to conserved framework regions within V genes in order to identify the most common complementarity determining region 3 (CDR3) sequences. Germline alignments were performed using the IMGT software HighV-Quest. Sheep germline sequences, which have been shown to have high identity to known goat sequences, were used for IMGT-based alignment to determine CDR motifs in goats.

Bioinformatic analysis of repertoires in rabbit, sheep, and goat revealed distinct differences as compared to murine repertoires. Primarily the repertoire polarity in the tBM samples for both heavy and light chain was lower than in the mice (Example 9). Thus, unlike the mice where antigen-specific V gene were identified solely based on relative cDNA abundance additional bioinformatics schemes were implemented to refine the data and aid the antigen-specific V gene identification. In one method, described herein PBMC repertoires to compare to bone marrow data. Antigen secreting cells in the bone marrow in other lymphoid compartments at early times following booster immunization (between 4-30 days, depending on species). Sequences present at high frequency in the bone marrow and also at moderate to high frequencies in other compartments account for antigen-specific monoclonal antibodies. The use of IgG-specific 5' RACE amplification affords the high resolution analysis of class-switched (IgG, IgA or IgE encoding) antibodies expressed predominantly by circulating plasmablasts and plasma cells (and to a lesser extent because of substantially lower transcription level, by class switched memory cells) in total peripheral blood monocytes without the need for prior purification of specific B cell populations. It should be noted that transcript levels (and thus cDNA levels) from class-switched memory B cells are much lower, as these cells do not actively secreting immunoglobulin. Table 28 contains the top 10 $V_H$ sequences for four of the five animals above the titer threshold of 1:25000, from both bone marrow and PBMC populations. As expected, correlation of the two populations is not immediately obvious and additional filters are necessary to select sequences common to both.

TABLE 28

Frequencies (%) of the most highly represented CDRH3 sequences in bone marrow and PBMCs.

| | | | | Total PBMC | | |
|---|---|---|---|---|---|---|
| CDRH3 | | Percent | SEQ ID | CDRH3 | Percent | SEQ ID |
| Total bone marrow | | | | | | |
| Goat 52 | | | | | | |
| GRGRYGGGYDYDFFQYGVDV | | 1.39 | 240 | ARRCGEGDGYGYNPDCYDY | 0.34 | 241 |
| VRCYTHWSDNNGRCYGPMY | | 0.31 | 242 | ARERSGWYSPYGAVDV | 0.25 | 243 |

TABLE 28-continued

Frequencies (%) of the most highly represented CDRH3 sequences in bone marrow and PBMCs.

| CDRH3 | Percent | SEQ ID | CDRH3 (Total PBMC) | Percent | SEQ ID |
|---|---|---|---|---|---|
| AKYFWTNNYADYVFFDI | 0.25 | 244 | ARDGDGAGGALSSGLDV | 0.24 | 245 |
| GRDGYYSDYYAVDV | 0.24 | 246 | ARSNGGGIGDVDV | 0.17 | 247 |
| GRGYDQVVS | 0.23 | 248 | VRSDYGYGAGYGWGFHH | 0.13 | 249 |
| ADGYSYPNAY | 0.22 | 250 | GRDGYYSDYYAVDV | 0.12 | 246 |
| TKSWDYDYANGAEF | 0.22 | 252 | VREAYGSDGLYYGIDV | 0.12 | 253 |
| GRDV | 0.20 | 254 | VTGGNGYGYDAP | 0.12 | 255 |
| ARGYSDYAYFYGGAIEV | 0.17 | 256 | ADGYSYPNAY | 0.12 | 250 |
| GKGVYYNYGADVED | 0.17 | 258 | ASAYGYSWNSYGIDD | 0.11 | 259 |
| Sheep 54 | | | | | |
| ARGPDYSTYGTAYIYYLDY | 0.40 | 260 | ASSILAISNY | 0.77 | 261 |
| ARGPDYSTYGSYYLYYLDY | 0.38 | 262 | ATSACGYT$_H$CIDY | 0.53 | 263 |
| ARGGGDY | 0.35 | 264 | ARYRYFAESLIDY | 0.49 | 265 |
| ASSILAISNY | 0.35 | 261 | VTGNMYSCDVDF | 0.47 | 267 |
| ARCHYGGHCETYGLPMDY | 0.32 | 268 | ARGLMPIFDR | 0.45 | 269 |
| VRDYEEYNHAYAYGGY | 0.29 | 270 | IREGGGGYGFNIDY | 0.38 | 271 |
| ECYNGYGYAYGYNIDT | 0.27 | 272 | VRVRRGYHAYGYNDY | 0.34 | 273 |
| GREGNIAYGYDYGPHNIDY | 0.24 | 274 | GREGNIAYGYDYGPHNIDY | 0.30 | 274 |
| ARNTGRYGICSTIDA | 0.23 | 276 | GRESRSVSGYHGVTNFDF | 0.27 | 277 |
| ARGCLLIDY | 0.22 | 278 | ECYNGYGYAYGYNIDT | 0.26 | 272 |
| Bone marrow plasma cells[a] | | | | | |
| Rabbit CCH1 | | | | | |
| ARGLNAAGYTTFAYGTTVMDL | 0.93 | 280 | ATYDGSIAYLAL | 1.47 | 281 |
| ARDMDGGNVGYGM | 0.88 | 282 | AKYSASSGAYYDGYYFNL | 0.71 | 283 |
| ARFDAAYADFGVANL | 0.63 | 284 | ARASSSSGHYYDGYYFNL | 0.64 | 285 |
| ARADRGFYAGTSDYTGYNL | 0.60 | 286 | ARGGYSTFDL | 0.29 | 287 |
| ARADRGFYAGTSDYSGYNL | 0.51 | 288 | ARDLVMLSYL | 0.28 | 289 |
| ARDAGGSYSYYFDL | 0.47 | 290 | ASNYAGNPGYGYAPFNL | 0.28 | 291 |
| ARDAGGYTGDGYYFKL | 0.42 | 292 | ARADRGFYAGTSDYSGYNL | 0.24 | 293 |
| ARGGPIHYSNL | 0.40 | 294 | ARNFKL | 0.24 | 295 |
| ARGSGWYGGLNL | 0.40 | 296 | ARGDDDWYYLNL | 0.23 | 297 |
| ASNYADPPGYNYTPFNL | 0.35 | 298 | ERHRHGDAYPNL | 0.23 | 299 |
| ATDRGPSGSGPLDL | 0.71 | 300 | AREGGNSDWSFTL | 1.05 | 301 |
| SRDGKYAGIAGYGSTYFDL | 0.67 | 302 | ARDSSYNYWVPDYFDL | 1.04 | 303 |
| AGDGRSYYADYAFVDL | 0.56 | 304 | ARE$_H$DDDNGALTL | 1.00 | 305 |
| ARDPVTRLVAGADYFDL | 0.48 | 306 | ARYYIYRGDWSGNL | 0.94 | 307 |

TABLE 28-continued

Frequencies (%) of the most highly represented CDRH3 sequences in bone marrow and PBMCs.

| | | | Total PBMC | | |
|---|---|---|---|---|---|
| CDRH3 | Percent | SEQ ID | CDRH3 | Percent | SEQ ID |
| ARDVYTYDADGDYRHFNL | 0.47 | 308 | ARMGGSDEDYHL | 0.87 | 309 |
| ARAPVYYNGGYAGFREFNL | 0.46 | 310 | ARDPFASSSGYYWWGMDL | 0.65 | 311 |
| ARDGGWGYNL | 0.46 | 312 | ARDSSSGGNRGFDL | 0.61 | 313 |
| ARDSFDGYGDFNL | 0.45 | 314 | ARLRSSSGYFIYDL | 0.45 | 315 |
| ARVGNHYGMDL | 0.45 | 316 | ARGEYGTKLDV | 0.42 | 317 |
| ARGAAGYAGYAYAYYYFDF | 0.44 | 318 | ARCGGFGIEYFNL | 0.42 | 319 |

Filtering by Mutual Abundance in Bone Marrow and PBMC Populations

The selection of antigen-specific $V_H$ sequences from each animal was based on both abundance in bone marrow and a filter for an adjustable threshold abundance in total PBMCs. The more stringent filter scores antigen-specific V genes as positive if they are represented among the top 10 most abundant in the bone marrow and among the top 50 most abundant among peripheral blood monocytes. Table 29 below lists the abundance ranking and frequency (as % of the total repertoire for V genes from different animals).

TABLE 29

Examples of $V_H$ sequence frequencies and rankings in terms of abundance[a] used in the filtering analysis.

| CDRH3 | SEQ ID NO: | % total BM | rank total BM | % total PBMC | rank PBMC |
|---|---|---|---|---|---|
| | | Goat 52 | | | |
| VRCYTHWSDNNGRCYGPMY | 320 | 0.31 | 2 | 0.07 | 31 |
| GRDGYYSDYYAVDV | 321 | 0.24 | 4 | 0.12 | 6 |
| ADGYSYPNAY | 322 | 0.22 | 6 | 0.12 | 9 |
| GRDV | 323 | 0.20 | 8 | 0.11 | 11 |
| ARGYSDYAYFYGGAIEV | 324 | 0.17 | 9 | 0.07 | 25 |
| GKGVYYNYGADVED | 325 | 0.17 | 10 | 0.06 | 41 |
| ARDTSIDYAYRYNYEIDY | 326 | 0.16 | 11 | 0.08 | 19 |
| ARGISDWDYGLVGLNV | 327 | 0.13 | 18 | 0.06 | 57 |
| ARSNGGGIGDVDI | 328 | 0.13 | 19 | 0.09 | 13 |
| VTGGNGYGYDAPF | 329 | 0.12 | 23 | 0.06 | 46 |
| ARDKEWPGASSIDY | 330 | 0.12 | 24 | 0.06 | 47 |
| ISGRSGVGDDWAAHY | 331 | 0.12 | 25 | 0.09 | 14 |
| VGGSGYNYRYVYDGVDI | 332 | 0.12 | 28 | 0.08 | 18 |
| ARDRTCCGAGYGSRPDIEV | 333 | 0.11 | 29 | 0.10 | 12 |
| ARVYADDTYDYEDAFDY | 334 | 0.11 | 30 | 0.07 | 27 |
| ARGRYSGYGYGYDQYYIDY | 335 | 0.10 | 34 | 0.06 | 55 |
| ARSNGGGIGDVDV | 336 | 0.10 | 36 | 0.17 | 4 |
| TSCYSVYGYNCADRDYGANF | 337 | 0.10 | 38 | 0.06 | 42 |

TABLE 29-continued

Examples of $V_H$ sequence frequencies and rankings in terms of abundance[a] used in the filtering analysis.

| Sheep 54 | | | | |
|---|---|---|---|---|
| ARGPDYSTYGTAYIYYLDY | 338 | 0.40 | 1 | 0.13 | 43 |
| ARGPDYSTYGSYYLYYLDY | 339 | 0.38 | 2 | 0.18 | 22 |
| ARGGGDY | 340 | 0.35 | 3 | 0.19 | 18 |
| ASSILAISNY | 341 | 0.35 | 4 | 0.77 | 1 |
| ARCHYGGHCETYGLPMDY | 342 | 0.32 | 5 | 0.12 | 48 |
| VRDYEEYNHAYAYGGY | 343 | 0.29 | 6 | 0.24 | 12 |
| ECYNGYGYAYGYNIDT | 344 | 0.27 | 7 | 0.26 | 10 |
| GREGNIAYGYDYGPHNIDY | 345 | 0.24 | 8 | 0.30 | 8 |
| VTGNMYSCDVDF | 346 | 0.21 | 13 | 0.47 | 4 |
| ATSACGYT$_H$CIDY | 347 | 0.21 | 14 | 0.53 | 2 |
| AGSIRWFDRPTSGV | 348 | 0.21 | 15 | 0.12 | 47 |
| VRVRRGYGHAYGYNDY | 349 | 0.21 | 16 | 0.34 | 7 |
| VRGYYSPPGYDICFDD | 350 | 0.18 | 20 | 0.15 | 34 |
| ARGLMPIFDR | 351 | 0.18 | 19 | 0.45 | 5 |
| ARGIGIPRLDY | 352 | 0.17 | 23 | 0.13 | 40 |
| TRNDIGYSYLPDY | 353 | 0.17 | 25 | 0.10 | 73 |
| VRDYYGGVGVAVSGDY | 354 | 0.17 | 22 | 0.25 | 11 |
| ARGLYDVSI | 355 | 0.17 | 24 | 0.17 | 28 |
| ARAAGFTRAAADVDY | 356 | 0.16 | 26 | 0.10 | 64 |
| ARGFYSTNSVARYYADY | 357 | 0.15 | 30 | 0.17 | 23 |
| VRDDGTIGYAGSIDY | 358 | 0.14 | 32 | 0.13 | 46 |
| GRESRSVSGYGHGVTNFDF | 359 | 0.13 | 37 | 0.27 | 9 |
| VSLSTLCDAAGAFYGEY | 360 | 0.13 | 40 | 0.14 | 35 |
| ARYSDFGSAGNYLDY | 361 | 0.13 | 41 | 0.17 | 24 |

| CDRH3 | SEQ ID NO: | % BMPC | rank BMPC | % total PBMC | rank PBMC |
|---|---|---|---|---|---|
| ARDMDGGNVGYGM | 362 | 0.88 | 2 | 0.10 | 95 |
| ARADRGFYAGTSDYTGYNL | 363 | 0.60 | 4 | 0.14 | 45 |
| ARADRGFYAGTSDYSGYNL | 364 | 0.51 | 5 | 0.24 | 7 |
| ARGSGWYGGLNL | 365 | 0.40 | 9 | 0.20 | 20 |
| ASNYADPPGYNYTPFNL | 366 | 0.35 | 10 | 0.09 | 129 |
| ARLYAGSSYSISPDYGMDL | 367 | 0.30 | 12 | 0.07 | 203 |
| ARDSYVGDEITTGYSFNL | 368 | 0.21 | 24 | 0.12 | 66 |
| ARNYAGYGGYVYLSEYHFNL | 369 | 0.19 | 27 | 0.13 | 54 |
| ASNYADGPGYGFAPFNL | 370 | 0.19 | 28 | 0.20 | 15 |
| ARDYYSSGWGGFNL | 371 | 0.19 | 30 | 0.06 | 277 |
| ARLNIGGADGL | 372 | 0.17 | 36 | 0.06 | 291 |
| ARDYGSSGWGGFNL | 373 | 0.15 | 52 | 0.19 | 24 |

TABLE 29-continued

Examples of V$_H$ sequence frequencies and rankings in terms of abundance[a] used in the filtering analysis.

| | | | | | |
|---|---|---|---|---|---|
| ASNYAGDAGYGYAPFNL | 374 | 0.14 | 59 | 0.20 | 22 |
| ARDLGAAEYGYGSPFNL | 375 | 0.13 | 60 | 0.17 | 31 |
| ASSHLSDDYYFNL | 376 | 0.12 | 69 | 0.06 | 301 |
| ARGLVMLVMSILPDL | 377 | 0.12 | 70 | 0.14 | 43 |
| ATYTYDYAGYSHAGFNL | 378 | 0.12 | 77 | 0.14 | 44 |
| ARDPPGYGINFVAMDL | 379 | 0.11 | 78 | 0.06 | 224 |
| AREFAAGSFNF | 380 | 0.11 | 85 | 0.18 | 26 |
| Rabbit CCH2 | | | | | |
| ATDRGPSGSGPLDL | 381 | 0.71 | 1 | 0.10 | 89 |
| SRDGKYAGIAGYGSTYFDL | 382 | 0.67 | 2 | 0.06 | 195 |
| AGDGRSYYADYAFVDL | 383 | 0.56 | 3 | 0.23 | 23 |
| ARDPVTRLVAGADYFDL | 384 | 0.48 | 4 | 0.08 | 122 |
| ARDVYTYDADGDYRHFNL | 385 | 0.47 | 5 | 0.06 | 189 |
| ARAPVYYNGGYAGFREFNL | 386 | 0.46 | 6 | 0.12 | 59 |
| ARVGNHYGMDL | 387 | 0.45 | 9 | 0.08 | 127 |
| ARGAAGYAGYAYAYYYFDF | 388 | 0.44 | 10 | 0.10 | 87 |
| ARDPVNRLQAGADYFNL | 389 | 0.44 | 11 | 0.20 | 30 |
| ARDFSYGYAGQAYVTPFIL | 390 | 0.40 | 12 | 0.10 | 84 |
| ARQPYTGTTL | 391 | 0.36 | 16 | 0.07 | 159 |
| VRDSFLDYGDFGL | 392 | 0.34 | 17 | 0.13 | 55 |
| ARGGGRGE$_L$NL | 393 | 0.34 | 19 | 0.06 | 209 |
| ARDFGASSYYLFDL | 394 | 0.32 | 22 | 0.05 | 226 |
| ARGVIYDDFGDYPYYLDL | 395 | 0.31 | 25 | 0.11 | 69 |
| ARDLDGYGDFIYFGL | 396 | 0.30 | 27 | 0.11 | 68 |
| AKYDDYAHYFHL | 397 | 0.30 | 28 | 0.10 | 82 |
| ARDGFPCASDYYRACLDL | 398 | 0.29 | 29 | 0.10 | 85 |
| ARTLIYASRPNYFDL | 399 | 0.28 | 32 | 0.11 | 72 |
| ARDGDGGSFGYTL | 400 | 0.27 | 34 | 0.09 | 100 |
| ARDFNL | 401 | 0.27 | 36 | 0.36 | 14 |
| ATNVGGGYVARLDL | 402 | 0.26 | 37 | 0.07 | 178 |
| ARDMLVVVGLNL | 403 | 0.25 | 39 | 0.08 | 132 |
| AKYNYDDYGDQYYFNL | 404 | 0.24 | 42 | 0.05 | 223 |
| ARDYNL | 405 | 0.18 | 63 | 0.10 | 86 |
| AGRSGWDGFNL | 406 | 0.16 | 73 | 0.06 | 182 |
| TREFAYAYSSGYYGFNL | 407 | 0.16 | 75 | 0.05 | 245 |
| ARYNYDDYGDQYYFNL | 408 | 0.14 | 94 | 0.05 | 241 |
| ASYGGGSFISPDYLNL | 409 | 0.14 | 97 | 0.08 | 141 |
| ARGNYDDYGAEYFGL | 410 | 0.12 | 106 | 0.06 | 192 |

TABLE 29-continued

Examples of $V_H$ sequence frequencies and rankings in terms of abundance[a] used in the filtering analysis.

| | | | | | |
|---|---|---|---|---|---|
| TRGGSYTDGDVGAVYATDFNL | 411 | 0.12 | 121 | 0.08 | 142 |
| ARDLGDTYYSGALWYWNL | 412 | 0.12 | 125 | 0.09 | 93 |
| ARFAYSYGYAGNIDYYGMDL | 413 | 0.11 | 129 | 0.06 | 208 |
| ARVDLAYYNGGDTTTPYATEFTL | 414 | 0.11 | 132 | 0.06 | 214 |
| ARGTYTYDDYGDYRAFDP | 415 | 0.11 | 138 | 0.09 | 97 |

[a]The abundance threshold can be modified for stringency to optimize the isolation of antigen-specific $V_H$ sequences. The inventors chose 0.05-0.1% cutoffs for PBMC frequency and have shown the top bone marrow sequences passing this threshold.

Selecting $V_L$ Sequences by Abundance in Bone Marrow

The selection of antigen-specific $V_L$ sequences relies upon abundance data in bone marrow. As with $V_H$, the $V_L$ sequences were also amplified via 5' RACE using constant region primers.

TABLE 30

Top $V_L$ sequences by abundance in bone marrow plasma cells

| CDRL3 | Percent | SEQ ID NO: |
|---|---|---|
| Rabbit CCH1 | | |
| QGYSSYPLT | 0.85 | 416 |
| QCTRYDRSDGGA | 0.78 | 417 |
| QSAYFSVTGDSYA | 0.56 | 418 |
| QSAYDASTYVPSA | 0.53 | 419 |
| QTAYGSSSSDNV | 0.52 | 420 |
| LGGYSGSADLT | 0.51 | 421 |
| AGGYSSSSDNA | 0.41 | 422 |
| GGDLGGGMDA | 0.39 | 423 |
| LGGYSSSTGTT | 0.38 | 424 |
| LGGYSYGSNT | 0.35 | 425 |
| Rabbit CCH2 | | |
| QQGYSTPLT | 2.42 | 426 |
| QGYRRYPHT | 1.20 | 427 |
| LGGDTSRTGLT | 1.05 | 428 |
| LGGVSGSADFVS | 0.77 | 429 |
| QSAYYSSNPDIT | 0.63 | 430 |
| LGGVSGSADFLS | 0.58 | 431 |
| QSADYTTFTDSHA | 0.55 | 432 |
| QSAYYGSSGKIT | 0.54 | 433 |
| QSAYYSSSADNA | 0.53 | 434 |
| QSYYYDSIPYNV | 0.51 | 435 |
| Rabbit HEL1 | | |
| LGGYISASDNG | 2.12 | 436 |
| AGAYTTSVSDAVRA | 2.12 | 437 |
| QGGYDCSSADCHV | 0.90 | 438 |
| LGGYNYDGTGRT | 0.67 | 439 |
| QGYSNYHLT | 0.67 | 440 |
| QGGYSGNIYD | 0.57 | 441 |
| QGYWHDGIWA | 0.56 | 442 |
| LGVGTYINGDGRGV | 0.49 | 443 |
| LGSYDCDRADCTA | 0.48 | 444 |
| QFTHSSSNSDGNP | 0.45 | 445 |
| Rabbit HEL2 | | |
| QSYVYGADTPA | 2.38 | 446 |
| QCSFVTNGDNSHNT | 1.40 | 447 |
| QSYYGVASKHA | 0.92 | 448 |
| QQEYESRDVPNP | 0.40 | 449 |
| QQSYTRHNAENI | 0.35 | 450 |
| QTSNAITTYGAA | 0.35 | 451 |
| LGVDTDINGDTTWA | 0.34 | 452 |
| QCTSYGSTYVGP | 0.33 | 453 |
| AGDFGASIVA | 0.31 | 454 |
| QSYDYSSSSTYVNI | 0.27 | 455 |
| Goat 52 | | |
| YDSSSSGV | 0.76 | 456 |
| FDSSSNYI | 0.42 | 457 |
| YDSTYGGSI | 0.39 | 458 |
| FSTDYIDV | 0.39 | 459 |

TABLE 30-continued

Top V_L sequences by abundance in bone marrow plasma cells

| CDRL3 | Percent | SEQ ID NO: |
|---|---|---|
| YDSSSTGV | 0.37 | 460 |
| TDSNNNAV | 0.37 | 461 |
| YSSSNYGV | 0.36 | 462 |
| YDSDSSYI | 0.35 | 463 |
| YQSDWSLL | 0.35 | 464 |
| IQSDWTGV | 0.32 | 465 |
| Sheep 54 | | |
| YDSSSYTV | 0.80 | 466 |
| YRSPYTGV | 0.77 | 467 |
| YKSGGIV | 0.45 | 468 |
| YDNNNSNL | 0.43 | 469 |
| DDTSDS_L | 0.39 | 470 |
| YRSPGTVV | 0.38 | 471 |
| YKTPYTGV | 0.37 | 472 |
| YDSSSYGV | 0.32 | 473 |
| YKSGGTGV | 0.31 | 474 |
| YDSGSYGV | 0.31 | 475 |

Example 13

ELISA Screening of Selected Highly Abundant V_H and V_L Synthetic Genes by Combinatorial Pairing The lower polarity of the rabbit, sheep, and goat V_H and V_L repertoires (as compared to murine V_H and V_L repertoires in Example 9) necessitates a modified approach to identify high affinity pairings of antigen-specific V_H and V_L. The use of ELISA screening of small combinatorial panels of different synthetic V_H and V_L pairings avoids the difficulty of manually pairing the synthetic V_H and V_L based solely on rank, as was done for the higher polarity murine repertoires.

Isolation of antigen-specific antibodies. Synthetic genes of highly abundant V_H and V_L sequences from sheep 54 were made as described in Example 9. The V_H and V_L genes were separately synthesized for cloning as Fab constructs, with Nco I/Not I sites appended onto the V_L and Nhe I/Hind III sites appended onto the V_H. This facilitates cloning of the synthetic genes into the pFab-S vector, a pMAZ360-based vector (Mazor et al., 2007) engineered for expression as soluble Fab in the periplasm of E. coli. In addition, the synthetic genes were subsequently amplified as scFvs with a glycine-serine linker (GGGGS)_4 (SEQ ID NO: 806)(as in Example 9) between the V_L and V_H sequences constructed using overlap extension PCR. For scFv cloning, Sfi I restriction endonuclease sites were added flanking each V_H-linker-V_L gene sequence to facilitate cloning of the synthetic gene constructs into compatible pMoPac16 vectors (Hayhurst et al., 2003). Expression and ELISA screening from E. coli lysates is accomplished as described in Example 9. Table 31 lists the sheep 54 V_H and V_L CDR3 sequences used to construct FAbs and scFvs and their relative abundance in the bone marrow and in PBMCs. Table 32 lists the full amino acid sequences of the 7 V_H and 5 V_L synthetic genes from sheep 54. The most abundant somatic variant of each CDRH3 was selected unless otherwise indicated. For the V_L, the amino acid consensus sequence of the CDRL3 group was synthesized.

TABLE 31

Sheep 54 V_H and V_L synthetic genes

| CDRH3 | SEQ ID NO: | % Bone marrow | % PBMC | rank PBMC |
|---|---|---|---|---|
| ARGPDYSTYGTAYIYYLDY | 476 | 0.40 | 0.13 | 43 |
| ARGPDYSTYGSYYLYYLDY | 477 | 0.38 | 0.18 | 22 |
| ARGGGDY | 478 | 0.35 | 0.19 | 18 |
| ASSILAISNY | 479 | 0.35 | 0.77 | 1 |
| ARCHYGGHCETYGLPMDY | 480 | 0.32 | 0.12 | 48 |
| VRDYEEYNHAYAYGGY | 481 | 0.29 | 0.24 | 12 |
| ECYNGYGYAYGYNIDT | 482 | 0.27 | 0.26 | 10 |

| CDRL3 | | % Bone marrow[a] | | |
|---|---|---|---|---|
| YDSSSYTV | 483 | 0.80 | | |
| YRSPYTGV | 484 | 0.77 | | |
| YKSGGIV | 485 | 0.45 | | |
| YDNNNSNL | 486 | 0.43 | | |
| DDTSDSVL | 487 | 0.39 | | |

[a]For CDRL3, percentages were based on PC-V repertoire for sheep 54 sorted using the 281-2 α-CD138 antibody.

TABLE 32

Sheep 54 V_H and V_L synthetic genes - full amino acid sequences and the corresponding CDR3 sequences (also listed in Table 1 above)

Full amino acid sequence

CDRH3

ASSILAISNY       QVRLQESGPSLVKPSQTLSLTCTVSRFSLTNYGVGWVRQAP
(SEQ ID NO: 488) GKALEWLGGIDKDGDTGYNPALKSRLSITRDTSKSQVSLSLS
                 STTTEDTAVYYCASSILAISNYWGPGVLVTVSS
                 (SEQ ID NO: 489)

TABLE 32-continued

Sheep 54 $V_H$ and $V_L$ synthetic genes - full amino acid sequences and the corresponding CDR3 sequences (also listed in Table 1 above)

Full amino acid sequence

| | |
|---|---|
| VRDYEEYNHAYAYGGY (SEQ ID NO: 490) | QVQLQESGPSLVKPSQTLSLTCTVSGFSLKTHGVGWVRQAP GKALESVGIIFTGGGTGYNPALKSRLSITRDTSKSQVSLSLSS VTTEDTAVYYCVRDYEEYNHAYAYGGYWGPGLLVTVSS (SEQ ID NO: 491) |
| ARGPDYSTYGSYYLYYL DY[a] (SEQ ID NO: 492) | QVQLQESGPSLVKPSQTLSLACTVSVFSLTSYTVGWVRQAP GKAPEWVGSIGGSGRRVYNPALKSRVSIARDTSKNQVSLSL SSVTTEDTAVYYCARGPDYSTYGSYYLYYLDYWGPGLLVT VSS (SEQ ID NO: 493) |
| ARGPDYSTYGTAYIYYLD Y (SEQ ID NO: 494) | QVQLQESGPSLVKPSQTLSLACTVSVFSLNSYTVGWVRQAP GKALEWVGSIGGSGRRVYNPALKSRVSIARDTSKSQVSLSLS SVTAEDTAVYYCARGPDYSTYGTAYIYYLDYVGPRTPGHRL L (SEQ ID NO: 495) |
| ARCHYGGHCETYGLPMD Y (SEQ ID NO: 496) | QVRLQESGPSLVKPSQTLSLTCTVSGFPLTSNAVGWVRQAP GKVPEWLGGISTRGSTYYNSALKSRLSITRDTSKSQVSLFLSS VTTEDTALYYCARCHYGGHCETYGLPMDYWGPGLLVTVSS (SEQ ID NO: 497) |
| ARGGGDY (SEQ ID NO: 498) | QVQLQESGPSLVKPSQTLSLTCTISGFSLTDHDVEWVRQAPG KALEWVGAIYDSGNAYYNPALKSRLSITRDTSRSRVSLSLSN VTTEDTALYYCARGGGDYWGPGLLVTVSS (SEQ ID NO: 499) |
| ECYNGYGYAYGYNIDT (SEQ ID NO: 500) | QVQLQESGPSLVKPSQTLSLTCTVSGFSLTRYGVGWVRQAP GKALEWVGYIYSDGGIYYNPALKSRLSITRDTSKSQVSLSLS SVTTEDTAVYYCECYNGYGYAYGYNIDTWGPGLLVTVSS (SEQ ID NO: 501) |

CDRL3

| | |
|---|---|
| YDSSSYTV (SEQ ID NO: 502) | QAVLTQPSSVSRSLGQSVSITCSGSSSNVGYGSYVGWFQQVP GSAPKLLIYGATSRASGVPDRFSGSRSGNTATLTITSLQAEDE ADYYCASYDSSSYTVFGSGTRLTVL (SEQ ID NO: 503) |
| YRSPYTGV (SEQ ID NO: 504) | QSALTQPASVSGNPGQTVTISCTGTNSDIGAANYIGWYQQLP GSAPKTLIYAVDKRPSGIPARFSGSKSGNTATLTISGLQAEDE ADYYCSSYRSPYTGVFGSGTRLTVL (SEQ ID NO: 505) |
| YKSGGIV (SEQ ID NO: 506) | QSALTQPASVSGNPGQTVTISCTGTSSDVGIYKYVGWYQQL PGSAPKTLIYHVNERPSGIPARFSGSKSGNTATLTISGLQAED EADYYCSSYKSGGIVFGSGTRLTVL (SEQ ID NO: 507) |
| YDNNNSNL (SEQ ID NO: 508) | QTVLTQPSSVSKSLGQAVSITCSGSSSNIGYGDYVRWFQQVP GSAPKLLIYGASSRASGVPDRFSGSRSGNTATLTISSLQAEDE ADYYCATYDNNNSNLFGSGTRLTVL (SEQ ID NO: 509) |
| DDTSDSVL (SEQ ID NO: 510) | QAVLTQPSSVSKSLGQSVSITCSGSSSNVGYGDYVSWFQQV PGSAPKLLIYGATRRASGVPDRFSGSRSGNTATMTISSLQAE DEADYYCASDDTSDSVLFGSGTRLTVL (SEQ ID NO: 511) |

[a]For this $V_H$, the second most abundant somatic variant was synthesized.

Example 14

Immunoinformatic Mining of Lymphoid Repertoires Via Clustering Analysis of High Resolution V Gene DNA Sequence Data Sets The V immunoglobulin cDNA repertoires from bone marrow in sheep, goats and to a lesser extent rabbits are less polarized than those of mice. This example describes a bioinformatics approach for identifying antigen-specific VH and VL genes and then pairing hem to produce desired, high affinity antibodies.

The inventors discovered that phylogenetic analysis (more specifically clustering analysis) can be used to help identify desired antigen-specific V genes. The high resolution provided by high sample sizes can aid in identifying antigen-specific monoclonal antibodies that will have resulted from high levels of somatic hypermutation during the affinity maturation process. Therefore, by identifying clusters of highly related sequences (somatic variants arising from a clonal expansion), an additional filter emerges for identifying antibodies arising as a result of a recent clonal expansion which occurred after immunization. Highly related sequences can be somatic variants within a single CDR3 group or somatic variants of the CDR3 group (e.g. somatic hypermutation within the CDR3 itself). By identifying clusters of highly related sequences within multiple lymphoid populations (bone marrow, spleen, lymph nodes, and PBMCs), a clear picture of recent clonal expansion and affinity maturation emerges. These events indicate a recent antigen-specific response and can aid in isolation of monoclonal antibody sequences, especially in instances where repertoire polarity is low.

Repertoire clustering using multiple sequence alignment and phylogenetic analysis. There are numerous computer programs available for multiple sequence alignment, but most are limited in the size of the data set that can be aligned. MUSCLE or Multiple Sequence Comparison by Log Expectation (Edgar, 2004) is ideally suited for extremely large data sets and was chosen to align the $V_H$ and $V_L$ repertoires, which often have upward of several thousand unique amino acid sequences depending on the read numbers vailable. The raw 454 sequencing data was processed as described in Example 9 to produce amino acid sequences aligned via homology-driven motif searches. To ensure only near full-length $V_H$ and $V_L$ sequences were analyzed, a series of filters were applied that removed highly truncated sequences and those containing stop codons. For example, the $V_H$ filter included the following criterion: 1) full length ≥100 residues, 2) FR4 length ≥2 residues, 3) sequences containing no stop codons, and 4) unique sequences (as defined from CDR1 to CDR3) with at least 2 reads (removes unique sequencing errors). Application of this filter to the rabbit CCH1 $V_H$ aligned PC-V data set (>30,000 identified VH amino acid sequences) limited the data to ~5000 unique amino acid sequences. These 5000 amino acid sequences were annotated by abundance (e.g. most abundant unique amino acid sequences named 1) in FASTA format and aligned with MUSCLE using default parameters for gap opening and gap extension penalties and the default scoring matrix. The alignment produced by MUSCLE was then processed by tree building software to cluster sequences. In ClustalX, a Phylip tree file was created using the Neighbor-Joining method. The tree file was then analyzed and manipulated using Dendroscope (Huson, 2007). In Dendroscope, it is easy to search the tree and quickly identify those annotated highly abundant sequences that are also located in highly branched limbs of the tree. The software is also very interactive in that you can then select large clusters of sequences and export for examination of the annotated data in Microsoft Excel. Table 33 shows a cluster of $V_H$ sequences identified from rabbit CCH1 PBMC using clustering analysis as described above. Table 34 provides CDRH3 abundances in PC-V (from bone marrow) and tLT-V (from PBMC) data compared by color coding to show somatic variants for the cluster identified in both bone marrow and blood populations. Large related cluster of sequences with similar CDRH3 sequence are found both in PBMC and BMPC populations. Representative CDRH3s that are very abundant are shown. Clustering analysis also identifies large clusters of sequences that are moderately abundant (with regards to representative CDRH3 groups), but again likely arise from antigen-specific clonal expansion.

TABLE 33

Cluster of unique highly related PBMC somatic variants identified by clustering analysis

| PBMC Rank (by full sequence) | CDRH3 group | SEQ ID NO: | # SM[a] |
|---|---|---|---|
| 92 | NYAGHPGYGYAPFNL | 512 | 16 |
| 782 | NYAGHSGYGYAPFNL | 513 | 17 |
| 1430 | NYAGHPGYGYAPFNL | 514 | 17 |
| 303 | NYAGHPGYGYAPFNL | 515 | 17 |
| 1429 | NYAGHPGYGYAPFNL | 516 | 17 |
| 2158 | NYAGHPGYGYAPFNL | 517 | 7 |
| 1106 | NYADGPGYGFAPFNL | 518 | 10 |
| 2029 | NYADGPGYGFAPFNL | 519 | 9 |
| 169 | NYADGPGYGFAPFNL | 520 | 12 |
| 1887 | NYADGPGYGFAPFNL | 521 | 12 |
| 240 | NYADGPGYGFAPFNL | 522 | 11 |
| 1891 | NYADGPGYGFAPFNL | 523 | 12 |
| 356 | NYADGPGYGFAPFNL | 524 | 13 |
| 61 | NYAGGPGYGFAPFNL | 525 | 8 |
| 2515 | NYAGGPGYGFAPFNL | 526 | 9 |
| 6 | NYAGNPGYGYAPFNL | 527 | 13 |
| 2662 | NYAGNPGYGYAPFNL | 528 | 14 |
| 2764 | NYAGNPGYGYAPFNL | 529 | 14 |
| 2770 | NYAGNPGYGYAPFNL | 530 | 17 |
| 2234 | NYAPFPGYGFAPFNL | 531 | 11 |
| 203 | NYAGDAGYGYAPFNL | 532 | 14 |
| 2744 | NYAADAGYGYAPFNL | 533 | 13 |
| 2745 | NYAADAGYGYAPFNL | 534 | 12 |
| 417 | NYAADAGYGYAPFNL | 535 | 10 |
| 1075 | NYAGDAGYGYAPFNL | 536 | 9 |
| 104 | NYAADAGYGYAPFNL | 537 | 9 |
| 382 | NYAADAGYGYAPFNL | 538 | 9 |
| 1076 | NYAGDAGYGYAPFNL | 539 | 9 |
| 1072 | NYAGNAGYGYAPFNL | 540 | 13 |
| 143 | NYADAGYGYAPFNL | 541 | 14 |
| 2591 | NYAGDAGYGYAPFNL | 542 | 13 |
| 764 | NADGNGGYRYAPFNL | 543 | 15 |
| 1071 | NYADPPGYNYTPFNL | 544 | 9 |
| 2236 | NYADPPGYNYTPFNL | 545 | 10 |

[a]#SM is the number of somatic mutations as determined by germline alignment using IMGT HighV-Quest. Each listed CDRH3 represents a unique somatic variant. Some somatic variants have the same number of somatic mutations, but are different unique sequences.

TABLE 34

CDRH3 abundance in CCH1 PBMC and BMPC sorted by percent PBMC (top) and percent BMPC (bottom). Color coded to match Table 1.

| CDRH3 | % PBMC | % BMPC | SEQ ID NO: |
|---|---|---|---|
| YDGSIAYLAL | 1.44 | 0.02 | 546 |
| YSASSGAYYDGYYFNL | 0.78 | #N/A | 547 |
| ASSSSGHYYDGYYFNL | 0.63 | 0.00 | 548 |
| DLVMLSYL | 0.28 | 0.01 | 549 |
| GGYSTFDL | 0.28 | 0.04 | 550 |
| NYAGNPGYGYAPFNL | 0.27 | 0.06 | 551 |
| HRHGDAYPNL | 0.24 | 0.06 | 552 |
| NFKL | 0.24 | 0.04 | 553 |
| GDDDYWYYLNL | 0.23 | #N/A | 554 |
| ADRGFYAGTSDYSGYNL | 0.23 | 0.47 | 555 |
| DYDL | 0.23 | 0.02 | 556 |
| NYADGPGYGFAPFNL | 0.22 | 0.18 | 557 |
| DSPTSGYYGGYYFDL | 0.22 | 0.01 | 558 |
| EIWSDGYYDL | 0.21 | 0.03 | 559 |
| EAESGNSYADFNL | 0.21 | 0.02 | 560 |
| NYAADAGYGYAPFNL | 0.20 | 0.03 | 561 |
| GIFDYNVDGAETL | 0.20 | #N/A | 562 |
| DYGSSGWGGFNL | 0.20 | 0.14 | 563 |
| DWSADIDYILTL | 0.20 | 0.04 | 564 |
| NYAGDAGYGYAPFNL | 0.19 | 0.14 | 565 |
| DMDGGNVGYGM | 0.87 | 0.13 | 566 |
| GLNAAGYTTFAYGTTVMDL | 0.84 | 0.01 | 567 |
| FDAAYADFGVANL | 0.60 | #N/A | 568 |
| ADRGFYAGTSDYTGYNL | 0.55 | 0.13 | 569 |
| ADRGFYAGTSDYSGYNL | 0.47 | 0.23 | 570 |
| DAGGSYSYYFDL | 0.42 | 0.04 | 571 |
| DAGGYTGDGYYFKL | 0.40 | 0.03 | 572 |
| GGPIHYSNL | 0.39 | 0.02 | 573 |
| GSGWYGGLNL | 0.35 | 0.19 | 574 |
| NYADPPGYNYTPFNL | 0.33 | 0.09 | 575 |
| LYAGSSYSISPDYGMDL | 0.31 | 0.06 | 576 |

Example 15

Proteomic Identification and Quantization of Antibodies in Rabbits and Other Mammals Rabbit serum Ig proteins from immunized animals as described in Example 6 were isolated by affinity chromatography using protein A beads with elution using glycine buffer, pH 2.5. Following elution, Ig protein solution was buffer exchanged to Phosphate Buffer Saline.

Protein A-purified serum IgG proteins were isolated from traces of rabbit serum albumin (RSA) that co-eluted with antibodies using size exclusion chromatography (SEC). SEC was carried out with Na-acetate, pH 5.0, as the mobile phase and TSKgel G3000SWxl column as the stationary phase (Tosoh Bioscience LLC). Samples were subsequent digested with immobilized papain (Pierce) to produce two FAB fragments and an Fc domain per IgG molecule. FAB fragments were isolated from the Fc fragments by applying the digestion solution to a protein A affinity column with elution as above. FAB fragments were collected in the flow through and washing steps.

Purified FAB fragments were denatured in freshly prepared 8M Urea solution pH 8.0 in 100 mM Sodium carbonate pH 10. A mixture of 97.5% v/v acetonitrile, 2% v/v Iodoethanol, 0.5% v/v Triethylphosphine was added to reduce and alkylate Fab fragments, and samples were incubated at 60° C. for 60 min. Samples were then lyophilized using speedvac centrifugation and resuspended to final concentration of 2M Urea. Samples were then subjected to protease digestion by trypsin. Proteolytic cleavage was accomplished using sequencing grade trypsin (Sigma) at 37° C. for 5 hr with the trypsin:protein ration of 1:50. Digestions were quenched with 1% formic acid. To remove contaminants, peptides were bound and washed on C-18 Hypersep SpinTips (Thermo Scientific) and filtered through 10 kDa Microcon YM-10 centrifugal filters (Amicon) prior to LC-MS/MS analysis.

Peptides were then separated on a reverse phase Zorbax C-18 column (Agilent) with a gradient from 5% to 38% acetonitrile, 0.1% formic acid over 230 mins. Peptides were eluted directly into an LTQ-Orbitrap mass spectrometer (Thermo Scientific) by nano-electrospray ionization. Data-dependant ion selection was enabled, with parent ion mass spectra (MS1) collected at 100K resolution. Ions with known charge >+1 were selected for CID fragmentation spectral analysis (MS2) in order of decreasing intensity, with a maximum of 12 parent ions selected per MS1 cycle. Dynamic exclusion was activated, with ions selected for MS2 twice within 30 sec. excluded from MS2 selection for 30 sec.

Ions identified in an LC-MS/MS run as corresponding to peptides from the constant regions of the heavy and light chains were excluded from data-dependant selection in subsequent experiments in order to increase selection of peptides from the CDR3 region. Moreover, in addition to the full range of m/z peptides, gas fractionation was carried out to lower ion sapreation of dominant peptides in the sample. Gas fractionation was with m/z of i) 300-800, ii) 800-900 and iii) 900-1500. This procedure improve the peptide coverage.

LC-MS/MS data were searched against database containing full V genes sequences obtained by NextGen sequencing of the V gene repertoires as described in Example 6 using the Sequest search algorithm as part of the Bioworks software package (Thermo Scientific). Filters were applied to ensure high confidence peptide identifications as follows: $\Delta CN \geq 0.250$; XCorr=2.0, 2.5, and 3.0 for +2, +3, and $\geq +4$ charge; and accuracy $\leq 10.0$ ppm. Alternatively, other label-free (Silva et al., 2006b; Gygi et al., 1999; Ross et al., 2004) or isotope label-based quantitative methods for mass spectrometry could be used to determine the abundancy of specific CDR3 families at the protein level.

Table 35 shows a comparison of V,D and J family abundance from 454 sequencing cDNA V gene abundance data (i.e., transcriptional abundance) and shotgun MS proteomic data (Table 35). The transcriptional profile correlates with the proteomic data, reported as peptide counts.

TABLE 35

Abundance of, D and J family from transcription data and MS data

| Family | mRNA seq counts | MS Peptide count |
|---|---|---|
| F_4 (J) | 987 | 264 |
| F_2 (J) | 199 | 63 |
| F_3 (J) | 87 | 38 |
| F_6 (J) | 11 | 12 |
| F_5 (J) | 8 | 4 |
| 8_1 (D) | 92 | 408 |
| 6_1 (D) | 80 | 120 |
| 2_1 (D) | 49 | 217 |
| 1_1 (D) | 45 | 190 |
| 4_2 (D) | 31 | 77 |
| 7_1 (D) | 10 | 34 |
| 4_1 (D) | 5 | 19 |
| 5_1 (D) | 2 | 5 |
| 3_3 (D) | 1 | 6 |
| 3_1 (D) | 0 | 0 |
| 1S40 (V) | 110 | 348 |
| 1S45 (V) | 102 | 420 |
| 1S47 (V) | 99 | 167 |
| 1S7 (V) | 44 | 244 |
| 1S21 (V) | 10 | 29 |
| 1S29 (V) | 9 | 5 |

In some embodiments, grouping of V genes based on CDR3 families substantially improves quantitation of the peptide dataset. Sample-specific protein sequence databases were created from the high-throughput V gene cDNA sequencing data. The sequence database was created by grouping of V genes based on CDR3 families substantially improves quantitation of the peptide dataset. This introduced a number of additional steps into the bioinformatics analysis pipeline: (1) After performing the shotgun proteomics experiments and identifying peptides based on the standard mass spectrometry analysis pipeline and the sample-specific sequence database, peptides that overlap CDR3 regions were identified. (2) These observed peptides were mapped to V gene cDNA-defined CDR3 families, and (3) Spectral counts attributable to each CDR3 family were defined.

CDR3 regions of the V gene and MS data were concatonated to the FR4 and the N-terminal of CH1 region. LC-MS/MS data were searched in this case against this database containing grouped CDR3 sequence using the Sequest search algorithm as part of the Bioworks software package (Thermo Scientific). Filters were applied to ensure high confidence peptide identifications as mentioned above.

Total count of peptides identified in FABs that were isolated from *Concholepas concholepas* hemocyanin (CCH) immunized rabbit CCH1 were compared to the VH cDNA repertoire data which reflects the transcript abundance of the respective V genes. In cases where peptides identified fit uniquely to the CDR3 from sequencing data (Table 36 italicized text) the corresponding CDR3 from the transcript sequence are shown. In the case where the peptide identified consists trypsin digestion site in the CDR3 region, no unique corresponding CDR3 from sequencing data is shown (since that CDR3 fragments corresponds to multiple sequences). These arise because the presence of Lys or Arg amino acids in the CDR3 region results in short peptides following trypsin digestion (Table 36, bolded text). As expected, the most abundance peptide identified in this example did not correlate with the most abundant VH gene transcript expressed by bone marrow cells because the latter reflects only a snapshot of transcription and protein synthesis. However, antibodies persist in circulation with a t½ of approx 14 days for IgGs. Putative antibodies originating from "declining" plasma cells that show modarate transcription levels but are nonetheless highly represented in the MS peptide counts are marked by underlining in Table 36.

TABLE 36

Example of CDR3 VH gene sequence abundance (frequency ranking) determined by NextGen seuencing of the total bone marrow repertoire and the corresponding abundance of the respective antibodies in serum as deduced from counting the CDR3 peptide identified by MS.

| mRNA CDR3 Sequences | SEQ ID NO: | mRNA seq counts | MS CDR3 peptides | SEQ ID NO: | Peptide counts |
|---|---|---|---|---|---|
| *ARRADGGTYNLWGPGT LVTVSSGQPK* | 577 | <u>29</u> | *RADGGTYNLWGP GTLVTVSSGQPK* | 578 | <u>23</u> |
| *ARLNIGGADGLWGPGT LVTVSSGQPK* | 579 | 24 | *LNIGGADGLWGP GTLVTVSSGQPK* | 580 | 15 |
| ARGYNTFDPWGPGTLV SVSSGQPK | 581 | 10 | GYNTFDPWGPGTL VSVSSGQPK | 582 | 8 |
| ARNFKLWGPGTLVTVS SGQPK | 583 | 15 | NFKLWGPGTLVTV SSGQPK | 584 | 8 |
| ARNVYGASRVCGMDL WGPGTLVTVSSGQPK | 585 | 12 | VCGMDLWGPGTL VTVSSGQPK | 586 | 8 |
| RRSGLWGPGTLVAVSS GQPK | 587 | 35 | *SGLWGPGTLVAVS SGQPK* | 588 | 7 |
| ARSSYVNSGGAANLWG PGTLVTVSSGQPK | 589 | 13 | SSYVNSGGAANLW GPGTLVTVSSGQP K | 590 | 7 |
| ARGGYGGYGYDRAFDF WGPGTLVTVSSGQPK | 591 | 11 | AFDFWGPGTLVTV SSGQPK | 592 | 7 |

TABLE 36-continued

Example of CDR3 VH gene sequence abundance (frequency ranking) determined by NextGen seuencing of the total bone marrow repertoire and the corresponding abundance of the respective antibodies in serum as deduced from counting the CDR3 peptide identified by MS.

| mRNA CDR3 Sequences | SEQ ID NO: | mRNA seq counts | MS CDR3 peptides | SEQ ID NO: | Peptide counts |
|---|---|---|---|---|---|
| ARSPSSGSSNLWGPGTLVTVSSGQPK | 593 | 5 | SPSSGSSNLWGPGTLVTVSSGQPK | 594 | 6 |
| ARNFGLWGQGTLVTVSSGQPK | 595 | 21 | NFGLWGQGTLVTVSSGQPK | 596 | 6 |
| ARNFGLGGQGTLVTVSSGQPK | 597 | 8 | NFGLGGQGTLVTVSSGQPK | 598 | 6 |
| ARGGGSDGDGYNLWGPGTLVTVSSGQPK | 599 | 10 | GGGSDGDGYNLWGPGTLVTVSSGQPK | 600 | 4 |
| ARNYGLWGPGTLVTVSSGQPK | 601 | 6 | NYGLWGPGTLVTVSSGQPK | 602 | 4 |
| VRNLYLWGPGTLVTVSSGQPK | 603 | 3 | NLYLWGPGTLVTVSSGQPK | 604 | 4 |
| ARVVPGVHSFNLWGPGTLVTVSSGQPK | 605 | 3 | VVPGVHSFNLWGPGTLVTVSSGQPK | 606 | 4 |
| ARGGNPNYDYGLWGPGTLVTVSSGQPK | 607 | 2 | GGNPNYDYGLWGPGTLVTVSSGQPK | 608 | 4 |
| ARGLFGRAFPFKLWGPGTLVTVSSGQPK | 609 | 6 | AFPFKLWGPGTLVTVSSGQPK | 610 | 4 |
| ARDLYGGSSDLWGPGTLVTVSSGQPK | 611 | 23 | DLYGGSSDLWGPGTLVTVSSGQPK | 612 | 3 |
| AREGLYNLWGPGTLVTVSSGQPK | 613 | 3 | EGLYNLWGPGTLVTVSSGQPK | 614 | 3 |
| ARGAGGSYNLWGPGTLVTVSSGQPK | 615 | 11 | GAGGSYNLWGPGTLVTVSSGQPK | 616 | 3 |
| SRGGGAGYGLWGPGTLVTVSSGQPK | 617 | 17 | GGGAGYGLWGPGTLVTVSSGQPK | 618 | 3 |
| ARKDTNPHWGLWGPGTLVTVSSGQPK | 619 | 25 | DTNPHWGLWGPGTLVTVSSGQPK | 620 | 3 |
| ARKDTNPHWGLWGPGTLVTVSSGQPK | 621 | 64 | KDSNPHWGLWGPGTLVTVSSGQPK | 622 | 3 |
| ARGAGGSYGLWGPGTLVTVSSGQPK | 623 | 6 | GAGGSYGLWGPGTLVTVSSGQPK | 624 | 3 |
| ARDDVGDGAFVHNLWGPGTLVTVSSGQPK | 625 | 25 | DDVGDGAFVHNLWGPGTLVTVSSGQPK | 626 | 3 |
| ARDHSGNSGWHPDLWGPGTLVTVSSGQPK | 627 | 10 | DHSGNSGWHPDLWGPGTLVTVSSGQPK | 628 | 2 |
| ARYYSGTGSDLWGPGTLVTVSSGQPK | 629 | 3 | YYSGTGSDLWGPGTLVTVSSGQPK | 630 | 2 |
| ARGVGGYGSDLWGPGTLVTVSSGQPK | 631 | 15 | GVGGYGSDLWGPGTLVTVSSGQPK | 632 | 2 |
| ARGNTYAVDGYNLWGPGTLVTVSSGQPK | 633 | 24 | GNTYAVDGYNLWGPGTLVTVSSGQPK | 634 | 2 |
| ARETAGDKNWLFHLWGPGTLVTVSSGQPK | 635 | 13 | NWLFHLWGPGTLVTVSSGQPK | 636 | 2 |

TABLE 36-continued

Example of CDR3 VH gene sequence abundance (frequency ranking) determined by NextGen seuencing of the total bone marrow repertoire and the corresponding abundance of the respective antibodies in serum as deduced from counting the CDR3 peptide identified by MS.

| mRNA CDR3 Sequences | SEQ ID NO: | mRNA seq counts | MS CDR3 peptides | SEQ ID NO: | Peptide counts |
|---|---|---|---|---|---|
| AREGYGGYVGYMGLW GPGTLVTVSSGQPK | 637 | 9 | EGYGGYVGYMGL WGPGTLVTVSSGQ PK | 638 | 2 |
| ARVVDDGDGCDLWGP GTLVTVSSGQPK | 639 | 5 | VVDDGDGCDLWG PGTLVTVSSGQPK | 640 | 2 |
| LRERSGVNTDLWGPGT LVTVSSGQPK | 641 | 25 | SGVNTDLWGPGTL VTVSSGQPK | 642 | 2 |
| AREALYNLWGPGTLVT VASGQPK | 643 | 6 | EALYNLWGPGTLV TVASGQPK | 644 | 2 |
| ARGAGGSGYDLWGPG TLVTVSSGQPK | 645 | 3 | GAGGSGYDLWGP GTLVTVSSGQPK | 646 | 2 |
| ARGAYGNTNTYYNLGG PGTLVTVSSGQPK | 647 | 4 | GAYGNTNTYYNLG GPGTLVTVSSGQP K | 648 | 1 |
| ARWAGSNGFSLWSPGT LVTVSSGQPK | 649 | 4 | WAGSNGFSLWSPG TLVTVSSGQPK | 650 | 1 |
| LRERSGVNTDLGAPGT LVTVSSGQPK | 651 | 2 | SGVNTDLGAPGTL VTVSSGQPK | 652 | 1 |
| ARNLGITNDNNLWGPG TLVTVSSGQPK | 653 | 21 | NLGITNDNNLWGP GTLVTVSSGQPK | 654 | 1 |
| ARGAGWVDYSLWGPG TLVTVSSGQPK | 655 | 30 | GAGWVDYSLWGP GTLVTVSSGQPK | 656 | 1 |
| VRDTIGLWGPGTLVTVS SGQPK | 657 | 7 | DTIGLWGPGTLVT VSSGQPK | 658 | 1 |
| ARGGNPNYDYGLGGP GTLVTVSSGQPK | 659 | 7 | GGNPNYDYGLGG PGTLVTVSSGQPK | 660 | 1 |
| AREFWASTTILWGPGTL VTVSSGQPK | 661 | 69 | EFWASTTILWGPG TLVTVSSGQPK | 662 | 1 |
| AREFGRSRNLWGPGTL VTVSSGQPK | 663 | 2 | EFGRSRNLWGPGT LVTVSSGQPK | 664 | 1 |
| | | | LDLWGQGTLVT VSSGQPK | 665 | 96 |
| | | | FNLWGPGTLVT VSSGQPK | 666 | 53 |
| | | | AFDPWGPGTLV TVSSGQPK | 667 | 36 |
| | | | FIDLWGPGTLVT VSSGQPK | 668 | 28 |
| | | | NLWGPGTLVTV SSGQPK | 669 | 26 |
| | | | SQNLWGPGTLV TVSSGQPK | 670 | 21 |
| | | | GGPIHYSNLWGP GTLVTVSSGQPK | 671 | 20 |
| | | | GDLWGPGTLVT VSSGQPK | 672 | 17 |
| | | | GMDLWGPGTLV TVSSGQPK | 673 | 16 |

TABLE 36-continued

Example of CDR3 VH gene sequence abundance (frequency ranking) determined by NextGen seuencing of the total bone marrow repertoire and the corresponding abundance of the respective antibodies in serum as deduced from counting the CDR3 peptide identified by MS.

| mRNA CDR3 Sequences | SEQ ID NO: | mRNA seq counts | MS CDR3 peptides | SEQ ID NO: | Peptide counts |
|---|---|---|---|---|---|
| | | | FFNLWGPGTLVTVSSGQPK | 674 | 12 |
| | | | WGPGTLVTVSSGQPK | 675 | 10 |
| | | | SFNLWGPGTLVTVSSGQPK | 676 | 10 |
| | | | FDLWGPGTLVTVSSGQPK | 677 | 10 |
| | | | HFNLWGPGTLVTVSSGQPK | 678 | 9 |
| | | | DYFLWGPGTLVTVSSGQPK | 679 | 9 |
| | | | DWGLWGPGTLVTVSSGQPK | 680 | 9 |
| | | | GVGLWGPGTLVTVSSGQPK | 681 | 8 |
| | | | GFFNLWGPGTLVTVSSGQPK | 682 | 7 |
| | | | SSLLWGPGTLVTVSSGQPK | 683 | 7 |
| | | | YLWGPGTLVTVSSGQPK | 684 | 6 |
| | | | YFSLWGPGTLVTVSSGQPK | 685 | 6 |
| | | | YAPFNLWGPGTLVTVSSGQPK | 686 | 5 |
| | | | FNFWGPGTLVTVSSGQPK | 687 | 5 |
| | | | SYILWGPGTLVTVSSGQPK | 688 | 4 |
| | | | GFNLWGPGTLVTVSSGQPK | 689 | 3 |
| | | | FDFWGPGTLVTVSSGQPK | 690 | 3 |
| | | | DLGLWGPGTLVTVSSGQPK | 691 | 3 |
| | | | LWGPGTVVTVSSGQPK | 692 | 3 |
| | | | LWGPGTLVTVSAGQPK | 693 | 3 |
| | | | YFTLWGPGTLVTVSSGQPK | 694 | 3 |
| | | | DLWGPGTLVTVSSGQPK | 695 | 2 |
| | | | LFNLWGPGTLVTVSSGQPK | 696 | 2 |

TABLE 36-continued

Example of CDR3 VH gene sequence abundance (frequency ranking) determined by NextGen seuencing of the total bone marrow repertoire and the corresponding abundance of the respective antibodies in serum as deduced from counting the CDR3 peptide identified by MS.

| mRNA CDR3 Sequences | SEQ ID NO: | mRNA seq counts | MS CDR3 peptides | SEQ ID NO: | Peptide counts |
|---|---|---|---|---|---|
| | | | ECGLWGPGTLVTVSSGQPK | 697 | 2 |
| | | | DYDLWGPGTLVTVSSGQPK | 698 | 2 |
| | | | ADGGTYNLWGPGTLVTVSSGQPK | 699 | 2 |
| | | | AFNLWGPGTLVTVSSGQPK | 700 | 2 |
| | | | VFNLWGPGTLVTVSSGQPK | 701 | 2 |
| | | | TGYIGDGYPFNLWGPGTLVTVSSGQPK | 702 | 2 |
| | | | EGIYFDLWGPGTLVTVSSGQPK | 703 | 2 |
| | | | SYGASDLWGPGTLVTVSSGQPK | 704 | 2 |
| | | | YAFDPWGPGTLVTVSSGQPK | 705 | 2 |
| | | | NYNLWGPGTLVTVSSGQPK | 706 | 2 |
| | | | NFGLWGPGTLVTVSSGQPK | 707 | 1 |
| | | | DLWGQGTLVTVSSGQPK | 708 | 1 |
| | | | DSGYLWGPGTLVTVSSGQPK | 709 | 1 |
| | | | DGSVDYDLWGPGTLVTVSSGQPK | 710 | 1 |
| | | | SADGSSASGMHLWGPGTLVTVSSGQPK | 711 | 1 |
| | | | NICPSTDINLWGPGTLVTVSSGQPK | 712 | 1 |
| | | | SYAPTLWGPGTLVTVSSGQPK | 713 | 1 |
| | | | QYLLWGPGTLVTVSSGQPK | 714 | 1 |
| | | | DFNLWGPGTLVTVSSGQPK | 715 | 1 |
| | | | YFMDLWGPGTLVTVSSGQPK | 716 | 1 |
| | | | NGGLWGPGTLVTVSSGQPK | 717 | 1 |

* * *

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,683,202
U.S. Pat. No. 5,302,523
U.S. Pat. No. 5,322,783
U.S. Pat. No. 5,384,253
U.S. Pat. No. 5,384,253
U.S. Pat. No. 5,464,765
U.S. Pat. No. 5,538,877
U.S. Pat. No. 5,538,880
U.S. Pat. No. 5,550,318
U.S. Pat. No. 5,563,055
U.S. Pat. No. 5,580,859
U.S. Pat. No. 5,589,466
U.S. Pat. No. 5,610,042
U.S. Pat. No. 5,656,610
U.S. Pat. No. 5,702,932
U.S. Pat. No. 5,736,524
U.S. Pat. No. 5,780,448
U.S. Pat. No. 5,789,215
U.S. Pat. No. 5,928,906
U.S. Pat. No. 5,945,100
U.S. Pat. No. 5,981,274
U.S. Pat. No. 5,994,624
Ausubel et al., In: *Current Protocols in Molecular Biology*, Greene Publishing Associates and Wiley Interscience, N.Y., 1994.
Bhattacharya and Cheah, *J. Immunol.*, 179:6808-6819, 2007.
Boyd et al., *Sci. Transl. Med.*, 1:12ra23, 2009.
Brochet et al., *Nucleic Acids Res.*, 36:W503-508, 2008.
Carbonelli et al., *FEMS Microbiol. Lett.*, 177(1):75-82, 1999.
Carlson, *Nat. Biotechnol.*, 27:1091-1094, 2009.
Chen and Okayama, *Mol. Cell. Biol.*, 7(8):2745-2752, 1987.
Clackson et al., *Nature*, 352:624-628, 1991.
Cocea, *Biotechniques*, 23(5):814-816, 1997.
Cox et al., *Protein Sci.*, 16:379-390, 2007.
EP 171496
EP 173494
EP 194276
EP 239400
Fechheimer et al., *Proc Natl. Acad. Sci. USA*, 84:8463-8467, 1987.
Feldhaus et al., *Nat. Biotechnol.*, 21:163-170, 2003.
Fox et al., *Methods Mol. Biol.*, 553:79-108, 2009.
Fraley et al., *Proc. Natl. Acad. Sci. USA*, 76:3348-3352, 1979.
Gao et al., *Nucleic Acids Res.*, 31:e143, 2003.
Ge et al., *Biotechnol. Bioeng.*, 106:347-357, 2010.
Glanville et al., *Proc. Natl. Acad. Sci. USA*, 106:20216-20221, 2009.
Gopal, *Mol. Cell. Biol.*, 5:1188-1190, 1985.
Graham and Van Der Eb, *Virology*, 52:456-467, 1973.
Gygi et al., *Nat. Biotechnol.*, 17(10):994-999, 1999.
Harland and Weintraub, *J. Cell Biol.*, 101(3):1094-1099, 1985.
Harlow and Lane, In: *Antibodies: A Laboratory Manual*, Cold Spring Harbor Laboratory, Cold Spring Harbor, N.Y., 346-348, 1988.
Harvey et al., *Proc. Natl. Acad. Sci. USA*, 101:9193-9198, 2004.
Hayhurst et al., *J. Immunol. Methods*, 276:185-196, 2003.
Hoogenboom, *Nat. Biotechnol.*, 23:1105-1116, 2005.
Hosse et al., *Protein Sci.*, 15:14-27, 2006.
Hu et al., *J. Mass. Spectrom.*, 40:430-443, 2005.
Hunt et al., *Proc. Natl. Acad. Sci. USA*, 83:6233-6237, 1986.
Ishihama et al., *Mol. Cell. Proteomics*, 4:1265-1272, 2005.
Jackson et al., *Adv. Immunol.*, 98:151-224, 2008.
Jin et al., *Nat. Med.*, 15:1088-1092, 2009.
Kaeppler et al., *Plant Cell Rep.*, 8:415-418, 1990.
Kaneda et al., *Science*, 243:375-378, 1989.
Kato et al, *J. Biol. Chem.*, 266:3361-3364, 1991.
Keller et al., *Anal. Chem.*, 74:5383-5392, 2002.
Kohler and Milstein, *Nature*, 256:495-497, 1975.
Krebber et al., *J. Immunol. Methods*, 201:35-55, 1997.
Krebber et al., *J. Immunol. Methods*, 201:35-55, 1997.
Kretzschmar and von Ruden, *Curr. Opin. Biotech.*, 13:598-602, 2002.
Kwakkenbos et al., *Nat. Med.*, 16:123-128, 2010.
Lanzavecchia and Sallusto, *Curr. Opin. Immunol.*, 21:298-304, 2009.
Levenson et al., *Hum. Gene Ther.*, 9(8):1233-1236, 1998.
Link et al., *Nat. Biotechnol.*, 17:676-682, 1999.
Liu et al., *Anal. Chem.*, 76:4193-4201, 2004.
Love et al., *Nat. Biotechnol.*, 24: 703-707, 2006.
Lu et al., *Nat. Biotechnol.*, 25:117-124, 2007.
Malmstrom et al., *Nature*, 460(7256):762-5, 2009.
Maniatis, et al., Molecular Cloning, A Laboratory Manual, Cold Spring Harbor Press, Cold Spring Harbor, N.Y., 1988.
Manz et al., *Annu. Rev. Immunol.*, 23:367-386, 2005.
Manz et al., *Nature*, 388:133-134, 1997.
Marcotte, *Nat. Biotechnol.*, 25:755-757, 2007.
Mazor et al., *J. Immunol. Methods*, 321, 41-59, 2007.
Mazor et al., *Nat. Biotechnol.*, 25:563-565, 2007.
Meijer, P.-J. et al., *J. Molec. Biol.*, 358:764-772, 2006.
Nesvizhskii et al., *Anal. Chem.*, 75:4646-4658, 2003.
Nicolau and Sene, *Biochim. Biophys. Acta*, 721:185-190, 1982.
Nicolau et al., *Methods Enzymol.*, 149:157-176, 1987.
Ong and Mann, *Nat. Chem. Biol.*, 1:252-262, 2005.
Pandey and Mann, *Nature*, 405:837-846, 2000.
PCT Appln. WO 89/01782
PCT Appln. WO 89/01974
PCT Appln. WO 89/02465
PCT Appln. WO 94/09699
PCT Appln. WO 95/06128
Phan et al., *J. Exp. Med.*, 203:2419-2424, 2006.
Potrykus et al., *Mol. Gen. Genet.*, 199(2):169-177, 1985.
Potrykus et al., *Mol. Gen. Genet.*, 199:183-188, 1985.
Radbruch et al., *Nat. Rev. Immunol.*, 6:741-750, 2006.
Rajewsky, *Nature*, 381:751-758, 1996.
Rippe, et al., *Mol. Cell. Biol.*, 10:689-695, 1990.
Ross et al., *Mol. Cell. Proteomics*, 3(12):1154-69, 2004.
Sambrook and Russell, Molecular Cloning: A Laboratory Manual, 3rd Edition, Cold Spring Harbor Laboratory, N.Y., 1989.
Schaffitzel et al., *J. Immunol. Meth.*, 231:119-135, 1999.
Scheid et al., *Nature*, 458:636-640, 2009.
Shapiro-Shelef and Calame, *Nat. Rev. Immunol.*, 5:230-242, 2005.

Shendure and Ji, *Nat. Biotechnol.*, 26:1135-1145, 2008.
Shevchenko et al., *Proc. Natl. Acad. Sci. USA*, 93:14440-14445, 1996.
Silva et al., *Mol. Cell. Proteomics*, 5(4):589-607, 2006b.
Silva et al., *Mol. Cell. Proteomics*, 5:144-156, 2006a.
Smith et al., *Nat. Protoc.*, 4:372-384, 2009.
Tatusova et al., *FEMS Microbiol Lett.*, 174(2):247-50, 1999.
Traggiai, E. et al., *Nat. Med.*, 10:871-875, 2004.
Vogel and Marcotte, *Nature Protocols*, 3:1444-1451, 2008.
Washburn et al., *Nat. Biotechnol.*, 19:242-247, 2001.
Weinstein et al., *Science*, 324:807-810, 2009.
Wong et al., *Gene*, 10:87-94, 1980.
Wrammert et al., *Nature*, 453:667-671, 2008.
Zahnd et al., *Nat. Methods*, 4:269-279, 2007.

What is claimed is:

1. A method for determining antibody sequences in circulation from a subject, wherein the subject has a tumor, an infectious disease, an autoimmune disease, has been immunized or has been exposed to an antigen which is an infectious agent, a tumor antigen, a tumor cell or a self-antigen, comprising:
   a) obtaining mature B cells from the subject;
   b) isolating nucleic acids encoding VH and VL gene repertoires encoded by the mature B cells of the subject, and sequencing the isolated nucleic acids using a high-throughput sequencing method, wherein the high-throughput sequencing method is selected from the group consisting of sequencing-by-synthesis, sequencing-by-ligation, sequencing-by-hybridization, single molecule DNA sequencing, multiplex polony sequencing and nanopore sequencing, and determining the nucleic acid sequence and the corresponding amino acid sequence information of the VH and VL gene repertoires encoded by mature B cells of a subject;
   c) isolating antibodies from the biological fluid of the subject and preparing CDR3-containing peptide fragments derived from the isolated antibodies, separating the peptide fragments using chromatography, and generating mass spectra of the separated CDR3-containing peptide fragments;
   d) using the nucleic acid sequence information and the mass spectra to determine the amino acid sequence of VH and VL regions of one or more antibodies in circulation of the subject;
   e) determining the abundancy level of the amino acid sequences of the antibodies in circulation of the subject, and identifying the antibody sequences that exhibit at least a threshold level of abundancy; and
   f) expressing the one or more antibodies or antigen-binding fragments identified in step e) comprising one or more of the abundant amino acid sequences.

2. The method of claim 1, where in the mature B cells are from peripheral blood.

3. The method of claim 1, where in the mature B cells are from a lymphoid organ.

4. The method of claim 1, wherein step a) comprises determining the nucleic acid sequences and the corresponding amino acid sequences of rearranged antibody VH and VL.

5. The method of claim 1, wherein the mature B cells comprise memory B cells.

6. The method of claim 1, wherein the mature B cells comprise plasma cells.

7. The method of claim 1, wherein step b) comprises the use of high performance liquid chromatography (HPLC).

8. The method of claim 1, wherein step c) further comprises isolating or enriching a selected class of serum antibodies.

9. The method of claim 1, wherein step c) further comprises isolating or enriching serum antibodies that bind to a predetermined antigen.

10. The method of claim 1, wherein each of the antibodies or antigen-binding fragments so expressed in step f) comprises similarly abundant amino acid sequences of VH and VL or is part of a cluster of highly homologous amino acid sequence which are similarly abundant.

11. The method of claim 1, wherein the antibodies or antigen-binding fragments so expressed in step f) bind an antigen the subject has or has been exposed to with a monovalent affinity of about 100 pM to 5 μM.

12. The method of claim 1, further comprising evaluating binding affinity of the antibody or antigen-binding fragments so expressed in step f) toward a predetermined antigen.

* * * * *